United States Patent
Honma et al.

(10) Patent No.: US 7,105,564 B1
(45) Date of Patent: Sep. 12, 2006

(54) PHARMACEUTICAL COMPOSITION COMPRISING A DUAL ANTAGONIST AGAINST PGD$_2$/TXA$_2$ RECEPTORS HAVING A [2.2.1] OR [3.1.1] BICYCLIC SKELETON

(75) Inventors: Tsunetoshi Honma, Osaka (JP); Yoshiharu Hiramatsu, Osaka (JP); Akinori Arimura, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/936,161

(22) PCT Filed: Mar. 2, 2000

(86) PCT No.: PCT/JP00/01223

§ 371 (c)(1),
(2), (4) Date: Sep. 10, 2001

(87) PCT Pub. No.: WO00/53573

PCT Pub. Date: Sep. 14, 2000

(30) Foreign Application Priority Data

Mar. 10, 1999 (JP) ................... 11/062721

(51) Int. Cl.
- A61P 11/00 (2006.01)
- A61K 31/40 (2006.01)
- A61K 31/47 (2006.01)
- A61K 31/44 (2006.01)
- A61K 31/425 (2006.01)

(52) U.S. Cl. .............. 514/422; 514/307; 514/336; 514/352; 514/365; 514/367; 514/369; 514/370; 514/371; 514/378; 514/379; 514/393; 514/397; 514/406; 514/415; 514/419; 514/424; 514/427; 514/438; 514/443; 514/444; 514/445; 514/447; 514/448; 514/469; 514/471; 514/539; 514/562; 514/563; 546/147; 546/280.4; 546/309; 548/180; 548/188; 548/194; 548/195; 548/200; 548/204; 548/241; 548/247; 548/303.1; 548/315.1; 548/365.7; 548/510; 548/517; 548/518

(58) Field of Classification Search .............. 514/307, 514/336, 352, 365, 367, 369, 370, 371, 378, 514/379, 393, 397, 406, 415, 419, 422, 424, 514/427, 438, 443, 444, 445, 447, 448, 469, 514/471, 539, 562, 563; 546/147, 280.4, 546/309; 548/180, 188, 194, 195, 200, 204, 548/241, 247, 303.1, 315.1, 365.7, 510, 517, 548/518, 525, 527, 542, 561; 549/43, 44, 549/50, 51, 57, 58, 59, 60, 64, 65, 68, 69, 549/72, 77, 467, 487; 560/17, 21; 562/427, 562/461, 462, 466

See application file for complete search history.

(56) References Cited

U.S. PATENT DOCUMENTS 6,172,113 B1 * 1/2001 Ohtani et al. ............... 514/562
6,384,075 B1 * 5/2002 Ohtani et al. ............... 514/538

FOREIGN PATENT DOCUMENTS

WO    WO 97/00853    *   1/1997
WO    WO99/15502    *   4/1999

OTHER PUBLICATIONS

Tsuri et al., Bicyclo[2.2.1]heptane and 6,6-dimethylbicyclo[3.1.1]heptane Derivative: Orally Active, Potent, and Selective Prostaglandin D.sub.2 Receptor Antagonists, Journal of Medicinal Chemistry, vol. 40, No. 22, pp. 3504-3507, 1997.*

* cited by examiner

Primary Examiner—Brenda Coleman
(74) Attorney, Agent, or Firm—Foley & Lardner LLP

(57) ABSTRACT

The present invention provides novel compounds having a dual antagonistic activity against thromboxane A2 receptor and prostaglandin D$_2$ receptor and pharmaceutical compositions comprising them.

A compound of the formula (I):

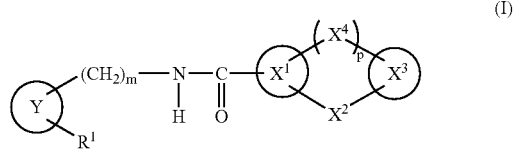

wherein R$^1$ is —CH$_2$—CH=CH—CH$_2$—CH$_2$—CH$_2$—COOR$_2$ or —CH=CH—CH$_2$—CH$_2$—CH$_2$—COOR$^2$; R$^2$ is hydrogen or alkyl; m is 0 or 1; p is 0 or 1; X$^1$ and X$^3$ each is independently optionally substituted aryl or optionally substituted heteroaryl; X$^2$ is a bond, —CH$_2$—, —S—, —SO$_2$—, —CH$_2$—O—, —O—CH$_2$—, —CH$_2$—S—, —S—CH$_2$—, or the like; X$^4$ is —CH$_2$—, —CH$_2$—CH$_2$—, —C(=O)—, or the like, have a dual antagonistic activity against both a thromboxane A$_2$ receptor and a prostaglandin D$_2$ receptor.

3 Claims, No Drawings

PHARMACEUTICAL COMPOSITION COMPRISING A DUAL ANTAGONIST AGAINST PGD₂/TXA₂ RECEPTORS HAVING A [2.2.1] OR [3.1.1] BICYCLIC SKELETON

This is a national stage application under 35 USC § 371 of PCT/JP00/01223, filed Mar. 2, 2000.

TECHNICAL FIELD

The present invention relates to a compound having a [2.2.1] or [3.1.1] bicyclic skeleton and a pharmaceutical composition comprising the same having a dual antagonistic activity against $PGD_2/TXA_2$ receptors.

BACKGROUND ART

Some compounds similar to those of the present invention having a [2.2.1] or [3.1.1] bicyclic skeleton have been described as thromboxane $A_2$ ($TXA_2$) antagonists in the Japanese Patent Publication (Kokoku) No. 53295/1991. $TXA_2$ is known to possess various activities such as platelet aggregation, thrombogenesis, contraction of airway smooth muscle, advance of respiratory anaphylaxis and the like. The $TXA_2$ antagonists have, therefore, been considered to be useful as anti-thrombotic agents, anti-vasoconstrictor, anti-respiratory contractile agents as well as medicines for treating myocardial infarction or asthma. The $TXA_2$ antagonists can be used for treating or improving conditions of diseases such as arteriosclerosis, myocardial infarction, acute myocardial ischemia angina, cardiovascular shock or preventing unexpected death and the like.

Further, other compounds similar to those of the present invention having a [2.2.1] or [3.1.1] bicyclic skeleton have been described as prostaglandin $D_2$ ($PGD_2$) antagonists in WO97/00853. $PGD_2$ is a prostanoid released from mast cells in which it is produced through $PGG_2$ and $PGH_2$ from arachidonic acid by the action of cyclooxygenase activated by immunological or unimmunological stimulation.

$PGD_2$ can cause strong contraction of smooth muscle of bronchus to lead to bronchial asthma, and dilate the peripheral vessels to cause an anaphylactic shook in a systemic allergic state.

Accordingly, $PGD_2$ antagonists are useful for the improvement of conditions caused by excessive production of $PGD_2$, particularly as medicines for treating diseases involved with mast cell dysfunction, for example, systemic mastocytosis and disorder of systemic mast cell activation as well as tracheal contraction, allergic rhinitis, allergic conjunctivitis, urticaria, itching, atopic dermatitis, alimentary allergy, ischemic reperfusion injury, cerebrovascular disorder, and inflammation.

As shown above, $PGD_2$ receptor antagonists have a quite different character from that of $TXA_2$ receptor antagonists in the site and mechanism of action and indications thereof.

On the other hand, a compound having a dual antagonistic activity against both a $TXA_2$ receptor and a $PGD_2$ receptor can be useful as therapeutic agents for various diseases caused by $TXA_2$ or $PGD_2$.

For example, in the case of bronchial asthma, it is known that $TXA_2$ cause potent tracheal contraction and respiratory anaphylaxis and $PGD_2$ effects infiltration of eosionophils. From these comprehension, $TXA_2$ and $PGD_2$ are thought to be one of causative substances of the pathopoiesis and advance of asthma, thus the dual antagonistic compounds are expected to be more potent agents for treating asthma than ever known antagonists.

Further, in the case of allergic rhinitis, it is recognized that $TXA_2$ and $PGD_2$ cause the swelling of nasal mucosa through the aggravation of vascular permeability, and $PGD_2$ induces the nasal blockage through the enlargement of vascular volume. Therefore, the dual antagonistic compounds are expected to be more potent agents for treating nasal blockage than ever known antagonists.

These diseases and condition thereof might be treated by administering both a $TXA_2$ receptor antagonist and a $PGD_2$ receptor antagonist at the same time, for example, in combination therapy or as a mixture thereof. But the administration of two or more agents often causes some problems due to the difference of their metabolic rate. For example, when the antagonists are different from each other in the time to reach a maximum blood concentration or the duration of action, they do not always efficiently exhibit each receptor antagonistic effect at the same time, failing to give a desired additive or synergic effect.

It has therefore been desired to develop medicines having a dual antagonistic activity against $TXA_2/PGD_2$ receptors, which exhibit new excellent therapeutic effects and can be used for many indications.

DISCLOSURE OF INVENTION

The present inventors have studied intensively to develop a pharmaceutical composition having a dual antagonistic activity against $TXA_2/PGD_2$ receptors and found out new compounds and pharmaceutical compositions comprising them.

The present invention provides:

(1) a pharmaceutical composition having a dual antagonistic activity against PGD₂/TXA2 receptors which comprises a compound of the formula (I):

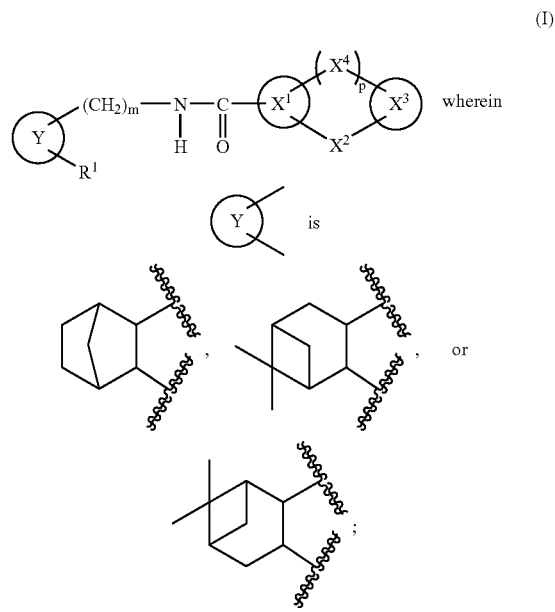

$R^1$ is —$CH_2$—CH=CH—$CH_2$—$CH_2$—$CH_2$—$COOR^2$ or —CH=CH—$CH_2$—$CH_2$—$CH_2$—$COOR_2$;

R2 is hydrogen or alkyl;

m is 0 or 1;

p is 0 or 1, provided that when p=0, $X^1$ is not bonded to $X^3$ via $X^4$;

$X^1$ and $X^3$ are independently optionally substituted aryl or optionally substituted heteroaryl;

$X^2$ is a single bond, —$CH_2$—, —$CH_2$—$CH_2$—, —C(=O)—, —O—, —S—, —SO—, —$SO_2$—, —NH—, —N($CH_3$)—, —C(=N—O—$CH_3$)—, —N=N—, —CH=CH—, —(C=O)—NH—, —NH—(C=O)—, —$CH_2$NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH— or —NH—$SO_2$—;

$X^4$ is —$CH_2$—, —$CH_2$—$CH_2$—, —C(=O)—, —SO—, —$SO_2$—, —(C=O)—NH—, —NH—(C=O)—, —$CH_2$NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH— or —NH—$SO_2$—, a prodrug, a pharmaceutically acceptable salt or a hydrate thereof, (2) the pharmaceutical composition having a dual antagonistic activity against $PGD_2/TXA_2$ receptors according to the above (1) wherein at least one of $X^1$ and $X^3$ is optionally substituted heteroaryl, (3) the pharmaceutical composition having a dual antagonistic activity against $PGD_2/TXA_2$ receptors according to the above (1) or (2) wherein $R^1$ is —$CH_2$—CH=CH—$CH_2$—$CH_2$—$CH_2$—COOH, m is 0 and p is 0, (4) the pharmaceutical composition having a dual antagonistic activity against $PGD_2/TXA_2$ receptors according to any one of the above (1) to (3) which is used for asthma, (5) the pharmaceutical composition having a dual antagonistic activity against $PGD_2/TXA_2$ receptors according to any one of the above (1) to (3) which is used for nasal blockage, (6) use of the compound according to any one of the above (1) to (3) for manufacturing a pharmaceutical composition for asthma or nasal blockage, (7) a method for treating asthma or nasal blockage which comprises administering the compound according to any one of the above (1) to (3), (8) a compound of the formula (I):

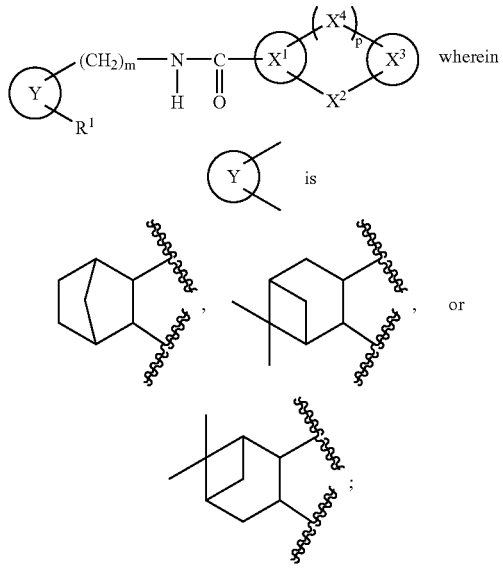

$R^1$ is —$CH_2$—CH=CH—$CH_2$—$CH_2$—$CH_2$—$COOR_2$ or —CH=CH—$CH_2$—$CH_2$—$CH_2$—$COOR_2$;

$R^2$ is hydrogen or alkyl;

m is 0 or 1;

p is 0 or 1, provided that when p=0, $X^1$ is not bonded to $X^3$ via $X^4$;

$X^1$ and $X^3$ are independently optionally substituted aryl or optionally substituted heteroaryl;

$X^2$ is a single bond, —$CH_2$—, —$CH_2$—$CH_2$—, —C(=O)—, —O—, —S—, —SO—, —$SO_2$—, —NH—, N($CH_3$)—, —C(=N—O—$CH_3$)—, —N=N—, —CH=CH—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH— or —NH—$SO_2$—;

$X^4$ is —$CH_2$—, —$CH_2$—$CH_2$—, —C(=O)—, —SO—, —$SO_2$—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH—, or —NH—$SO_2$—;

provided that when

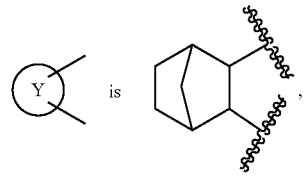

a compound wherein $R^1$ is —$CH_2$—CH=CH—$CH_2$—$CH_2$—$CH_2$—$COOR^2$, $R^2$ is hydrogen or methyl, m is 0, p is 0, $X^1$ is phenyl optionally substituted with methoxy, $X^2$ is a bond, —O—, —$CH_2$—, —C(=O)—NH—, —S— or —N=N—, and $X^3$ is phenyl optionally substituted with hydroxy, acetoxy or methoxy, and a compound wherein $R^1$ is —$CH_2$—CH=CH—$CH_2$—$CH_2$—$CH_2$—COOH, m is 1, p is 0, $X^1$ is phenyl, $X^2$ is —N=N—, and $X^3$ is phenyl, are excluded, and when

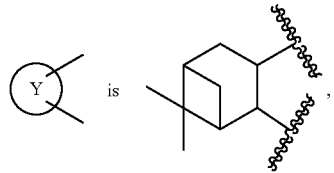

$R^1$ is —$CH_2$—CH=$CH_2$—$CH_2$—$CH_2$—$COOR^2$, $R^2$ is hydrogen or methyl, m is 0, and p is 0, a compound wherein $X^1$ is phenyl optionally substituted with methyl or methoxy, $X^2$ is a single bond, —$CH_2$—$CH_2$—, —C(=O)—, —NH—, —O—, —S—, —SO—, —$SO_2$—, —CH=CH—, —N=N—, —C(=O)—NH— or —NH—C(=O)—, and $X^3$ is phenyl optionally substituted with methyl, hydroxy, acetoxy, methoxy, ethoxy, isopropoxy, dimethylamino, hydroxymethyl, methoxymethyl or carboxy, a compound wherein $X^1$ is phenyl, $X^2$ is a single bond, —$CH_2$— or —CH=CH—, and $X^3$ is imidazolyl, thienyl, pyridyl or tetrazolyl optionally substituted with methyl or phenyl, and a compound wherein $X^1$ is benzothienyl, isoxazolyl or thienyl optionally substituted with methyl, $X^2$ is a single bond or —S—, and $X^3$ is phenyl optionally substituted with methoxy or methyl, are excluded, a prodrug, a pharmaceutically acceptable salt, a hydrate thereof, (9) the compound according to the above (8) wherein at least one of $X^1$ and $X^3$ is optionally substituted heteroaryl, the prodrug, the pharmaceutically acceptable salt, the hydrate thereof,

(10) the compound according to the above (8) wherein $X^1$ and $X^3$ each is independently optionally substituted heteroaryl, the prodrug, the pharmaceutically acceptable salt, the hydrate thereof,

(11) the compound according to the above (8) wherein at least one of $X^1$ and $X^3$ is optionally substituted thienyl or optionally substituted benzothienyl, the prodrug, the pharmaceutically acceptable salt, the hydrate thereof,

(12) the compound according to any one of the above (8) to (11) wherein $X^2$ is a single bond, —$CH_2$—, —S—, —$SO_2$—, —$CH_2$—O—, —O—$CH_2$—, —$CH_2$—S— or —S—$CH_2$—, the prodrug, the pharmaceutically acceptable salt, the hydrate thereof,

(13) the compound according to any one of the above (8) to (12) wherein $R^1$ is —$CH_2$—CH=CH—$CH_2$—$CH_2$—$CH_2$—COOH, m is 0, and p is 0, the prodrug, the pharmaceutically acceptable salt, the hydrate thereof,

(14) a pharmaceutical composition which comprises a compound according to any one of the above (8) to (13),

(15) a pharmaceutical composition having a dual antagonistic activity against $PGD_2/TXA_2$ receptors which comprises a compound according to any one of the above (8) to (13),

(16) the pharmaceutical composition according to the above (14) or (15), which is used for asthma, and

(17) the pharmaceutical composition according to the above (14) or (15), which is used for nasal blockage.

BEST MODE FOR CARRYING OUT THE INVENTION

A compound of the present invention is characterized in that (A) a bicyclic ring represented by the Y ring of the above formula (I) is [2.2.1] or [3.1.1] skeleton, (B) an ω chain attached to the bicyclic ring, a group represented by the formula:

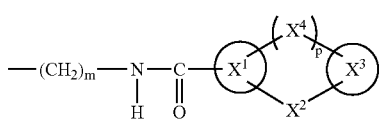

of the above formula (I), includes —NH—CO—, and $X^1$ and $X^3$ each is independently optionally substituted aryl or optionally substituted heteroaryl, (C) $X^1$ and $X^3$ bond via $X^2$, and the like A more preferred embodiment is a compound of the formula (I) wherein (1) at least one of $X^1$ and $X^3$ is optionally substituted heteroaryl, (2) $X^1$ and $X^3$ each is independently optionally substituted heteroaryl, (3) at least one of $X^1$ and $X^3$ is optionally substituted thienyl or optionally substituted benzothienyl, (4) $R^1$ is —$CH_2$—CH=CH—$CH_2$—$CH_2$—$CH_2$—COOH, m is 0 and p is 0, (5) $X^2$ is a bond, —$CH_2$—, —S—, —$SO_2$—, —$CH_2$—O—, —O—$CH_2$—, —$CH_2$—S— or —S—$CH_2$—, (6) $R^1$ is —CH=CH—$CH_2$—$CH_2$—$CH_2$—COOH and m is 1, or (7) p is 0.

The term "heteroaryl" includes a 5- to 7-membered aromatic heterocycle containing one or more oxygen atom, sulfur atom and/or nitrogen atom in the ring, or such an aromatic heterocycle as fused with one or more carbocycle or other aromatic heterocycle, which has a bond at any substitutable. Any one of aromatic heterocycle and aromatic carbocycle may have a bond. "Heteroaryl" may have a bond at a nitrogen atom as well as a carbon atom of aromatic heterocycle or aromatic carbocycle. Examples of "heteroaryl" include pyrrolyl (e.g., 1-pyrrolyl, 2-pyrrolyl, 3-pyrrolyl), pyridyl (e.g., 2-pyridyl, 3-pyridyl, 4-pyridyl), pyrazolyl (e.g., 1-pyrazolyl, 3-pyrazolyl, 4-pyrazolyl), imidazolyl (e.g., 1-imidazolyl, 2-imidazolyl, 4-imidazolyl), pyrimidinyl (e.g., 2-pyrimidinyl, 4-pyrimidinyl, 5-pyrimidinyl), pyrazinyl (e.g., 2-pyrazinyl), indolyl (e.g., 1-indolyl, 2-indolyl, 3-indolyl, 4-indolyl, 5-indolyl, 6-indolyl, 7-indolyl), carbazolyl (e.g., 1-carbazolyl, 2-carbazolyl, 3-carbazolyl, 4-carbazolyl, 9-carbazolyl), benzimidazolyl (e.g., 1-benzimidazolyl, 2-benzimidazolyl, 4-benzimidazolyl, 5-benzimidazolyl), indazolyl (e.g., 1-indazolyl, 2-indazolyl, 3-indazolyl, 4-indazolyl, 5-indazolyl, 6-indazolyl, 7-indazolyl), quinolyl (e.g., 2-quinolyl, 3-quinolyl, 4-quinolyl, 5-quinolyl, 6-quinolyl, 7-quinolyl, 8-quinolyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), furyl (e.g., 2-furyl, 3-furyl), benzofuryl (e.g., 2-benzofuryl, 3-benzofuryl, 4-benzofuryl, 5-benzofuryl, 6-benzofuryl, 7-benzofuryl), thienyl (e.g., 2-thienyl, 3-thienyl), benzothienyl (e.g., benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), dibenzothienyl (e.g., 2-dibenzothienyl, 3-dibenzothienyl), dibenzofuryl (e.g., 2-dibenzofuryl, 3-dibenzofuryl), naphthothienyl (e.g., naphtho[2,3-b]thiophen-2-yl, naphtho [2,3-b]thiophen-3-yl, naphtho[1.2-b]thiophen-2-yl, naphtho[1.2-b]thiophen-3-yl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), imidazothiazolyl (e.g., imidazo[2.1-b]thiazol-2-yl, imidazo[2.1-b]thiazol-3-yl), benzoisoxazolyl (e.g., benzo[d]isoxazol-3-yl), benzothiazolyl (e.g., benzo[d]thiazol-2-yl) or the like.

"Aromatic carbocycle or other aromatic heterocycle" which may fuse the above "heteroaryl" includes 5- to 7-membered aromatic cycle which may contains one or more oxygen atom, sulfur atom and/or nitrogen atom in the ring, or such a aromatic ring as fused with one or more other aromatic rings.

"Aryl" includes mono aromatic carbocyclyl (e.g., phenyl) or fused aromatic heterocyclyl (e.g., 1-naphthyl, 2-naphthyl, 1-anthryl, 9-anthryl, 1-phenanthryl, 10-phenanthryl).

"Aryl" or "heteroaryl" may be fused 4- to 7-membered cycloalkane or 4- to 7-membered non-aromatic heterocycle. Examples of cycloalkane include cyclobutane, cyclopentane, cyclohexane, cycloheptane. Examples of nonaromatic heterocycle includes pyrrolidine, piperazine, oxorane, 1,3-dioxorane, 1,4-dioxane, thiorane, or the like. "cycloalkane" or "non-aromatic heterocycle" may be fused with aromatic carbocycle or aromatic heterocycle. Examples of aryl or heteroaryl fused with 4- to 7-membered cycloalkane or 4- to 7-membered non-aromatic heterocycle are illustrated below.

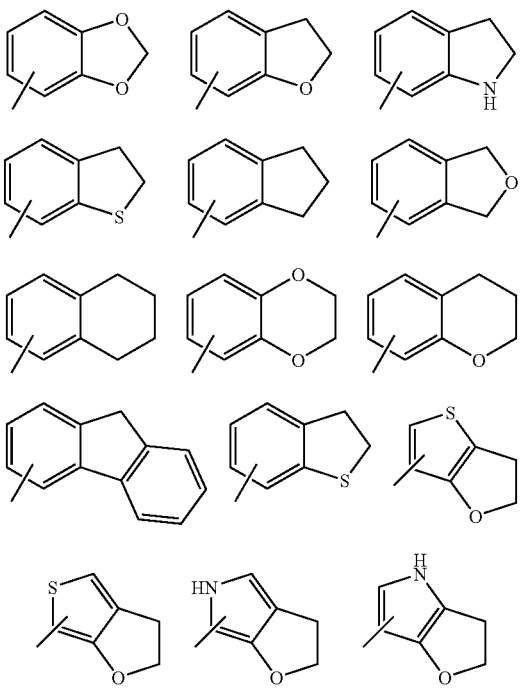

Examples of the substituent on "optionally substituted aryl" or "optionally substituted heteroaryl" include a group of the formula: $-Z^1-Z^2$ wherein $Z^1$ is a single bond, —O—, —S—, —NH—, —NH—C(=O)—, —NH—C(=O)—O—, —NH—SO$_2$—, —C(=O)—, —O—C(=O)—, —C(=O)—O—, or —SO$_2$-; and $Z^2$ is alkyl, haloalkyl, alkenyl, alkynyl, aryl optionally substituted alkyl or halogen, heteroaryl optionally substituted with alkyl or halogen, arylalkyl optionally substituted with alkyl or halogen, heteroarylalkyl optionally substituted with alkyl or halogen, carboxy, halogen (F, Cl, Br, I), hydroxyalkyl, hydroxy, nitro, cyano, mercapto, thioformyl, thioacetyl, thiocarboxy, dithiocarboxy, thiocarbamoyl, sulfino, sulfo, sulfamoyl, sulfoamino, optionally substituted amino, optionally substituted aminoalkyl, hydroxyamino, carbamoyl, hydorazino. One to three substituents may be at any suitable position on the above aryl or heteroaryl.

"Alkyl" includes a straight or branched C1 to C8 alkyl group or a C3 to C8 cycloalkyl group , for example, methyl, ethyl, n-propyl, isopropyl, n-butyl, isobutyl, tert-butyl, n-pentyl, isopentyl, n-hexyl, n-heptyl, n-octyl, cyclopropyl, cyclobutyl, cyclopentyl, cyclohexyl, cycloheptyl or the like.

"Haloalkyl" includes a straight or branched C1 to C8 alkyl or C3 to C8 cycloalkyl group substituted with one or more halogen, for example, chloromethyl, fluoromethyl, trifluoromethyl, 2,2,2-trifluoroethyl, 1,1-difluoroethyl, trichloromethyl, 2,2,2-trichloroethyl, 1,1-dichloroethyl or the like.

"Alkenyl" includes a straight or branched C2 to C8 alkenyl or C3 to C8 cycloalkenyl group having one or more double bonds, for example, vinyl, 1-propenyl, 2-propenyl, isopropenyl, 2-cyclobuten-1-yl, 2-cyclopenten-1-yl, 3-cyclopenten-1-yl, 2-cyclohexen-1-yl or the like.

"Alkynyl" includes a straight or branched C2 to C8 alkynyl or C3 to C8 cycloalkynl group having one or more triple bonds, for example, ethynyl, 1-propynyl, 2-propynyl, 1-butynyl, 2-butynyl, 3-butynyl or the like.

"Halogen" means fluoro, chloro, bromo, iodo.

"Alkyl", "aryl" and "heteroaryl" used in the term "arylalkyl" or "heteroarylalkyl" have the same meaning of the above "alkyl", "aryl" and "heteroaryl".

"Hydroxy alkyl" includes the above "alkyl" substituted with one or two hydroxy, for example, hydroxymethyl, 1-hydroxyethyl, 2-hydroxyethyl, 1,2-dihydroxyethyl, 1,2-dihydroxy-n-propyl or the like.

Examples of the substituent of "optionally substituted amino" or "optionally substituted amino alkyl" include the above "alkyl", the above "arylalkyl", the above "aryl", the above "heteroaryl", the above "heteroarylalkyl" or the like. They may be mono- or di-substituted with these substituents. When the substituent is alkyl, alkyl may form a ring together with a nitrogen atom of an amino group.

Example of "optionally substituted amino" includes amino, dimethylamino, methylethylamino, diethylamino, pyrrolidino, piperidino, phenylmethylamino, isopropylamino, diisopropylamino or the like.

Examples of "optionally substituted aminoalkyl" include dimethylaminomethyl, methylethylaminomethyl, diethylaminomethyl, pyrrolidinomethyl, piperidinomethyl, phenylmethylaminomethyl, isopropylaminomethyl, diisopropylaminomethyl or the like.

"A pharmaceutical composition having a dual antagonistic activity against PGD$_2$/TXA$_2$ receptors" means a pharmaceutical composition comprising a compound having at least one compound of the formula (I) having an antagonistic activity against both a PGD$_2$ receptor and a TXA$_2$ receptor.

The present invention includes a method for treating asthma or nasal blockage which comprises administering a compound of the formula (I) and use of a compound of the formula (I) for manufacturing a medicine for asthma or nasal blockage.

A compound of the present invention can be any of the following stereo isomers of [2.2.1] and [3.1.1] bicyclic skeleton.

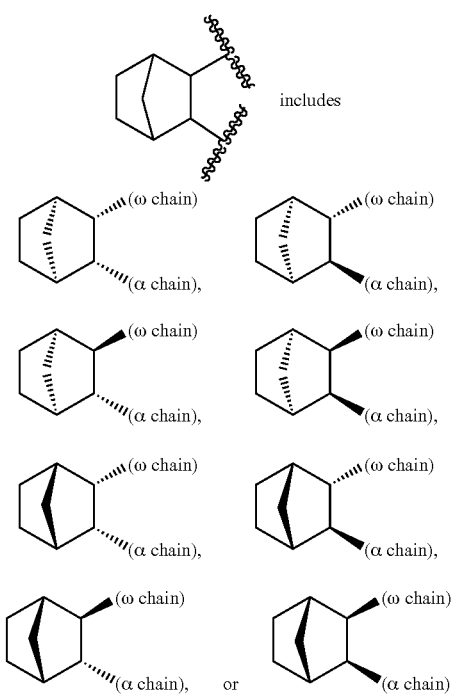

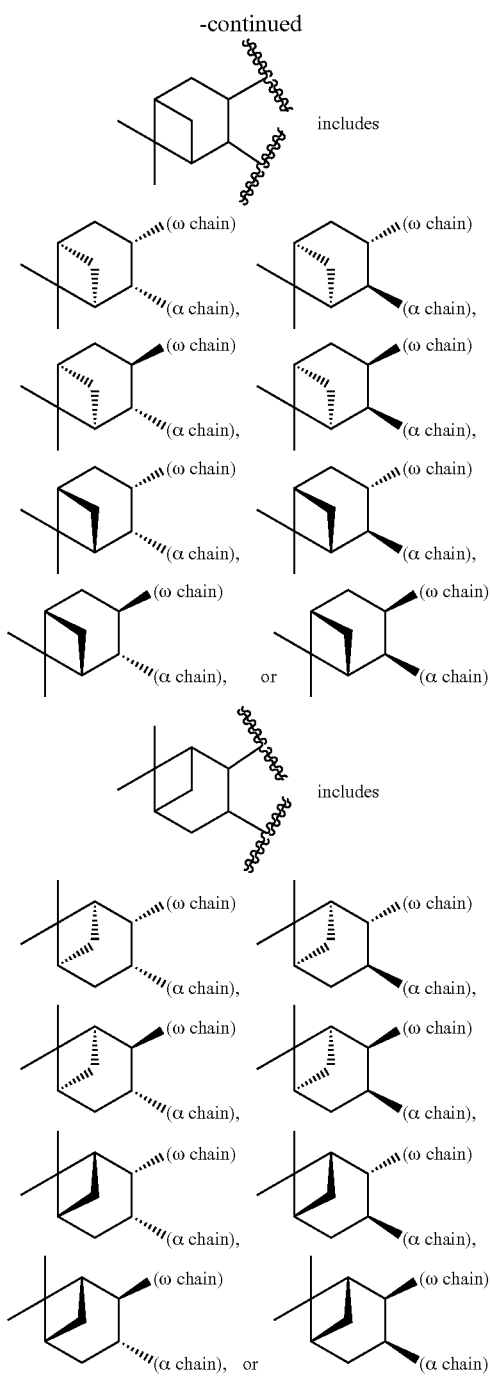

In these stereo isomers, the most preferable is a compound having the skeleton of the formula:

"α chain" means a group represented by the formula: —R¹, and "ω chain" means a group represented by the formula:

$$-(CH_2)_m-N-C-\begin{pmatrix}X^1\\X^2\end{pmatrix}\begin{pmatrix}X^4\\ \end{pmatrix}_p X^3$$

The present invention includes all stereo isomers of them and the optional mixtures thereof. Namely, the bond binding to the bicyclic ring is in R configuration or S configuration, and all of the stereo isomers (diastereomer, epimer, enantiomer and the like), racemates, and optional mixture thereof are included in the present invention.

Moreover, the α chain of the compound of the present invention can be in Z configuration or E configuration, thus a compound having any of the configurations and the mixture thereof are included in the present invention.

A prodrug of a compound of the formula (I) is a derivative of the compound of the present invention having a group which can be decomposed chemically or metabolically, and such prodrug is converted to a pharmaceutically active compound of the present invention by means of solvolysis or by placing the compound in vivo under a physiological condition. Method for the selection and process of an appropriate prodrug derivative are described in the literature such as Design of Prodrugs, Elsevier, Amsterdam 1985.

When the compound of the formula (I) has a carboxyl group, an ester derivative prepared by reacting a basal acid compound with a suitable alcohol or an amide derivative prepared by reacting a basal acid compound with a suitable amine is exemplified as a prodrug. A particularly preferred ester derivative as an prodrug is an optionally substituted alkyl ester derivative (e.g., methyl ester, ethyl ester, n-propyl ester, isopropyl ester, n-butyl ester, isobutyl ester, tert-butyl ester, morpholinoethyl ester), an arylalkyl ester derivative (e.g., benzyl ester, phenethyl ester, benzhydryl ester), or the like. A particularly preferred amide derivative as a prodrug is alkyl amide derivative (e.g., N-methyl amide, N-ethyl amide, N-(n-propyl)amide, N-isopropyl amide, N-(n-butyl) amide, N-isobutyl amide, N-(tert-butyl)amide), aryl alkyl amide (e.g., N-benzyl amide, N-phenethyl amide, benzhydryl amide), or the like.

When the compound of the formula (I) has a hydroxy group, an acyloxy derivative prepared by reacting with a suitable acyl halide (e.g., acid chloride, halogenated acid) or a suitable acid anhydride (e.g., mixed acid anhydride) is exemplified as a prodrug. A particularly preferred acyloxy derivative as a prodrug is a derivative substituted with optionally substituted alkylcarbonyloxy (e.g., —OCOC$_2$H$_5$, —OCO(tert-Bu), —OCOC$_{15}$H$_{31}$, —OCOCH$_2$CH$_2$COON$_a$, —OCOCH(NH$_2$)CH$_3$, —OCOCH$_2$N(CH$_3$)$_2$—), optionally substituted arylcarbonyloxy (e.g., —OCO(m—COON$_a$—Ph) or the like.

When the compound of the formula (I) has an amino group, an amide derivative prepared by reacting with a suitable acid halide or a suitable acid anhydride is exemplified as a prodrug. A particularly preferred amide derivative as a prodrug is a derivative substituted with optionally substituted alkylcarbonyl (e.g., —NHCO(CH$_2$)$_{20}$CH$_3$, —NHCOCH(NH$_2$)CH$_3$) or the like.

Examples of a salt of the compound of the formula (I) or its prodrug include alkali metal salts such as lithium salts, sodium salts or potassium salts, alkaline-earth metal salts such as calcium salts, salts with organic bases such as tromethamine, trimethylamine, triethylamine, 2-aminobutane, tert-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthylene methylamine, diphenylbenzylamine, triphenylamine, 1-naphthylamine, 1-aminoanthorathene, 2-aminoanthorathene, dehydroabiethylamine, N-methylmorpholine, pyridine), basic amino acid salts such as arginine salts or lysine salts.

A hydrate means a hydrate of the compound of the formula (I), its prodrug or its pharmaceutically acceptable salt, for example, monohydrate, dihydrate or the like.

General processes for the preparation of the compounds of the formula (I) are illustrated as follows.

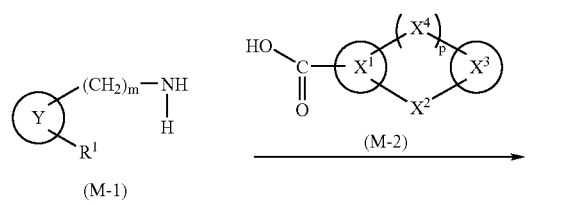

wherein

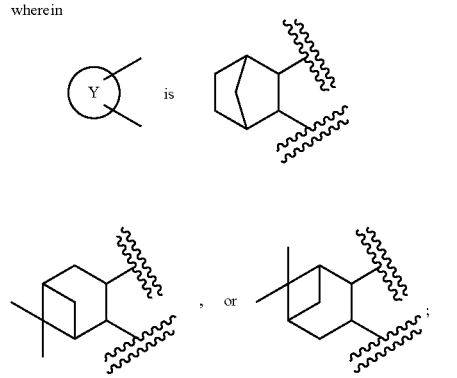

$R^1$ is —$CH_2$—CH=CH—$CH_2$—$CH_2$—$CH_2$—COOR2 or —CH=CH—$CH_2$—$CH_2$—$CH_2$—COOR$^2$;

$R^2$ is hydrogen or alkyl;

m is 0 or 1;

p is 0 or 1, provided that when p is 0, $X^1$ is not bonded to $X^3$ via $X^4$;

$X^1$ and $X^3$ each is independently optionally substituted aryl or optionally substituted heteroaryl;

$X^2$ is a bond, —$CH_2$—, —$CH_2$—$CH_2$—, —C(=O)—, —O—, —S—, —SO—, —$SO_2$—, —NH—, —N($CH_3$)—, —C(=N—O—$CH_3$)—, —N=N—, —CH=CH—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH— or —NH—$SO_2$—;

$X^4$ is —$CH_2$—, —$CH_2$—$CH_2$—, —C(=O)—, —SO—, —$SO_2$—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH— or —NH—$SO_2$—.

As shown in the above process, the compound of the formula (I) can be prepared by reacting a carboxylic acid of the formula (M-2) or its reactive derivative with an amino compound of the formula (M-1).

In this process, the starting compound (M-1) wherein $R^1$ is —$CH_2$—CH=CH—$CH_2$—$CH_2$—$CH_2$—COOMe, m is 0, Y is [2.2.1]bicyclic skeleton, 7-(3-amino-bicyclo[2.2.1]hept-2-yl)-5-heptenoic acid methyl ester is described in the Japanese Patent Publication (Kokoku) No. 79060/1993. The other starting compounds can be prepared in accordance with methods as described in the above publication.

When p is 0, the carboxylic acid of the formula (M-2) can be prepared by reacting a carboxylic acid having $X^1$ or its reactive derivative with a compound having $X^3$. A person ordinary skilled in the art can carry out such a reaction by selecting the kinds of reactions and their conditions depending on the kind of $X^2$.

The reactive derivatives of carboxylic acid of the formula (M-2) mean the corresponding acid halides (e.g., chloride, bromide, iodide), acid anhydrides (e.g., mixed acid anhydride with formic acid or acetic acid), active esters (e.g., succinimide ester), and the like, and include acylating agents used for the usual acylation of amino group.

For example, an acid halide is obtained by reacting the compound (M2) with a thionyl halide (e.g., thionyl chloride), phosphorous halide (e.g., phosphorous trichloride, phosphorous pentachloride), oxalyl halide (e.g., oxalyl chloride), and the like, in accordance with known methods as described in the literatures (e.g., Shin-Jikken-Kagaku-Koza, Vol. 14, 1787 (1978); Synthesis 852–854 (1986); Shin-Jikken-Kagaku-Koza Vol. 22, 115 (1992)).

The reaction can be conducted under a condition generally used for the acylation of amino group. For example, in the case of condensation with the acid halide, the reaction is carried out in a solvent such as an ether solvent (e.g., diethyl ether, tetrahydrofuran, dioxane), benzene solvent (e.g., benzene, toluene, xylene), halogenated hydrocarbon solvent (e.g., dichloromethane, dichloroethane, chloroform) as well as ethyl acetate, dimethylformamide, dimethyl sulfoxide, acetonitrile, or the like, if necessary, in the presence of a base (e.g., organic base such as triethylamine, pyridine, N,N-dimethylaminopyridine, N-methylmorpholine; inorganic base such as sodium hydroxide, potassium hydroxide, potassium carbonate, or the like) under cooling, at room temperature, or under heating, preferably at a temperature ranging from −20° C. to ice-cooling temperature, or from a room temperature to a refluxing temperature of the reaction system, for a period of several min to several hr, preferably for 0.5 hr to 24 hr, particularly, for 1 hr to 12 hr.

In the case of using the carboxylic acid (M-2) in a free form without converting into the reactive derivatives, the reaction is conducted in the presence of a condensing agent (e.g., dicyclohexylcarbodiimide (DCC), 1-ethyl-3-(3-methylaminopropyl)carbodiimide, N,N'-carbonyldiimidazole) usually used in the condensation reaction of amine and carboxylic acid.

When "optionally substituted aryl" or "optionally substituted heteroaryl" in $X^1$ or $X^3$ of the compound of the formula (M-2) is substituted with a hydroxy group or an amino group, such a compound can be used after protection by acetyl group or the like in accordance with the well known method.

In the reaction of the other reactive derivatives or free acid (M-2) with the amine (M-1), the reaction conditions are determined according to the property of each reactive derivative or free acid, in accordance with a known method. The reaction product can be purified in accordance with a conventional purification, such as the extraction with a solvent, chromatography, recrystallization, and the like.

When p is O, a group of the formula: —NHCO—X$^1$—X$^2$—X$^3$ of the compound (I) can be introduced by reacting a carboxylic acid of the formula: X$^3$—X$^2$—X$^1$—COOH (M-2) or its reactive derivative with amine (M-1), or by reacting a carboxylic acid having X$^1$ or its reactive derivatives with amine (M-1) and reacting the obtained compound with a compound having X$^3$.

In case of the introduction of a substituent(s) into the "optionally substituted aryl" or "optionally substituted heteroaryl", the change of the functional group can be performed before or after reacting a carboxylic acid or its reactive derivative thereof (M-2) with the amine (M-1). For example, the compound having an aromatic heterocycle substituted with a nitro group can be prepared through the nitration of the compound with a nitrating acid. Moreover, the compound having an aromatic heterocycle substituted with an amino group can be prepared through the reduction of the above-obtained compound with tin in the presence of hydrochloride. Moreover, the compound having an aromatic heterocycle substituted with hydroxy group can be prepared through the diazonization of the above-obtained compound and the hydrolysis with alkali. On the other hand, the compound having an aromatic heterocycle substituted with an alkoxy group can be prepared through the reaction of the diazonium derivative with alcohol. The compound having an aromatic heterocycle substituted with halogen can be prepared through Sandmeyer reaction, the reaction of the diazonium derivative with a copper salt (e.g., CuCl$_2$, CuBr$_2$). The compound having an aromatic heterocycle substituted with halogen can be also prepared through the direct reaction of the compound having an aromatic heterocycle with chlorine and the like. Using the above-mentioned methods appropriately, halogen can be introduced into a desired position(s). The group of alkyl, alkenyl or acyl group can be directly introduced into an aromatic heterocycle through Friedel Crafts reaction with alkylating agent, an alkenylating agent, or an acylating agent, respectively, in the presence of anhydrous aluminum chloride.

The objective compound (I) of the present invention can be converted into a corresponding ester derivative, if desired. For example, the ester derivative can be prepared by esterification of a carboxylic acid in accordance with a known method.

When using the compound (I) of the present invention in treatment, it can be formulated into ordinary formulations for oral and parenteral administration. A pharmaceutical composition containing the compound (I) of the present invention can be in the form for oral and parenteral administration. Specifically, it can be formulated into formulations for oral administration such as tablets, capsules, granules, powders, syrup, and the like; or those for parenteral administration such as injectable solution or suspension for intravenous, intramuscular, or subcutaneous injection, inhalant, eye drops, nasal drops, suppositories, or percutaneous formulations such as ointment.

In preparing the formulations, carriers, excipients, solvents, and bases known to one having ordinary skill in the art may be used. In case of tablets, they are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated appropriately. In case of liquid formulations such as syrups, solutions, or suspensions, they may contain suspending agents (e.g., methyl cellulose), emulsifiers (e.g., lecithin), preservatives, and the like. In case of injectable formulations, it may be in the form of solution, suspension, or oily or aqueous emulsion, which may contain suspension-stabilizing agents or dispersing agent, and the like. In case of an inhalant, it is formulated into a liquid formulation applicable to an inhaler. In case of eye drops, it is formulated into a solution or a suspension.

Especially, in case of a nasal drug for treating nasal blockage, it can be used as a solution or suspension prepared by a conventional formulating method, or administered as a powder formulated using a powdering agent (e.g., hydroxypropyl cellulose, carbopole) into the nasal cavity. Alternatively, it can be used as an aerosol filled into a special container together with a solvent of low boiling point.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between 0.01–100 mg, preferably 0.01–10 mg, more preferably 0.01–1 mg, per kg body weight. In case of parenteral administration, the daily dosage can generally be between 0.001–100 mg, preferably 0.001–1 mg, more preferably 0.001–0.1 mg, per kg body weight. The daily dosage can be administered in 1–4 divisions.

The following examples are provided to further illustrate the present invention and are not to be construed as limiting the scope.

EXAMPLE 1

Preparation of (5Z)-7-{(1R,2S,3S,4S)-3-[5-(pyrrol-1-ylsulfonyl)-thiophen-2-ylcarbonylamino]-bicyclo[2.2.1]hept-2-yl}-5-heptenoic acid (I-1b)

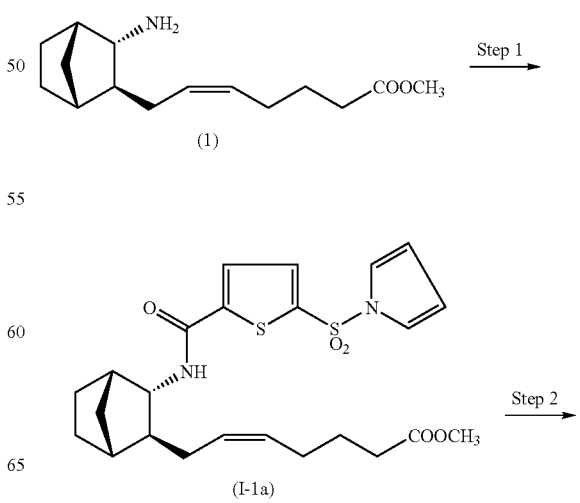

-continued

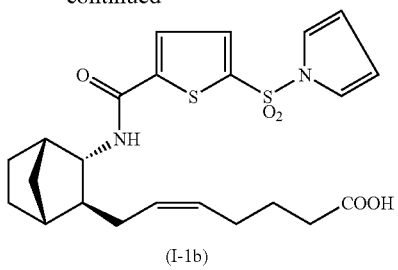

(I-1b)

(Step 1)

To a solution of 251 mg (1.0 mmol) of (5Z)-7-[(1R,2S,3S,4S)-3-aminobicyclo[2.2.1]hept-2-yl]-5-heptenoic acid methyl ester (1) in 4 ml of tetrahydrofuran were added 257 mg (1.0 mmol) of 5-(pyrrol-1-ylsulfonyl)thiophen-2-carboxylic acid and 13.5 mg (0.1 mmol) of 1-hydroxybenzotriazole. Under ice-cooling, 186 mg (1.2 mmol) of 1-ethyl-3-(3-dimethylaminopropyl)carbodiimide was added thereto. The mixture was warmed to room temperature and stirred at 25° C. for 16 h. The mixture was diluted with water and extracted with toluene. The organic layer was washed with dilute hydrochloric acid and water, dried over anhydrous magnesium sulfate, and concentrated under reduced pressure. The residue was chromatographed on silica gel (toluene/ethyl acetate=6:1) to give 412 mg of (5Z)-7-{(1R,2S,3S,4S)-3-[5-(pyrrol-1-ylsulfonyl)-thiophen-2-ylcarbonylamino]-bicyclo[2.2.1]hept-2-yl}-5-heptenoic acid methyl ester (I-1a). Yield 83.9%.

Colorless oil.

300MHz $^1$H-NMR(CDCl$_3$) δ: 1.08 (1H, m), 1.16–1.32 (2H, m), 1.56–1.73 (4H, m), 1.98–2.13 (5H, m), 2.31 (2H, t, J=7.2Hz), 2.56 (1H, m), 3.63 (3H, s), 3.79 (1H, m), 5.30–5.45 (2H, m), 6.28 (1H, d, J=7.5Hz), 6.33 and 7.16 (each 2H, each t, each J=2.1Hz), 7.40 and 7.57 (each 1H, each d, each J=3.9Hz).

(Step 2)

To a solution of 350 mg (0.713 mmol) of (5Z)-7-{(1R,2S,3S,4S)-3-[5-(pyrrol-1-ylsulfonyl)thiophen-2-ylcarbonylamino]-bicyclo[2.2.1]hept-2-yl}-5-heptenoic acid methyl ester (I-1a) in 1 ml of methanol and 0.5 ml of tetrahydrofuran was added under ice-cooling 0.5 ml (2.0 mmol) of 4N sodium hydroxide. The mixture was warmed to room temperature and stirred at 25° C. for 2 h. The reaction mixture was diluted with water and washed with ether. The aqueous layer was acidified with 0.5 ml of 5N hydrochloric acid and extracted with ethyl acetate. The organic layer was washed with water, dried over anhydrous magnesium sulfate, and concentrated under reduced pressure. The residue was recrystallized from ethyl acetate/hexane (3:4) to give 234 mg of (5Z)-7-{(1R,2S,3S,4S)-3-[5-(pyrrol-1-ylsulfonyl)-thiophen-2-ylcarbonylamino]-bicyclo[2.2.1]hept-2-yl}-5-heptenoic acid (I-1b) as needles.

Yield 68.8%. Mp. 113–114 ° C.

300MHz $^1$H-NMR(CDCl$_3$) δ: 1.09(1H, m), 1.17–1.32 (2H, m), 1.34–1.52(2H, m), 1.56–1.75(4H, m), 2.00–2.18 (5H, m), 2.35(2H, t, J=7.2Hz), 2.52(1H, m), 3.80(1H, m), 5.31–5.43(2H, m), 6.22(1H, d, J=6.0Hz), 6.35 and 7.17(each 2H, each t, each J=2.1Hz), 7.37 and 7.56(each 1H, each d, each J=3.9Hz).

IR(Nujol): 3369, 3143, 3124, 3068, 2678, 1710, 1626, 1593, 1374, 1200, 1171 cm$^{-1}$.

$[α]_D^{26.5}$+75.5±1.2° (c=1.004, MeOH)

Elemental Analysis (C$_{23}$H$_{28}$N$_2$O$_6$S$_2$) Calcd. (%): C, 57.96; H, 5.92; N, 5.88; S, 13.45 Found (%): C, 57.99; H, 5.88; N, 5.66; S, 13.50

EXAMPLE 2

Preparation of (5Z)-7-[(1S,2R,3R,4R)-3-(4-biphenyl)carbonylamino-bicyclo[2.2.1]hept-2-yl]-5-heptenoic acid (I-2b)

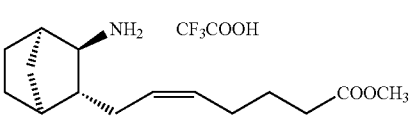
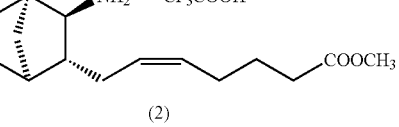

(2)

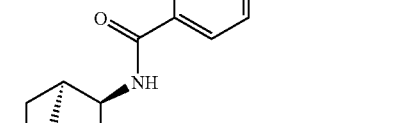

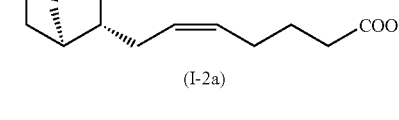

(I-2a)

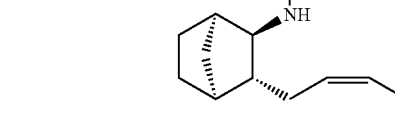

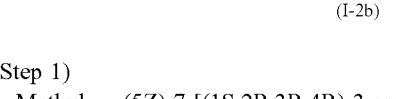

(I-2b)

(Step 1)

Methyl (5Z)-7-[(1S,2R,3R,4R)-3-aminobicyclo[2.2.1]hept-2-yl]-5-heptenoate trifluoroacetate (2) (232 mg, 0.636 mmol), which was prepared by the method described in Reference Example 4 of the Japanese Patent Publication (Kokoku) No. 79060/1993, was dissolved in methylene chloride (5 ml). To the solution were added triethylamine (0.279 ml, 2.00 mmol) and 4-biphenylcarbonyl chloride under ice-cooling and stirred for 7 h at the same temperature. The reaction mixture was purified by column chromatography on silica gel (ethyl acetate/hexane (1:4)) to yield methyl (5Z)-7-[(1S,2R, 3R,4R)-3-(4-biphenyl)carbonylaminobicyclo[2.2.1]hept-2-yl]-5-heptenoate(I-2b) (221 mg, 0.512 mmol).

(Step 2)

The compound (I-2a) (190 mg, 0.440 mmol) was dissolved in methanol (6 ml). To the solution was added 1 N KOH (1.10 ml, 1.10 mmol) under ice-cooling and stirred for 15 h at room temperature. The reaction mixture was concentrated in vacuo. The residue, after the addition of water (20 ml) and 1 N HCl (2 ml), was extracted with ethyl acetate. The organic layer was washed with saturated brine, dried over anhydrous sodium sulfate and concentrated. The residue was purified by column chromatography on silica gel (ethyl acetate/hexane (1:1) containing 0.3% acetic acid) to yield (5Z)-7-[(1S,2R,3R,4R)-3-(4-biphenyl)carbonylamino-bicyclo[2.2.1]hept-2-yl]-5-heptenoic acid (I-2b) (172 mg, 0.412 mmol). Yield 94%.

EXAMPLE 3

Preparation of Sodium (5Z)-7-[(1R,2R,3S,5S)-2-(4-phenylthio)benzoylamino-10-norpinan-3-yl]-5-heptenoate (I-1c)

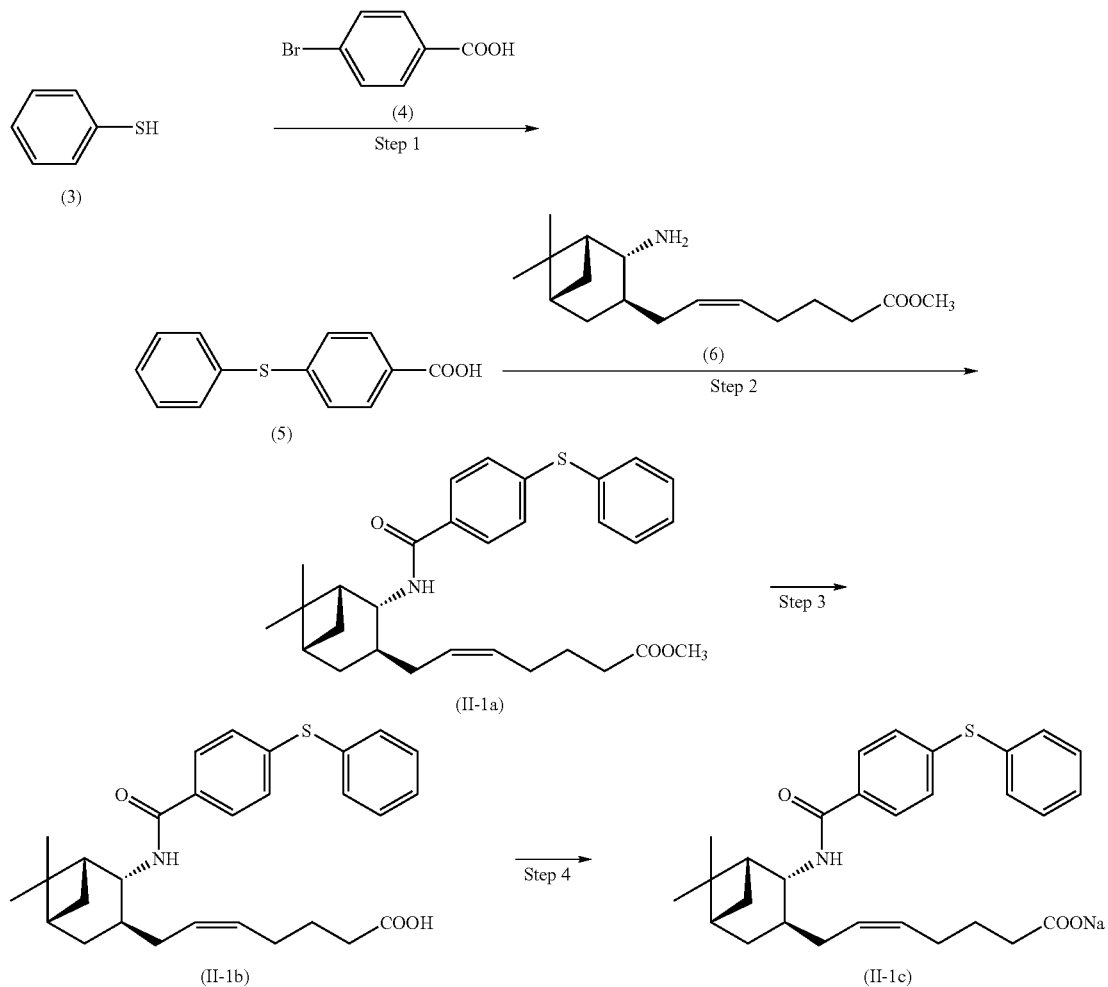

(Step 1)

A mixture of 4.06 g (37 mmol) of thiophenol (3), 7.07 g (35 mmol) of 4-bromobenzoic acid (4), and 2,67 g (18.7 mmol) of copper oxide in 18 ml of quinoline was stirred under nitrogen gas at 190° C. for 1 h. The reaction mixture, cooled at 110° C. was added to 52 ml of 6N hydrochloric acid. The resulting precipitate was washed with 6N hydrochloric acid and water and recrystallized from ethyl acetate/hexane to yield 4.28 g of the compound (5).

Mp. 178–179° C. Yield 53%.

$^1$H-NMR(CDCl$_3$) δ:7.21(2H,d,J=8.7Hz),7.40–7.42(3H,m), 7.50–7.53(2H,m),7.95(2H,d,J=8.7Hz).

IR(Nujol): 3523, 3062, 3007, 2884, 2670, 2549, 1730, 1690, 1595, 1561, 1491cm$^{-1}$ This preparation was carried out according to D. Hands, H. Marley, S. J. Skittrall and S. H B. Wright, J. Heterocyclic Chem., 23, 1333 (1986).

(Step2)

To a solution of 1.83 g (6.56 mmol) of methyl (5Z)-7-[(1R,2R,3S,5S)-2-amino-10-norpinan-3-yl]-5-heptenoate (6) in 3 ml of tetrahydrofuran were added 1.51 g (6.56 mmol) of 4-phenylthiobenzoic acid (5), 88 mg of 1-hydroxy benzotriazole and 1.32 g (8.53 mmol) of 1-ethyl-3-(3-dimethylaminopropyl)carbodiimide. The mixture was allowed to stand at room temperature over night. The reaction mixture was diluted by diluted hydrochloric acid and extracted with toluene. The organic layer was washed with water, dried over anhydrous magnesium sulfate and concentrated under reduced pressure. The obtained residue was purified by column chromatography on silica gel (ethyl acetate/hexane (1:1)) to yield 3.181 g of the compound (II-1a) as oil. Yield: 98.4%.

[α]$_D^{22}$+61.8° (c=1.00, CH$_3$OH)

Elemental Analysis (C$_{30}$H$_{37}$NO$_3$S) Calcd.(%):C,73.28;H, 7.59;N,2.85;S,6.52   Found(%):C,73.02;H,7.63;N,2.91;S, 6.53

$^1$H-NMR(CDCl$_3$) δ:0.96(1H,d,J=10.5Hz), 1.10 and 1.22 (each 3H, eachs), 1.49–1.73(3H,m),1.83–2.45(11H,m),3.62 (3H,s),4.27(1H,m),5.32–5.49(2H,m),6.19(1H,d,J=8.1Hz), 7.26(2H,d,J=8.4Hz),7.34–7.46(5H,m),7.62(2H,d,J=8.4Hz)

IR(CHCl$_3$): 3453, 3030, 3015, 2924, 2870, 1730, 1652, 1595, 1583, 1557, 1513, 1480 cm$^{-1}$ (Step 3)

To a solution of 3.181 g (6.47 mmol) of the compound (II-1a) in 32 ml of methanol was added 5.7 ml (22.6 mmol)

of 4N sodium hydroxide. The mixture was stirred at 45° C. for 4.5 h. The mixture was neutralized with 1N hydrochloric acid and extracted with ethyl acetate. The organic layer was washed with water, dried over anhydrous magnesium sulfate, and concentrated under reduced pressure to yield 3.113 g of the compound (II-1b) as a colorless amorphous. Yield 99.5%.

$[\alpha]_D^{22}$ +61.0° (c=1.01,CH$_3$OH)

Elemental Analysis (C$_{29}$H$_{35}$NO$_3$S•0.1H$_2$O) Calcd.(%):C, 72.65;H,7.48;N,2.92;S,6.69 Found(%):C,72.50;H,7.45;N, 3.19;S,6.69

$^1$H-NMR(CDCl$_3$) δ:0.96(1H,d,J=10.2Hz), 1.10 and 1.22 (each 3H, each s),1.51–1.79(3H,m),1.83–2.44(11H,m),4.26 (1H,m),5.33–5.49(2H,m),6.21(1H,d,J=8.7Hz),7.25(2H,d, J=9.0Hz),7.34–7.47(5H,m),7.60(2H,d,J=9.0Hz)

IR(CHCl$_3$):3453, 3062, 3029, 3014, 2925, 2870, 1739, 1708, 1651, 1595, 1583, 1557,1515, 1481cm$^{-1}$ (Step 4)

To a solution of 3.113 g (6.5 mmol) of the above obtained compound (II-1b) in 30 ml of methanol was added 6.2 ml of 1 N sodium hydroxide. The mixture was concentrated under reduced pressure. The residue was dissolved in a small amount of ethyl acetate and mixed with hexane. The insoluble product was dissolved in 60 ml of water and freeze-dried to yield 3.138 g of the compound (I-1c) as a colorless amorphous. Yield 96.4%.

$[\alpha]_D^{23}$ +47.0° (c=1.00,CH$_3$OH)

Elemental Analysis (C$_{29}$H$_{34}$NO$_3$SNa•H$_2$O) Calcd.(%):C, 67.29;H,7.01;N;2.71;S,6.19,Na,4.44 Found(%):C,67.17;H, 7.00;N,2.75;S,6.29;Na,4.35

$^1$H-NMR(CD$_3$OD) δ:0.964(1H,d,J=9.9Hz),1.13 and 1.22 (each 3H, eachs), 1.54–1.69(3H,m),1.94–2.39(11H,m),4.12 (1H,bs),5.38–5.49(2H,m),7.25(1H,d,J=8.4Hz),7.36–7.46 (5H,m),7.68(2H,d,J=8.4Hz)

IR (KBr): 3435, 3058, 2985, 2921, 2867, 1635, 1595, 1562, 1522, 1482, 1439, 1412cm$^{-1}$

The structure and physical property of the compound prepared in accordance with the above examples are shown below.

TABLE 1

TABLE 1-continued

| Comp. No. | R |
|---|---|
| I-17 | 3-methylphenyl-SO₂-N-pyrrolyl |
| I-18 | 4-methylphenyl-SO₂-N(2-methyl)pyrrolyl |
| I-19 | 4-methylphenyl-CH₂-N-pyrrolyl |
| I-20 | 4-methylphenyl-SO₂-N-indolyl |
| I-21 | 4-methylphenyl-SO₂-N(2-CH₂OH)pyrrolyl |
| I-22 | 4-methylphenyl-SO₂-NH-(2-thiazolyl) |

TABLE 2

| Comp. No. | R |
|---|---|
| I-23 | 4-methylphenyl-CONH-(2-thiazolyl) |
| I-24 | 2-methylbenzothiophene-5-SO₂-N-pyrrolyl |
| I-25 | 4-methylphenyl-S-(2-thienyl) |
| I-26 | 4-methylphenyl-SO₂-(2-thienyl) |
| I-27 | 4-methylphenyl-CONH-(2-pyridyl) |
| I-28 | 4-methylphenyl-S-(3-thienyl) |
| I-29 | 4-methylphenyl-SO₂-(3-thienyl) |
| I-30 | 5-methylfuran-2-N-pyrrolyl |
| I-31 | 5-methylthiophene-2-CH₂-phenyl |
| I-32 | 3-methylbenzothiophene-5-SO₂NH-phenyl |
| I-33 | 3-methylbenzothiophene-5-SO₂-N-pyrrolyl |
| I-34 | 5-methylfuran-2-SO₂-N-pyrrolyl |

TABLE 2-continued
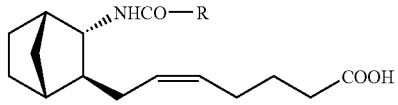
| Comp. No. | R |
|---|---|
| I-35 | 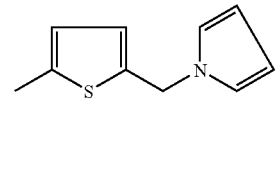 |
| I-36 | 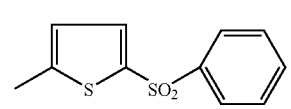 |
| I-37 | 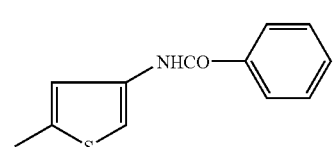 |
| I-38 | 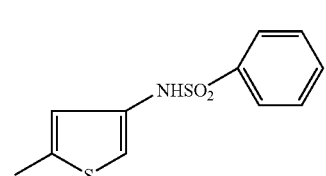 |
| I-39 | 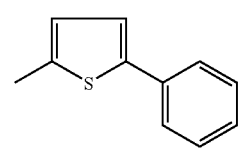 |
| I-40 | 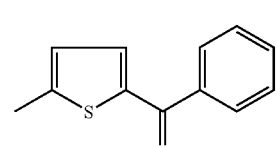 |
| I-41 | 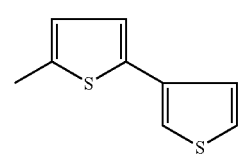 |
| I-42 | 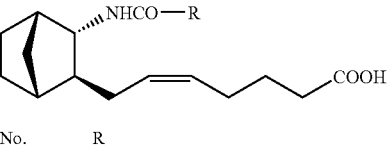 |
TABLE 3
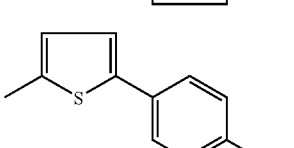
| Comp. No. | R |
|---|---|
| I-43 | 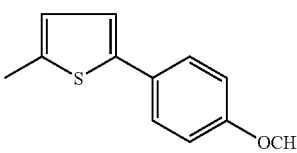 |
| I-44 | 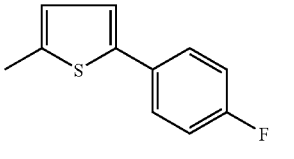 |
| I-45 | 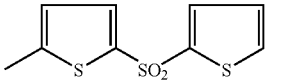 |
| I-46 |  |
| I-47 |  |
| I-48 | 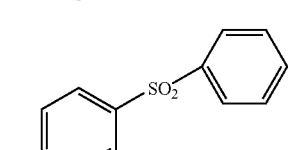 |
| I-49 | 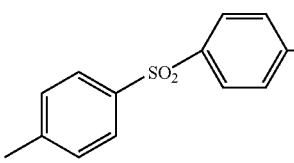 |
| I-50 | 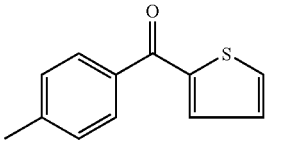 |
| I-51 |  |
| I-52 |  |

TABLE 3-continued
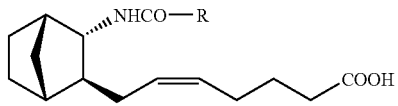
| Comp. No. | R |
|---|---|
| I-53 | 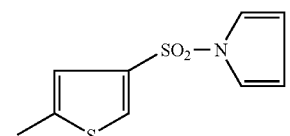 |
| I-54 | 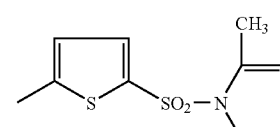 |
| I-55 | 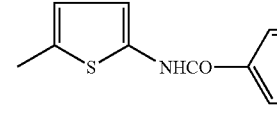 |
| I-56 | 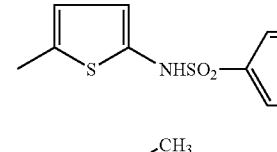 |
| I-57 | 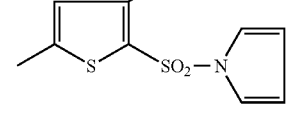 |
| I-58 | 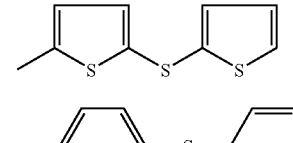 |
| I-59 | 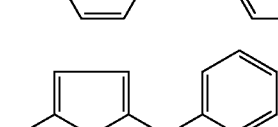 |
| I-60 | 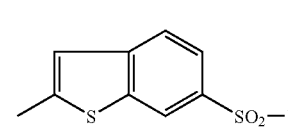 |
| I-61 | 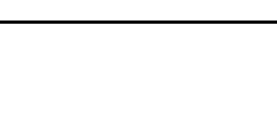 |
| I-62 | 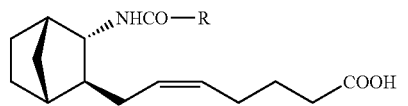 |
TABLE 4
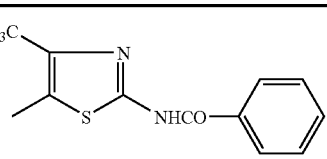
| Comp. No. | R |
|---|---|
| I-63 | 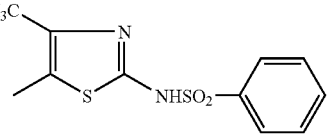 |
| I-64 | 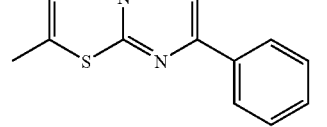 |
| I-65 | 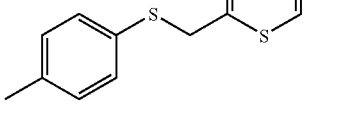 |
| I-66 | 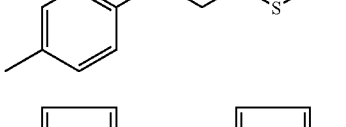 |
| I-67 | 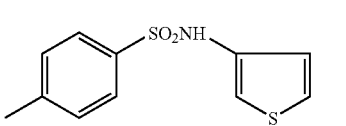 |
| I-68 | 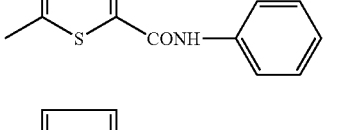 |
| I-69 | 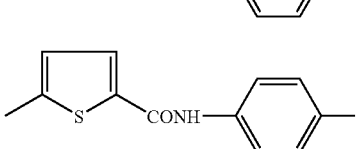 |
| I-70 |  |
| I-71 |  |
| I-72 |  |

TABLE 4-continued
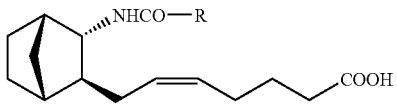
| Comp. No. | R |
|---|---|
| I-73 | 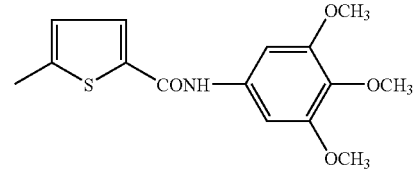 |
| I-74 | 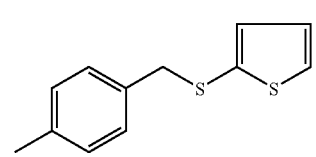 |
| I-75 | 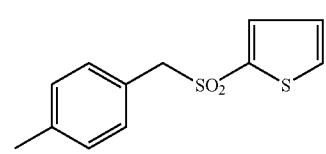 |
| I-76 | 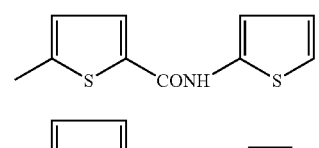 |
| I-77 | 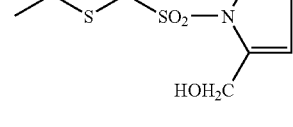 |
| I-78 | 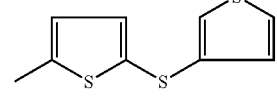 |
| I-79 | 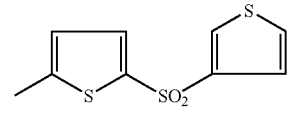 |
| I-80 | 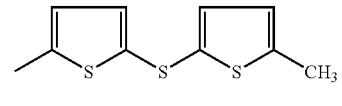 |
| I-81 | 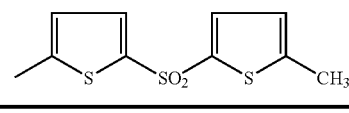 |
| I-82 | 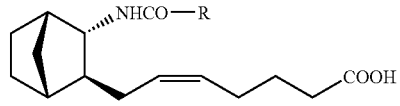 |
TABLE 5
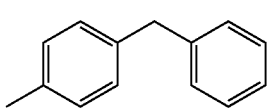
| Comp. No. | R |
|---|---|
| I-83 | 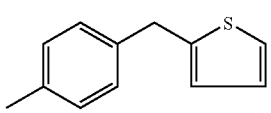 |
| I-84 | 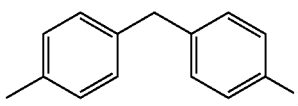 |
| I-85 | 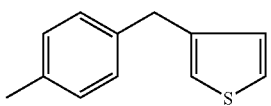 |
| I-86 | 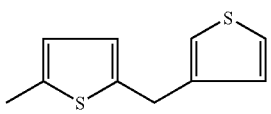 |
| I-87 | 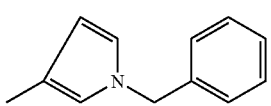 |
| I-88 | 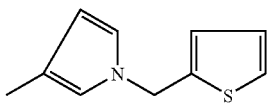 |
| I-89 | 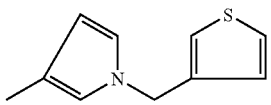 |
| I-90 | 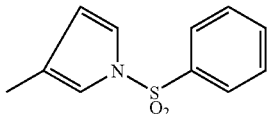 |
| I-91 | 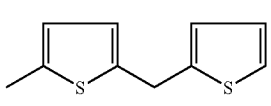 |
| I-92 | 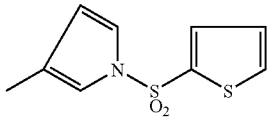 |
| I-93 | |
| I-94 | |

TABLE 5-continued

| Comp. No. | R |
|---|---|
| I-95 | 4-methyl-2-(1H-pyrrol-1-yl)thiazole |
| I-96 | 5-methyl-2-(thiophen-2-ylthio)thiophene |
| I-97 | 5-methyl-2-(thiophen-2-ylsulfonyl)thiophene |
| I-98 | (E)-5-methyl-2-(2-(thiophen-3-yl)vinyl)thiophene |
| I-99 | (Z)-5-methyl-2-(2-(thiophen-3-yl)vinyl)thiophene |
| I-100 | 5-methyl-2-((5-methylthiophen-3-yl)thio)thiophene |
| I-101 | 5-methyl-2-((5-methylthiophen-3-yl)sulfonyl)thiophene |
| I-102 | (Z)-5-methyl-2-(2-(thiophen-2-yl)vinyl)thiophene |

TABLE 6

| Comp. No. | R |
|---|---|
| I-103 | (E)-5-methyl-2-(2-(thiophen-2-yl)vinyl)thiophene |
| I-104 | 2-methyl-5-((thiophen-2-ylthio)methyl)thiophene |
| I-105 | 2-methyl-5-((thiophen-2-ylsulfonyl)methyl)thiophene |
| I-106 | 2-methyl-5-((thiophen-2-ylmethyl)thio)thiophene |
| I-107 | 5-methyl-2-(thiophen-2-ylsulfinyl)thiophene |
| I-108 | 5-methyl-2-((5-methylthiophen-2-yl)sulfinyl)thiophene |
| I-109 | (5-methylthiophen-2-yl)(thiophen-2-yl)methanone |
| I-110 | (5-methylthiophen-2-yl)(thiophen-2-yl)methanone O-methyl oxime |
| I-111 | N-phenyl-5-methylthiophen-2-amine |
| I-112 | N-methyl-N-phenyl-5-methylthiophen-2-amine |
| I-113 | 5-methyl-2-((3-methylphenyl)thio)thiophene |
| I-114 | 5-methyl-2-((3-methylphenyl)sulfonyl)thiophene |

TABLE 6-continued

| Comp. No. | R |
|---|---|
| I-115 | 5-methylthien-2-yl-S-(3-methoxyphenyl) |
| I-116 | 5-methylthien-2-yl-SO₂-(3-methoxyphenyl) |
| I-117 | 5-methylthien-2-yl-SO₂-(3-hydroxyphenyl) |
| I-118 | 5-methylthien-2-yl-S-(3-hydroxyphenyl) |
| I-119 | 5-methylthien-2-yl-CH₂-(3-methoxyphenyl) |
| I-120 | 5-methylthien-2-yl-CH₂-(3-hydroxyphenyl) |
| I-121 | 5-methylthien-2-yl-CH₂-(3-acetoxyphenyl) |
| I-122 | 5-methylthien-2-yl-CH₂-S-phenyl |

TABLE 7

| Comp. No. | R |
|---|---|
| I-123 | 5-methylthien-2-yl-CH₂-O-phenyl |
| I-124 | 5-methylthien-2-yl-CH₂-NH-phenyl |
| I-125 | 5-methylthien-2-yl-CH₂-(2-methylphenyl) |
| I-126 | 5-methylthien-2-yl-CH₂-(2-methoxyphenyl) |
| I-127 | 5-methylthien-2-yl-CH₂-(2-ethylphenyl) |
| I-128 | 5-methylthien-2-yl-CH₂-(2,4-dimethylphenyl) |
| I-129 | 5-methylthien-2-yl-CH₂-(5-methylthien-2-yl) |
| I-130 | 5-methylthien-2-yl-CH₂-(4-methylphenyl) |
| I-131 | 5-methylthien-2-yl-CH₂-(3-methylphenyl) |
| I-132 | 5-methylthien-2-yl-CH₂-S-(3-methylphenyl) |
| I-133 | 5-methylthien-2-yl-CH₂-(furan-2-yl) |

TABLE 7-continued
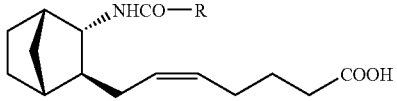
| Comp. No. | R |
|---|---|
| I-134 | 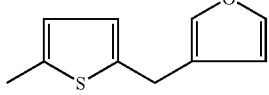 |
| I-135 | 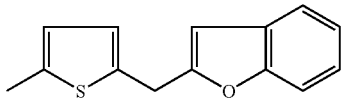 |
| I-136 | 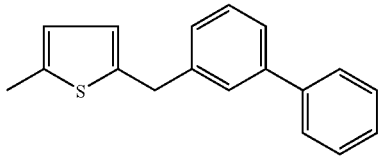 |
| I-137 | 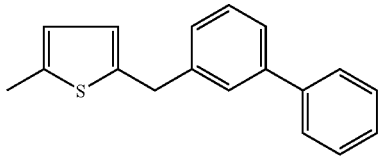 |
| I-138 | 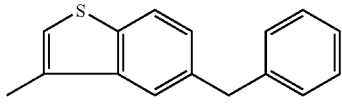 |
| I-139 | 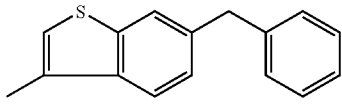 |
| I-140 | 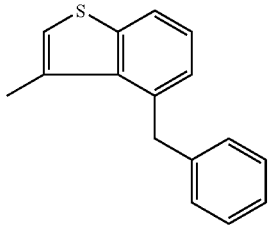 |
| I-141 | 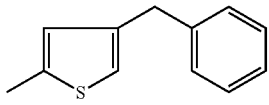 |
| I-142 | 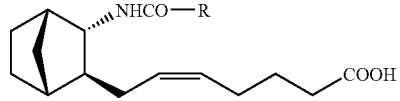 |
TABLE 8
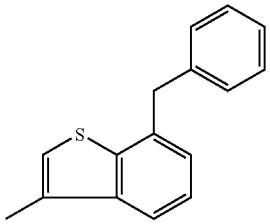
| Comp. No. | R |
|---|---|
| I-143 | 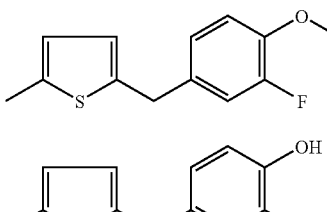 |
| I-144 | 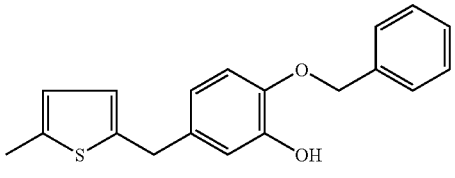 |
| I-145 | 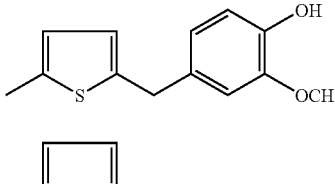 |
| I-146 | 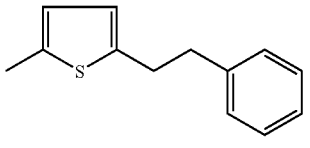 |
| I-147 | 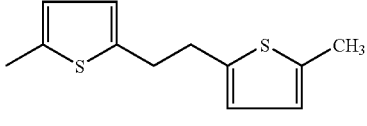 |
| I-148 | 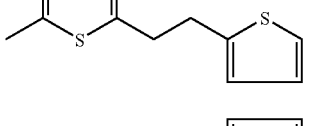 |
| I-149 | 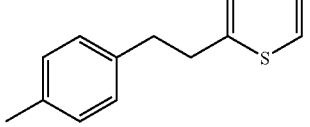 |
| I-150 | |
| I-151 | |

TABLE 8-continued

[Structure: norbornane with NHCO-R substituent and CH2-CH=CH-CH2-CH2-COOH chain]

| Comp. No. | R |
|---|---|
| I-152 | 5-methylthiophen-2-yl-CH2CH2-(4-fluorophenyl) |
| I-153 | 5-methylthiophen-2-yl-CH2-(3,5-dimethylphenyl) |
| I-154 | 5-methylthiophen-2-yl-CH2-(4-fluorophenyl) |
| I-155 | 5-methylthiophen-2-yl-CH2-(4-trifluoromethylphenyl) |
| I-156 | 2-methylbenzothiophen-5-yl-CH2-phenyl |
| I-157 | 5-methylthiophen-2-yl-CH2-(2-naphthyl) |
| I-158 | 5-methylthiophen-2-yl-CH2CH2-(2-methoxyphenyl) |
| I-159 | 5-methylthiophen-2-yl-CH2CH2-(2-hydroxyphenyl) |
| I-160 | 2-methylbenzothiophen-6-yl-CH2-phenyl |
| I-161 | 2-methylbenzothiophen-5-yl-CH2-(3-thienyl) |
| I-162 | 2-methylbenzothiophen-5-yl-CH2-(2-thienyl) |

TABLE 9

[Structure: norbornane with NHCO-R substituent and CH2-CH=CH-CH2-CH2-COOH chain]

| Comp. No. | R |
|---|---|
| I-163 | 5-methylthiophen-3-yl-CH2-(2-thienyl) |
| I-164 | 5-methylthiophen-3-yl-CH2-(3-thienyl) |
| I-165 | 5-methylthiophen-3-yl-CH2-(3-furyl) |
| I-166 | 5-methylthiophen-2-yl-CH2-(1-naphthyl) |
| I-167 | 5-methylthiophen-3-yl-(1-naphthyl) |
| I-168 | 3-methylbenzothiophen-7-yl-CH2-(2-thienyl) |

TABLE 9-continued

[Structure: norbornane with NHCO-R substituent and CH2-CH=CH-CH2-CH2-COOH chain]

| Comp. No. | R |
|---|---|
| I-169 | 3-methylbenzothiophen-7-yl-methyl-(thiophen-3-yl) |
| I-170 | 3-methylbenzothiophen-7-yl-methyl-(furan-3-yl) |
| I-171 | (5-methylthiophen-2-yl)methyl-(2-SCH3-phenyl) |
| I-172 | (5-methylthiophen-2-yl)methyl-(2-SO2CH3-phenyl) |
| I-173 | 2-methylfluoren-7-yl |
| I-174 | (5-methylthiophen-2-yl)methyl-(5-bromo-2,3-dihydrobenzofuran-7-yl) |
| I-175 | 2-methylbenzothiophen-7-yl-methyl-phenyl |
| I-176 | 2-methylbenzothiophen-7-yl-methyl-(thiophen-3-yl) |
| I-177 | 2-methylbenzothiophen-7-yl-methyl-(4-methylphenyl) |
| I-178 | 2-methylbenzothiophen-7-yl-methyl-(thiophen-2-yl) |
| I-179 | (5-methylthiophen-2-yl)methyl-(2-phenylphenyl) |
| I-180 | 3-methyl-9-oxofluorenyl |
| I-181 | (5-methylthiophen-2-yl)methyl-(4-methoxyphenyl) |
| I-182 | (5-methylthiophen-2-yl)methyl-(benzothiophen-3-yl) |

TABLE 10
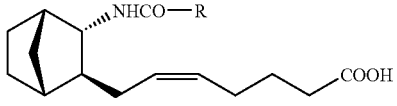
TABLE 10-continued
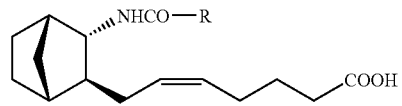

TABLE 10-continued
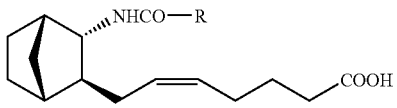
| Comp. No. | R |
|---|---|
| I-202 | 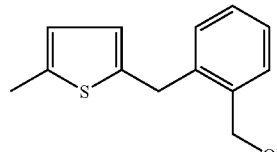 |
TABLE 11
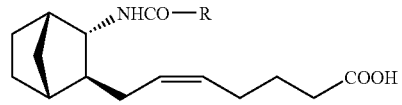
| Comp. No. | R |
|---|---|
| I-203 | 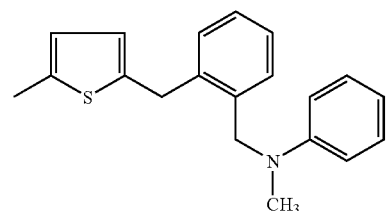 |
| I-204 | 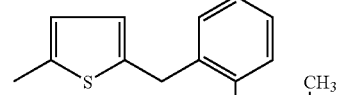 |
| I-205 | 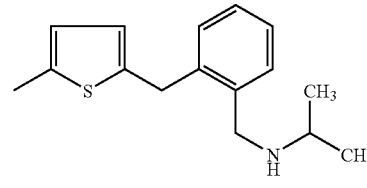 |
| I-206 | 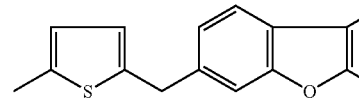 |
| I-207 | 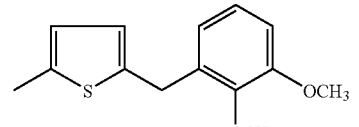 |
| I-208 | 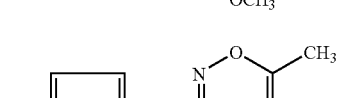 |
TABLE 11-continued
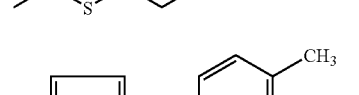
| Comp. No. | R |
|---|---|
| I-209 | 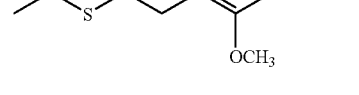 |
| I-210 | 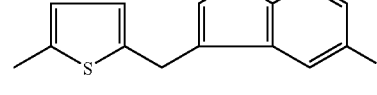 |
| I-211 | 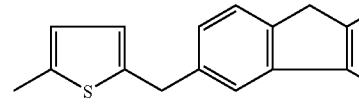 |
| I-212 | 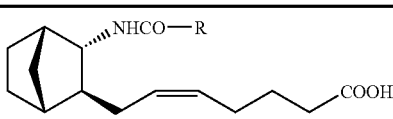 |
| I-213 | 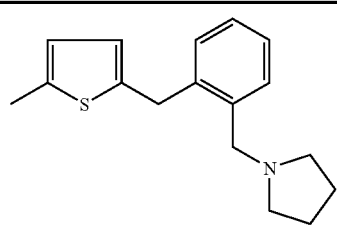 |
| I-214 | 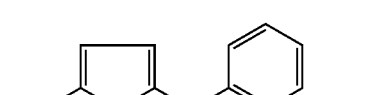 |
| I-215 | 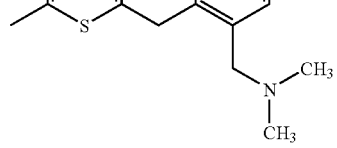 |
| I-216 | 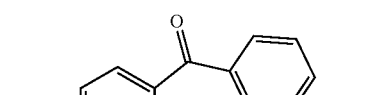 |
| I-217 | 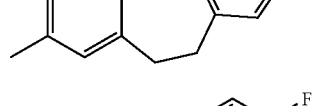 |

TABLE 11-continued

[Structure: norbornane with NHCO-R and CH2-CH=CH-CH2-CH2-COOH chain]

| Comp. No. | R |
|---|---|
| I-218 | 5-methylthiophene-CH2-(2,3,4-trimethoxyphenyl) |
| I-219 | 5-methylthiophene-CH2-(2,3-dimethylphenyl) |
| I-220 | 5-methylthiophene-CH2-(3,4,5-trimethoxyphenyl) |
| I-221 | 5-methylthiophene-CH2-(benzo[1,3]dioxol-4-yl) |
| I-222 | 5-methylthiophene-CH2-(3-NHCOCH3-phenyl) |

TABLE 12

[Structure: norbornane with NHCO-R and CH2-CH=CH-CH2-CH2-COOH chain]

| Comp. No. | R |
|---|---|
| I-223 | 5-methylthiophene-CH2-(3-NHSO2CH3-phenyl) |
| I-224 | 5-methylthiophene-CH2-(5-phenylthiophen-2-yl) |

TABLE 12-continued

[Structure: norbornane with NHCO-R and CH2-CH=CH-CH2-CH2-COOH chain]

| Comp. No. | R |
|---|---|
| I-225 | 5-methylthiophene-CH2-(2,3-dihydro-1,4-benzodioxin-5-yl) |
| I-226 | 5-methylthiophene-CH2-(3-methyl-2-methoxyphenyl) |
| I-227 | 5-methylthiophene-CH2-(4-NHCOCH3-phenyl) |
| I-228 | 5-methylthiophene-CH2-(4-NHSO2CH3-phenyl) |
| I-229 | 5-methylthiophene-CH2-(dibenzothiophen-4-yl) |
| I-230 | 5-methylthiophene-CH2-(fluoren-4-yl) |
| I-231 | 5-methylthiophene-CH2-(3,4-dimethyl-2-methoxyphenyl) |
| I-232 | 5-methylthiophene-CH2-(fluoren-1-yl) |

TABLE 12-continued
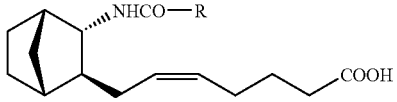
| Comp. No. | R |
|---|---|
| I-233 | 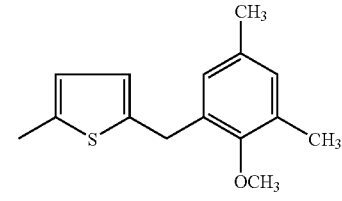 |
| I-234 | 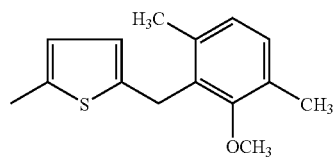 |
| I-235 | 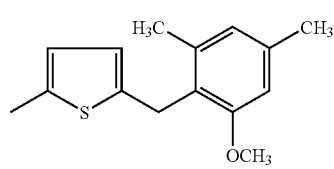 |
| I-236 | 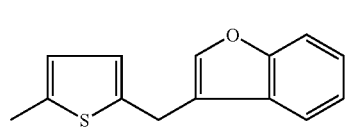 |
| I-237 | 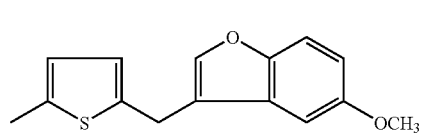 |
| I-238 | 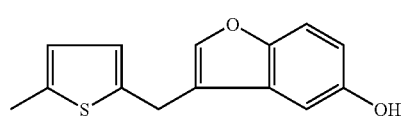 |
| I-239 | 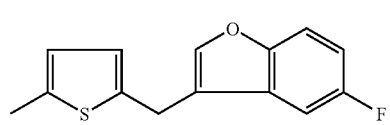 |
| I-240 | 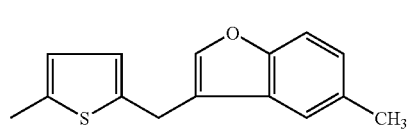 |
| I-241 | 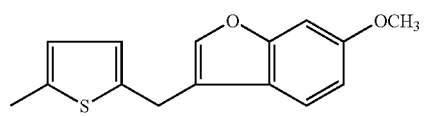 |
| I-242 | 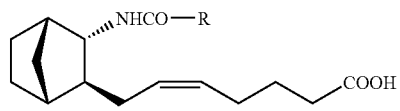 |
TABLE 13
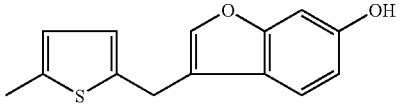
| Comp. No. | R |
|---|---|
| I-243 | 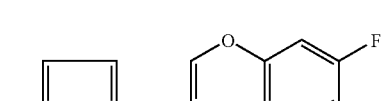 |
| I-244 | 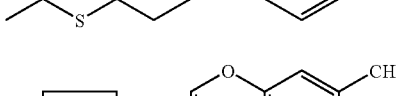 |
| I-245 | 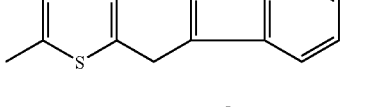 |
| I-246 | 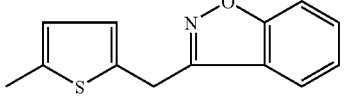 |
| I-247 | 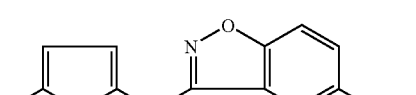 |
| I-248 | 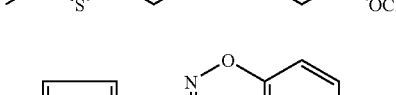 |
| I-249 | 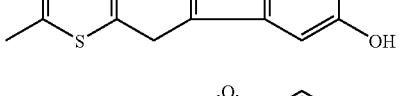 |
| I-250 | 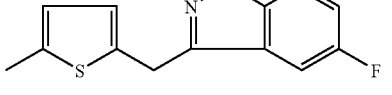 |
| I-251 | 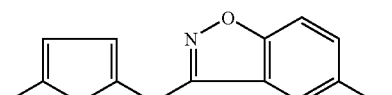 |
| I-252 |  |

TABLE 13-continued

![structure: norbornane with NHCO-R and CH2-CH=CH-CH2-CH2-COOH chain]

| Comp. No. | R |
|---|---|
| I-253 | 5-methylthiophene-CH2-thiophene-C6H4-OCH3 (para) |
| I-254 | 5-methylthiophene-CH2-thiophene-C6H4-OH (para) |
| I-255 | 5-methylthiophene-CH2-thiophene-C6H4-F (para) |
| I-256 | 5-methylthiophene-CH2-thiophene-C6H4-CH3 (para) |
| I-257 | 5-methylthiophene-CH2-(5-chlorothiophene) |
| I-258 | 5-methylthiophene-CH2-(5-phenylthiophene) |
| I-259 | 5-methylthiophene-CH2-(3-phenylthiophene) |
| I-260 | 5-methylthiophene-CH2-thiophene-CH2-C6H5 |
| I-261 | 5-methylthiophene-CH2-thiazole |

TABLE 13-continued

![structure: norbornane with NHCO-R and CH2-CH=CH-CH2-CH2-COOH chain]

| Comp. No. | R |
|---|---|
| I-262 | 5-methylthiophene-CH2-benzothiazole |

TABLE 14

![structure: norbornane with NHCO-R and CH2-CH=CH-CH2-CH2-COOH chain]

| Comp. No. | R |
|---|---|
| I-263 | 5-methylthiophene-CH2-(3-pyridyl) |
| I-264 | 5-methylthiophene-CH2-(7-isoquinolinyl) |
| I-265 | 5-methylthiophene-CH2-(6-isoquinolinyl) |
| I-266 | 5-methylthiophene-CH2-(2,3-dihydrobenzofuran-4-yl) |
| I-267 | 5-methylthiophene-CH2-(2,3-dihydrobenzofuran-6-yl) |
| I-268 | 5-methylthiophene-CH2-(2,3-dihydrobenzofuran-5-yl) |
| I-269 | 5-methylthiophene-CH2-(2,4-difluorophenyl) |
| I-270 | 5-methylthiophene-SO2-(2,5-dimethylpyrrol-1-yl) |

TABLE 14-continued
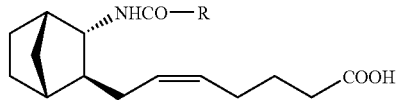
| Comp. No. | R |
|---|---|
| I-271 | 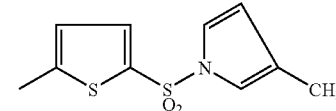 |
| I-272 | 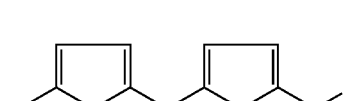 |
| I-273 | 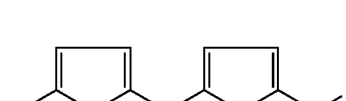 |
| I-274 | 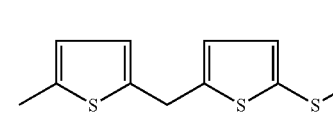 |
| I-275 |  |
| I-276 |  |
| I-277 |  |
| I-278 | 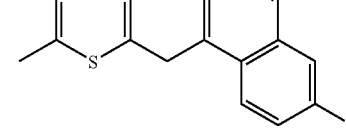 |
| I-279 | 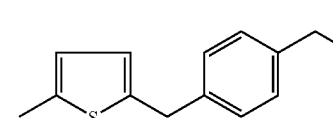 |
| I-280 |  |
TABLE 14-continued
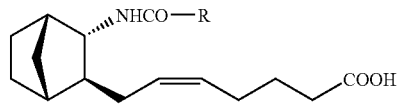
| Comp. No. | R |
|---|---|
| I-281 |  |
| I-282 |  |
TABLE 15
| Comp. No. | R |
|---|---|
| I-283 | 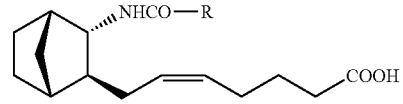 |
| I-284 | 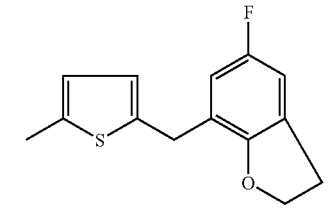 |
| I-285 | 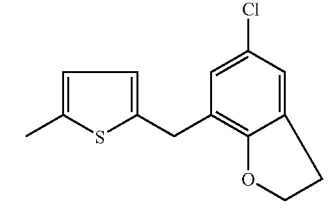 |
| I-286 | 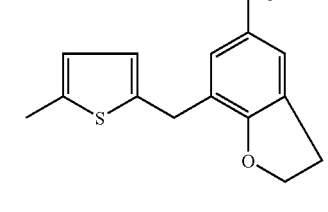 |

TABLE 15-continued

| Comp. No. | R |
|---|---|
| I-287 | 5-methylthiophen-2-yl-methyl-(4-phenyl-2,3-dihydrobenzofuran-7-yl) |
| I-288 | 5-methylthiophen-2-yl-methyl-(2,3-dihydrothieno[2,3-b]furan-6-yl) |
| I-289 | 5-methylthiophen-2-yl-methyl-(3-methyl-2,3-dihydrothieno[2,3-b]furan-6-yl) |
| I-290 | benzyl-(3-methylbenzofuran-7-yl) |
| I-291 | thiophen-3-yl-methyl-(3-methylbenzofuran-7-yl) |
| I-292 | thiophen-2-yl-methyl-(3-methylbenzofuran-7-yl) |
| I-293 | furan-3-yl-methyl-(3-methylbenzofuran-7-yl) |

TABLE 15-continued

| Comp. No. | R |
|---|---|
| I-294 | furan-2-yl-methyl-(3-methylbenzofuran-7-yl) |

TABLE 16

| Comp. No. | R |
|---|---|
| II-2 | 4-methylthiophen-2-yl-NH-SO$_2$-phenyl |
| II-3 | 4-methylthiophen-2-yl-NH-CO-phenyl |
| II-4 | 4-methyl-5-benzyl-thiophen-2-yl |
| II-5 | 4-methylphenyl-pyrrol-1-yl |
| II-6 | 4-methylphenyl-SO$_2$NH-phenyl |
| II-7 | 4-methylphenyl-NHSO$_2$-phenyl |
| II-8 | 4-methylphenyl-SO$_2$-pyrrolidin-1-yl |
| II-9 | 5-methyl-2-phenyl-benzothiophen-3-yl |

TABLE 16-continued

[Structure: bicyclic terpene with NHCO—R substituent and (Z)-heptenoic acid chain ending in COOH]

| Comp. No. | R |
|---|---|
| II-10 | 3-methylphenyl-SO₂-N(pyrrolyl) |
| II-11 | 4-methylphenyl-SO₂-N(2-methylpyrrolyl) |
| II-12 | 4-methylbenzyl-N(pyrrolyl) |
| II-13 | 4-methylphenyl-SO₂-N(indolyl) |
| II-14 | 4-methylthiophen-2-yl-SO₂-N(pyrrolyl) |
| II-15 | 5-methylthiophen-2-yl-SO₂-N(pyrrolyl) |
| II-16 | 4-methylphenyl-SO₂-N(2-hydroxymethylpyrrolyl) |
| II-17 | 4-methylthiophen-3-yl-SO₂-N(pyrrolyl) |
| II-18 | 5-methylthiophen-2-yl-SO₂-thien-2-yl |
| II-19 | 3-methyl-1-(thien-2-ylsulfonyl)pyrrole |

TABLE 16-continued

[Same parent structure]

| Comp. No. | R |
|---|---|
| II-20 | 3-methyl-1-(phenylsulfonyl)pyrrole |
| II-21 | 5-methylthien-2-yl-S-thien-2-yl |

TABLE 17

[Structure: bicyclic terpene with NHCO—R substituent and hexenoic acid chain ending in COOH]

| Comp. No. | R |
|---|---|
| II-22 | 5-methylthien-2-yl-S-5-methylthien-2-yl |
| II-23 | 5-methylthien-2-yl-SO₂-5-methylthien-2-yl |
| II-24 | 3-methyl-1-(4-fluorophenylsulfonyl)pyrrole |
| II-25 | 3-methyl-1-(4-methoxyphenylsulfonyl)pyrrole |
| II-26 | 5-methyl-2-(thien-2-yl)pyrrole (NH) |
| II-27 | 5-methylthien-2-yl-CH=CH-thien-3-yl |
| II-28 | 5-methylthien-2-yl-CH=CH-thien-3-yl |

TABLE 17-continued

| Comp. No. | R |
|---|---|
| II-29 | 5-methylthiophen-2-yl-thio-(5-methylthiophen-3-yl) |
| II-30 | 5-methylthiophen-2-yl-sulfonyl-(5-methylthiophen-3-yl) |
| II-31 | 5-methylthiophen-2-yl-CH2-phenyl |
| II-32 | (Z)-5-methylthiophen-2-yl-CH=CH-thiophen-2-yl |
| II-33 | (E)-5-methylthiophen-2-yl-CH=CH-thiophen-2-yl |
| II-34 | 5-methylthiophen-2-yl-SO2-N(2-methylpyrrol-1-yl) |
| II-35 | 5-methylthiophen-2-yl-S(O)-thiophen-2-yl |
| II-36 | 5-methylthiophen-2-yl-S(O)-(5-methylthiophen-2-yl) |
| II-37 | 5-methylthiophen-2-yl-CH2-(2-methoxyphenyl) |
| II-38 | 5-methylthiophen-2-yl-CH2-(2-hydroxyphenyl) |
| II-39 | 5-methylthiophen-2-yl-CH2-(2-acetoxyphenyl) |
| II-40 | 5-methylthiophen-2-yl-SO2-phenyl |
| II-41 | 5-methylthiophen-2-yl-S-(3-methylphenyl) |

TABLE 18

| Comp. No. | R |
|---|---|
| II-42 | 5-methylthiophen-2-yl-SO2-(3-methylphenyl) |
| II-43 | 5-methylthiophen-2-yl-S-(3-methoxyphenyl) |
| II-44 | 5-methylthiophen-2-yl-SO2-(3-methoxyphenyl) |
| II-45 | 5-methylthiophen-2-yl-SO2-(3-hydroxyphenyl) |
| II-46 | 5-methylthiophen-2-yl-S-(3-hydroxyphenyl) |
| II-47 | 5-methylthiophen-2-yl-CH2-(3-methoxyphenyl) |
| II-48 | 5-methylthiophen-2-yl-N(CH3)-phenyl |

TABLE 18-continued

Structure: bicyclic terpene with NHCO—R substituent, connected to a chain with COOH (cis-alkene)

| Comp. No. | R |
|---|---|
| II-49 | 5-methylthiophen-2-yl-CH₂-(2-methylphenyl) |
| II-50 | 5-methylthiophen-2-yl-CH₂-(thiophen-2-yl) |
| II-51 | 5-methylthiophen-2-yl-CH₂-(5-methylthiophen-2-yl) |
| II-52 | 5-methylthiophen-2-yl-CH₂-S-(3-methylphenyl) |
| II-53 | 5-methylthiophen-2-yl-SO₂-(2-methylphenyl) |
| II-54 | 5-methylthiophen-2-yl-SO₂-(4-methylphenyl) |
| II-55 | 5-methylthiophen-2-yl-CH₂-(furan-2-yl) |
| II-56 | 5-methylthiophen-2-yl-CH₂-(furan-3-yl) |
| II-57 | 5-methylthiophen-2-yl-CH₂-(benzothiophen-2-yl) |
| II-58 | 5-methylthiophen-2-yl-CH₂-(benzofuran-2-yl) |
| II-59 | 5-methylthiophen-2-yl-CH₂-(biphenyl-3-yl) |
| II-60 | 3-methylbenzothiophen-5-yl-CH₂-phenyl |

TABLE 19

Structure: bicyclic terpene with NHCO—R substituent, connected to a chain with COOH (cis-alkene)

| Comp. No. | R |
|---|---|
| II-61 | 3-methylbenzothiophen-6-yl-CH₂-phenyl |
| II-62 | 3-methylbenzothiophen-4-yl-CH₂-phenyl |
| II-63 | 5-methylthiophen-3-yl-CH₂-phenyl |
| II-64 | 3-methylbenzothiophen-7-yl-CH₂-phenyl |
| II-65 | 5-methylthiophen-2-yl-CH₂-(4-hydroxy-3-methoxyphenyl) |

TABLE 19-continued

| Comp. No. | R |
|---|---|
| II-66 | 5-methylthiophen-2-yl-CH₂CH₂-phenyl |
| II-67 | 5-methylthiophen-2-yl-CH₂CH₂-5-methylthiophen-2-yl |
| II-68 | 5-methylthiophen-2-yl-CH₂CH₂-thiophen-2-yl |
| II-69 | 4-methylphenyl-CH₂CH₂-thiophen-2-yl |
| II-70 | 5-methylthiophen-2-yl-CH₂CH₂-(4-fluorophenyl) |
| II-71 | 2-methylbenzothiophen-5-yl-CH₂-phenyl |
| II-72 | 5-methylthiophen-2-yl-CH₂-naphthalen-2-yl |
| II-73 | 5-methylthiophen-2-yl-CH₂CH₂-(2-methoxyphenyl) |
| II-74 | 5-methylthiophen-2-yl-CH₂CH₂-(2-hydroxyphenyl) |
| II-75 | 5-methylthiophen-2-yl-CH₂-thiophen-3-yl |

TABLE 19-continued

| Comp. No. | R |
|---|---|
| II-76 | 2-methylbenzothiophen-6-yl-CH₂-phenyl |
| II-77 | 2-methylbenzothiophen-5-yl-CH₂-thiophen-3-yl |
| II-78 | 2-methylbenzothiophen-5-yl-CH₂-thiophen-2-yl |
| II-79 | 5-methylthiophen-3-yl-CH₂-thiophen-2-yl |
| II-80 | 5-methylthiophen-3-yl-CH₂-thiophen-3-yl |

TABLE 20

| Comp. No. | R |
|---|---|
| II-81 | 3-methylbenzothiophen-7-yl-CH₂-thiophen-3-yl |
| II-82 | 5-methylthiophen-3-yl-CH₂-furan-3-yl |
| II-83 | 5-methylthiophen-2-yl-CH₂-naphthalen-1-yl |

TABLE 20-continued
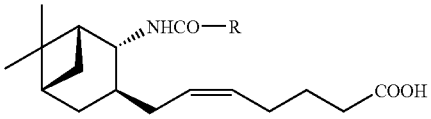
| Comp. No. | R |
|---|---|
| II-84 | 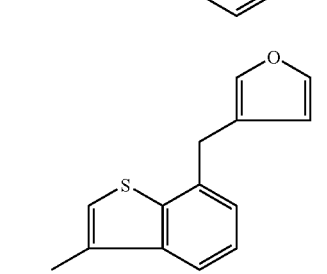 |
| II-85 | 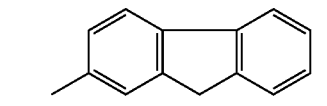 |
| II-86 | 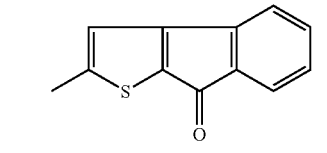 |
| II-87 | 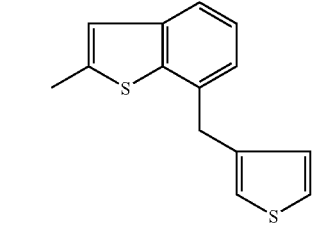 |
| II-88 | 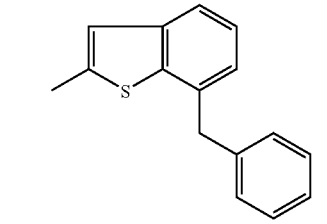 |
| II-89 | 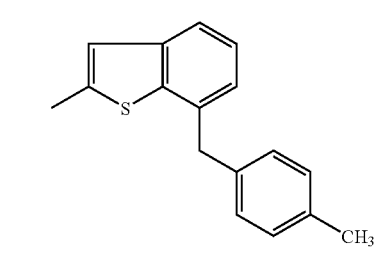 |
| II-90 | 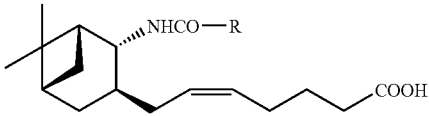 |
TABLE 20-continued
| Comp. No. | R |
|---|---|
| II-91 | 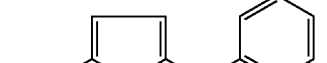 |
| II-92 |  |
| II-93 |  |
| II-94 | 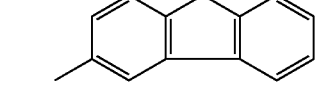 |
| II-95 |  |
| II-96 | 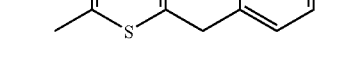 |
| II-97 |  |
| II-98 | 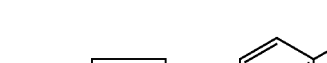 |
| II-99 | 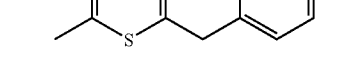 |

TABLE 20-continued
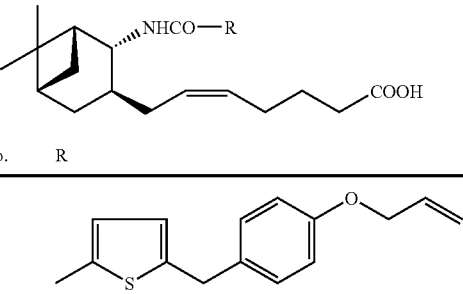
| Comp. No. | R |
|---|---|
| II-100 | 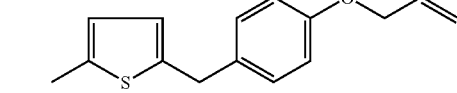 |
TABLE 21
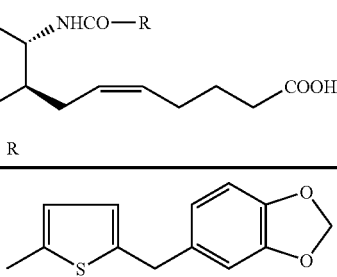
| Comp. No. | R |
|---|---|
| II-101 | 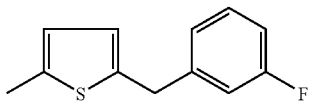 |
| II-102 | 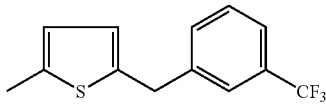 |
| II-103 | 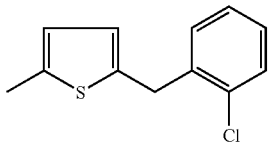 |
| II-104 | 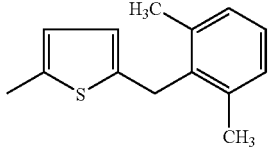 |
| II-105 | 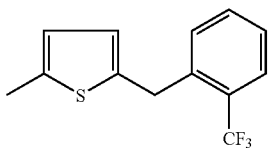 |
| II-106 | 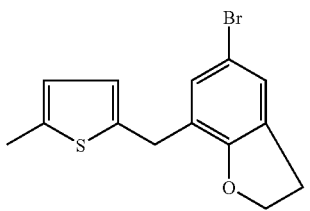 |
| II-107 | 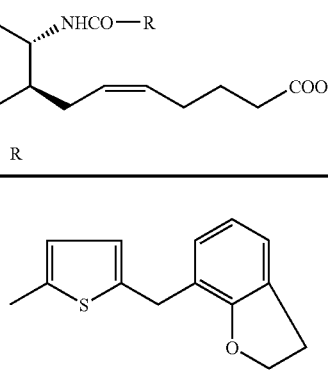 |
TABLE 21-continued
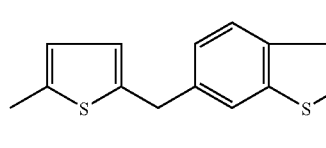
| Comp. No. | R |
|---|---|
| II-108 | 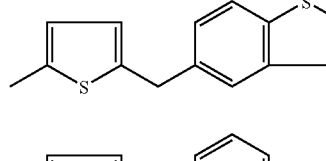 |
| II-109 | 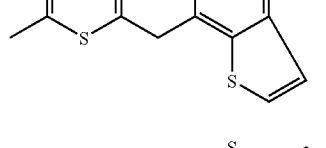 |
| II-110 | 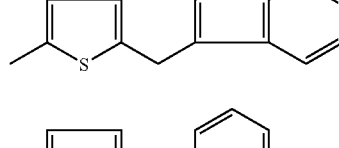 |
| II-111 | 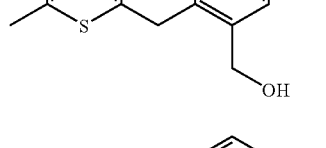 |
| II-112 | 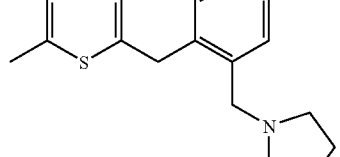 |
| II-113 | 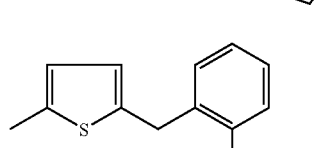 |
| II-114 | |
| II-115 | |

TABLE 21-continued
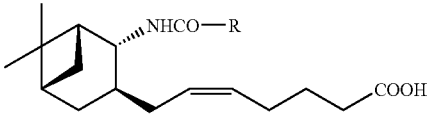
| Comp. No. | R |
|---|---|
| II-116 | 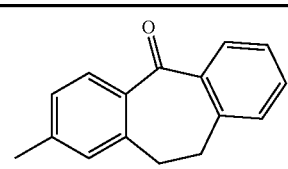 |
| II-117 | 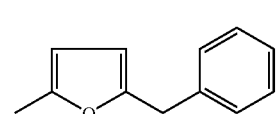 |
| II-118 | 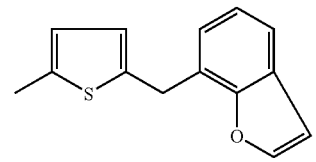 |
| II-119 | 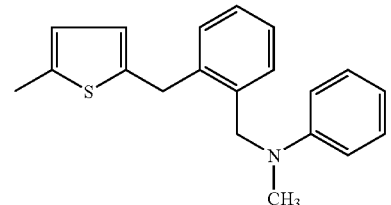 |
| II-120 | 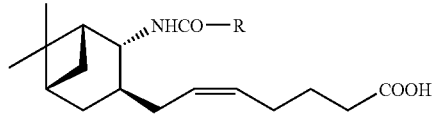 |
TABLE 22
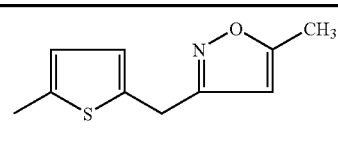
| Comp. No. | R |
|---|---|
| II-121 | 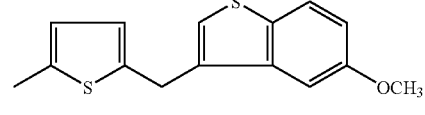 |
| II-122 | 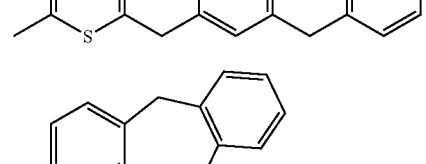 |
TABLE 22-continued
| Comp. No. | R |
|---|---|
| II-123 | 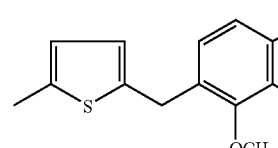 |
| II-124 | 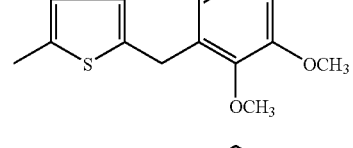 |
| II-125 | 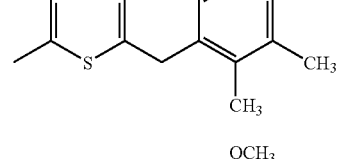 |
| II-126 | 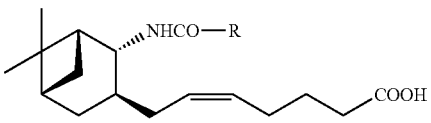 |
| II-127 | 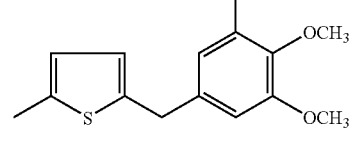 |
| II-128 | 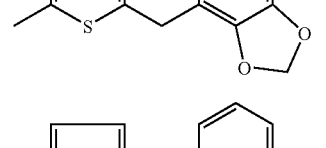 |
| II-129 | |
| II-130 | |
| II-131 | |
| II-132 | |

TABLE 22-continued
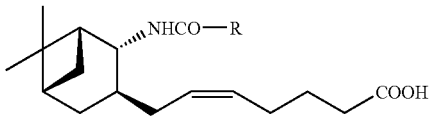
| Comp. No. | R |
|---|---|
| II-133 | 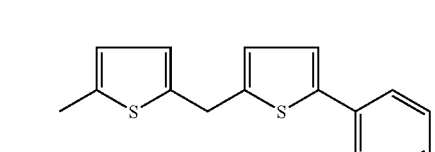 |
| II-134 | 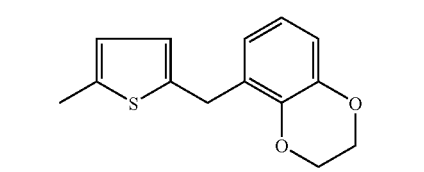 |
| II-135 | 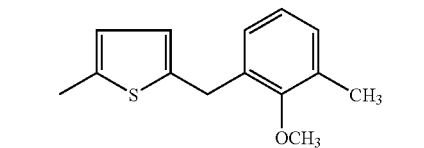 |
| II-136 | 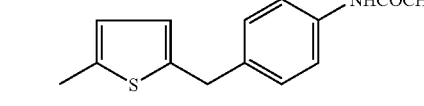 |
| II-137 | 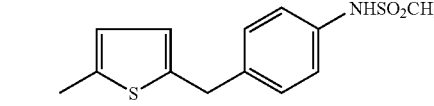 |
| II-138 | 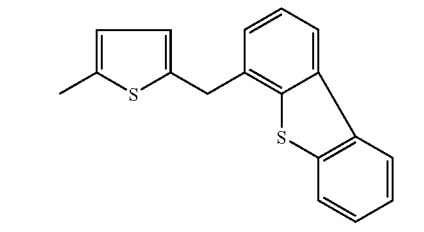 |
| II-139 | 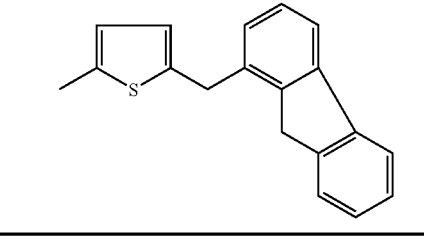 |
| II-140 | 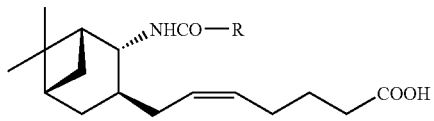 |
TABLE 23
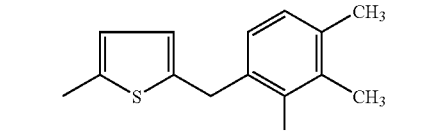
| Comp. No. | R |
|---|---|
| II-141 | 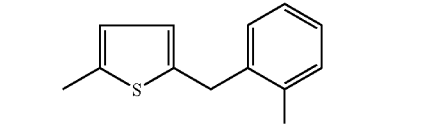 |
| II-142 | 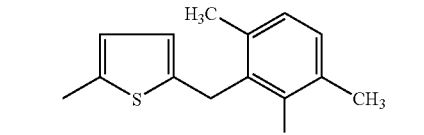 |
| II-143 | 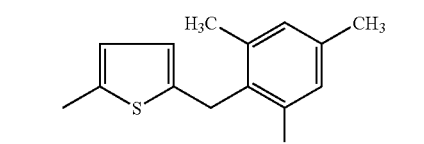 |
| II-144 | 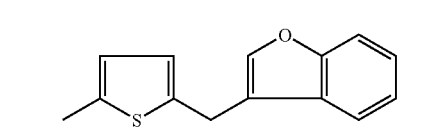 |
| II-145 | 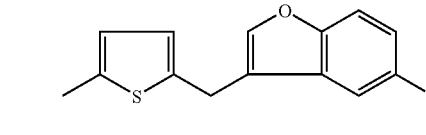 |
| II-146 | 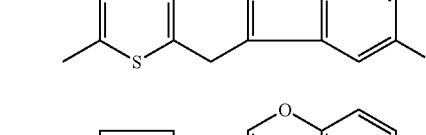 |
| II-147 | 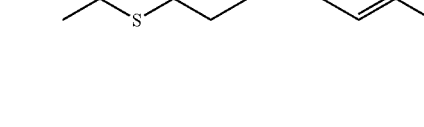 |
| II-148 | |
| II-149 | |

TABLE 23-continued

| Comp. No. | R |
|---|---|
| II-150 | 5-methyl-thiophene-CH2-(5-methylbenzofuran-3-yl) |
| II-151 | 5-methyl-thiophene-CH2-(6-methoxybenzofuran-3-yl) |
| II-152 | 5-methyl-thiophene-CH2-(6-hydroxybenzofuran-3-yl) |
| II-153 | 5-methyl-thiophene-CH2-(6-fluorobenzofuran-3-yl) |
| II-154 | 5-methyl-thiophene-CH2-(6-methylbenzofuran-3-yl) |
| II-155 | 5-methyl-thiophene-CH2-(benzo[d]isoxazol-3-yl) |
| II-156 | 5-methyl-thiophene-CH2-(5-methoxybenzo[d]isoxazol-3-yl) |
| II-157 | 5-methyl-thiophene-CH2-(5-hydroxybenzo[d]isoxazol-3-yl) |
| II-158 | 5-methyl-thiophene-CH2-(5-fluorobenzo[d]isoxazol-3-yl) |
| II-159 | 5-methyl-thiophene-CH2-(5-methylbenzo[d]isoxazol-3-yl) |
| II-160 | 5-methyl-thiophene-CH2-(5-chloro-4-phenyl-thiophen-2-yl) |

TABLE 24

| Comp. No. | R |
|---|---|
| II-161 | 5-methyl-thiophene-CH2-(4-phenyl-thiophen-2-yl) |
| II-162 | 5-methyl-thiophene-CH2-(4-(4-methoxyphenyl)-thiophen-2-yl) |
| II-163 | 5-methyl-thiophene-CH2-(4-(4-hydroxyphenyl)-thiophen-2-yl) |
| II-164 | 5-methyl-thiophene-CH2-(4-(4-fluorophenyl)-thiophen-2-yl) |
| II-165 | 5-methyl-thiophene-CH2-(4-(4-methylphenyl)-thiophen-2-yl) |
| II-166 | 5-methyl-thiophene-CH2-(5-chloro-thiophen-2-yl) |
| II-167 | 5-methyl-thiophene-CH2-(5-phenyl-thiophen-3-yl) |
| II-168 | 5-methyl-thiophene-CH2-(4-phenyl-thiophen-3-yl) |

TABLE 24-continued

R structure with NHCO—R, COOH

| Comp. No. | R |
|---|---|
| II-169 | 5-methylthiophene-CH2-thiophene-CH2-phenyl |
| II-170 | 5-methylthiophene-CH2-thiazole |
| II-171 | 5-methylthiophene-CH2-benzothiazole |
| II-172 | 5-methylthiophene-CH2-pyridin-3-yl |
| II-173 | 5-methylthiophene-CH2-isoquinolin-7-yl |
| II-174 | 5-methylthiophene-CH2-isoquinolin-6-yl |
| II-175 | 5-methylthiophene-CH2-(2,3-dihydrobenzofuran-4-yl) |
| II-176 | 5-methylthiophene-CH2-(2,3-dihydrobenzofuran-6-yl) |
| II-177 | 5-methylthiophene-CH2-(2,3-dihydrobenzofuran-5-yl) |
| II-178 | 5-methylthiophene-CH2-(2,4-difluorophenyl) |
| II-179 | 5-methylthiophene-SO2-N(2,5-dimethylpyrrole) |

TABLE 24-continued

R structure with NHCO—R, COOH

| Comp. No. | R |
|---|---|
| II-180 | 5-methylthiophene-SO2-N(3-methylpyrrole) |

TABLE 25

R structure with NHCO—R, COOH

| Comp. No. | R |
|---|---|
| II-181 | 5-methylthiophene-CH2-thiophene-SO2-N(pyrrole) |
| II-182 | 5-methylthiophene-CH2-thiophene-SO2-N(2-methylpyrrole) |
| II-183 | 5-methylthiophene-CH2-thiophene-SO2-thiophene |
| II-184 | 5-methylthiophene-CH2-(6-hydroxynaphthalen-2-yl) |
| II-185 | 5-methylthiophene-CH2-(1-hydroxynaphthalen-2-yl) |
| II-186 | 5-methylthiophene-CH2-(6-hydroxynaphthalen-1-yl) |
| II-187 | 5-methylthiophene-CH2-phenyl-CH2-thiophene |

TABLE 25-continued

| Comp. No. | R |
|---|---|
| II-188 | (5-methylthiophen-2-yl)methyl-phenyl-SO2-N(pyrrole) |
| II-189 | (5-methylthiophen-2-yl)methyl-phenyl-SO2-N(2-methylpyrrole) |
| II-190 | (5-methylthiophen-2-yl)methyl-thieno-dihydrofuran |
| II-191 | (5-methylthiophen-2-yl)methyl-thieno-dihydrofuran isomer |
| II-192 | (5-methylthiophen-2-yl)methyl-(F-substituted dihydrobenzofuran) |
| II-193 | (5-methylthiophen-2-yl)methyl-(Cl-substituted dihydrobenzofuran) |
| II-194 | (5-methylthiophen-2-yl)methyl-(CH3-substituted dihydrobenzofuran) |
| II-195 | (5-methylthiophen-2-yl)methyl-(OH-substituted dihydrobenzofuran) |
| II-196 | (5-methylthiophen-2-yl)methyl-(phenyl-substituted dihydrobenzofuran) |
| II-197 | (5-methylthiophen-2-yl)methyl-thieno-dihydrofuran |
| II-198 | (5-methylthiophen-2-yl)methyl-(CH3-substituted thieno-dihydrofuran) |
| II-199 | (3-methylbenzofuran-7-yl)-benzyl |
| II-200 | (3-methylbenzofuran-7-yl)methyl-thiophene |

TABLE 26
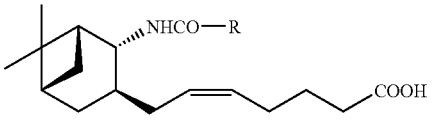
| Comp. No. | R |
|---|---|
| II-201 | 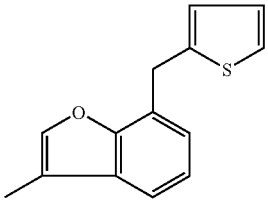 |
| II-202 | 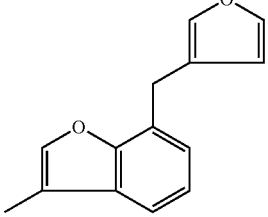 |
| II-203 | 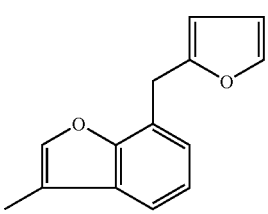 |
| II-204 |  |
TABLE 27
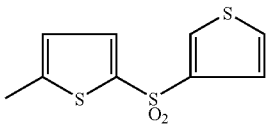
| Comp. No. | R |
|---|---|
| III-1 | 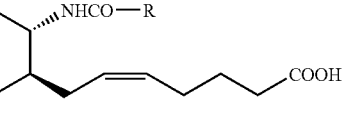 |
| III-2 | 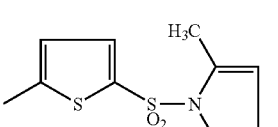 |
| III-3 | 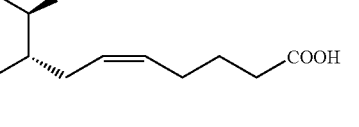 |
| III-4 | 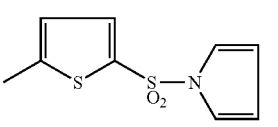 |
TABLE 28
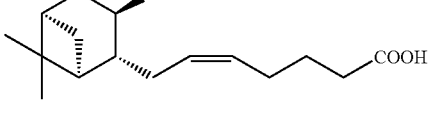
| Comp. No. | R |
|---|---|
| IV-1 | 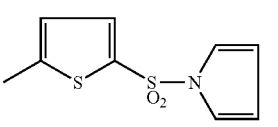 |
| IV-2 | 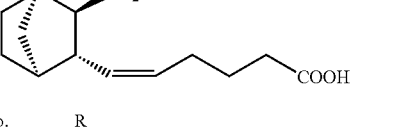 |
TABLE 29
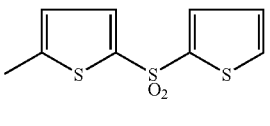
| Comp. No. | R |
|---|---|
| V-1 | 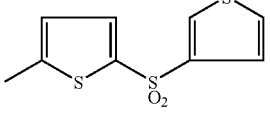 |
| V-2 | |
| V-3 | |

TABLE 29-continued

[Structure: bicyclic core with CH₂NHCO—R substituent and pendant chain terminating in COOH]

| Comp. No. | R |
|---|---|
| V-4 | 5-methyl-thiophen-2-yl-SO₂-N(2-methylpyrrole) |
| V-5 | 5-methyl-thiophen-2-yl-CH₂-phenyl |
| V-6 | 5-methyl-thiophen-2-yl-phenyl |
| V-7 | 4-methylphenyl-O-4-methoxyphenyl |
| V-8 | 5-methyl-thiophen-2-yl-CH₂-S-thiophen-2-yl |
| V-9 | 5-methyl-thiophen-2-yl-CH₂-O-phenyl |
| V-10 | 5-methyl-thiophen-2-yl-CH₂-NH-phenyl |
| V-11 | 5-methyl-thiophen-2-yl-CH₂-S-phenyl |
| V-12 | 5-methyl-thiophen-2-yl-CH₂-furan-2-yl |

TABLE 30

| Comp. No. | R |
|---|---|
| VI-1 | 5-methyl-thiophen-2-yl-CH₂-thiophen-2-yl |

PHYSICAL PROPERTY

Compound I-3

300 MHz $^1$H-NMR (CDCl$_3$-CD$_3$OD) δ: 1.23(1H, m), 1.28–1.32(2H, m), 1.44–1.53(2H, m), 1.57–1.74(4H, m), 2.03–2.14(5H, m), 2.32(2H, t, J=7.2Hz), 2.56(1H, m), 3.82 (1H, m), 5.33–5.47(2H, m), 6.80(1H, m), 7.09–7.12(2H, m), 7.22(1H, t, J=8.1Hz), 7.63 and 7.86(each 1H, each d, each J=8.1Hz).

IR(CHCl$_3$): 3593 3442, 3111, 1710, 1644, 1519, 1449 cm$^{-1}$.

[α]$_D^{25}$+77.6±1.2° (c=1.010, MeOH)

Elemental Analysis (C$_{25}$H$_{29}$NO$_4$S•0.2H$_2$O) Calcd.(%): C, 67.76; H, 6.69; N, 3.16; S, 7.23 Found(%): C, 67.64; H, 6.77; N, 3.17; S, 7.18

Compound I-4

300MHz $^1$H-NMR(CDCl$_3$) δ: 1.06(1H, m), 1.17–1.32 (2H, m), 1.40–1.50(2H, m), 1.56–1.80(4H, m), 2.00–2.22 (5H, m), 2.33(2H, t, J=7.2Hz), 2.53(1H, m), 3.84(3H, s), 3.85(1H, m), 5.29–5.42(2H, m), 6.18(1H, d, J=6.9Hz), 6.93, 7.10, 7.44 and 7.59(each 2H, each d-like).

IR(CHCl$_3$): 3516, 3448, 1708, 1650, 1594, 1514, 1494, 1483, 1288, 1248, 1032 cm$^{-1}$.

[α]$_D^{26}$+82.8±1.2° (c=1.000, MeOH)

Elemental Analysis (C$_{28}$H$_{33}$NO$_4$S•0.2H$_2$O) Calcd.(%): C, 69.59; H, 6.97; N, 2.90; S, 6.64 Found(%): C, 69.69; H, 6.93; N, 3.20; S, 6.57

Compound I-5

300MHz $^1$H-NMR(CDCl$_3$) δ: 1.06(1H, m), 1.16–1.32 (2H, m), 1.36–1.50(2H, m), 1.54–1.80(4H, m), 2.00–2.22 (5H, m), 2.34(2H, t, J=7.2Hz), 2.53(1H, m), 3.82(1H, m), 3.83(3H, s), 5.29–5.42(2H, m), 6.14(1H, d, J=7.2Hz), 6.92 (2H, d-like), 7.20–7.30(2H, m), 7.41–7.51(4H, m).

IR(CHCl$_3$): 3509, 3444, 2666, 1708, 1654, 1592, 1570, 1510, 1494, 1468, 1288, 1247, 1082 cm$^{-1}$.

[α]$_D^{26}$+58.4±1.4° (c=0.704, MeOH)

Elemental Analysis (C$_{28}$H$_{33}$NO$_4$S•0.2H$_2$O) Calcd.(%): C, 69.59; H, 6.97; N, 2.90; S, 6.64 Found(%): C, 69.55; H, 6.93; N, 3.03; S, 6.57

Compound I-6

300MHz $^1$H-NMR(CDCl$_3$) δ: 1.11(1H, m), 1.20–1.34 (2H, m), 1.42–1.52(2H, m), 1.56–1.78(4H, m), 2.00–2.23 (5H, m), 2.35(2H, t, J=7.2Hz), 2.57(1H, m), 3.89(1H, m), 5.31–5.45(2H, m), 6.30(1H, d, J=7.2Hz), 6.37 and 7.12(each 2H, each 2H, each J=2.1Hz), 7.42 and 7.83(each 2H, each d-like).

IR(CHCl$_3$): 3518, 3448, 2662, 1708, 1653, 1609, 1499, 1334 cm$^{-1}$.

$[\alpha]_D^{23}$+94.9±1.3° (c=1.005, MeOH)

Elemental Analysis (C$_{25}$H$_{30}$N$_2$O$_3$•0.1H$_2$O) Calcd.(%): C, 73.54; H, 7.45; N, 6.86 Found(%): C, 73.43; H, 7.46; N, 7.01

Compound I-7

300MHz $^1$H-NMR(CDCl$_3$) δ: 1.12–1.76(9H, m), 1.96–2.24(5H, m), 2.33(2H, t, J=7.2Hz), 2.53(1H, m), 3.86(1H, m), 5.30–5.47(2H, m), 6.60(1H, d, J=6.9Hz), 7.05–7.23(5H, m), 7.55(1H, brs), 7.67 and 7.74(each 2H, each d, each J=8.7Hz).

IR(CHCl$_3$): 3516, 3439, 3368, 1708, 1653, 1600, 1519, 1496, 1487, 1401, 1347, 1165 cm$^{-1}$.

$[\alpha]D^{25}$+69.9±1.1° (c=1.019, MeOH)

Elemental Analysis (C$_{27}$H$_{34}$N$_2$O$_5$S•0.1H$_2$O) Calcd.(%): C, 64.80; H, 6.89; N, 5.60; S, 6.41 Found(%): C, 64.73; H, 6.56; N, 5.74; S, 6.41

Compound I-8

300MHz $^3$H-NMR(CDCl$_3$) δ: 1.19–1.27(3H, m), 1.35–1.43(2H, m), 1.55–1.80(4H, m), 1.90–2.08(3H, m), 2.11–2.21(2H, m), 2.34(2H, t, J=7.2Hz), 2.53(1H, m), 3.74(1H, m), 5.29–5.48(2H, m), 6.44(1H, d, J=6.9Hz), 7.15(1H, d, J=1.5Hz), 7.46(2H, t, J=7.8Hz), 7.57(1H, m), 7.60(1H, d, J=1.5Hz), 7.76–7.78(2H, m), 7.89(1H, s).

IR(CHCl$_3$): 3440, 3360, 3107, 1708, 1637, 1518, 1448, 1329, 1163 cm$^{-1}$.

$[\alpha]_D^{20}$+55.5±1.0° (c=1.003, MeOH)

Elemental Analysis (C$_{25}$H$_{30}$N$_2$O$_5$S$_2$•0.2H$_2$O) Calcd.(%): C, 59.31; H, 6.05; N, 5.53; S, 12.67 Found(%): C, 59.19; H, 6.12; N, 5.66; S, 12.50

Compound I-9 mp.193–194° C.

300MHz $^1$H-NMR(d$_6$-DMSO) δ: 1.18–1.59(9H, m), 1.93(1H, d, J=2.4Hz), 1.99–2.07(4H, m), 2.21(2H, t, J=7.2Hz), 2.36(1H, m), 5.30–5.40(2H; m), 7.25(1H, d, J=1.5Hz), 7.54–7.63(3H, m), 7.69(1H, d, J=1.5Hz), 7.99–8.02(3H, m), 11.6(1H, s), 12.00(1H, brs).

IR(Nujol): 3367, 3221, 3186, 3091, 3055, 2654, 1711, 1631, 1566, 1541, 1321 cm$^{-1}$.

$[\alpha]_D^2$+74.6±1.1° (c=1.006, MeOH)

Elemental Analysis (C$_{26}$H$_{30}$N$_2$O$_4$S) Calcd.(%): C, 66.93; H, 6.48; N, 6.00; S, 6.87 Found(%): C, 66.76; H, 6.44; N, 5.88; S, 6.76

Compound I-10

300MHz $^1$H-NMR(CDCl$_3$) δ: 1.08(1H, m), 1.18–1.34(2H, m), 1.40–1.50(2H, m), 1.56–1.77(4H, m), 2.00–2.20(5H, m), 2.35(2H, t, J=7.2Hz), 2.55(1H, m), 3.86(1H, m), 5.31–5.54(2H, m), 6.26(1H, d, J=7.8Hz), 6.31 and 7.14(each 2H, each t, each J=2.1Hz), 7.84 and 7.88(each 2H, each d, each J=8.4Hz).

IR(CHCl$_3$): 3515, 3441, 3144, 2669, 1708, 1662, 1515, 1486, 1455, 1376 cm$^{-1}$.

$[\alpha]_D^{22}$+77.4±1.2° (c=1.004, MeOH)

Elemental Analysis (C$_{25}$H$_{30}$N$_2$O$_5$S•0.2H$_2$O) Calcd.(%): C, 63.32; H, 6.46; N, 6.91; S, 6.76 Found(%): C, 63.23; H, 6.49; N, 5.88; S, 6.67

Compound I-11

300MHz $^1$H-NMR(CDCl$_3$) δ: 1.06(1H, m), 1.18–1.29(2H, m), 1.42–1.46(2H, m), 1.56–1.79(4H, m), 2.03–2.20(5H, m), 2.34(2H, t, J=7.2Hz), 2.52(1H, m), 3.82(1H, m), 4.12(2H, s), 5.29–5.43(2H, m), 6.04(1H, d, J=7.5Hz), 7.09(1H, d, J=1.5Hz), 7.22–7.34(5H, m), 7.67(1H, d, J=1.5Hz).

IR(CHCl$_3$): 3517, 3446, 2669, 1708, 1647, 1549, 1508, 1454 cm$^{-1}$.

$[\alpha]_D^{21.5}$+68.8±1.1° (c=1.016, MeOH)

Elemental Analysis (C$_{26}$H$_{31}$NO$_3$S•0.1H$_2$O) Calcd.(%): C, 71.07; H, 7.16; N, 3.19; S, 7.30 Found(%): C, 71.05; H, 7.11; N, 3.38; S, 7.33

Compound I-12

300MHz $^1$H-NMR(CDCl$_3$) δ: 1.09(1H, m), 1.10–1.30(2H, m), 1.40–1.46(2H, m), 1.56–1.77(4H, m), 2.00–2.22(5H, m), 2.33(2H, t, J=7.2Hz), 2.52(1H, m), 3.83(1H, m), 5.28–5.42(2H, m), 6.26(1H, d, J=6.9Hz), 7.15 and 7.63(each 2H, each d, each J=8.7Hz), 7.53(1H, m), 7.78–7.82(2H, m).

IR(CHCl$_3$): 3515, 3446, 3371, 3138, 1708, 1648, 1610, 1496, 1163 cm$^{-1}$.

$[\alpha]_D^{22.5}$+66.5±1.1° (c=1.004, MeOH)

Elemental Analysis (C$_{27}$H$_{34}$N$_2$O$_5$S•0.4H$_2$O) Calcd.(%): C, 64.11; H, 6.93; N, 5.54; S, 6.34 Found(%): C, 64.05; H, 6.63; N, 5.56; S, 6.12

Compound I-13

300MHz $^1$H-NMR(CDCl$_3$) δ: 1.19–1.31(3H, m), 1.36–1.44(2H, m), 1.55–1.78(4H, m), 1.85–2.02(2H, m), 2.05(1H, m), 2.13–2.47(4H, m), 2.57(1H, m), 3.71(1H, m), 5.31–5.54(2H, m), 6.53(1H, d, J=6.9Hz), 7.14–7.32(5H, m), 7.47(1H, br), 8.05 and 8.13(each 1H, each d, each J=1.5Hz).

IR(CHCl$_3$): 3509, 3360, 3262, 1709, 1649, 1542, 1496, 1349, 1160 cm$^{-1}$.

$[\alpha]_D^{23}$+59.1±1.1° (c=1.001, MeOH)

Elemental Analysis (C$_{25}$H$_{30}$N$_2$O$_5$S$_2$•0.2H$_2$O) Calcd.(%): C, 59.31; H, 6.05; N, 5.53; S, 12.67 Found(%): C, 59.17; H, 6.01; N, 5.49; S, 12.37

Compound I-14

300MHz $^1$H-NMR(CDCl$_3$) δ: 1.18–1.32(3H, m), 1.38–1.47(2H, m), 1.55–1.78(4H, m), 1.90–2.08(3H, m), 2.15–2.31(2H, m), 2.32–2.49(2H, m), 2.59(1H, m), 3.74(1H, m), 5.33–5.53(2H, m), 6.35 and 7.17(each 2H, each t, each J=2.4Hz), 6.47(1H, d, J=6.3Hz), 8.21 and 8.22(each 1H, each d, each J=1.5Hz).

IR(CHCl$_3$): 3506, 3412, 3144, 3107, 1727, 1709, 1656, 1540, 1504, 1456, 1382, 1166 cm$^{-1}$.

$[\alpha]_D^{23}$+63.8±1.0° (c=1.005, MeOH)

Elemental Analysis (C$_{23}$H$_{28}$N$_2$O$_5$S$_2$•0.2H$_2$O) Calcd.(%): C, 57.53; H, 5.96; N, 5.83; S, 13.35 Found(%): C, 57.44; H, 5.96; N, 6.00; S, 13.35

Compound I-15 mp.128–130° C.

300MHz $^1$H-NMR(CDCl$_3$) δ: 1.16–1.34(3H, m), 1.40–1.81(6H, m), 2.37(2H, t, J=7.2Hz), 2.57(1H, m), 3.89(1H, m), 5.35–5.51(2H, m), 6.37 and 7.20(each 2H, each d, each J=2.4Hz), 7.23(1H, d, J=8.7Hz).

IR(Nujol): 3371, 3097, 2662, 1716, 1703, 1671, 1652, 1530, 1367, 1361, 1187, 1162 cm$^{-1}$.

$[\alpha]_D^{25}$+47.5±0.9° (c=1.003, MeOH)

Elemental Analysis (C$_{23}$H$_{28}$N$_2$O$_5$S$_2$) Calcd.(%): C, 57.96; H, 5.92; N, 5.88; S, 13.45 Found(%): C, 58.05; H, 5.91; N, 5.83; S, 13.38

Compound I-16

300MHz $^1$H-NMR(CDCl$_3$) δ: 1.09(1H, m), 1.20–1.32 (2H, m), 1.42–1.47(2H, m), 1.58–1.75(4H, m), 2.01(3H, d, J=1.2Hz), 2.00–2.16(5H, m), 2.35(2H, t, J=7.2Hz), 2.55(1H, m), 3.86(1H, m), 5.31–5.44(2H, m), 6.14(1H, dd, J=1.5 and 3.0Hz), 6.29(1H, d, J=7.5Hz), 6.86(1H, m), 7.04(1H, t, J=3.0Hz), 7.84(4H, s).

IR(CHCl$_3$): 3517, 3441, 2667, 1708, 1661, 1515, 1485, 1375, 1260, 1178 cm$^{-1}$.

[α]$_D^{25}$+73.8±1.1° (c=1.001, MeOH)

Elemental Analysis (C$_{26}$H$_{32}$N$_2$O$_5$S•0.1H$_2$O) Calcd.(%): C, 64.20; H, 6.67; N, 5.76; S, 6.59 Found(%): C, 64.14; H, 6.65; N, 5.85; S, 6.86

Compound I-17

300MHz $^1$H-NMR(CDCl$_3$) δ: 1.20–1.31(3H, m), 1.40–1.47(2H, m), 1.57–1.80(4H, m), 2.00–2.30(5H, m), 2.37(2H, t, J=6.9Hz), 2.60(1H, m), 3.84(1H, m), 5.32–5.50 (2H, m), 6.32(2H, t, J=2.4Hz), 6.63(1H, d, J=6.6Hz), 7.16 (2H, t, J=2.4Hz), 7.55(1H, t, J=8.0Hz), 7.89(1H, m), 8.06 (1H, d, J=7.8Hz), 8.30(1H, t, J=1.7Hz).

IR(CHCl$_3$): 3394, 3145, 1726, 1709, 1659, 1374 cm$^{-1}$.

[α]$_D^{25}$+6.03±1.0° (c=1.000, MeOH)

Elemental Analysis (C$_{25}$H$_{30}$N$_2$O$_5$S•0.2H$_2$O) Calcd.(%): C, 63.32; H, 6.46; N, 5.91; S, 6.76 Found(%): C, 63.39; H, 6.50; N, 6.16; S, 6.80

Compound I-18

300MHz $^1$H-NMR(CDCl$_3$) δ: 1.10(1H, m), 1.20–1.32 (2H, m), 1.45(2H, t, J=6.9Hz), 1.58–1.74(4H, m), 2.04–2.16 (5H, m), 2.28(3H, s), 2.35(2H, t, J=6.9Hz), 2.55(1H, m), 3.87(1H, m), 5.31–5.44(2H, m), 5.96(1H, m), 6.18(1H, t, J=3.3Hz), 6.32(1H, d, J=7.5Hz), 7.25(1H, dd, J=1.8 and 3.3Hz), 7.78 and 7.85(each 2H, each d, each J=8.7Hz).

IR(CHCl$_3$): 3514, 3441, 1708, 1661, 1515, 1487, 1368, 1164 cm$^{-1}$.

[α]$_D^{25}$+74.0±1.1° (c=1.004, MeOH)

Elemental Analysis (C$_{26}$H$_{32}$N$_2$O$_5$S•0.2H$_2$O) Calcd.(%): C, 63.96; H, 6.69; N, 5.74; S, 6.57 Found(%): C, 63.97; H, 6.69; N, 5.98; S, 6.54

Compound I-19

300MHz $^1$H-NMR(CDCl$_3$) δ: 1.07(1H, m), 1.18–1.31 (2H, m), 1.41–1.49(2H, m), 1.56–1.76(4H, m), 2.00–2.21 (5H, m), 2.34(2H, t, J=7.2Hz), 2.55(1H, m), 3.86(1H; m), 5.09(2H, s), 5.29–5.43(2H, m), 6.19(2H, t, J=2.1Hz), 6.25 (1H, d, J=7.5Hz), 6.67(2H, t, J=2.1Hz), 7.13 and 7.70(each 2H, each d, each J=8.4Hz).

IR(CHCl$_3$): 3517, 3446, 3103, 2667, 1708, 1653, 1523, 1497 cm$^{-1}$.

[α]$_D^{25}$+57.7±1.0° (c=1.010, MeOH)

Elemental Analysis (C$_{26}$H$_{32}$N$_2$O$_3$) Calcd.(%): C, 73.63; H, 7.70; N, 6.60 Found(%): C, 73.72; H, 7.77; N, 6.76

Compound I-20

300MHz $^1$H-NMR(CDCl$_3$) δ: 1.05(1H, m), 1.15–1.30 (2H, m), 1.36–1.45(2H, m), 1.55–1.72(4H, m), 2.00–2.14 (5H, m), 2.32(2H, t, J=7.2Hz), 2.51(1H, m), 3.82(1H, m), 5.28–5.42(2H, m), 6.22(2H, d, J=7.5Hz), 6.68(1H, d, J=3.6Hz), 7.22–7.34(2H, m), 7.52–7.55(2H, m), 7.76 and 7.88(each 2H, each d, each J=8.7Hz), 7.97(1H, d, J=8.1Hz).

IR(CHCl$_3$): 3510, 3480, 3440, 3145, 3117, 1708, 1661, 1516, 1485, 1445, 1377, 1130 cm$^{-1}$.

[α]$_D^{25}$+65.9±1.1° (c=1.010, MeOH)

Elemental Analysis (C$_{29}$H$_{32}$N$_2$O$_5$S•S0.3H$_2$O) Calcd.(%): C, 66.21; H, 6.25; N, 5.33; S,6.10 Found(%): C, 66.34; H, 6.30; N, 5.63; S,5.84

Compound I-21

300MHz $^1$H-NMR(CDCl$_3$) δ: 1.13(1H, m), 1.20–1.31 (2H, m), 1.44(2H, t, J=6.8Hz), 1.59–1.72(4H, m), 2.03–2.20 (5H, m), 2.32(2H, t, J=7.2Hz), 2.54(1H, m), 3.83(1H, m), 4.62(2H, s), 5.31–5.45(2H, m), 6.25–6.26(2H, m), 6.57(1H, d, J=7.2Hz), 7.25(1H, m), 7.81(4H, s).

IR(CHCl$_3$): 3581, 3518, 3440, 3149, 1708, 1660, 1517, 1486, 1371, 1150 cm$^{-1}$.

[α]$_D^{27}$+72.2±1.1° (c=1.007, MeOH)

Elemental Analysis (C$_{26}$H$_{32}$N$_2$O$_6$S) Calcd.(%): C, 62.38; H, 6.44; N, 5.60; S,6.40 Found(%): C, 62.17; H, 6.52; N, 5.71; S,6.40

Compound I-22

300MHz $^1$H-NMR(d$_6$-DMSO) δ: 1.18–1.33(3H, m), 1.43–1.60(6H, m), 1.92–2.30(5H, m), 2.20(2H, t, J=7.5Hz), 2.38(1H, m), 3.67(1H, m), 5.30–5.36(2H, m), 6.85(1H, d, J=4.8Hz), 7.27(1H, d, J=4.8Hz), 7.86 and 7.94(each 2H, each d, each J=8.7Hz), 8.37(1H, d, J=6.9Hz).

IR(KBr): 3360, 3151, 3103, 1707, 1635, 1569, 1530, 1328, 1284, 1140 cm$^{-1}$.

[α]$_D^{27}$+67.4±1.1° (c=1.007, DMSO)

Elemental Analysis (C$_{24}$H$_{29}$N$_3$O$_5$S$_2$•0.3H$_2$O) Calcd.(%): C, 56.62; H, 5.86; N, 8.24; S,12.60 Found(%): C, 56.74; H, 5.96; N, 8.30; S,12.31

Compound I-23 mp.231–232° C.

300MHz $^1$H-NMR(d$_6$-DMSO) δ: 1.19–1.61(9H, m), 1.95–2.08(5H, m), 2.21(2H, t, J=7.2Hz), 2.40(1H, m), 3.71 (1H, m), 5.34–5.37(2H, m), 7.31 and 7.59(each 1H, each d, each J=3.6Hz), 7.98 and 8.16(each 2H, each d, each J=8.7Hz), 8.41(1H, d, J=7.2Hz).

IR(KBr): 3336, 3185, 2541, 1675, 1631, 1548, 1324, 1295, 1163 cm$^{-1}$.

[α]$_D^{27}$+84.5±1.3° (c=1.000, DMSO)

Elemental Analysis (C$_{24}$H29N$_3$O$_4$S) Calcd.(%): C, 64.22; H, 6.25; N, 8.99; S,6.86 Found(%): C, 64.13; H, 6.10; N, 8.92; S,7.08

Compound I-24

300MHz $^1$H-NMR(CDCl$_3$) δ: 1.14(1H, m), 1.22–1.35 (2H, m), 1.44–1.53(2H, m), 1.58–1.78(4H, m), 2.02–2.28 (5H, m), 2.36(2H, t, J=7.2Hz), 2.58(1H, m), 3.87(1H, m), 5.15–5.48(2H, m), 6.29 and 7.18(each 2H, each t, J=2.4Hz), 6.38(1H, d, J=7.2Hz), 7.77(1H, dd, J=1.8 and 8.7Hz), 7.82 (1H, s), 7.91(1H, d, J=8.7Hz), 8.34(1H, d, J=1.8Hz).

IR(CHCl$_3$): 3512, 3441, 3423, 3144, 2670, 1708, 1530, 1501, 1374, 1164 cm$^{-1}$.

[α]$_D^{26}$+96.1±1.4° (c=1.006, MeOH)

Elemental Analysis (C$_{27}$H$_{30}$N$_2$O$_5$S$_2$•0.2H$_2$O) Calcd.(%): C, 61.16; H, 5.78; N, 5.28; S, 12.09 Found(%): C, 61.17; H, 5.74; N, 5.35; S, 12.12

Compound I-25

300MHz $^1$H-NMR(CDCl$_3$) δ: 1.06(1H, m), 1.17–1.31 (2H, m), 1.39–1.48(2H, m), 1.56–1.77(4H, m), 1.99–2.20 (5H, m), 2.34(2H, t, J=7.2Hz), 2.53(1H, m), 3.84(1H, m), 5.29–5.42(2H, m), 6.20(1H, d, J=7.2Hz), 7.10–7.17(3H, m), 7.32(1H, dd, J=1.2 and 3.6Hz), 7.54(1H, dd, J=1.2 and 5.4Hz), 7.60–7.64(2H, m).

IR(CHCl$_3$): 3518, 3447, 2669, 1708, 1651, 1596, 1515, 1483 cm$^{-1}$.

[α]$_D^{26}$+84.7±1.2° (c=1.003, MeOH)

Elemental Analysis (C$_{25}$H$_{29}$NO$_3$S$_2$•0.1H$_2$O) Calcd.(%): C, 65.64; H, 6.43; N, 3.06; S, 14.02 Found(%): C, 65.58; H, 6.41; N, 3.10; S, 13.82

Compound I-26

300MHz $^1$H-NMR(CDCl$_3$) δ: 1.13(1H, m), 1.20–1.33 (2H, m), 1.41–1.50(2H, m), 1.56–1.77(4H, m), 2.00–2.21 (5H, m), 2.37(2H, t, J=7.2Hz), 2.55(1H, m), 3.87(1H, m), 5.31–5.45(2H, m), 6.48(1H, d, J=7.2Hz), 7.10(1H, dd, J=3.9 and 5.1Hz), 7.68(1H, dd, J=1.2 and 5.1Hz), 7.69(1H, dd, J=1.2 and 3.9Hz), 7.84–7.88 and 7.95–7.99(each 2H, each m).

IR(CHCl$_3$): 3518, 3441, 3382, 1708, 1659, 1515, 1329, 1158 cm$^{-1}$.

[α]$_D^{26}$+75.7±1.2° (c=1.000, MeOH)

Elemental Analysis (C$_{25}$H$_{29}$NO$_5$S$_2$) Calcd.(%): C, 61.58; H, 5.99; N, 2.87; S, 13.15 Found(%): C, 61.36; H, 6.05; N, 2.91; S, 13.13

Compound I-27 mp.213–215° C.

300MHz $^1$H-NMR(d$_6$-DMSO) δ: 1.18–1.61(9H, m), 1.95–2.10(5H, m), 2.21(2H, t, J=7.5Hz), 2.40(1H, m), 3.71 (1H, m), 5.33–5.38(2H, m), 7.19(1H, m), 7.87(1H, m), 7.96 and 8.10(each 2H, each d, each J=8.2Hz), 8.21(1H, d, J=8.6Hz), 8.40(1H, m), 10.92(1H, s), 12.05(1H, brs).

IR(Nujol): 3337, 3249, 3205, 3132, 2524, 1678, 1632, 1545, 1433, 1305 cm$^{-1}$.

[α]$_D^{23}$+85.2±2.5° (c=0.505, MeOH)

Elemental Analysis (C$_{27}$H$_{31}$N$_3$O$_4$•0.3H$_2$O) Calcd.(%): C, 69.72; H, 6.80; N, 9.03 Found(%): C, 69.76; H, 6.75; N, 8.76

Compound I-28

300MHz $^1$H-NMR(CDCl$_3$) δ: 1.07(1H, m), 1.18–1.32 (2H, m), 1.40–1.50(2H, m), 1.56–1.78(4H, m), 2.00–2.21 (5H, m), 2.34(2H, t, J=7.2Hz), 2.54(1H, m), 3.85(1H, m), 5.29–5.42(2H, m), 6.17(1H, d, J=6.9Hz), 7.07(1H, dd, J=1.2 and 5.1Hz), 7.15(2H, d J=8.7Hz), 7.43(1H, dd, J=3.0 and 5.1Hz), 7.51(1H, dd, J=1.2 and 3.0Hz), 7.62(2H, d, J=8.7Hz).

IR(CHCl$_3$): 3510, 3447, 3110, 2666, 1708, 1651, 1596, 1515, 1482 cm$^{-1}$.

[α]$_D^{27}$+85.9±1.3° (c=1.007, MeOH)

Elemental Analysis (C$_{25}$H$_{29}$NO$_3$S$_2$) Calcd.(%): C, 65.90; H, 6.42; N, 3.07; S, 14.07 Found(%): C, 65.60; H, 6.36; N, 3.36; S, 13.86

Compound I-29 mp. 123–125° C.

300MHz $^1$H-NMR(CDCl$_3$) δ: 1.12(1H, m), 1.18–1.34 (2H, m), 1.42–1.50(2H, m), 1.56–1.78(4H, m), 2.02–2.21 (5H, m), 2.35(2H, t, J=7.2Hz), 2.55(1H, m), 3.88(1H, m), 5.31–5.45(2H, m), 6.42(1H, d, J=6.0Hz), 7.31(1H, d, J=5.1Hz), 7.40(1H, dd, J=3.0 and 5.1Hz), 7.87 and 7.96 (each 2H, each d, each J=8.7Hz), 8.11(1H, d, J=3.0Hz).

IR(Nujol): 3286, 3108, 2671, 1701, 1641, 1546, 1327, 1156 cm$^{-1}$.

[α]$_D^{27}$+75.3±1.2° (c=1.004, MeOH)

Elemental Analysis (C$_{25}$H$_{29}$NO$_5$S$_2$) Calcd.(%): C, 61.58; H, 5.99; N, 2.87; S, 13.15 Found(%): C, 61.39; H, 5.94; N, 3.02; S, 12.99

Compound I-30

300MHz $^1$H-NMR(CDCl$_3$) δ: 1.12(1H, m), 1.23–1.34 (2H, m), 1.43–1.52(2H, m), 1.58–1.79(4H, m), 2.02–2.24 (5H, m), 2.36(2H, t, J=7.2Hz), 2.53(1H, m), 3.87(1H, m), 5.32–5.45(2H, m), 6.11(1H, d, J=3.6Hz), 6.28(1H, d, J=7.5Hz), 6.35 and 7.09(each 2H, each t, each J=2.1Hz), 7.16(1H, d, J=3.6Hz).

IR(CHCl$_3$): 3512, 3438, 3142, 1741, 1709, 1653, 1623, 1564, 1508 cm$^{-1}$.

[α]$_D^{25}$+102.4±1.4° (c=1.006, MeOH)

Elemental Analysis (C$_{23}$H$_{28}$N$_2$O$_4$•0.2H$_2$O) Calcd.(%): C, 69.05; H, 7.15; N, 7.00 Found(%): C, 69.12; H, 7.10; N, 6.95

Compound I-31

300MHz $^1$H-NMR(CDCl$_3$) δ: 1.04(1H, m), 1.08–1.28 (2H, m), 1.41–1.46(2H, m), 1.55–1.78(4H, m), 1.99–2.16 (5H, m), 2.34(2H, t, J=7.2Hz), 2.51(1H, m), 3.81(1H, m), 4.13(2H, s), 5.29–5.42(2H, m), 5.96(1H, d, J=8.1Hz), 6.77 (1H, ddd, J=0.9, 0.9 and 3.9Hz), 7.20–7.35(5H, m), 7.37 (1H, d, J=3.9Hz).

IR(CHCl$_3$): 3511, 3445, 2670, 1708, 1642, 1544, 1507, 1455 cm$^{-1}$.

[α]$_D^{26}$+67.1±1.1° (c=1.015, MeOH)

Elemental Analysis (C$_{26}$H$_{31}$NO$_3$S) Calcd.(%): C, 71.36; H, 7.14; N, 3.20; S, 7.33 Found(%): C, 71.19; H, 7.16; N, 3.34; S, 7.26

Compound I-32

300MHz $^1$H-NMR(CDCl$_3$) δ: 1.22–1.85(9H, m), 1.95–2.53(7H, m), 2.66(1H, m), 3.84(1H, m), 5.37–5.60(2H, m), 6.79(1H, d, J=6.0Hz), 7.01–7.17(5H, m), 7.83(1H, dd, J=1.5 and 8.7Hz), 7.53(1H, d, J=8.7Hz), 7.89(1H, s), 8.35 (1H, s), 8.83(1H, d, J=1.5Hz).

IR(CHCl$_3$): 3509, 3437, 3364, 3209, 1710, 1634, 1495, 1344, 1158 cm$^{-1}$.

[α]$_D^{26}$+36.6±0.8° (c=1.005, MeOH)

Elemental Analysis (C$_{29}$H$_{32}$N$_2$O$_5$S$_2$•0.2H$_2$O) Calcd.(%): C, 62.61; H, 5.87; N, 5.04; S, 11.53 Found(%): C, 62.53; H, 5.87; N, 5.21; S, 11.42

Compound I-33

300MHz $^1$H-NMR(CDCl$_3$) δ: 1.13(1H, m), 1.20–1.37 (2H, m), 1.46–1.56(2H, m), 1.60–1.80(4H, m), 2.02–2.28 (5H, m), 2.38(2H, t, J=7.2Hz), 2.64(1H, m), 3.94(1H, m), 5.35–5.50(2H, m), 6.21(1H, d, J=7.2Hz), 6.28 and 7.21(each 2H, each t, each J=2.4Hz), 7.81(1H, dd, J=1.8 and 8.7Hz), 7.91(1H, d, J=8.7Hz), 7.99(1H, s), 8.97(1H, d, J=1.8Hz).

IR(CHCl$_3$): 3513, 3438, 3144, 3096, 1708, 1656, 1518, 1374 cm$^{-1}$.

[α]$_D^{26}$+40.1±0.8° (c=1.010, MeOH)

Elemental Analysis (C$_{27}$H$_{30}$N$_2$O$_5$S$_2$•0.2H$_2$O) Calcd.(%): C, 61.16; H, 5.78; N, 5.28; S,12.09 Found(%): C, 61.16; H, 5.76; N, 5.43; S,12.05

Compound I-34

300MHz $^1$H-NMR(CDCl$_3$) δ: 1.18–1.35(3H, m), 1.40–1.48(2H, m), 1.57–1.79(4H, m), 1.99–2.21(5H, m), 2.37(2H, t, J=7.2Hz), 2.50(1H, m), 3.80(1H, m), 5.32–5.47 (2H, m), 6.38(2H, t, J=2.4Hz), 6.54(1H, d, J=7.5Hz), 7.12 and 7.13(each 1H, each d, each J=3.6Hz), 7.20(2H, t, J=2.4Hz).

IR(CHCl$_3$): 3512, 3433, 3144, 2686, 1708, 1669, 1591, 1528, 1475, 1457, 1394 cm$^{-1}$.

[α]$_D^{26}$+74.3±1.1° (c=1.007, MeOH)

Elemental Analysis (C$_{23}$H$_{28}$N$_2$O$_5$S) Calcd.(%): C, 59.98; H, 6.13; N, 6.08; S, 6.96 Found(%): C, 59.71; H, 6.22; N, 6.10; S, 7.02

Compound I-35 mp.102–103° C.

300MHz $^1$H-NMR(CDCl$_3$) δ: 1.05(1H, m), 1.18–1.30 (2H, m), 1.38–1.48(2H, m), 1.55–1.78(4H, m), 1.99–2.19 (5H, m), 2.35(2H, t, J=7.2Hz), 2.52(1H, m), 3.81(1H, m), 5.20(2H, d, J=0.9Hz), 5.30–5.42(2H, m), 5.99(1H, d, J=7.2Hz), 6.20 and 6.71 (each 2H, each t, each J=2.1Hz), 6.86(1H, td, J=0.9 and 3.9Hz), 7.37(1H, d, J=3.9Hz).

IR(Nujol): 3393, 3093, 6064, 2669, 1704, 1616, 1523, 1522 cm$^{-1}$.

[α]$_D^{26}$+71.1±1.1° (c=1.005, MeOH)

Elemental Analysis (C$_{24}$H$_{30}$N$_2$O$_3$S) Calcd.(%): C, 67.58; H, 7.09; N, 6.57; S, 7.52 Found(%): C, 67.45; H, 7.09; N, 6.58; S, 7.67

Compound I-36

300MHz $^1$H-NMR(CDCl$_3$) δ: 1.07(1H, m), 1.18–1.31 (2H, m), 1.40–1.48(2H, m), 1.56–1.78(4H, m), 2.00–2.20 (5H, m), 2.35(2H, t, J=7.2Hz), 2.53(1H, m), 3.82(1H, m), 5.31–5.43(2H, m), 6.02(1H, d, J=7.2Hz), 7.15 and 7.44 (each 1H, each d, each J=3.9Hz), 7.20–7.33(5H, m).

IR(CHCl$_3$): 3511, 3444, 3426, 3031, 2665, 1708, 1646, 1530, 1499, 1477, 1421, 1318 cm$^{-1}$.

[α]D$^{26}$+74.8±1.1° (c=1.004, MeOH)

Elemental Analysis (C$_{25}$H$_{29}$NO$_3$S$_2$) Calcd.(%): C, 65.90; H, 6.42; N, 3.07; S, 14.07 Found(%): C, 65.61; H, 6.40; N, 3.19; S, 14.18

Compound I-37

300MHz $^1$H-NMR(CDCl$_3$) δ: 1.09(1H, m), 1.17–1.31 (2H, m), 1.38–1.47(2H, m), 1.54–1.74(4H, m), 2.00–2.17 (5H, m), 2.34(2H, t, J=7.2Hz), 2.52(1H, m), 3.80(1H, m), 5.30–5.43(2H, m), 6.27(1H, d, J=7.2Hz), 7.41(1H, d, J=4.2Hz), 7.51–7.64(4H, m), 7.98(2H, m).

IR(CHCl$_3$): 3515, 3442, 3366, 1708, 1656, 1530, 1504, 1327, 1156 cm$^{-1}$.

[α]$_D^{26}$+73.1±1.1° (c=1.004, MeOH)

Elemental Analysis (C$_{25}$H$_{29}$NO$_5$S$_2$•0.2H$_2$O) Calcd.(%): C, 61.13; H, 6.03; N, 2.85; S, 13.05 Found(%): C, 60.94; H, 6.02; N, 2.86; S, 13.12

Compound I-38 mp. 163–165° C.

300MHz $^1$H-NMR(CDCl$_3$) δ: 1.24–1.43(3H, m), 1.52–1.87(8H, m), 2.10(1H, d, J=3.0Hz), 2.30–2.55(4H, m), 2.71(1H, m), 3.66(1H, m), 5.38 and 5.63(each 1H, each m), 7.13(1H, d, J=1.5Hz), 7.34(1H, d, J=5.4Hz), 7.49–7.60(3H, m), 7.86–7.89(2H, m), 8.49(1H, s), 8.69(1H, d, J=1.5Hz).

IR(KBr): 3367, 3261, 3090, 1726, 1645, 1618, 1589, 1577, 1535, 1513, 1426, 1396, 1289, 1197 cm$^{-1}$.

[α]$_D^{23}$+84.5∓1.2° (c=1.006, MeOH)

Elemental Analysis (C$_{26}$H$_{30}$N$_2$O$_4$S) Calcd.(%): C, 66.93; H, 6.48; N, 6.00; S, 6.87 Found(%): C, 66.97; H, 6.36; N, 6.01; S, 6.89

Compound I-39

300MHz $^1$H-NMR(CDCl$_3$) δ: 1.25–1.80(9H, m), 1.87–2.05(3H, m), 2.14–2.29(2H, m), 2.37(2H, t, J=6.9Hz), 2.57(1H, m), 3.73(1H, m), 5.35 and 5.49(each 1H, each m), 6.71(1H, d, J=6.6Hz), 6.87(1H, d, J=1.5Hz), 7.43–7.48(2H, m), 7.56(1H, m), 7.63(1H s), 7.64((1H, j, J=1.5Hz), 7.73–7.76(2H, m).

IR(CHCl$_3$): 3510, 3379, 3247, 3108, 1709, 1637, 1556, 1516, 1448, 1365, 1319, 1161 cm$^{-1}$.

[α]$_D^{23}$+61.1±1.0° (c=1.004, MeOH)

Elemental Analysis (C$_{25}$H$_{30}$N$_2$O$_5$S$_2$•0.2H$_2$O) Calcd.(%): C, 59.31; H, 6.05; N, 5.53; S, 12.67 Found(%): C, 59.38; H, 6.11; N, 5.75; S, 12.41

Compound I-40

300MHz $^1$H-NMR(CDCl$_3$) δ: 1.11(1H, m), 1.24–1.31 (2H, m), 1.44–1.52(2H, m), 1.60–1.79(4H, m), 2.00–2.21 (5H, m), 2.37(2H, t, J=7.2Hz), 2.56(1H, m), 3.86(1H, m), 5.32–5.46(2H, m), 6.11(1H, d, J=7.8Hz), 7.25 and 7.49(each 1H, each d, each J=4.2Hz), 7.30–7.43(3H, m), 7.60–7.63 (2H, m).

IR(CHCl$_3$): 3510, 3445, 3428, 1739, 1708, 1643, 1540, 1510, 1491, 1454 cm$^{-1}$.

[α]$_D^{35}$+88.0±1.3° (c=1.012, MeOH)

Elemental Analysis (C$_{25}$H$_{29}$NO$_3$S•0.2H$_2$O) Calcd.(%): C, 70.29; H, 6.94; N, 3.28; S, 7.51 Found(%): C, 70.35; H, 7.01; N, 3.59; S, 7.46

Compound I-41

300MHz $^1$H-NMR(CDCl$_3$) δ: 1.13(1H, m), 1.22–1.32 (2H, m), 1.46–1.51(2H, m), 1.60–1.76(4H, m), 2.04–2.17 (5H, m), 2.36(2H, t, J=7.2Hz), 2.57(1H, m), 3.86(1H, m), 5.32–5.46(2H, m), 6.30(1H, d, J=8.4Hz), 7.48–7.65(5H, m), 7.84–7.88(2H, m).

IR(CHCl$_3$): 3511, 3443, 3425, 1708, 1643, 1529, 1506, 1448 cm$^{-1}$.

[α]$_D^{25}$+92.4±1.3° (c=1.000, MeOH)

Elemental Analysis (C$_{26}$H$_{29}$NO$_4$S$_2$•0.2H$_2$O) Calcd.(%): C, 68.61; H, 6.51; N, 3.08; S, 7.04 Found(%): C, 68.55; H, 6.52; N, 3.13; S, 7.03

Compound I-42

300MHz $^1$H-NMR(CDCl$_3$) δ: 1.10(1H, m), 1.27–1.31 (2H, m), 1.49(2H, brs), 1.59–1.80(4H, m), 2.00–2.20(5H, m), 2.36(2H, t, J=7.2Hz), 2.55(1H, m), 3.85(1H, m), 5.31–5.45(2H, m), 6.14(1H, d, J=7.2Hz), 7.13(1H, d, J=3.9Hz), 7.30(1H, dd, J=1.2 and 5.1Hz), 7.36(1H, dd, J=3.0 and 5.1Hz), 7.45–7.46(2H, m).

IR(CHCl$_3$): 3511, 3445, 3428, 3109, 1708, 1642, 1523, 1499, 1456 cm$^{-1}$.

[α]$_D^{25}$+82.9±1.2° (c=1.006, MeOH)

Elemental Analysis (C$_{23}$H$_{27}$NO$_3$S$_2$•0.1H$_2$O) Calcd.(%): C, 64.04; H, 6.36; N, 3.25; S, 14.86 Found(%): C, 63.99; H, 6.52; N, 3.23; S, 14.85

Compound I-43

300MHz $^1$H-NMR(CDCl$_3$) δ: 1.10(1H, m), 1.22–1.31 (2H, m), 1.46–1.51(2H, m), 1.60–1.80(4H, m), 2.03–2.22 (5H, m), 2.37(2H, t, J=7.2Hz), 2.55(1H, m), 3.85(1H, m), 5.32–5.45(2H, m), 6.07(1H, d, J=7.5Hz), 7.04(1H, dd, J=3.6 and 5.4Hz), 7.11(1H, d, J=3.9Hz), 7.24(1H, dd, J=1.2 and 3.6Hz), 7.28(1H, dd, J=1.2 and 5.4Hz), 7.42(1H, d J=3.9Hz).

IR(CHCl$_3$): 3511, 3445, 3428, 3113, 3073, 2667, 1708, 1643, 1521, 1498, 1455 cm$^{-1}$.

$[α]_D^{25}$+89.5±1.3° (c=1.005, MeOH)

Elemental Analysis (C$_{23}$H$_{27}$NO$_3$S$_2$•0.1H$_2$O) Calcd.(%): C, 64.04; H, 6.36; N, 3.25; S, 14.86 Found(%): C, 63.93; H, 6.39; N, 3.46; S, 14.61

Compound I-44 mp.146–147° C.

300MHz $^1$H-NMR(CDCl$_3$) δ: 1.10(1H, m), 1.24–1.31 (2H, m), 1.46–1.51(2H, m), 1.61–1.82(4H, m), 2.00–2.24 (5H, m), 2.37(2H, t, J=7.2Hz), 2.37(3H, s), 2.56(1H, m), 3.85(1H, m), 5.31–5.45(2H, m), 6.06(1H, d, J=6.9Hz), 7.20 and 7.51(each 2H, each d, each J=9.0Hz), 7.21 and 7.48 (each 1H, each d, each J=3.9Hz).

IR(CHCl$_3$): 3517, 3445, 3428, 1740, 1708, 1642, 1542, 1518, 1498, 1451 cm$^{-1}$.

$[α]_D^{26}$+89.3±1.3° (c=1.009, MeOH)

Elemental Analysis (C$_{26}$H$_{31}$NO$_3$S) Calcd.(%): C, 71.36; H, 7.14; N, 3.20; S, 7.33 Found(%): C, 71.51; H, 7.10; N, 3.20; S, 7.33

Compound I-45 mp.110–116° C.

300MHz $^1$H-NMR(CDCl$_3$) δ: 1.10(1H, m), 1.24–1.31 (2H, m), 1.46–1.51(2H, m), 1.61–1.83(4H, m), 2.00–2.25 (5H, m), 2.37(2H, t, J=7.2Hz), 2.56(1H, m), 3.84(3H, s), 3.85(1H, m), 5.31–5.45(2H, m), 6.04(1H, d, J=7.5Hz), 6.93 and 7.55(each 2H, each d, each J=8.7Hz), 7.15 and 7.46 (each 2H, each d, each J=4.2Hz).

IR(CHCl$_3$): 3515, 3445, 3428, 1740, 1708, 1640, 1608, 1541, 1499, 1453, 1178 cm$^{-1}$.

$[α]_D^{26}$+88.0±1.3° (c=1.010, MeOH)

Elemental Analysis (C$_{26}$H$_{31}$NO$_4$S) Calcd.(%): C, 68.85; H, 6.89; N, 3.09; S, 7.07 Found(%): C, 68.87; H, 6.82; N, 3.11; S, 7.19

Compound I-46 mp.124–125° C.

300MHz $^1$H-NMR(CDCl$_3$) δ: 1.10(1H, m), 1.24–1.32 (2H, m), 1.46–1.51(2H, m), 1.61–1.82(4H, m), 2.00–2.24 (5H, m), 2.37(2H, t, J=7.2Hz), 2.56(1H, m), 3.85(1H, m), 5.32–5.45(2H, m), 6.06(1H, d, J=7.2Hz), 7.10(2H, t, J=8.7Hz), 6.19 and 7.47(each 1H, each d, each J=3.6Hz), 7.56–5.60(2H, m).

IR(CHCl$_3$): 3516, 3445, 3428, 2672, 1740, 1708, 1643, 1542, 1519, 1498, 1452 cm$^{-1}$.

$[α]_D^{26}$+83.3±1.2° (c=1.005, MeOH)

Elemental Analysis (C$_{25}$H$_{28}$FNO$_3$S) Calcd.(%): C, 68.00; H, 6.39; N, 3.17; F, 4.30; S, 7.26 Found(%): C, 67.90; H, 6.34; N, 3.25; F, 4.31; S, 7.20

Compound I-47

300MHz $^1$H-NMR(CDCl$_3$) δ: 1.10(1H, m), 1.18–1.32 (2H, m), 1.38–1.48(2H, m), 1.56–1.76(4H, m), 2.00–2.18 (5H, m), 2.35(2H, t, J=7.2Hz), 2.53(1H, m), 3.81(1H, m), 5.31–5.43(2H, m), 6.32(1H, d, J=7.5Hz), 7.11(1H, dd, J=3.9 and 5.1Hz), 7.42 and 7.62(each 1H, each d, each J=3.9Hz), 7.70(1H, dd, J=1.5 and 5.1Hz), 7.74(1H, dd, J=1.5 and 3.9Hz).

IR(CHCl$_3$): 3516, 3442, 3378, 1708, 1655, 1530, 1504, 1336, 1153 cm$^{-1}$.

$[α]_D^{25}$+74.3±1.1° (c=1.000, MeOH)

Elemental Analysis (C$_{23}$H$_{27}$NO$_5$S$_3$•0.1H$_2$O) Calcd.(%): C, 55.76; H, 5.53; N, 2.83; S, 19.41 Found(%): C, 55.49; H, 5.64; N, 3.09; S, 19.32

Compound I-48 mp.112–115° C.

300MHz $^1$H-NMR(CDCl$_3$) δ: 1.13–1.30(3H, m), 1.34–1.45(2H, m), 1.50–1.82(4H, m), 1.94–2.27(5H, m), 2.34(2H, t, J=7.2Hz), 2.56(1H, m), 3.74(1H, m), 5.22(2H, s), 5.31–5.50(2H, m), 6.64(1H, d, J=6.6Hz), 6.84(1H, d, J=3.9Hz), 6.93 and 7.05(each 1H, each s), 7.47(1H, d, J=3.9Hz), 7.66(1H, s).

IR(Nujol): 3339, 3102, 2464, 1691, 1635, 1622, 1551, 1288 cm$^{-1}$.

$[α]_D^{25}$+71.2±1.1° (c=1.005, MeOH)

Elemental Analysis (C$_{23}$H$_{29}$N$_3$O$_3$S) Calcd.(%): C, 64.61; H, 6.84; N, 9.83; S, 7.50 Found(%): C, 64.54; H, 6.85; N, 9.78; S, 7.42

Compound I-49

300MHz $^1$H-NMR(CDCl$_3$) δ: 1.08(1H, m), 1.16–1.30 (2H, m), 1.38–1.47(2H, m), 1.54–1.77(4H, m), 1.98–2.20 (5H, m), 2.34(2H, t, J=7.2Hz), 2.52(1H, m), 3.79(1H, m), 5.30–5.42(2H, m), 5.47(2H, s), 6.16(1H, d, J=6.9Hz), 6.30 (1H, t, J=2.1Hz), 6.94 and 7.41(each 1H, each d, each J=3.6Hz), 7.47 and 7.57(each 1H, each d, each J=2.1 Hz).

IR(CHCl$_3$): 3510, 3444, 3426, 1709, 1646, 1546, 1512 cm$^{-1}$.

$[α]_D^{25}$+68.6±1.1° (c=1.011, MeOH)

Elemental Analysis (C$_{23}$H$_{29}$N$_3$O$_3$S•0.1H$_2$O) Calcd.(%): C, 64.34; H, 6.85; N, 9.79; S, 7.47 Found(%): C, 64.10; H, 6.93; N, 9.90; S, 7.52

Compound I-50 mp.126–128° C.

300MHz $^1$H-NMR(CDCl$_3$) δ: 1.12(1H, m), 1.18–1.33 (2H, m), 1.40–1.50(2H, m), 1.55–1.78(4H, m), 2.00–2.21 (5H, m), 2.54(1H, m), 3.87(1H, m), 5.30–5.44(2H, m), 6.43(1H, d, J=6.6Hz), 7.48–7.62(3H, m), 7.83–7.95(5H, m).

IR(Nujol): 3284, 3058, 2669, 1701, 1641, 1546, 1326, 1294, 1160 cm$^{-1}$.

$[α]_D^{25}$+77.2±1.2° (c=1.007, MeOH)

Elemental Analysis (C$_{27}$H$_{31}$NO$_5$S) Calcd.(%): C, 67.34; H, 6.49; N, 2.91; S, 6.66 Found(%): C, 67.20; H, 6.38; N, 2.88; S, 6.58

Compound I-51 mp.103–107° C.

300MHz $^1$H-NMR(CDCl$_3$) δ: 1.14(1H, m), 1.18–1.33 (2H, m), 1.40–1.50(2H, m), 1.54–1.77(4H, m), 2.00–2.20

(5H, m), 2.34(2H, t, J=7.2Hz), 2.54(1H, m), 3.85(3H, s), 3.86(1H, m), 5.30–5.45(2H, m), 6.48(1H, d, J=6.9Hz), 6.96 (2H, m), 7.81–7.91(6H, m).

IR(Nujol): 3273, 3067, 2669, 1702, 1639, 1560, 1548, 1323, 1301, 1274, 1156 cm$^{-1}$.

$[\alpha]_D^{25}$+75.4±1.2° (c=1.002, MeOH)

Elemental Analysis ($C_{28}H_{33}NO_6S$) Calcd.(%): C, 65.73; H, 6.50; N, 2.74; S, 6.27 Found(%): C, 65.50; H, 6.46; N, 2.82; S, 6.25

Compound I-52

300MHz $^1$H-NMR(CDCl$_3$) δ: 1.17(1H, m), 1.26–1.34 (2H, m), 1.47–1.53(2H, m), 1.60–1.76(4H, m), 2.04–2.21 (5H, m), 2.36(2H, t, J=7.2Hz), 2.60(1H, m), 3.91(1H, m), 5.32–5.47(2H, m), 6.46(1H, d, J=8.4Hz), 7.17(1H, dd, J=3.9 and 5.1Hz), 7.61(1H, dd, J=1.2 and 3.9Hz), 7.76(1H, dd, J=1.2 and 5.1Hz), 7.87(4H, s-like).

IR(CHCl$_3$): 3518, 3444, 2663, 1708, 1638, 1517, 1494, 1414 cm$^{-1}$.

$[\alpha]_D^{25}$+86.6±1.3° (c=1.008, MeOH)

Elemental Analysis ($C_{26}H_{29}NO_4S$) Calcd.(%): C, 69.15; H, 6.47; N, 3.10; S, 7.10 Found(%): C, 68.86; H, 6.70; N, 3.15; S, 6.95

Compound I-53 mp.144–145° C.

300MHz $^1$H-NMR(CDCl$_3$) δ: 1.20–2.54(16H, m), 2.62 (1H, m), 3.69(3H, s), 5.35–5.56(2H, m), 6.36 and 7.17(each 2H, each t, each J=2.4Hz), 6.66(1H, d, J=6.3Hz), 8.05 and 8.07(each 1H, each d, each J=1.5Hz).

IR(Nujol): 3509, 3406, 3146, 3110, 1728, 1708, 1653, 1535, 1375, 1189, 1166 cm$^{-1}$.

$[\alpha]_D^{25}$+67.9±1.1° (c=1.007, MeOH)

Elemental Analysis ($C_{23}H_{28}N_2O_5S_2$) Calcd.(%): C, 57.96; H, 5.92; N, 5.88; S, 13.45 Found(%): C, 58.19; H, 5.95; N, 5.75; S, 13.09

Compound I-54

300MHz $^1$H-NMR(CDCl$_3$) δ: 1.22–2.57(16H, m), 2.68 (1H, m), 3.66(3H, s), 5.37–5.63(2H, m), 6.20, 6.35, 6.74 and 6.87(each 2H, each t, each J=2.4Hz), 6.92(1H, d, J=5.4Hz), 8.27(1H, s).

IR(CHCl$_3$): 3402, 3143, 3108, 1725, 1710, 1650, 1516, 1375 cm$^{-1}$.

$[\alpha]_D^{26}$+70.0±1.1° (c=1.006, MeOH)

Elemental Analysis ($C_{27}H_{31}N_3O_5S_2$•0.3H$_2$O) Calcd.(%): C, 59.28; H, 5.82; N, 7.68; S, 11.72 Found(%): C, 59.28; H, 5.77; N, 5.58; S, 11.68

Compound I-55

300MHz $^1$H-NMR(CDCl$_3$) δ: 1.10(1H, m), 1.18–1.31 (2H, m), 1.40–1.45(2H, m), 1.57–1.74(4H, m), 2.00–2.10 (5H, m), 2.35(2H, t, J=7.2Hz), 2.38(3H, s), 2.52(1H, m), 3.80(1H, m), 5.31–5.43(2H, m), 5.99(1H, m), 6.20(1H, t, J=3.3Hz), 6.30(1H, d, J=6.9Hz), 7.18(1H, dd, J=1.8 and 3.3Hz), 7.40 and 7.53(each 1H, each d, each J=3.9Hz).

IR(CHCl$_3$): 3513, 3442, 3149, 3100, 1708, 1657, 1530, 1504, 1375, 1183, 1161 cm$^{-1}$.

$[\alpha]_D^{27}$+70.3±1.5° (c=0.730, MeOH)

Elemental Analysis ($C_{24}H_{30}N_2O_5S_2$•0.4H$_2$O) Calcd.(%): C, 57.90; H, 6.24; N, 5.63; S, 12.88 Found(%): C, 58.08; H, 6.28; N, 5.77; S, 12.54

Compound I-56

300MHz $^1$H-NMR(d$_6$-DMSO) δ: 1.06–1.59(9H, m), 1.93–2.07(5H, m), 2.21(2H, t, J=7.2Hz), 2.35(1H, m), 3.65 (1H, m), 5.30–5.41(2H, m), 6.90 and 7.69(each 1H, each d, each J=4.2Hz), 7.55–7.64(3H, m), 7.99–8.04(3H, m), 11.73 (1H, s), 12.01(1H, brs).

IR(KBr): 3562, 1708, 1616, 1564, 1523, 1454, 1295 cm$^{-1}$.

$[\alpha]_D^{27}$+71.2±1.1° (c=1.000, MeOH)

Elemental Analysis ($C_{26}H_{30}N_2O_4S$•0.2H$_2$O) Calcd.(%): C, 66.42; H, 6.52; N, 5.96; S, 6.82 Found(%): C, 66.43; H, 6.32; N, 6.17; S, 6.75

Compound I-57

300MHz $^1$H-NMR(d$_6$-DMSO) δ: 1.05–1.56(9H, m), 1.91–2.05(5H, m), 2.19(2H, t, J=7.2Hz), 2.29(1H, m), 3.56 (1H, m), 5.28–5.38(2H, m), 6.54 and 7.56(each 1H, each d, each J=4.2Hz), 7.59–7.62(3H, m), 7.76–7.79(2H, m), 8.06 (1H, d, J=6.9Hz), 11.10(1H, s), 11.99(1H, brs).

IR(KBr): 3384, 3084, 1707, 1616, 1553, 1523, 1459, 1350, 1322, 1161 cm$^{-1}$.

$[\alpha]_D^{27}$+62.4±1.0° (c=1.005, MeOH)

Elemental Analysis ($C_{25}H_{30}N_2O_5S_2$•0.2H$_2$O) Calcd.(%): C, 59.31; H, 6.05; N, 5.53; S, 12.66 Found(%): C, 59.36; H, 5.75; N, 5.55; S, 12.38

Compound I-58

300MHz $^1$H-NMR(CDCl$_3$) δ: 1.07(1H, m), 1.17–1.33 (2H, m), 1.36–1.50(2H, m), 1.54–1.75(4H, m), 2.00–2.20 (5H, m), 2.35(2H, t, J=7.2Hz), 2.45(3H, s), 2.52(1H, m), 3.80(1H, m), 5.31–5.43(2H, m), 6.12(1H, d, J=7.5Hz), 6.32 and 7.18(each 2H, each t, each J=2.4Hz), 7.22(1H, s).

IR(CHCl$_3$): 3316, 3442, 3145, 2668, 1708, 1657, 1545, 1509, 1455, 1375, 1190, 1165, 1057 cm$^{-1}$.

$[\alpha]_D^{26}$+75.8±1.2° (c=1.002, MeOH)

Elemental Analysis ($C_{24}H_{30}N_2O_5S_2$•0.1H$_2$O) Calcd.(%): C, 58.54; H, 6.18; N, 5.69; S, 13.02 Found(%): C, 58.35; H, 6.29; N, 5.74; S, 12.92

Compound I-59

300MHz $^1$H-NMR(CDCl$_3$) δ: 1.05(1H, m), 1.16–1.30 (2H, m), 1.38–1.48(2H, m), 1.53–1.79(4H, m), 1.98–2.17 (5H, m), 2.34(2H, t, J=7.2Hz), 2.50(1H, m), 3.79(1H, m), 5.30–5.42(2H, m), 6.00(1H, d, J=7.5Hz), 7.01(1H, dd, J=3.6 and 5.4Hz), 7.03(1H, d, J=3.9Hz), 7.29(1H, dd, J=1.2 and 3.6Hz), 7.33(1H, d, J=3.9) 7.43(1H, dd, J=1.2 and 5.4Hz).

IR(CHCl$_3$): 3517, 3444, 3426, 2670, 1708, 1645, 1530, 1499, 1421, 1318 cm$^{-1}$.

$[\alpha]_D^{26}$+70.8±1.1° (c=1.018, MeOH)

Elemental Analysis ($C_{23}H_{27}NO_3S_3$) Calcd.(%): C, 59.84; H, 5.89; N, 3.03; S, 20.84 Found(%): C, 59.73; H, 5.99; N, 3.15; S, 20.70

Compound I-60

300MHz $^1$H-NMR(CDCl$_3$) δ: 1.07(1H, m), 1.17–1.32 (2H, m), 1.40–1.50(2H, m), 1.56–1.80(4H, m), 1.99–2.21 (5H, m), 2.34(2H, t, J=7.2Hz), 2.54(1H, m), 3.85(1H, m), 5.29–5.42(2H, m), 6.20(1H, d, J=6.9Hz), 7.23–7.45(7H, m), 7.55(2H, d, J=8.1Hz).

IR(CHCl$_3$): 3516, 3447, 2667, 1708, 1651, 1596, 1514, 1481 cm$^{-1}$.

$[\alpha]_D^{26}$+89.1±1.3° (c=1.006, MeOH)

Elemental Analysis (C$_{27}$H$_{31}$NO$_3$S•0.2H$_2$O) Calcd.(%): C, 71.56; H, 6.98; N, 3.09; S, 7.07 Found(%): C, 71.39; H, 6.97; N, 3.16; S, 6.94

Compound I-61

300MHz $^1$H-NMR(CDCl$_3$) δ: 1.06(1H, m), 1.18–1.31 (2H, m), 1.41–1.50(2H, m), 1.55–1.80(4H, m), 1.99–2.20 (5H, m), 2.35(2H, t, J=7.2Hz), 2.52(1H, m), 3.82(1H, m), 5.31–5.43(2H, m), 5.97(1H, d, J=6.6Hz), 6.45(1H, d, J=4.2Hz), 7.11–7.20(3H, m), 7.28(1H, d, J=4.2Hz), 7.33–7.40(2H, m).

IR(CHCl$_3$): 3515, 3445, 3427, 2667, 1740, 1708, 1640, 1506, 1475 cm$^{-1}$.

[α]D$^{27}$+71.3±1.1° (c=1.002, MeOH)

Elemental Analysis (C$_{25}$H$_{29}$NO$_4$S) Calcd.(%): C, 68.31; H, 6.65; N, 3.19; S, 7.29 Found(%): C, 68.41; H, 6.87; N, 3.22; S, 7.35

Compound I-62

300MHz $^1$H-NMR(CDCl$_3$) δ: 1.14(1H, m), 1.20–1.35 (2H, m), 1.42–1.54(2H, m), 1.57–1.77(4H, m), 2.00–2.23 (5H, m), 2.35(2H, t, J=7.2Hz), 2.58(1H, m), 3.88(1H, m), 5.32–5.46(2H, m), 6.31 and 7.19(each 2H, each t, each J=2.4Hz), 6.33(1H, d, J=7.5Hz), 7.77(1H, dd, J=1.8 and 8.4Hz), 7.77(1H, s), 7.87(1H, d, J=8.4Hz), 8.38(1H, d, J=1.8Hz).

IR(CHCl$_3$): 3514, 3442, 3422, 3144, 2670, 1708, 1654, 1525, 1375, 1193, 1171 cm$^{-1}$.

[α]$_D^{26}$+89.8±1.3° (c=1.000, MeOH)

Elemental Analysis (C$_{27}$H$_{30}$N$_2$O$_5$S$_2$) Calcd.(%): C, 61.58; H, 5.74; N, 5.32; S, 12.17 Found(%): C, 61.42; H, 5.86; N, 5.57; S, 11.98

Compound I-63 mp.180–181° C.

300MHz $^1$H-NMR(CDCl$_3$) δ: 1.04(1H, m), 1.22–1.30 (2H, m), 1.41–1.46(2H, m), 1.59–1.82(4H, m), 1.94–2.16 (3H, m), 2.25–2.37(2H, m), 2.42(2H, t, J=6.9Hz), 2.52(1H, m), 2.52(3H, s), 3.79(1H, m), 5.41–5.59(2H, m), 5.73(1H, d, J=6.6Hz), 7.48–7.53(2H, m), 7.60(1H, m), 8.07–8.10(2H, m).

IR(Nujol): 3372, 3173, 3053, 2544, 1690, 1672, 1632, 1559, 1496, 1362, 1317 cm$^{-1}$.

[α]D$^{28}$+77.7±1.2° (c=1.007, MeOH)

Elemental Analysis (C$_{26}$H$_{31}$N$_3$O$_4$S) Calcd.(%): C, 64.84; H, 6.49; N, 8.72; S, 6.66 Found(%): C, 64.66; H, 6.31; N, 8.73; S, 6.65

Compound I-64

300MHz $^1$H-NMR(d$_6$-DMSO) δ: 1.07(1H, m), 1.28–1.58 (8H, m), 1.91–2.08(5H, m), 2.20(2H, t, J=7.2Hz), 2.31(3H, s), 2.32(1H, s), 3.96(1H, m), 5.28–5.40(2H, m), 7.52–7.62 (3H, m), 7.80–7.83(2H, m), 7.94(1H, d, J=6.9Hz).

IR(Nujol): 3316, 3161, 3106, 2677, 1709, 1629, 1531, 1284, 1142 cm$^{-1}$.

[α]$_D^{27}$+76.2±1.2° (c=1.002, MeOH)

Elemental Analysis (C$_{25}$H$_{31}$N$_3$O$_5$S$_2$•0.1H$_2$O) Calcd.(%): C, 57.80; H, 6.05; N, 8.09; S, 12.34 Found(%): C, 57.59; H, 6.15; N, 8.10; S, 12.57

Compound I-65

300MHz $^1$H-NMR(CDCl$_3$) δ: 1.28–1.31(2H, m), 1.47 (2H, brs), 1.56–1.84(4H, m), 1.94–2.30(5H, m), 2.39(2H, t, J=6.9Hz), 2.62(1H, s), 2.63(3H, s), 3.77(1H, m), 5.35–5.67 (2H, m), 6.42(1H, d, J=6.3Hz), 7.29–7.43(3H, m), 7.46(1H, s), 7.72(2H, d, J=7.2Hz).

IR(CHCl$_3$): 3517, 3421, 3350, 3150, 2538, 1708, 1651, 1590, 1512, 1474, 1442, 1164 cm$^{-1}$.

[ ]D$^{28}$+100.8±1.4° (c=1.002, MeOH)

Elemental Analysis (C$_{27}$H$_{31}$N$_3$O$_3$S•0.5H$_2$O) Calcd.(%): C, 66.64; H, 6.63; N, 8.63; S, 6.59 Found(%): C, 66.55; H, 6.59; N, 8.68; S, 6.76

Compound I-66

300MHz $^1$H-NMR(CDCl$_3$) δ: 1.08(1H, m), 1.19–1.33 (2H, m), 1.42–1.50(2H, m), 1.58–1.79(4H, m), 2.01–2.22 (5H, m), 2.35(2H, t, J=7.2Hz), 2.55(1H, m), 3.86(1H, m), 4.37(2H, s), 5.30–5.43(2H, m), 6.19(1H, d, J=7.5Hz), 6.90 (1H, dd, J=3.6 and 5.1Hz), 6.93(1H, m), 7.17(1H, dd, J=1.2 and 5.1Hz), 7.33 and 7.65(each 2H, each d, J=8.4Hz).

IR(CHCl$_3$): 3518, 3447, 2665, 1708, 1651, 1596, 1515, 1484 cm$^{-1}$.

[α]$_D^{26}$+82.4±1.4° (c=0.900, MeOH)

Elemental Analysis (C$_{26}$H$_{31}$NO$_3$S$_2$•0.1H$_2$O) Calcd.(%): C, 66.24; H, 6.67; N, 2.97; S, 13.60 Found(%): C, 66.14; H, 6.72; N, 2.96; S, 13.53

Compound I-67

300MHz $^1$H-NMR(CDCl$_3$) δ: 1.16(1H, m), 1.21–1.34 (2H, m), 1.43–1.52(2H, m), 1.57–1.76(4H, m), 2.04–2.22 (5H, m), 2.35(2H, t, J=7.2Hz), 2.56(1H, m), 3.89(1H, m), 4.53(2H, s), 5.33–5.48(2H, m), 6.58(1H, d, J=6.9Hz), 6.83 (1H, dd, J=1.2 and 3.9Hz), 6.93(1H, dd, J=3.9 and 5.1Hz), 7.28(1H, dd, J=1.2 and 5.1Hz), 7.65 and 7.81(each 2H, each d, J=8.4Hz).

IR(CHCl$_3$): 3518, 3442, 3373, 2666, 1708, 1658, 1516, 1483, 1323, 1153 cm$^{-1}$.

[α]$_D^{26}$+69.6±1.1° (c=1.003, MeOH)

Elemental Analysis (C$_{26}$H$_{31}$NO$_5$S$_2$•0.5H$_2$O) Calcd.(%): C, 61.15; H, 6.32; N, 2.74; S, 12.56 Found(%): C, 66.16; H, 6.25; N, 2.90; S, 12.57

Compound I-68

300MHz $^1$H-NMR(CDCl$_3$) δ: 1.13(1H, m), 1.20–1.32 (2H, m), 1.38–1.50(2H, m), 1.54–1.77(4H, m), 1.98–2.20 (5H, m), 2.35(2H, t, J=7.2Hz), 2.53(1H, m), 3.80(1H, m), 5.31–5.46(2H, m), 6.47(1H, d, J=7.5Hz), 6.87(1H, dd, J=1.5 and 3.6Hz), 6.84(1H, dd, J=3.6 and 5.4Hz), 7.03(1H, dd, J=1.5 and 5.4Hz), 7.33 and 7.38(each 1H, each d, each J=3.9Hz), 7.90(1H, br).

IR(CHCl$_3$): 3510, 3440, 3358, 3109, 1708, 1647, 1533, 1505, 1364, 1331, 1161 cm$^{-1}$.

[α]$_{436}^{29}$+151.3±1.9° (c=1.010, MeOH) Elemental Analysis (C$_{23}$H$_{28}$N$_2$O$_5$S$_3$•0.1H$_2$O) Calcd.(%): C, 54.12; H, 5.57; N, 5.49; S, 18.84 Found(%): C, 53.84; H, 5.46; N, 5.38; S, 18.62

Compound I-69

300MHz $^1$H-NMR(CDCl$_3$) δ: 1.20(1H, m), 1.26–1.38 (2H, m), 1.42–1.52(2H, m), 1.57–1.76(4H, m), 2.00–2.24 (5H, m), 2.34(2H, t, J=7.2Hz), 2.53(1H, m), 3.88(1H, m), 5.31–5.49(2H, m), 6.63(1H, dd, J=1.2 and 3.9Hz), 6.69(1H, d, J=7.5Hz), 6.77(1H, dd, J=3.9 and 5.4Hz), 6.98(1H, dd, J=1.2 and 5.4Hz), 7.66 and 7.76(each 2H, each d, each J=8.4Hz).

IR(CHCl$_3$): 3509, 3439, 3363, 3111, 1707, 1651, 1520, 1328, 1167 cm$^{-1}$.

$[\alpha]_{436}^{29}$ +155.7±2.0° (c=1.003, MeOH)

Elemental Analysis (C$_{25}$H$_{30}$N$_2$O$_5$S$_3$•0.3H$_2$O) Calcd.(%): C, 59.10; H, 6.07; N, 5.51; S, 12.62 Found(%): C, 59.00; H, 5.95; N, 5.51; S, 12.46

Compound I-70 mp. 187–188° C.

300MHz $^1$H-NMR(d$_6$-DMSO) δ: 1.16–1.62(9H, m), 1.90–2.14(5H, m), 2.21(2H, t, J=7.2Hz), 2.38(1H, m), 3.66 (1H, m), 5.27–5.41(2H, m), 7.10–7.15(1H, m), 7.34–7.39 (2H, m), 7.42–7.75(2H, m), 7.91 and 7.99(each 1H, each d, each J=3.9Hz), 8.04(1H, d, J=6.6Hz), 10.32(1H, s), 12.02 (1H, s).

IR(Nujol): 3316, 3075, 2678, 1704, 1635, 1614, 1544, 1323 cm$^{-1}$.

$[\alpha]_D^{28}$ +83.3±1.2° (c=1.003, MeOH)

Elemental Analysis (C$_{26}$H$_{30}$N$_2$O$_4$S) Calcd.(%): C, 66.93; H, 6.48; N, 6.00; S, 6.87 Found(%): C, 67.04; H, 6.45; N, 5.98; S, 6.96

Compound I-71 mp.192–194° C.

300MHz $^1$H-NMR(d$_6$-DMSO) δ: 1.16–1.62(9H, m), 1.90–2.14(5H, m), 2.21(2H, t, J=7.2Hz), 2.37(1H, m), 3.65 (1H, m), 5.29–5.41(2H, m), 7.18–7.24(2H, m), 7.33–7.78 (2H, m), 7.91 and 7.97(each 1H, each d, each J=3.9Hz), 8.04(1H, d, J=6.9Hz), 10.38(1H, s), 12.01(1H, s).

IR(Nujol): 3322, 3278, 3150, 3098, 3077, 2678, 1704, 1635, 1615, 1546, 1521, 1508, 1322 cm$^{-1}$.

$[\alpha]_D^{28}$ +83.3±1.2° (c=1.000, MeOH)

Elemental Analysis (C$_{26}$H$_{29}$FN$_2$O$_4$S) Calcd.(%): C, 64.44; H, 6.03; N, 5.78; F, 3.92; S, 6.62 Found(%): C, 64.36; H, 6.00; N, 5.81; F, 3.94; S, 6.46

Compound I-72 mp.192–193° C.

300MHz $^1$H-NMR(d$_6$-DMSO) δ: 1.16–1.62(9H, m), 1.92–2.14(5H, m), 2.21(2H, t, J=7.2Hz), 2.37(1H, m), 3.66 (1H, m), 3.75(3H, s), 5.30–5.41(2H, m), 6.94 and 7.63(each 2H, each d-like), 7.89 and 7.94(each 1H, each d, each J=3.9Hz), 8.38(1H, d, J=6.9Hz), 10.21(1H, s), 12.01(1H, s).

IR(Nujol): 3316, 3075, 2678, 1704, 1635, 1614, 1544, 1323 cm$^{-1}$.

$[\alpha]_D^{27}$ +81.6±1.2° (c=1.000, MeOH)

Elemental Analysis (C$_{27}$H$_{32}$N$_2$O$_5$S) Calcd.(%): C, 65.30; H, 6.49; N, 5.64; S, 6.46 Found(%): C, 65.19; H, 6.49; N, 5.45; S, 6.31

Compound I-73

300MHz $^1$H-NMR(CDCl$_3$) δ: 1.14(1H, m), 1.18–1.32 (2H, m), 1.40–1.78(6H, m), 1.94–2.20(5H, m), 2.35(2H, t, J=7.2Hz), 2.51(1H, m), 3.80(1H, m), 3.81(6H, s), 3.82(3H, s), 5.30–5.44(2H, m), 6.56(1H, d, J=7.2Hz), 6.97(2H, s), 7.47 and 7.58(each 1H, each d, each J=3.9Hz), 8.43(1H, s).

IR(CHCl$_3$): 3515, 3438, 3317, 1708, 1650, 1607, 1537, 1508, 1454, 1412, 1131 cm$^{-1}$.

$[\alpha]_D^{27}$ +75.8±1.2° (c=1.009, MeOH)

Elemental Analysis (C$_{29}$H$_{36}$N$_2$O$_7$S•0.4H$_2$O) Calcd.(%): C, 61.77; H, 6.58; N, 4.97; S, 5.69 Found(%): C, 61.74; H, 6.64; N, 4.89; S, 5.89

Compound I-74

300MHz $^1$H-NMR(CDCl$_3$) δ: 1.10(1H, m), 1.20–1.33 (2H, m), 1.43–1.52(2H, m), 1.57–1.78(4H, m), 2.00–2.21 (5H, m), 2.36(2H, t, J=7.2Hz), 2.55(1H, m), 3.85(1H, m), 5.32–5.45(2H, m), 6.09(1H, d, J=6.9Hz), 6.32 and 7.00(each 2H, each t, each J=2.1Hz), 6.81 and 7.34(each 1H, each d, each J=3.9Hz).

IR(CHCl$_3$): 3515, 3445, 3109, 2678, 1740, 1708, 1642, 1507, 1489 cm$^{-1}$.

$[\alpha]_D^{26}$ +83.5±1.2° (c=1.007, MeOH)

Elemental Analysis (C$_{23}$H$_{28}$N$_2$O$_3$S) Calcd.(%): C, 66.96; H, 6.84; N, 6.79; S, 7.77 Found(%): C, 66.66; H, 6.74; N, 6.74; S, 7.61

Compound I-75

300MHz $^1$H-NMR(CDCl$_3$) δ: 1.09(1H, m), 1.20–1.32 (2H, m), 1.39–1.49(2H, m), 1.57–1.66(4H, m), 2.01–2.22 (5H, m), 2.35(2H, t, J=7.2Hz), 2.56(1H, m), 3.88(1H, m), 3.95(2H, s), 5.30–5.44(2H, m), 6.27(1H, d, J=7.5Hz), 6.89–6.91(2H, m), 7.32(1H, dd, J=2.4 and 3.9Hz), 7.19 and 7.66(each 2H, each d, J=8.4Hz).

IR(CHCl$_3$): 3516, 3447, 2670, 1708, 1651, 1523, 1496 m$^{-1}$.

$[\alpha]_D^{26}$ +71.8±1.1° (c=1.016, MeOH)

Elemental Analysis (C$_{26}$H$_{31}$NO$_3$S$_2$•0.1H$_2$O) Calcd.(%): C, 66.24; H, 6.67; N, 2.97; S, 13.60 Found(%): C, 66.36; H, 6.67; N, 3.27; S, 13.62

Compound I-76 mp. 135–136° C.

300MHz $^1$H-NMR(CDCl$_3$) δ: 1.12(1H, m), 1.22–1.33 (2H, m), 1.43–1.51(2H, m), 1.59–1.78(4H, m), 2.03–2.22 (5H, m), 2.35(2H, t, J=7.2Hz), 2.56(1H, m), 3.87(1H, m), 4.44(2H, s), 5.31–5.45(2H, m), 6.30(1H, d, J=7.2Hz), 7.08 (1H, dd, J=3.9 and 5.1Hz), 7.23(2H, d, J=8.4Hz), 7.40(1H, dd, J=1.5 and 3.9Hz), 7.69–7.71(3H, m).

IR(CHCl$_3$): 3516, 3445, 3096, 2665, 1708, 1655, 1523, 1496, 1403, 1327, 1152, 1127 m$^{-1}$.

$[\alpha]_D^{26}$ +65.0±1.1° (c=1.000, MeOH)

Elemental Analysis (C$_{26}$H$_{31}$NO$_5$S$_2$•0.2H$_2$O) Calcd.(%): C, 61.81; H, 6.26; N, 2.77; S, 12.69 Found(%): C, 61.76; H, 6.20; N, 2.90; S, 12.57

Compound I-77 mp.215–217° C.

300MHz $^1$H-NMR(d$_6$-DMSO) δ: 1.16–1.62(9H, m), 1.90–2.14(5H, m), 2.21(2H, t, J=7.2Hz), 2.38(1H, m), 3.66 (1H, m), 5.29–5.41(2H, m), 6.91–6.94(2H, m), 7.05(1H, dd, J=2.4 and 4.2Hz), 7.93 and 7.96(each 1H, each d, each J=4.2Hz), 8.4391H, d, J=6.6Hz), 10.67(1H, br), 12.01(1H, br).

IR(Nujol): 3315, 3222, 3097, 3049, 2672, 1705, 1621, 1548, 1504, 1311 cm$^{-1}$.

$[\alpha]_D^{27}$ +88.2±1.3° (c=1.009, MeOH)

Elemental Analysis (C$_{24}$H$_{28}$N$_2$O$_4$S$_2$) Calcd.(%): C, 60.99; H, 5.97; N, 5.93; S, 13.57 Found(%): C, 60.94; H, 5.74; N, 5.91; S, 13.61

Compound I-78

300MHz $^1$H-NMR(CDCl$_3$) δ: 1.09(1H, m), 1.18–1.31 (2H, m), 1.40–1.47(2H, m), 1.57–1.73(4H, m), 2.00–2.12 (5H, m), 2.31(2H, t, J=7.2Hz), 2.56(1H, m), 3.79(1H, m), 4.70(2H, s), 5.30–5.45(2H, m), 6.26–6.30(2H, m), 6.34(1H, d, J=6.9Hz), 7.22(1H, dd, J=1.8 and 3.3Hz), 7.41 and 7.62(each 1H, each d, each J=4.2Hz).

IR(CHCl$_3$): 3589, 3516, 3441, 3355, 3100, 1708, 1656, 1530, 1504, 1377, 1180, 1147 cm$^{-1}$.

$[α]_D^{26.5}$+70.8±1.1° (c=1.009, MeOH)

Elemental Analysis (C$_{24}$H$_{30}$N$_2$O$_6$S$_2$•0.2H$_2$O) Calcd.(%): C, 56.50; H, 6.01; N, 5.49; S, 12.57 Found(%): C, 56.43; H, 6.02; N, 5.61; S, 12.47

Compound I-79

300MHz $^1$H-NMR(CDCl$_3$) δ: 1.06(1H, m), 1.16–1.30 (2H, m), 1.38–1.50(2H, m), 1.54–1.77(4H, m), 1.98–2.18 (5H, m), 2.35(2H, t, J=7.2Hz), 2.51(1H, m), 3.80(1H, m), 5.30–5.42(2H, m), 6.03(1H, d, J=7.2Hz), 7.04–7.06(2H, m), 7.32–7.35(2H, m), 7.37(1H, d, J=3.6Hz).

IR(CHCl$_3$): 3509, 3444, 3426, 3110, 2667, 1708, 1645, 1530, 1499, 1421 cm$^{-1}$.

$[α]_D^{26.5}$+69.5±1.1° (c=1.001, MeOH)

Elemental Analysis (C$_{23}$H$_{27}$NO$_3$S$_3$•0.1H$_2$O) Calcd.(%): C, 59.61; H, 5.92; N, 3.02; S, 20.76 Found(%): C, 59.66; H, 5.90; N, 3.15; S, 20.52

Compound I-80

300MHz $^1$H-NMR(CDCl$_3$) δ: 1.10(1H, m), 1.17–1.32 (2H, m), 1.38–1.48(2H, m), 1.54–1.77(4H, m), 2.00–2.20 (5H, m), 2.35(2H, t, J=7.2Hz), 2.53(1H, m), 3.81(1H, m), 5.31–5.43(2H, m), 6.31(1H, d, J=7.2Hz), 7.37–7.44(3H, m), 7.61(1H, d, J=3.9Hz), 8.15(1H, dd, J=1.2 and 3.0Hz).

IR(CHCl$_3$): 3517, 3441, 3371, 3114, 1708, 1655, 1530, 1504, 1331, 1152 cm$^{-1}$.

$[α]_D^{26.5}$+73.9±1.1° (c=1.001, MeOH)

Elemental Analysis (C$_{23}$H$_{27}$NO$_5$S$_3$•0.3H$_2$O) Calcd.(%): C, 55.35; H, 5.57; N, 2.81; S, 19.28 Found(%): C, 55.47; H, 5.50; N, 2.80; S, 19.09

Compound I-81

300MHz $^1$H-NMR(CDCl$_3$) δ: 1.05(1H, m), 1.16–1.30 (2H, m), 1.38–1.48(2H, m), 1.54–1.77(4H, m), 1.98–2.17 (5H, m), 2.34(2H, t, J=7.2Hz), 2.46(3H, d, J=0.9Hz), 2.50 (1H, m), 3.79(1H, m), 5.29–5.41(2H, m), 5.99(1H, d, J=7.2Hz), 6.67(1H, m), 6.99, 7.10 and 7.32(each 1H, each d, each J=3.9Hz).

IR(CHCl$_3$): 3517, 3445, 3426, 2668, 1708, 1644, 1530, 1499, 1420, cm$^{-1}$.

$[α]_D^{26.5}$+66.1±1.1° (c=1.002, MeOH)

Elemental Analysis (C$_{24}$H$_{29}$NO$_3$S$_3$•0.1H$_2$O) Calcd.(%): C, 60.37; H, 6.16; N, 2.93; S, 20.15 Found(%): C, 60.21; H, 6.10; N, 2.90; S, 20.45

Compound I-82

300MHz $^1$H-NMR(CDCl$_3$) δ: 1.11(1H, m), 1.18–1.32 (2H, m), 1.38–1.50(2H, m), 1.54–1.74(4H, m), 2.00–2.20 (5H, m), 2.35(2H, t, J=7.2Hz), 2.53(4H, d and m, J=0.6Hz), 3.80(1H, m), 5.31–5.43(2H, m), 6.34(1H, d, J=6.6Hz), 6.77 (1H, m), 7.41, 7.55 and 7.58(each 1H, each d, each J=3.9Hz).

IR(CHCl$_3$): 3511, 3442, 3373, 3096, 1708, 1655, 1530, 1504, 1436, 1335, 1152 cm$^{-1}$.

$[α]_D^{26.5}$+73.0±1.1° (c=1.002, MeOH)

Elemental Analysis (C$_{24}$H$_{29}$NO$_5$S$_3$•0.3H$_2$O) Calcd.(%): C, 56.18; H, 5.81; N, 2.73; S, 18.75 Found(%): C, 56.26; H, 5.74; N, 2.65; S, 18.50

Compound I-83

300MHz $^1$H-NMR(CDCl$_3$) δ: 1.17(1H, m), 1.24–1.36 (2H, m), 1.37–1.82(6H, m), 2.01–2.23(5H, m), 2.36(2H, t, J=7.2Hz), 2.51(1H, m), 3.83(1H, m), 5.31–5.45(2H, m), 7.17(1H, dd, J=3.9 and 5.4Hz), 7.36(1H, d, J=7.8Hz), 7.47 (1H, dd, J=1.5 and 3.9Hz), 7.66(1H, dd, J=1.5 and 5.4Hz).

IR(CHCl$_3$): 3514, 3404, 3121, 1709, 1657, 1544, 1488, 1425 cm$^{-1}$.

$[α]_D^{25}$+73.2±2.2° (c=0.518, MeOH)

Elemental Analysis (C$_{22}$H$_{26}$N$_2$O$_3$S$_3$•0.2H$_2$O) Calcd.(%): C, 56.67; H, 5.71; N, 6.01; S, 20.63 Found(%): C, 56.55; H, 5.71; N, 6.03; S, 20.93

Compound I-84

300MHz $^1$H-NMR(CDCl$_3$) δ: 1.07(1H, m), 1.20–1.32 (2H, m), 1.43–1.48(2H, m), 1.57–1.82(4H, m), 2.02(1H, d, J=3.3Hz), 2.00–2.20(5H, m), 2.35(2H, t, J=7.2Hz), 2.55(1H, m), 3.86(1H, m), 4.01(2H, s), 5.29–5.43(2H, m), 6.17(1H, d, J=7.2Hz), 7.15–7.31(7H, m), 7.67(2H, d, J=8.1Hz).

IR(CHCl$_3$): 3517, 3447, 2669, 1708, 1651, 1523, 1495 cm$^{-1}$.

$[α]_D^{25}$+77.9±1.2° (c=1.016, MeOH)

Elemental Analysis (C$_{28}$H$_{33}$NO$_3$) Calcd.(%): C, 77.93; H, 7.71; N, 3.25 Found(%): C, 77.65; H, 7.93; N, 3.32

Compound I-85

300MHz $^1$H-NMR(CDCl$_3$) δ: 1.08(1H, m), 1.21–1.31 (2H, m), 1.44–1.49(2H, m), 1.58–1.82(4H, m), 2.00–2.20 (5H, m), 2.35(2H, t, J=7.2Hz), 2.56(1H, m), 3.87(1H, m), 4.19(2H, s), 5.30–5.43(2H, m), 6.19(1H, d, J=7.2Hz), 6.80 (1H, m), 6.93(1H, dd, J=2.6 and 5.1Hz), 7.16(1H, dd, J=1.5 and 5.1Hz), 7.30 and 8.69(each 2H, each d, each J=8.1Hz).

IR(CHCl$_3$): 3510, 3446, 2664, 1708, 1651, 1523, 1496 cm$^{-1}$.

$[α]_D^{25}$+73.2±1.1° (c=1.009, MeOH)

Elemental Analysis (C$_{26}$H$_{31}$NO$_3$S) Calcd.(%): C, 71.36; H, 7.14; N, 3.20; S, 7.33 Found(%): C, 71.48; H, 7.05; N, 3.29; S, 7.13

Compound I-86

300MHz $^1$H-NMR(CDCl$_3$) δ: 1.07(1H, m), 1.19–1.31 (2H, m), 1.43–1.48(2H, m), 1.58–1.81(4H, m), 2.00–2.17 (5H, m), 2.34(2H, t, J=7.2Hz), 2.55(1H, m), 3.87(1H, m), 3.98(2H, s), 5.30–5.43(2H, m), 6.19(1H, d, J=7.2Hz), 6.93–7.00(2H, m), 7.09–7.13(2H, m), 7.22 and 7.70(each 2H, each d, each J=8.4Hz).

IR(CHCl$_3$): 3516, 3447, 2664, 1709, 1651, 1612, 1522, 1509, 1496, cm$^{-1}$.

$[α]_D^{25}$+71.6±1.1° (c=1.019, MeOH)

Elemental Analysis (C$_{28}$H$_{32}$FNO$_3$) Calcd.(%): C, 74.81; H, 7.17; N, 3.12; F, 4.23 Found(%): C, 74.66; H, 7.19; N, 3.13; F, 4.10

Compound I-87

300MHz $^1$H-NMR(CDCl$_3$) δ: 1.08(1H, m), 1.20–1.31 (2H, m), 1.44–1.49(2H, m), 1.58–1.82(4H, m), 2.00–2.22 (5H, m), 2.35(2H, t, J=7.2Hz), 2.56(1H, m), 3.87(1H, m), 4.02(2H, s), 5.30–5.43(2H, m), 6.18(1H, d, J=7.2Hz), 6.88 (1H, dd, J=1.5 and 4.8Hz), 6.92(1H, m), 7.25–7.28(3H, m), 7.68(2H, d, J=8.1Hz).

IR(CHCl$_3$): 3516, 3446, 2668, 1709, 1651, 1612, 1523, 1496 cm$^{-1}$.

$[α]_D^{25}$+72.7±1.1° (c=1.014, MeOH)

Elemental Analysis (C$_{26}$H$_{31}$NO$_3$S•0.1H$_2$O) Calcd.(%): C, 71.07; H, 7.16; N, 3.18; S, 7.30 Found(%): C, 70.90; H, 7.08; N, 3.21; S, 7.46

Compound I-88 mp. 103–105° C.

300MHz $^1$H-NMR(CDCl$_3$) δ: 1.05(1H, m), 1.19–1.29 (2H, m), 1.42–1.47(2H, m), 1.58–1.81(4H, m), 2.00–2.15 (5H, m), 2.35(2H, t, J=7.2Hz), 2.52(1H, m), 3.82(1H, m), 4.16(2H, s), 5.30–5.43(2H, m), 5.97(1H, d, J=7.5Hz), 6.79 (1H, dt, J=0.9 and 3.9Hz), 6.96(1H, dd, J=1.5 and 4.8Hz), 7.05(1H, m), 7.28(1H, dd, J=3.0 and 4.8Hz), 7.37(1H, d, J=3.9Hz).

IR(CHCl$_3$): 3516, 3445, 3427, 2670, 1708, 1642, 1544, 1507 cm$^{-1}$.

$[α]_D^{25}$+67.3±1.1° (c=1.002, MeOH)

Elemental Analysis (C$_{24}$H$_{29}$NO$_3$S$_2$•0.3H$_2$O) Calcd.(%): C, 64.20; H, 6.64; N, 3.12; S, 14.28 Found(%): C, 64.29; H, 6.49; N, 3.10; S, 14.11

Compound I-89

300MHz $^1$H-NMR(CDCl$_3$) δ: 1.07(1H, m), 1.20–1.29 (2H, m), 1.40–1.49(2H, m), 1.56–1.89(4H, m), 2.00–2.25 (5H, m), 2.32–2.38(2H, m), 2.51(1H, m), 3.80(1H, m), 5.04(2H, s), 5.27–5.41(2H, m), 5.90(1H, d, J=6.6Hz), 6.38 (1H, m), 6.63(1H, t, J=2.4Hz), 7.14–7.17(2H, m), 7.29–7.35 (4H, m).

IR(CHCl$_3$): 3510, 3448, 2663, 1736, 1709, 1636, 1555, 1497 cm$^{-1}$.

$[α]_D^{25}$+60.8±1.0° (c=1.003, MeOH)

Elemental Analysis (C$_{26}$H$_{32}$N$_2$O$_3$•0.3H$_2$O) Calcd.(%): C, 73.62; H, 7.70; N, 6.60 Found(%): C, 73.68; H, 7.62; N, 6.73

Compound I-90

300MHz $^1$H-NMR(CDCl$_3$) δ: 1.06(1H, m), 1.20–1.29 (2H, m), 1.40–1.48(2H, m), 1.56–1.87(4H, m), 2.00–2.24 (5H, m), 2.32–2.38(2H, m), 2.50(1H, m), 3.80(1H, m), 5.19(2H, s), 5.27–5.41(2H, m), 5.90(1H, d, J=7.5Hz), 6.37 (1H, dd, J=2.1 and 3.0Hz), 6.67(1H, t, J=2.4Hz), 6.95–6.98 (2H, m), 7.27(1H, dd, J=1.8 and 4.5Hz), 7.31(1H, dd, J=1.8 and 2.1Hz).

IR(CHCl$_3$): 3513, 3448, 2661, 1709, 1637, 1555, 1497 cm$^{-1}$.

$[α]_D^{25}$+59.4±1.0° (c=1.011, MeOH)

Elemental Analysis (C$_{24}$H$_{30}$N$_2$O$_3$S•0.2H$_2$O) Calcd.(%): C, 67.01; H, 7.12; N, 6.51; S, 7.45 Found(%): C, 67.07; H, 7.03; N, 6.62; S, 7.55

Compound I-91

300MHz $^1$H-NMR(CDCl$_3$) δ: 1.06(1H, m), 1.23–1.26 (2H, m), 1.39–1.48(2H, m), 1.57–1.82(4H, m), 2.00–2.16 (5H, m), 2.34(2H, t, J=7.2Hz), 2.50(1H, m), 3.82(1H, m), 5.03(2H, s), 5.27–5.42(2H, m), 5.98(1H, brs), 6.40(1H, m), 6.91(1H, dd, J=1.2 and 4.8Hz), 7.08(1H, brs), 7.28–7.31 (2H, m).

IR(CHCl$_3$): 3516, 3448, 3108, 2663, 1736, 1709, 1636, 1555, 1497 cm$^{-1}$.

$[α]_D^{25}$+59.8±1.0° (c=1.008, MeOH)

Elemental Analysis (C$_{24}$H$_{30}$N$_2$O$_3$S•0.2H$_2$O) Calcd.(%): C, 67.01; H, 7.12; N, 6.51; S, 7.45 Found(%): C, 67.26; H, 7.06; N, 6.61; S, 7.55

Compound I-92

300MHz $^1$H-NMR(CDCl$_3$) δ: 1.08(1H, m), 1.18–1.28 (2H, m), 1.38–1.43(2H, m), 1.54–1.78(4H, m), 1.96–2.23 (5H, m), 2.36(2H, dt, J=1.8 and 6.9Hz), 2.52(1H, m), 3.77(1H, m), 5.30–5.45(2H, m), 6.07(1H, d, J=6.9Hz), 6.58 (1H, dd, J=1.5 and 3.3Hz), 7.14(1H, dd, J=2.1 and 3.3Hz), 7.51–7.57(2H, m), 7.65(1H, m), 7.77(1H, t, J=2.1Hz), 7.88–7.92(2H, m).

IR(CHCl$_3$): 3510, 3444, 3144, 1732, 1708, 1651, 1570, 1509, 1382, 1176 cm$^{-1}$.

$[α]_D^{24}$+55.9±0.9° (c=1.013, MeOH)

Elemental Analysis (C$_{25}$H$_{30}$N$_2$O$_5$S•0.3H$_2$O) Calcd.(%): C, 63.08; H, 6.48; N, 5.88; S, 6.74 Found(%): C, 63.24; H, 6.27; N, 6.03; S, 6.74

Compound I-93

300MHz $^1$H-NMR(CDCl$_3$) δ: 1.06(1H, m), 1.18–1.29 (2H, m), 1.39–1.47(2H, m), 1.56–1.78(4H, m), 1.98–2.18 (5H, m), 2.35(2H, t, J=7.2Hz), 2.52(1H, m), 3.81(1H, m), 4.33(2H, s), 5.29–5.42(2H, m), 6.03(1H, d, J=7.5Hz), 6.84 (1H, d, J=3.9Hz), 6.90(1H, m), 6.95(1H, dd, J=3.6 and 5.1Hz), 7.19(1H, dd, J=1.2 and 5.1Hz), 7.38(1H, d, J=3.9Hz).

IR(CHCl$_3$): 3510, 3554, 3427, 1708, 1643, 1544, 1507 m$^{-1}$.

$[α]_D^{27}$+70.1±1.10 (c=1.010, MeOH)

Elemental Analysis (C$_{24}$H$_{29}$NO$_3$S$_2$•0.1H$_2$O) Calcd.(%): C, 64.72; H, 6.61; N, 3.14; S, 14.40 Found(%): C, 64.83; H, 6.60; N, 3.31; S, 14.46

Compound I-94

300MHz $^1$H-NMR(CDCl$_3$) δ: 1.09(1H, m), 1.20–1.27 (2H, m), 1.40–1.44(2H, m), 1.56–1.78(4H, m), 2.00–2.19 (5H, m), 2.36(2H, d, 7.2Hz), 2.51(1H, m), 3.78(1H, m), 5.30–5.44(2H, m), 6.13(1H, d, J=6.9Hz), 6.59(1H, dd, J=1.5 and 3.3Hz), 7.10(1H, dd, J=3.6 and 5.1Hz), 7.16(1H, dd, J=2.1 and 3.3Hz), 7.69–7.76(3H, m).

IR(CHCl$_3$): 3510, 3444, 3143, 1708, 1651, 1571, 1508, 1387, 1179 cm$^{-1}$.

$[α]_D^{24}$+56.0±1.0° (c=1.005, MeOH)

Elemental Analysis (C$_{23}$H$_{28}$N$_2$O$_5$S$_2$•0.2H$_2$O) Calcd.(%): C, 57.53; H, 5.96; N, 5.83; S, 13.35 Found(%): C, 57.54; H, 6.07; N, 5.93; S, 12.91

Compound I-95

300MHz $^1$H-NMR(CDCl$_3$) δ: 1.16(1H, m), 1.26–1.37 (2H, m), 1.40–1.81(6H, m), 2.04–2.25(5H, m), 2.36(2H, t, J=7.2Hz), 2.53(1H, m), 3.87(1H, m), 5.32–5.46(2H, m), 6.37(2H, t, J=2.1Hz), 7.31(1H, d, J=7.5Hz), 7.33(2H, t, J=2.1Hz), 7.82(1H, m).

IR(CHCl$_3$): 3512, 3408, 3127, 1708, 1658, 1540, 1525, 1493, 1341 m$^{-1}$.

$[α]_D^{25}$+88.2±1.3° (c=1.003, MeOH)

Compound I-96

300MHz $^1$H-NMR(CDCl$_3$) δ: 1.07(1H, m), 1.18–1.30 (2H, m), 1.39–1.48(2H, m), 1.57–1.78(4H, m), 2.01–2.22 (5H, m), 2.35(2H, t, J=7.2Hz), 2.52(1H, m), 3.80(1H, m), 5.30–5.43(2H, m), 6.11(1H, m), 6.98(1H, dd, J=3.6 and 5.4Hz), 7.24(1H, dd, J=1.2 and 3.6Hz), 7.38(1H, dd, J=1.2 and 5.4Hz), 7.43(1H, d, J=1.5Hz), 7.85(1H, d, J=1.5Hz).

IR(CHCl$_3$): 3510, 3445, 3108, 1708, 1650, 1535, 1498 m$^{-1}$.

$[α]_D^{25}$+70.7±1.1° (c=1.004, MeOH)

Elemental Analysis (C$_{23}$H$_{27}$NO$_3$S$_3$•0.3H$_2$O) Calcd.(%): C, 59.15; H, 5.96; N, 3.00; S, 20.60 Found(%): C, 59.06; H, 5.66; N, 3.07; S, 20.87

Compound I-97

300MHz $^1$H-NMR(CDCl$_3$) δ: 1.20–2.52(16H, m), 2.61 (1H, m), 3.72(1H, m), 5.34–5.55(2H, m), 6.66(1H, d, J=6.3Hz), 71.2(1H, m), 7.71(1H, m), 7.75(1H, m), 8.29(1H, m), 8.37(1H, brs).

IR(CHCl$_3$): 3512, 3405, 3096, 1726, 1710, 1653, 1542, 1505, 1402, 1329, 1152 m$^{-1}$.

$[α]_D^{25}$+65.4±1.1° (c=1.005, MeOH)

Elemental Analysis (C$_{23}$H$_{27}$NO$_5$S$_3$•0.2H$_2$O) Calcd.(%): C, 55.55; H, 5.55; N, 2.82; S, 19.35 Found(%): C, 55.47; H, 5.54; N, 3.09; S, 19.21

Compound I-98 mp.103–104° C.

300MHz $^1$H-NMR(CDCl$_3$) δ: 1.09(1H, m), 1.23–1.31 (2H, m), 1.45–1.50(2H, m), 1.60–1.80(4H, m), 2.00–2.23 (5H, m), 2.37(2H, t, J=7.2Hz), 2.55(1H, m), 3.85(1H, m), 5.31–5.45(2H, m), 6.05(1H, d, J=7.5Hz), 6.98 and 7.04(each 1H, each d, each J=16.2Hz), 6.97(1H, d, J=3.9Hz), 7.25–7.33(3H, m), 7.41(1H, d, J=3.9Hz).

IR(CHCl$_3$): 3511, 3445, 3428, 2665, 1708, 1641, 1538, 1519, 1499 cm$^{-1}$.

$[α]_D^{24}$+77.8±1.2° (c=1.007, MeOH)

Elemental Analysis (C$_{25}$H$_{29}$NO$_3$S$_2$•0.25AcOEt) Calcd. (%): C, 65.38; H, 6.54; N, 2.93; S, 13.43 Found(%): C, 65.64; H, 6.62; N, 2.95; S, 13.26

Compound I-99

300MHz $^1$H-NMR(CDCl$_3$) δ: 1.05(1H, m), 1.20–1.30 (2H, m), 1.41–1.46(2H, m), 1.59–1.80(4H, m), 2.00–2.20 (5H, m), 2.35(2H, t, J=7.2Hz), 2.52(1H, m), 3.80(1H, m), 5.30–5.43(2H, m), 5.94(1H, d, J=6.9Hz), 6.57(2H, s), 6.94 (1H, d, J=3.9Hz), 7.03(1H, dd, J=1.5 and 4.5Hz), 7.29(1H, s), 7.30(1H, m), 7.34(1H, d, J=3.9Hz).

IR(CHCl$_3$): 3511, 3445, 3427, 2670, 1708, 1642, 1536, 1518, 1500 cm$^{-1}$.

$[α]_D^{24}$+62.8±1.0° (c=1.003, MeOH)

Elemental Analysis (C$_{25}$H$_{29}$NO$_3$S$_2$•0.2AcOEt) Calcd. (%): C, 65.48; H, 6.52; N, 2.96; S, 13.55 Found(%): C, 65.36; H, 6.47; N, 2.13; S, 13.58

Compound I-100

300MHz $^1$H-NMR(CDCl$_3$) δ: 1.06(1H, m), 1.17–1.32 (2H, m), 1.38–1.50(2H, m), 1.56–1.80(4H, m), 1.98–2.20 (5H, m), 2.35(2H, t, J=7.2Hz), 2.44(3H, d, J=0.9Hz), 2.52 (1H, m), 3.80(1H, m), 5.30–5.43(2H, m), 5.99(1H, d, J=7.5Hz), 5.99(1H, d, J=7.5Hz), 6.70(1H, m), 7.03(1H, d, J=3.9Hz), 7.10(1H, d, J=1.5Hz), 7.36(1H, d, J=3.9Hz).

IR(CHCl$_3$): 3510, 3445, 3426, 2671, 1708, 1644, 1530, 1499, 1420, 1318 cm$^{-1}$.

$[α]_D^{25}$+69.1±1.1° (c=1.018, MeOH)

Elemental Analysis (C$_{24}$H$_{29}$NO$_3$S$_3$) Calcd.(%): C, 60.60; H, 6.14; N, 2.94; S, 20.22 Found(%): C, 60.49; H, 6.26; N, 2.98; S, 20.25

Compound I-101

300MHz $^1$H-NMR(CDCl$_3$) δ: 1.10(1H, m), 1.18–1.32 (2H, m), 1.38–1.50(2H, m), 1.54–1.77(4H, m), 2.00–2.20 (5H, m), 2.36(2H, t, J=7.2Hz), 2.47(3H, d, J=0.9Hz), 2.53 (1H, m), 3.81(1H, m), 5.31–5.44(2H, m), 6.30(1H, d, J=7.2Hz), 7.03(1H, m), 7.42 and 7.59(each 1H, each d, each J=3.9Hz), 7.90(1H, d, J=1.5Hz).

IR(CHCl$_3$): 3517, 3441, 3370, 3115, 2671, 1708. 1655, 1530, 1504, 1442, 1328, 1156, 1142 cm$^{-1}$.

$[α]_D^{24}$+7.6±1.1° (c=1.018, MeOH)

Elemental Analysis (C$_{24}$H$_{29}$NO$_5$S$_3$•0.2H$_2$O) Calcd.(%): C, 56.38; H, 5.80; N, 2.74; S, 18.81 Found(%): C, 56.28; H, 5.74; N, 2.79; S, 18.92

Compound I-102

300MHz $^1$H-NMR(CDCl$_3$) δ: 1.09(1H, m), 1.21–1.28 (2H, m), 1.42–1.47(2H, m), 1.57–1.74(4H, m), 2.00–2.18 (5H, m), 2.35(2H, t, J=7.2Hz), 2.53(1H, m), 3.82(1H, m), 5.30–5.43(2H, m), 6.15(1H, d, J=7.5Hz), 6.51 and 6.68(each 1H, each d, J=11.7Hz), 6.98(1H, dd, J=3.6 and 5.1Hz), 7.06(1H, dd, J=0.9 and 3.9Hz), 7.13(1H, dt, J=0.9 and 3.6Hz), 7.25(1H, dd, J=0.9 and 5.1Hz), 7.41(1H, d, J=3.9Hz).

IR(CHCl$_3$): 3510, 3445, 3427, 2665, 1708, 1643, 1535, 1501 cm$^{-1}$.

$[α]_D^{24}$+68.6±1.1° (c=1.006, MeOH)

Elemental Analysis (C$_{25}$H$_{29}$NO$_3$S$_2$•0.2H$_2$O) Calcd.(%): C, 65.45; H, 6.45; N, 3.05; S, 13.98 Found(%): C, 65.44; H, 6.37; N, 3.28; S, 13.82

Compound I-103 mp.107–108° C.

300MHz $^1$H-NMR(CDCl$_3$) δ: 1.09(1H, m), 1.26–1.32 (2H, m), 1.45–1.50(2H, m), 1.60–1.81(4H, m), 2.01–2.23 (5H, m), 2.37(2H, t, J=7.2Hz), 2.55(1H, m), 3.84(1H, m), 5.31–5.45(2H, m), 6.03(1H, d, J=7.5Hz), 6.97 and 7.14(each 1H, each d, J=15.9Hz), 6.97(1H, d, J=3.9Hz), 7.01(1H, dd, J=3.6 and 5.4Hz), 7.08(1H, d, J=3.6Hz), 7.23(1H, d, J=5.4Hz), 7.40(1H, d, J=3.9Hz).

IR(CHCl$_3$): 3517, 3445, 3428, 2670, 1708, 1641, 1536, 1518, 1500 cm$^{-1}$.

$[α]_D^{24}$+85.0±1.2° (c=1.009, MeOH)

Elemental Analysis (C$_{25}$H$_{29}$NO$_3$S$_2$•0.15AcOEt) Calcd. (%): C, 65.58; H, 6.49; N, 2.99; S, 13.68 Found(%): C, 65.88; H, 6.74; N, 2.98; S, 13.35

Compound I-104

300MHz $^1$H-NMR(CDCl$_3$) δ: 1.07(1H, m), 1.19–1.30 (2H, m), 1.42–1.50(2H, m), 1.57–1.79(4H, m), 2.01–2.24 (5H, m), 2.36(2H, t, J=7.2Hz), 2.53(1H, m), 3.82(1H, m), 4.10(sH, s), 5.31–5.44(2H, m), 6.03(1H, d, J=7.2Hz), 6.70

(1H, d, J=3.6Hz), 6.95(1H, dd, J=3.6 and 5.4Hz), 7.03(1H, dd, J=1.5 and 3.6Hz), 7.30(1H, d, J=3.6Hz), 7.36(1H, dd, J=1.5 and 5.4Hz).

IR(CHCl$_3$): 3518, 3445, 3427, 1708, 1644, 1542, 1507 cm$^{-1}$.

$[\alpha]_D^{24.5}$ +65.0±1.0° (c=1.008, MeOH)

Elemental Analysis ($C_{24}H_{29}NO_3S_3 \cdot 0.4H_2O$) Calcd.(%): C, 59.69; H, 6.22; N, 2.90; S, 19.92 Found(%): C, 59.40; H, 5.98; N, 2.95; S, 20.06

Compound I-105

300MHz $^1$H-NMR(CDCl$_3$) δ: 1.11(1H, m), 1.21–1.31 (2H, m), 1.42–1.49(2H, m), 1.58–1.76(4H, m), 2.01–2.21 (5H, m), 2.36(2H, t, J=7.2Hz), 2.53(1H, m), 3.81(1H, m), 4.60(sH, s), 5.32–5.45(2H, m), 6.18(1H, d, J=7.2Hz), 6.91 (1H, d, J=3.9Hz), 7.12(1H, dd, J=3.9 and 5.1Hz), 7.40(1H, d, J=3.9Hz), 7.52(1H, dd, J=1.2 and 3.9Hz), 7.72(1H, dd, J=1.2 and 5.1Hz).

IR(CHCl$_3$): 3517, 3444, 3425, 3097, 1708, 1648, 1524, 1508, 1402, 1328, 1147 cm$^{-1}$.

$[\alpha]_D^{24.5}$ +61.5±1.0° (c=1.008, MeOH)

Elemental Analysis ($C_{24}H_{29}NO_3S_3 \cdot 0.4H_2O$) Calcd.(%): C, 55.98; H, 5.83; N, 2.72; S, 18.68 Found(%): C, 55.77; H, 5.71; N, 2.84; S, 18.73

Compound I-106

300MHz $^1$H-NMR(CDCl$_3$) δ: 1.07(1H, m), 1.19–1.31 (2H, m), 1.41–1.49(2H, m), 1.57–1.78(4H, m), 2.00–2.21 (5H, m), 2.36(2H, t, J=7.2Hz), 2.53(1H, m), 3.81(1H, m), 4.23(sH, s), 5.31–5.44(2H, m), 6.00(1H, d, J=7.2Hz), 6.82 (1H, m), 6.88(1H, dd, J=3.6 and 5.1Hz), 6.92(1H, d, J=3.6Hz), 7.21(1H, dd, J=1.2 and 5.1Hz), 7.33(1H, d, J=3.6Hz).

IR(CHCl$_3$): 3514, 3444, 3427, 2665, 1709, 1645, 1529, 1498, 1421, 1317 cm$^{-1}$.

$[\alpha]_D^{24}$ +67.1±1.1° (c=1.006, MeOH)

Elemental Analysis ($C_{24}H_{29}NO_3S_3 \cdot 0.1H_2O$) Calcd.(%): C, 60.37; H, 6.16; N, 2.90; S, 20.15 Found(%): C, 60.46; H, 6.14; N, 2.96; S, 20.02

Compound I-107

300MHz $^1$H-NMR(CDCl$_3$) δ: 1.09–1.32(3H, m), 1.38–1.48(2H, m), 1.53–1.79(4H, m), 1.96–2.20(5H, m), 2.34(2H, t, J=7.2Hz), 2.54(4H, d and m, J=0.6Hz), 3.79(1H, m), 5.30–5.45(2H, m), 6.48 and 6.51(total 1H, each d, J=7.8 and 7.5Hz), 7.12(1H, dd, J=3.9 and 5.1Hz), 7.42 and 7.43 (total 1H, each d, each J=3.9Hz), 7.52 and 7.53(total 1H, each d, each J=3.9Hz), 7.58(1H, m), 7.69(1H, dd, J=1.2 and 5.1Hz).

IR(CHCl3): 3509, 3443, 3425, 3092, 2666, 1708, 1650, 1532, 1503, 1403, 1322 cm$^{-1}$.

$[\alpha]_D^{23}$ +70.4±1.1° (c=1.007, MeOH)

Elemental Analysis ($C_{23}H_{27}NO_4S_3 \cdot 0.4H_2O$) Calcd.(%): C, 56.97; H, 5.78; N, 2.89; S, 19.84 Found(%): C, 57.03; H, 5.67; N, 3.19; S, 19.73

Compound I-108

300MHz $^1$H-NMR(CDCl$_3$) δ: 1.09–1.32(3H, m), 1.39–1.50(2H, m), 1.54–1.77(4H, m), 1.97–2.20(5H ,m), 2.35(2H, t, J=7.2Hz), 2.52 and 2.53(total 3H, each s), 2.54(1H, m), 3.79(1H, m), 5.31–5.45(2H, m), 6.43 and 6.47(total 1H, each d, J=7.5 and 6.6Hz), 6.76(1H, m), 7.39(1H, t-like), 7.40(1H, dd, J=2.1 and 3.6Hz), 7.52(1H, dd, J=2.1 and 4.2Hz).

IR(CHCl$_3$): 3510, 3443, 3425, 3092, 1708, 1650, 1531, 1503, 1437, 1237 cm$^{-1}$.

$[\alpha]_D^{23}$ +68.6±1.1° (c=1.011, MeOH)

Elemental Analysis ($C_{24}H_{29}NO_4S_3 \cdot 0.2H_2O$) Calcd.(%): C, 58.20; H, 5.98; N, 2.83; S, 19.42 Found(%): C, 58.18; H, 5.67; N, 2.90; S, 19.11

Compound I-109

300MHz $^1$H-NMR(CDCl$_3$) δ: 1.13(1H, m), 1.21–1.34 (2H, m), 1.45–1.52(2H, m), 1.59–1.78(4H, m), 2.03–2.23 (5H, m), 2.37(2H, t, J=7.2Hz), 2.58(1H, m), 3.86(1H, m), 5.32–5.46(2H, m), 6.28(1H, d, J=6.6Hz), 7.20(1H, dd, J=3.9 and 5.1Hz), 7.59(1H, d, J=3.9Hz), 7.75(1H, dd, J=1.2 and 5.1Hz), 7.81(1H, d, J=3.9Hz), 7.92(1H, dd, J=1.2 and 3.9Hz).

IR(CHCl$_3$): 3518, 3442, 3425, 3109, 1709, 1651, 1622, 1529, 1508, 1442, 1414, 1356, 1286, 1267 cm$^{-1}$.

$[\alpha]_D^{23}$ +89.2±1.3° (c=1.002, MeOH)

Elemental Analysis ($C_{24}H_{27}NO_4S_2 \cdot 0.2H_2O$) Calcd.(%): C, 62.50; H, 5.99; N, 3.04; S, 13.90 Found(%): C, 62.63; H, 6.07; N, 2.97; S, 13.60

Compound I-110

300MHz $^1$H-NMR(CDCl$_3$) δ: 1.12(1H, m), 1.22–1.33 (2H, m), 1.44–1.52(2H, m), 1.59–1.79(4H, m), 2.03–2.24 (5H, m), 2.37(2H, t, J=7.2Hz), 2.57(1H, m), 3.87(1H, m), 4.14(3H, s), 5.32–5.47(2H, m), 6.14(1H, d, J=7.5Hz), 7.08 (1H, dd, J=3.9 and 5.4Hz), 7.27(1H, dd, J=1.2 and 3.9Hz), 7.39(1H, dd, J=1.2 and 5.4Hz), 7.41(1H, d, J=3.9Hz), 7.49 (1H, d, J=3.9Hz).

IR(CHCl$_3$): 3516, 3444, 3425, 2665, 1709, 1649, 1529, 1498, 1049 cm$^{-1}$.

$[\alpha]_D^{24}$ +73.3±1.1° (c=1.003, MeOH)

Elemental Analysis ($C_{26}H_{30}N_2O_4S_2 \cdot 0.6H_2O$) Calcd.(%): C, 60.36; H, 6.32; N, 5.63; S, 12.89 Found(%): C, 60.30; H, 6.14; N, 5.84; S, 12.95

Compound I-111

300MHz $^1$H-NMR(CDCl$_3$) δ: 1.08(1H, m), 1.19–1.30 (2H, m), 1.40–1.50(2H, m), 1.55–1.82(4H, m), 1.98–2.21 (5H ,m), 2.36(2H, t, J=7.2Hz), 2.53(1H, m), 3.83(1H, m), 5.30–5.44(2H, m), 5.96(1H, d, J=7.5Hz), 6.43(1H, br), 6.52 (1H, d, J=3.9Hz), 6.90(1H, m), 7.08–7.11(2H, m), 7.26–7.32 (3H, m).

IR(CHCl$_3$): 3514, 3444, 3419, 1739, 1709, 1633, 1601, 1500, 1456 cm$^{-1}$.

$[\alpha]_D^{22}$ +86.6±1.3° (c=1.005, MeOH)

Elemental Analysis ($C_{25}H_{30}N_2O_3S \cdot 0.1H_2O$) Calcd.(%): C, 68.18; H, 6.91; N, 6.36; S, 7.28 Found(%): C, 68.11; H, 6.95; N, 6.43; S, 7.31

Compound I-112

300MHz $^1$H-NMR(CDCl$_3$) δ: 1.05(1H, m), 1.18–1.30 (2H, m), 1.39–1.48(2H, m), 1.54–1.83(4H, m), 1.98–2.21 (5H ,m), 2.35(2H, t, J=7.2Hz), 2.51(1H, m), 3.38(3H, s), 3.80(1H, m), 5.29–5.42(2H, m), 5.82(1H, d, J=6.0Hz), 6.15 (1H, d, J=4.2Hz), 7.11–7.39(6H, m).

IR(CHCl$_3$): 3514, 3446, 3425, 1741, 1709, 1628, 1597, 1477, 1415 cm$^{-1}$.

$[\alpha]_D^{22}$ +83.2±1.2° (c=1.001, MeOH)

Compound I-113

300MHz ¹H-NMR(CDCl₃) δ: 1.07(1H, m), 1.18–1.31 (2H, m), 1.40–1.49(2H, m), 1.55–1.75(4H, m), 1.99–2.16 (5H, m), 2.31(3H, s), 2.35(2H, t, J=7.2Hz), 2.52(1H, m), 3.82(1H, m), 5.31–5.43(2H, m), 6.06(1H, d, J=7.5Hz), 7.03–7.20(5H, m), 7.44(1H, d, J=3.9Hz).

IR(CHCl₃): 3516, 3444, 3425, 2671, 1709, 1647, 1529, 1498, 1421, 1317 cm⁻¹.

$[\alpha]_D^{23}$+70.2±1.1° (c=1.001, MeOH)

Elemental Analysis (C₂₆H₃₁NO₃S₂) Calcd.(%): C, 66.49; H, 6.65; N, 2.98; S, 13.65 Found(%): C, 66.34; H, 6.74; N, 2.94; S, 13.78

Compound I-114 mp.114–116° C.

300MHz ¹H-NMR(CDCl₃) δ: 1.09(1H, m), 1.18–1.32 (2H, m), 1.37–1.47(2H, m), 1.55–1.75(4H, m), 2.00–2.18 (5H, m), 2.35(2H, t, J=7.2Hz), 2.42(3H, s), 2.52(1H, m), 3.80(1H, m), 5.30–5.43(2H, m), 6.23(1H, d, J=7.5Hz), 7.41 (3H, m), 7.59(1H, d, J=3.9Hz), 7.78(2H, m).

IR(CHCl₃): 3514, 3442, 3371, 2669, 1707, 1655, 1529, 1504, 1329, 1151 cm⁻¹.

$[\alpha]_D^{23}$+72.4±1.1° (c=1.004, MeOH)

Elemental Analysis (C₂₆H₃₁NO₅S₂) Calcd.(%): C, 62.25; H, 6.23; N, 2.79; S, 12.78 Found(%): C, 61.83; H, 6.39; N, 2.73; S, 12.78

Compound I-115

300MHz ¹H-NMR(CDCl₃) δ: 1.07(1H, m), 1.18–1.31 (2H, m), 1.40–1.50(2H, m), 1.56–1.78(4H, m), 1.99–2.20 (5H, m), 2.35(2H, t, J=7.2Hz), 2.53(1H, m), 3.77(3H, s), 3.82(1H, m), 5.31–5.43(2H, m), 6.06(1H, d, J=7.2Hz), 6.74–6.89(3H, m), 7.16–7.23(2H, m), 7.45(1H, d, J=3.9Hz).

IR(CHCl₃): 3516, 3444, 3425, 2665, 1709, 1647, 1591, 1529, 1498, 1477, 1423 cm⁻¹.

$[\alpha]_D^{23}$+68.7±1.1° (c=1.014, MeOH)

Elemental Analysis (C₂₆H₃₁NO₄S₂) Calcd.(%): C, 64.30; H, 6.43; N, 2.88; S, 13.20 Found(%): C, 64.04; H, 6.56; N, 2.87; S, 13.43

Compound I-116 mp.67–70° C.

300MHz ¹H-NMR(CDCl₃) δ: 1.09(1H, m), 1.17–1.32 (2H, m), 1.39–1.47(2H, m), 1.55–1.75(4H, m), 2.00–2.20 (5H, m), 2.35(2H, t, J=7.2Hz), 2.52(1H, m), 3.80(1H, m), 3.86(3H, s), 5.30–5.43(2H, m), 6.26(1H, d, J=7.2Hz), 7.12 (1H, m), 7.40–7.47(2H, m), 7.55(1H, m), 7.59(1H, d, J=3.9Hz).

IR(CHCl₃): 3514, 3442, 3373, 1707, 1655, 1599, 1529, 1504, 1481, 1327, 1151 cm⁻¹.

$[\alpha]_D^{23}$+70.0±1.1° (c=1.008, MeOH)

Elemental Analysis (C₂₆H₃₁NO₆S₂·0.7H₂O) Calcd.(%): C, 58.89; H, 6.16; N, 2.64; S, 12.09 Found(%): C, 58.87; H, 6.15; N, 2.74; S, 12.10

Compound I-117

300MHz ¹H-NMR(CDCl₃) δ: 1.10–1.32(3H, m), 1.37–1.46(2H, m), 1.55–1.73(4H, m), 1.94–2.18(5H, m), 2.34(2H, t, J=7.2Hz), 2.55(1H, m), 3.78(1H, m), 5.29–5.45 (2H, m), 6.56(1H, d, J=6.6Hz), 7.09(1H, m), 7.37(1H, t, J=8.1Hz), 7.45(1H, d, J=3.9Hz), 7.47–7.53(2H, m), 7.55 (1H, d, J=3.9Hz).

IR(KBr): 3365, 3095, 1707, 1628, 1543, 1448, 1306, 1147 cm⁻¹.

$[\alpha]_D^{23}$+70.8±1.1° (c=1.003, MeOH)

Elemental Analysis (C₂₅H₂₉NO₆S₂·0.3H₂O) Calcd.(%): C, 58.99; H, 5.86; N, 2.75; S, 12.60 Found(%): C, 58.85; H, 5.85; N, 2.67; S, 12.77

Compound I-118 mp. 133–134° C.

300MHz ¹H-NMR(CDCl₃) δ: 1.08(1H, m), 1.18–1.32 (2H, m), 1.40–1.49(2H, m), 1.55–1.78(4H, m), 1.96–2.24 (5H, m), 2.34(2H, t, J=7.2Hz), 2.52(1H, m), 3.81(1H, m), 5.31–5.46(2H, m), 6.14(1H, d, J=6.6Hz), 6.71(2H, m), 6.86 (1H, m), 7.14(2H, m), 7.42(1H, d, J=3.9Hz).

IR(Nujol): 3336, 3091, 2656, 1703, 1603, 1581, 1545 cm⁻¹.

$[\alpha]_D^{23}$+73.2±1.1° (c=1.007, MeOH)

Elemental Analysis (C₂₅H₂₉NO₄S₂) Calcd.(%): C, 63.67; H, 6.20; N, 2.97; S, 13.60 Found(%): C, 63.78; H, 6.17; N, 3.10; S, 13.73

Compound I-119

300MHz ¹H-NMR(CDCl₃) δ: 1.05(1H, m), 1.17–1.30 (2H, m), 1.38–1.48(2H, m), 1.54–1.80(4H, m), 1.98–2.20 (5H, m), 2.34(2H, t, J=7.2Hz), 2.51(1H, m), 3.79(3H, s), 3.81(1H, m), 4.10(2H, s), 5.29–5.42(2H, m), 5.97(1H, d, J=7.5Hz), 6.77–6.84(4H, m), 7.23(2H, m), 7.37(1H, d, J=3.9Hz).

IR(CHCl₃): 3514, 3446, 3427, 1741, 1709, 1641, 1543, 1506, 1456 cm⁻¹.

$[\alpha]_D^{22}$+64.3±1.0° (c=1.005, MeOH)

Elemental Analysis (C₂₇H₃₃NO₄S·0.1H₂O) Calcd.(%): C, 69.08; H, 7.13; N, 2.98; S, 6.83 Found(%): C, 69.03; H, 7.25; N, 3.06; S, 7.00

Compound I-120

300MHz ¹H-NMR(CDCl₃) δ: 1.07(1H, m), 1.16–1.28 (2H, m), 1.36–1.46(2H, m), 1.52–1.78(4H, m), 1.96–2.17 (5H, m), 2.32(2H, t, J=7.2Hz), 2.50(1H, m), 3.80(1H, m), 4.02(2H, s), 5.28–5.42(2H, m), 6.16(1H, d, J=7.5Hz), 6.72–6.77(4H, m), 7.14(1H, m), 7.36(1H, d, J=3.9Hz).

IR(CHCl₃): 3595, 3423, 3207, 1707, 1635, 1599, 1545, 1508, 1456 cm⁻¹.

$[\alpha]_D^{23}$+66.8±1.1° (c=1.009, MeOH)

Elemental Analysis (C₂₆H₃₁NO₄S·0.4H₂O) Calcd.(%): C, 67.77; H, 6.96; N, 3.04; S, 6.96 Found(%): C, 67.83; H, 6.92; N, 3.18; S, 7.14

Compound I-121

300MHz ¹H-NMR(CDCl₃) δ: 1.06(1H, m), 1.18–1.31 (2H, m), 1.40–1.48(2H, m), 1.55–1.82(4H, m), 1.98–2.22 (5H, m), 2.29(3H, s), 2.35(2H, t, J=7.2Hz), 2.52(1H, m), 3.80(1H, m), 4.14(2H, s), 5.29–5.43(2H, m), 5.97(1H, d, J=7.5Hz), 6.78(1H,m), 6.94–7.00(2H, m), 7.10(1H, m), 7.33 (1H, m), 7.36(1H, d, J=3.9Hz).

IR(CHCl₃): 3514, 3446, 3427, 2669, 1763, 1745, 1709, 1643, 1545, 1506, 1371 cm⁻¹.

$[\alpha]_D^{23}$+61.3±1.0° (c=1.019, MeOH)

Compound I-122

300MHz $^1$H-NMR(CDCl$_3$) δ: 1.06(1H, m), 1.18–1.30 (2H, m), 1.40–1.48(2H, m), 1.56–1.76(4H, m), 1.99–2.17 (5H, m), 2.35(2H, t, J=7.2Hz), 2.52(1H, m), 3.81(1H, m), 4.25(2H, s), 5.30–5.43(2H, m), 6.00(1H, d, J=7.5Hz), 6.81 (1H, d, J=3.9Hz), 7.20–7.36(6H, m).
IR(CHCl$_3$): 3516, 3446, 3427, 2667, 1709, 1643, 1543, 1506 cm$^{-1}$.
$[α]_D^{23}$+65.0±1.0° (c=1.008, MeOH)
Elemental Analysis (C$_{26}$H$_{31}$NO$_3$S$_2$•0.1H$_2$O) Calcd.(%): C, 66.24; H, 6.67; N, 2.97; S, 13.60 Found(%): C, 66.14; H, 6.63; N, 3.05; S, 13.49

Compound I-123

300MHz $^1$H-NMR(CDCl$_3$) δ: 1.08(1H, m), 1.20–1.32 (2H, m), 1.40–1.50(2H, m), 1.56–1.80(4H, m), 2.00–2.20 (5H, m), 2.36(2H, t, J=7.2Hz), 2.54(1H, m), 3.84(1H, m), 5.20(2H, s), 5.31–5.44(2H, m), 6.06(1H, d, J=7.5Hz), 6.94–7.05(4H, m), 7.27–7.33(2H, m), 7.42(1H, d, J=3.9Hz).
IR(CHCl$_3$): 3516, 3444, 3427, 2669, 1709, 1645, 1599, 1545, 1508, 1497 cm$^{-1}$.
$[α]_D^{24}$+65.4±1.1° (c=1.003, MeOH)
Elemental Analysis (C$_{26}$H$_{31}$NO$_4$S•0.2H$_2$O) Calcd.(%): C, 68.30; H, 6.92; N, 3.06; S, 7.01 Found(%): C, 68.32; H, 6.83; N, 3.08; S, 6.99

Compound I-124

300MHz $^1$H-NMR(CDCl$_3$) δ: 1.06(1H, m), 1.18–1.32 (2H, m), 1.40–1.50(2H, m), 1.55–1.80(4H, m), 2.00–2.20 (5H, m), 2.35(2H, t, J=7.2Hz), 2.52(1H, m), 3.81(1H, m), 4.51(2H, d, J=0.9Hz), 5.30–5.43(2H, m), 6.01(1H, d, J=7.5Hz), 6.65–6.97(3H, m), 6.96(1H, d, J=3.9Hz), 7.16–7.21(1H, m), 7.41(1H, d, J=3.9Hz).
IR(CHCl$_3$): 3516, 3444, 3427, 1709, 1643, 1603, 1545, 1504, 1309, 1260 cm$^{-1}$.
$[α]_D^{22}$+65.7±1.0° (c=1.014, MeOH)
Elemental Analysis (C$_{26}$H$_{32}$N$_2$O$_3$S•0.2H$_2$O) Calcd.(%): C, 68.45; H, 7.16; N, 6.14; S, 7.03 Found(%): C, 68.43; H, 7.18; N, 6.27; S, 6.94

Compound I-125

300MHz $^1$H-NMR(CDCl$_3$) δ: 1.05(1H, m), 1.18–1.27 (2H, m), 1.40–1.45(2H, m), 1.5.6–1.77(4H, m), 2.00–2.13 (5H, m), 2.28(3H, s), 2.34(2H, t, J=7.5Hz), 2.51(1H, m), 3.80(1H, m), 4.12(2H, s), 5.29–5.41(2H, m), 5.98(1H, d, J=7.2Hz), 6.69(1H, d, J=3.6Hz), 7.18(4H, s), 7.36(1H, d, J=3.6Hz).
IR(CHCl$_3$): 3518, 3446, 3426, 1741, 1709, 1641, 1543, 1506, 1458 cm$^{-1}$.
$[α]_D^{22.5}$+66.8±1.1° (c=1.003, MeOH)
Elemental Analysis (C$_{27}$H$_{33}$NO$_3$S•H$_2$O) Calcd.(%): C, 69.05; H, 7.51; N, 2.98; S, 6.83 Found(%): C, 69.07; H, 7.11; N, 3.23; S, 7.04

Compound I-126

300MHz $^1$H-NMR(CDCl$_3$) δ: 1.04(1H, m), 1.17–1.28 (2H, m), 1.41–1.46(2H, m), 1.55–1.77(4H, m), 2.00–2.20 (5H, m), 2.34(2H, t, J=7.2Hz), 2.51(1H, m), 3.80(1H, m), 4.12(2H, s), 5.29–5.41(2H, m), 5.91(1H, d, J=7.2Hz), 6.77 (1H, d, J=3.3Hz), 6.86–6.90(2H, m), 7.15(1H, dd, J=1.8 and 7.5Hz), 7.20–7.26(1H, m), 7.34(1H, d, J=3.6Hz).
IR(CHCl$_3$): 3519, 3446, 3427, 2669, 1741, 1709, 1641, 1543, 1504, 1458, 1248 cm$^{-1}$.
$[α]_D^{22.5}$64.2±1.0° (c=1.005, MeOH)
Elemental Analysis (C$_{27}$H$_{33}$NO$_4$S•0.1H$_2$O) Calcd.(%): C, 69.08; H, 7.13; N, 2.98; S, 6.83 Found(%): C, 68.97; H, 6.90; N, 3.09; S, 6.77

Compound I-127

300MHz $^1$H-NMR(CDCl$_3$) δ: 1.04(1H, m), 1.18(3H, t, J=7.7Hz), 1.15–1.29(2H, m), 1.41–1.46(2H, m), 1.56–1.80 (4H, m), 2.00–2.15(5H, m), 2.35(2H, t, J=7.2Hz), 2.51(1H, s), 2.64(2H, q, J=7.7Hz), 3.80(1H, m), 4.16(2H, s), 5.29–5.41(2H, m), 5.91(1H, d, J=7.5Hz), 6.69(1H, d, J=3.6Hz), 7.16–7.25(4H, m), 7.35(1H, d, J=3.6Hz).
IR(CHCl$_3$): 3516, 3447, 3427, 2669, 1709, 1641, 1543, 1506, 1456 cm$^{-1}$.
$[α]_D^{21}$+65.8±1.1° (c=1.011, MeOH)
Elemental Analysis (C$_{28}$H$_{35}$NO$_3$S•0.2H$_2$O) Calcd.(%): C, 71.67; H, 7.60; N, 2.98; S, 6.83 Found(%): C, 71.83; H, 7.49; N, 3.12; S, 6.89

Compound I-128

300MHz $^1$H-NMR(CDCl$_3$) δ: 1.04(1H, m), 1.18–1.29 (2H, m), 1.41–1.46(2H, m), 1.56–1.80(4H, m), 2.00–2.20 (5H, m), 2.24 and 2.31(each 3H, each s), 2.35(2H, t, J=7.4Hz), 2.51(1H, s), 3.80(1H, m), 4.19(2H, s), 5.29–5.41 (2H, m), 5.91(1H, d, J=7.2Hz), 6.70(1H, d, J=3.6Hz), 6.99 (1H, d, J=7.5Hz), 7.00(1H, s), 7.07(1H, d, J=7.5Hz), 7.35 (1H, d, J=3.6Hz).
IR(CHCl$_3$): 3514, 3446, 3426, 1741, 1709, 1641, 1543, 1506, 1456 cm$^{-1}$.
$[α]_D^{2}$+65.2±1.0° (c=1.014, MeOH)
Elemental Analysis (C$_{28}$H$_{35}$NO$_3$S•0.2H$_2$O) Calcd.(%): C, 71.67; H, 7.60; N, 2.98; S, 6.83 Found(%): C, 71.53; H, 7.49; N, 3.31; S, 6.90

Compound I-129

300MHz $^1$H-NMR(CDCl$_3$) δ: 1.05(1H, m), 1.18–1.29 (2H, m), 1.42–1.47(2H, m), 1.56–1.78(4H, m), 2.00–2.20 (5H, m), 2.35(2H, t, J=7.5Hz), 2.43(3H, s), 2.52(1H, s), 3.81 (1H, m), 4.24(2H, s), 5.30–5.42(2H, m), 5.97(1H, d, J=7.5Hz), 6.57(1H, m), 6.67(1H, d, J=3.3Hz), 6.83(1H, d, J=3.9Hz), 7.37(1H, d, J=3.9Hz).
IR(CHCl$_3$): 3514, 3446, 3427, 1709, 1643, 1545, 1506, 1456 cm$^{-1}$.
$[α]_D^{22}$+67.1±1.1° (c=1.002, MeOH)
Elemental Analysis (C$_{25}$H$_{31}$NO$_3$S$_2$) Calcd.(%): C, 65.61; H, 6.83; N, 3.06; S, 14.01 Found(%): C, 65.42; H, 6.76; N, 3.20; S, 13.73

Compound I-130

300MHz $^1$H-NMR(CDCl$_3$) δ: 1.04(1H, m), 1.18–1.28 (2H, m), 1.41–1.45(2H, m), 1.55–1.78(4H, m), 1.99–2.16 (5H, m), 2.34(2H, t, J=7.2Hz), 2.38(3H, s), 2.51(1H, m), 3.80(1H, m), 4.09(2H, s), 5.29–5.41(2H, m), 5.96(1H, d, J=6.9Hz), 6.76(1H, d, J=3.6Hz), 7.12(4H, s), 7.37(1H, d, J=3.6Hz).
IR(CHCl$_3$): 3510, 3446, 3427, 1741, 1709, 1641, 1543, 1508, 1458 cm$^{-1}$.
$[α]_D^{22}$+67.0±1.1° (c=1.014, MeOH)

Elemental Analysis (C$_{27}$H$_{33}$NO$_3$S) Calcd.(%): C, 71.81; H, 7.36; N, 3.10; S, 7.10 Found(%): C, 71.53; H, 7.24; N, 3.21; S, 7.36

Compound I-131

300MHz $^1$H-NMR(CDCl$_3$) δ: 1.04(1H, m), 1.18–1.28 (2H, m), 1.41–1.46(2H, m), 1.56–1.78(4H, m), 1.99–2.19 (5H, m), 2.33(3H, s), 2.34(2H, t, J=7.5Hz), 2.51(1H, m), 3.81(1H, m), 4.09(2H, s), 5.29–5.42(2H, m), 5.96(1H, d, J=7.2Hz), 6.77(1H, d, J=3.6Hz), 7.02–7.07(3H, m), 7.21 (1H, m), 7.37(1H, d, J=3.6Hz).

IR(CHCl$_3$): 3516, 3446, 3427, 1741, 1709, 1641, 1543, 1506, 1458 cm$^{-1}$.

[α]$_D^{23}$+66.1±1.1° (c=1.006, MeOH)

Elemental Analysis (C$_{27}$H$_{33}$NO$_3$S•0.2H$_2$O) Calcd.(%): C, 71.24; H, 7.40; N, 3.08; S, 7.04 Found(%): C, 71.26; H, 7.20; N, 3.19; S, 7.12

Compound I-132

300MHz $^1$H-NMR(CDCl$_3$) δ: 1.06(1H, m), 1.19–1.30 (2H, m), 1.41–1.49(2H, m), 1.57–1.78(4H, m), 2.00–2.21 (5H, m), 2.30(3H, s), 2.35(2H, t, J=7.2Hz), 2.52(1H, m), 3.81(1H, m), 4.25(2H, s), 5.30–5.43(2H, m), 6.01(1H, d, J=6.9Hz), 6.82(1H, d, J=3.9Hz), 7.02(1H, m), 7.10–7.19 (3H, m), 7.31(1H, d, J=3.9Hz).

IR(CHCl$_3$): 3516, 3446, 3427, 2671, 1739, 1709, 1643, 1543, 1506, 1475, 1456 cm$^{-1}$.

[α]$_D^{23}$+63.2±1.0° (c=1.007, MeOH)

Elemental Analysis (C$_{27}$H$_{33}$NO$_3$S$_2$•0.2H$_2$O) Calcd.(%): C, 66.55; H, 6.91; N, 2.87; S, 13.16 Found(%): C, 66.44; H, 6.87; N, 2.99; S, 13.11

Compound I-133

300MHz $^1$H-NMR(CDCl$_3$) δ: 1.07(1H, m), 1.20–1.30 (2H, m), 1.45–1.51(2H, m), 1.56–1.82(4H, m), 2.00–2.20 (5H, m), 2.35(2H, t, J=7.2Hz), 2.52(1H, m), 3.82(1H, m), 4.16(2H, s), 5.30–5.43(2H, m), 5.98(1H, d, J=7.2Hz), 6.13 (1H, dd, J=3.3 and 0.9Hz), 6.32(1H, dd, J=3.3 and 1.8Hz), 6.84(1H, d, J=3.6Hz), 7.35(1H, dd, J=1.8 and 0.9Hz), 7.37 (1H, d, J=3.6Hz).

IR(CHCl$_3$): 3512, 3446, 3427, 2669, 1709, 1643, 1545, 1506 cm$^{-1}$.

[α]$_D^{22}$+69.6±1.1° (c=1.015, MeOH)

Elemental Analysis (C$_{24}$H$_{29}$NO$_4$S•0.2H$_2$O) Calcd.(%): C, 66.86; H, 6.87; N, 3.25; S, 7.44 Found(%): C, 66.75; H, 6.63; N, 3.32; S, 7.50

Compound I-134

300MHz $^1$H-NMR(CDCl$_3$) δ: 1.07(1H, m), 1.19–1.29 (2H, m), 1.45–1.60(2H, m), 1.61–1.80(4H, m), 2.00–2.21 (5H, m), 2.36(2H, t, J=7.2Hz), 2.52(1H, m), 3.81(1H, m), 3.96(2H, s), 5.29–5.42(2H, m), 5.96(1H, d, J=6.9Hz), 6.30 (1H, m), 6.80(1H, m), 7.32(1H, m), 7.35–7.39(2H, m).

IR(CHCl$_3$): 3516, 3446, 3427, 2663, 1709, 1643, 1545, 1506 cm$^{-1}$.

[α]$_D^{21}$+70.2±1.1° (c=1.007, MeOH)

Elemental Analysis (C$_{24}$H$_{29}$NO$_4$S) Calcd.(%): C, 67.42; H, 6.84; N, 3.28; S, 7.50 Found(%): C, 67.13; H, 6.57; N, 3.40; S, 7.40

Compound I-135

300MHz $^1$H-NMR(CDCl$_3$) δ: 1.06(1H, m), 1.20–1.29 (2H, m), 1.42–1.47(2H, m), 1.58–1.82(4H, m), 2.00–2.15 (5H, m), 2.35(2H, t, J=7.2Hz), 2.52(1H, m), 3.81(1H, m), 4.41(2H, s), 5.29–5.41(2H, m), 5.96(1H, d, J=7.2Hz), 6.91 (1H, d, J=3.6Hz), 7.11(1H, s), 7.25–7.35(3H, m), 7.39(1H, d, J=3.6Hz), 7.76(1H, d, J=7.8Hz).

IR(CHCl$_3$): 3510, 3444, 3427, 2667, 1709, 1643, 1543, 1508 cm$^{-1}$.

[α]$_D^{24}$+66.5±1.1° (c=1.012, MeOH)

Elemental Analysis (C$_{28}$H$_{31}$NO$_3$S$_2$•0.5H$_2$O) Calcd.(%): C, 66.90; H, 6.42; N, 2.79; S, 12.76 Found(%): C, 66.99; H, 6.12; N, 2.81; S, 12.48

Compound I-136

300MHz $^1$H-NMR(CDCl$_3$) δ: 1.07(1H, m), 1.20–1.42 (2H, m), 1.44–1.49(2H, m), 1.55–1.80(4H, m), 2.00–2.20 (5H, m), 2.35(2H, t, J=7.2Hz), 2.52(1H, m), 3.81(1H, m), 4.30(2H, s), 5.29–5.41(2H, m), 5.98(1H, d, J=7.8Hz), 6.51 (1H, d, J=0.6Hz), 6.92(1H, d, J=3.9Hz), 7.17–7.25(2H, m), 7.38–7.51(3H, m).

IR(CHCl$_3$): 3514, 3444, 3427, 2669, 1709, 1643, 1545, 1508, 1454 cm$^{-1}$.

[α]$_D^{23}$+63.8±1.0° (c=1.004, MeOH)

Elemental Analysis (C$_{25}$H$_{31}$NO$_4$S•0.3H$_2$O) Calcd.(%): C, 69.62; H, 6.59; N, 2.90; S, 6.64 Found(%): C, 69.51; H, 6.52; N, 2.92; S, 6.63

Compound I-137

300MHz $^1$H-NMR(CDCl$_3$) δ: 1.05(1H, m), 1.18–1.29 (2H, m), 1.40–1.48(2H, m), 1.55–1.78(4H, m), 1.98–2.18 (5H, m), 2.34(2H, t, J=7.2Hz), 2.51(1H, m), 3.81(1H, m), 4.17(2H, s), 5.29–5.42(2H, m), 5.98(1H, d, J=7.5Hz), 6.81 (1H, d, J=3.6Hz), 7.29–7.46(6H, m), 7.52–7.60(4H, m).

IR(CHCl$_3$): 3510, 3446, 3427, 1741, 1709, 1643, 1543, 1506, 1489 cm$^{-1}$.

[α]$_D^{23}$+59.4±1.0° (c=1.007, MeOH)

Elemental Analysis (C$_{32}$H$_{35}$NO$_3$S•0.2H$_2$O) Calcd.(%): C, 74.30; H, 6.90; N, 2.71; S, 6.20 Found(%): C, 74.24; H, 6.78; N, 2.97; S, 6.16

Compound I-138

300MHz $^1$H-NMR(CDCl$_3$) δ: 1.04(1H, m), 1.17–1.29 (2H, m), 1.39–1.47(2H, m), 1.54–1.76(4H, m), 1.97–2.38 (5H, m), 2.33(2H, t, J=7.5Hz), 2.51(1H, m), 3.80(1H, m), 4.19(2H, s), 5.28–5.41(2H, m), 5.98(1H, d, J=7.5Hz), 6.79 (1H, d, J=3.6Hz), 7.21(1H, d, J=7.8Hz), 7.31–7.49(7H, m), 7.56(2H, m).

IR(CHCl$_3$): 3512, 3446, 3427, 2669, 1741, 1709, 1643, 1543, 1506, 1479, 1456 cm$^{-1}$.

[α]$_D^{24}$+59.2±1.0° (c=1.006, MeOH)

Elemental Analysis (C$_{32}$H$_{35}$NO$_3$S•0.2H$_2$O) Calcd.(%): C, 74.30; H, 6.90; N, 2.71; S, 6.20 Found(%): C, 74.26; H, 6.92; N, 3.00; S, 6.20

Compound I-139

300MHz $^1$H-NMR(CDCl$_3$) δ: 1.05(1H, m), 1.17–1.32 (2H, m), 1.43–1.48(2H, m), 1.58–1.80(4H, m), 2.02–2.24 (5H, m), 2.34(2H, t, J=7.2Hz), 2.58(1H, s), 3.91(1H, m), 4.11 (2H, s), 5.30–5.44(2H, m), 6.11(1H, d, J=7.2Hz), 7.18–7.30 (6H, m), 7.75(1H, d, J=8.4Hz), 7.86(1H, s), 8.16(1H, s).

IR(CHCl$_3$): 3516, 3430, 2665, 1741, 1709, 1651, 1513, 1494, 1454, 1435 cm$^{-1}$.

[α]$_D^{24}$+45.6±0.9° (c=1.004, MeOH)

Elemental Analysis (C$_{30}$H$_{33}$NO$_3$S•0.1H$_2$O) Calcd.(%): C, 73.62; H, 6.84; N, 2.86; S, 6.55 Found(%): C, 73.57; H, 6.71; N, 3.07; S, 6.30

Compound I-140

300MHz $^1$H-NMR(CDCl$_3$) δ: 1.09(1H, m), 1.20–1.32 (2H, m), 1.46–1.51(2H, m), 1.58–1.78(4H, m), 2.02–2.24 (5H, m), 2.35(2H, t, J=7.4Hz), 2.60(1H, s), 3.92(1H, m), 4.10 (2H, s), 5.32–5.46(2H, m), 6.14(1H, d, J=7.2Hz), 7.19–7.32 (6H, m), 7.64(1H, s), 7.81(1H, s), 8.20(1H, d, J=8.4Hz).

IR(CHCl$_3$): 3516, 3438, 2669, 1709, 1651, 1516, 1494, 1406 cm$^{-1}$.

[α]$_D^{24}$+53.0±0.9° (c=1.002, MeOH)

Elemental Analysis (C$_{30}$H$_{33}$NO$_3$S) Calcd.(%): C, 73.89; H, 6.82; N, 2.87; S, 6.58 Found(%): C, 73.57; H, 7.05; N, 3.08; S, 6.63

Compound I-141 mp.54–56° C.

300MHz $^1$H-NMR(CDCl$_3$) δ: 0.97(1H, m), 1.10–1.43 (4H, m), 1.53–1.72(4H, m), 1.97–2.15(5H, m), 2.31(2H, t, J=7.4Hz), 2.45(1H, s), 3.83(1H, m), 4.39 and 4.52(each 1H, each d, J=16.5Hz), 5.25–5.40(2H, m), 5.98(1H, d, J=7.5Hz), 7.00–7.31(7H, m), 7.57(1H, s), 7.73(1H, d, J=7.5Hz).

IR(CHCl$_3$): 3514, 3433, 2671, 1709, 1655, 1512, 1454 cm$^{-1}$.

[α]$_D^{25}$+76.7±1.2° (c=1.005, MeOH)

Elemental Analysis (C$_{30}$H$_{33}$NO$_3$S•0.1H$_2$O) Calcd.(%): C, 73.62; H, 6.84; N, 2.86; S, 6.55 Found(%): C, 73.45; H, 6.91; N, 3.21; S, 6.34

Compound I-142 mp. 118–119° C.

300MHz $^1$H-NMR(CDCl$_3$) δ: 1.07(1H, m), 1.20–1.27 (2H, m), 1.42–1.46(2H, m), 1.55–1.73(4H, m), 1.99–2.12 (5H, m), 2.33(2H, t, J=7.5Hz), 2.52(1H, s), 3.82(1H, m),3.93 (2H, s), 5.29–5.42(2H, m), 6.10(1H, d, J=7.2Hz), 7.05(1H, d, J=0.9Hz), 7.16–7.32(6H, m).

IR(CHCl$_3$): 3516, 3444, 3429, 2669, 1739, 1709, 1665, 1549, 1508, 1454 cm$^{-1}$.

[α]$_D^{24}$+72.7±0.1.1° (c=1.001, MeOH)

Elemental Analysis (C$_{26}$H$_{31}$NO$_3$S) Calcd.(%): C, 71.36; H, 7.14; N, 3.20; S, 7.33 Found(%): C, 71.31; H, 7.27; N, 3.36; S, 7.31

Compound I-143

300MHz $^1$H-NMR(CDCl$_3$) δ: 1.09(1H, m), 1.19–1.32 (2H, m), 1.46–1.51(2H, m), 1.58–1.78(4H, m), 2.02–2.24 (5H, m), 2.35(2H, t, J=7.2Hz), 2.60(1H, s), 3.92(1H, m),4.24 (2H, s), 5.32–5.47(2H, m), 6.14(1H, d, J=7.5Hz), 7.18–7.30 (6H, m), 7.43(1H, t, J=7.8Hz), 7.83(1H, s), 8.17(1H, d, J=7.8Hz).

IR(CHCl$_3$): 3516, 3438, 2671, 1709, 1651, 1518, 1495, 1454 cm$^{-1}$.

[α]$_D^{25}$+62.8±1.0° (c=1.011, MeOH)

Elemental Analysis (C$_{30}$H$_{33}$NO$_3$S•0.1H$_2$O) Calcd.(%): C, 73.62; H, 6.84; N, 2.86; S, 6.55 Found(%): C, 73.52; H, 6.87; N, 3.13; S, 6.47

Compound I-144

300MHz $^1$H-NMR(CDCl$_3$) δ: 1.05(1H, m), 1.23–1.29 (2H, m), 1.41–1.49(2H, m), 1.58–1.77(4H, m), 2.00–2.21 (5H, m), 2.35(2H, t, J=7.2Hz), 2.52(1H, m), 3.81(1H, m), 4.05(2H, s), 5.12(2H, s), 5.29–5.42(2H, m), 5.94(1H, d, J=7.8Hz), 6.76(1H, d, J=3.9Hz), 6.90–6.98(3H, m), 7.32–7.45(6H, m).

IR(CHCl$_3$): 3516, 3446, 3427, 1741, 1709, 1643, 1543, 1510, 1456, 1273 cm$^{-1}$.

[α]$_D^{23}$+53.7±0.9° (c=1.006, MeOH)

Elemental Analysis (C$_{33}$H$_{36}$FNO$_4$S•0.2H$_2$O) Calcd.(%): C, 70.11; H, 6.49; N, 2.48; S, 5.67; F,3.36 Found(%): C, 70.00; H, 6.44; N, 2.50; S, 5.75; F,3.32

Compound I-145 mp.136–137° C.

300MHz $^1$H-NMR(CDCl$_3$) δ: 1.06(1H, m), 1.23–1.29 (2H, m), 1.41–1.49(2H, m), 1.58–1.77(4H, m), 2.00–2.21 (5H, m), 2.35(2H, t, J=7.2Hz), 2.52(1H, m), 3.78(1H, m), 4.05(2H, s), 5.29–5.42(2H, m), 5.93(1H, d, J=10.8Hz), 6.77(1H, d, J=3.6Hz), 6.88–6.98(3H, m), 7.36(1H, d, J=3.6Hz).

IR(Nujol): 3377, 3101, 2752, 1703, 1618, 1601, 1550, 1518 cm$^{-1}$.

[α]$_D^{23}$+64.2±1.0° (c=1.009, MeOH)

Elemental Analysis (C$_{26}$H$_{30}$FNO$_4$S) Calcd.(%): C, 66.23; H, 6.41; N, 2.97; S, 6.80; F, 4.03 Found(%): C, 66.15; H, 6.38; N, 2.94; S, 6.76; F, 3.94

Compound I-146

300MHz $^1$H-NMR(CDCl$_3$) δ: 1.06(1H, m), 1.20–1.29 (2H, m), 1.41–1.46(2H, m), 1.61–1.81(4H, m), 2.00–2.16 (5H, m), 2.35(2H, t, J=7.2Hz), 2.51(1H, m), 3.79(1H, m), 4.03(2H, s), 5.08(2H, s), 5.29–5.40(2H, m), 5.63(1H, brs), 5.93(1H, d, J=7.5Hz), 6.70(1H, dd, J=2.1 and 8.4Hz), 6.77 (1H, d, J=3.9Hz), 6.83(1H, d, J=5.7Hz). 6.86(1H, d, J=8.4Hz), 7.36–7.41(6H, m).

IR(CHCl$_3$): 3539, 3446, 3425, 1741, 1709, 1641, 1543, 1508, 1475, 1273 cm$^{-1}$.

[α]$_D^{23}$+53.8±0.9° (c=1.003, MeOH)

Elemental Analysis (C$_{33}$H$_{37}$NO$_5$S•0.5H$_2$O) Calcd.(%): C, 69.69; H, 6.73; N, 2.46; S, 5.64 Found(%): C, 69.68; H, 6.85; N, 2.68; S, 5.76

Compound I-147 mp.150–151° C.

300MHz $^1$H-NMR(CDCl$_3$) δ: 1.06(1H, m), 1.20–1.29 (2H, m), 1.41–1.46(2H, m), 1.58–1.79(4H, m), 2.00–2.16 (5H, m), 2.35(2H, t, J=7.2Hz), 2.51(1H, m), 3.79(1H, m), 3.86(3H, s), 4.06(2H, s), 5.29–5.41(2H, m), 5.56(1H, brs), 5.93(1H, d, J=8.4Hz), 6.72–6.77(3H, m), 6.87(1H, d, J=8.1Hz), 7.37(1H, d, J=3.6Hz).

IR(Nujol): 3452, 3361, 3130, 1743, 1707, 1620, 1599, 1550, 1522, 1286 cm$^{-1}$.

[α]$_D^{23}$+62.6±1.0° (c=1.002, MeOH)

Elemental Analysis (C$_{27}$H$_{33}$NO$_5$S) Calcd.(%): C, 67.05; H, 6.88; N, 2.90; S, 6.63 Found(%): C, 67.20; H, 7.04; N, 2.98; S, 6.58

Compound I-148

300MHz $^1$H-NMR(CDCl$_3$) δ: 1.07(1H, m), 1.19–1.31 (2H, m), 1.41–1.50(2H, m), 1.56–1.81(4H, m), 1.99–2.21

(5H, m), 2.35(2H, t, J=7.2Hz), 2.53(1H, m), 2.95–3.00(2H, m), 3.10–3.15(2H, m),3.83(1H, m), 5.31–5.44(2H, m), 6.02 (1H, d, J=7.2Hz), 6.70(1H, d, J=3.9Hz), 7.15–7.32(5H, m), 7.33(1H, d, J=3.9Hz).

IR(CHCl$_3$): 3510, 3446, 3429, 2671, 1741, 1709, 1641, 1543, 1506, 1456 cm$^{-1}$.

$[\alpha]_D^{23}$+68.4±1.1° (c=1.004, MeOH)

Elemental Analysis (C$_{27}$H$_{33}$NO$_3$S•0.1H$_2$O) Calcd.(%): C, 71.52; H, 7.38; N, 3.09; S, 7.07 Found(%): C, 71.35; H, 7.37; N, 3.19; S, 7.19

Compound I-149

300MHz $^1$H-NMR(CDCl$_3$) δ: 1.07(1H, m), 1.19–1.32 (2H, m), 1.41–1.50(2H, m), 1.56–1.81(4H, m), 1.99–2.23 (5H, m), 2.36(2H, t, J=7.2Hz), 2.43(3H, s), 2.53(1H, m), 3.05–3.19(4H,m), 3.83(1H, m), 5.31–5.44(2H, m), 6.00(1H, d, J=6.9Hz), 6.23–6.56(2H, m), 6.75 and 7.34(each 1H, each d, each J=3.6Hz).

IR(CHCl$_3$): 3510, 3446, 3429, 2669, 1709, 1641, 1543, 1506, 1458 cm$^{-1}$.

$[\alpha]_D^{23}$+64.6±1.0° (c=1.014, MeOH)

Elemental Analysis (C$_{26}$H$_{33}$NO$_3$S$_2$•0.1H$_2$O) Calcd.(%): C,.65.96; H, 7.07; N, 2.96; S, 13.54 Found(%): C, 65.87; H, 7.03; N, 3.02; S, 13.50

Compound I-150

300MHz $^1$H-NMR(CDCl$_3$) δ: 1.07(1H, m), 1.19–1.31 (2H, m), 1.41–1.50(2H, m), 1.56–1.80(4H, m), 1.99–2.20 (5H, m), 2.35(2H, t, J=7.5Hz), 2.53(1H, m), 3.18(3H, s), 3.83(1H, m), 5.31–5.44(2H, m), 6.05(1H, d, J=7.2Hz), 6.741H, d, J=3.6Hz), 6.79(1H, m), 6.91(1H, dd, J=3.6 and 5.4Hz), 7.13(1H, dd, J=1.2 and 5.4Hz), 7.34(1H, d, J=3.6Hz).

IR(CHCl$_3$): 3516, 34446, 3429, 2669, 1709, 1641, 1543, 1506 cm$^{-1}$.

$[\alpha]_D^{24}$+66.1±1.0° (c=1.019, MeOH)

Elemental Analysis (C$_{25}$H$_{31}$NO$_3$S$_2$) Calcd.(%): C, 65.61; H, 6.83; N, 3.06; S,14.01 Found(%): C, 65.47; H, 6.89; N, 3.12; S,13.82

Compound I-151

300MHz $^1$H-NMR(CDCl$_3$) δ: 1.09(1H, m), 1.20–1.32 (2H, m), 1.42–1.51(2H, m), 1.57–1.81(4H, m), 2.00–2.22 (5H, m), 2.33(2H, t, J=7.5Hz), 2.56(1H, m), 2.99–3.05(2H, m), 3.11–3.17(2H, m), 3.88(1H, m), 5.30–5.44(2H, m), 6.22(1H, d, J=7.2Hz), 6.74(1H, m), 6.89(1H, dd, J=3.3 and 5.1Hz), 7.11(1H, dd, J=1.2 and 5.1Hz), 7.23 and 7.67(each 2H, each d, each J=8.1Hz).

IR(CHCl$_3$): 3516, 3448, 2665, 1709, 1651, 1523, 1496 cm$^{-1}$.

$[\alpha]_D^{24}$+71.8±1.1° (c=1.009, MeOH)

Elemental Analysis (C$_{27}$H$_{33}$NO$_3$S) Calcd.(%): C, 71.81; H, 7.37; N, 3.10; S, 7.10 Found(%): C, 71.68; H, 7.40; N, 3.18; S, 6.96

Compound I-152

300MHz $^1$H-NMR(CDCl$_3$) δ: 1.07(1H, m), 1.19–1.31 (2H, m), 1.42–1.50(2H, m), 1.56–1.81(4H, m), 2.00–2.21 (5H, m), 2.36(2H, t, J=7.2Hz), 2.53(1H, m), 2.92–2.97(2H, m), 3.07–3.12(2H, m), 3.83(1H, m), 5.31–5.44(2H, m), 5.99(1H, d, J=7.2Hz), 6.68(1H, d, J=3.6Hz), 6.92–7.00(2H, m), 7.08–7.15(2H, m), 7.32(1H, d, J=3.6Hz).

IR(CHCl$_3$): 3516, 3446, 3429, 1741, 1709, 1641, 1543, 1510, 1458 cm$^{-1}$.

$[\alpha]_D^{23}$+64.1±1.0° (c=1.012, MeOH)

Elemental Analysis (C$_{27}$H$_{32}$FNO$_3$S) Calcd.(%): C, 69.06; H, 6.87; N, 2.98; S, 6.83; F, 4.05 Found(%): C, 68.92; H, 6.90; N, 3.03; S, 6.81; F, 4.02

Compound I-153

300MHz 1H-NMR(CDCl$_3$) δ: 1.05(1H, m), 1.19–1.29 (2H, m), 1.41–1.46(2H, m), 1.56–1.78(4H, m), 2.00–2.19 (5H, m), 2.29(6H, s), 2.34(2H, t, J=7.5Hz), 2.51(1H, m), 3.81(1H, m), 4.05(2H, s), 5.29–5.42(2H, m), 5.96(1H, d, J=7.5Hz), 6.77(1H, td, J=0.9 and 3.6Hz), 6.85(2H, s), 6.88 (1H, s), 7.37(1H, d, J=3.6Hz).

IR(CHCl$_3$): 3516, 3446, 3427, 1739, 1709, 1641, 1606, 1543, 1506, 1458 cm$^{-1}$.

$[\alpha]_D^{23}$+64.6±1.0° (c=1.004, MeOH)

Elemental Analysis (C$_{28}$H$_{35}$NO$_3$S•0.1H$_2$O) Calcd.(%): C, 71.94; H, 7.59; N, 3.00; S, 6.86 Found(%): C, 71.87; H, 7.52; N, 3.31; S, 6.94

Compound I-154

300MHz $^1$H-NMR(CDCl$_3$) δ: 1.05(1H, m), 1.18–1.29 (2H, m), 1.41–1.46(2H, m), 1.56–1.78(4H, m), 2.00–2.19 (5H, m), 2.34(2H, t, J=7.5Hz), 2.51(1H, m), 3.81(1H, m), 4.10(2H, s), 5.29–5.42(2H, m), 5.98(1H, d, J=7.2Hz), 6.75 (1H, td, J=0.9 and 3.9Hz), 6.97–7.03(2H, m), 7.17–7.22(2H, m), 7.36(1H, d, J=3.9Hz).

IR(CHCl$_3$): 3512, 3446, 3427, 1741, 1709, 1643, 1543, 1508 cm$^{-1}$.

$[\alpha]_D^{24}$+66.1±1.1° (c=1.008, MeOH)

Elemental Analysis (C$_{26}$H$_{30}$FNO$_3$S) Calcd.(%): C, 68.54; H, 6.64; N, 3.07; S, 7.04; F,4.17 Found(%): C, 68.41; H, 6.70; N, 3.19; S, 6.90; F,3.98

Compound I-155

300MHz $^1$H-NMR(CDCl$_3$) δ: 1.05(1H, m), 1.19–1.29 (2H, m), 1.42–1.46(2H, m), 1.58–1.78(4H, m), 2.00–2.17 (5H, m), 2.35(2H, t, J=7.5Hz), 2.52(1H, m), 3.81(1H, m), 4.19(2H, s), 5.29–5.42(2H, m), 5.97(1H, d, J=7.8Hz), 6.75 (1H, td, J=0.9 and 3.6Hz), 7.34–7.37(3H, m), 7.56–7.59(2H, m).

IR(CHCl$_3$): 3512, 3444, 3427, 1741, 1709, 1643, 1543, 1506, 1325, 1167, 1130, 1066 cm$^{-1}$.

$[\alpha]_D^{24}$+60.3+1.0° (c=1.001, MeOH)

Elemental Analysis (C$_{27}$H$_{30}$F$_3$NO$_3$S) Calcd.(%): C, 64.14; H, 5.98; N, 2.77; S, 6.34; F,11.27 Found(%): C, 64.16; H, 6.04; N, 3.02; S, 6.19; F,11.17

Compound I-156 mp.66–70° C.

300MHz $^1$H-NMR(CDCl$_3$) δ: 1.11(1H, m), 1.22–1.30 (2H, m), 1.43–1.50(2H, m), 1.60–1.78(4H, m), 2.03–2.22 (5H, m), 2.36(2H, t, J=7.5Hz), 2.54(1H, m), 3.87(1H, m), 4.08(2H, s), 5.31–5.45(2H, m), 6.21(1H, d, J=7.2Hz), 7.18–7.32(6H, m), 7.60(1H, d, J=0.9Hz), 7.70(1H, d, J=0.6Hz), 7,74(1H, d, J=8.1Hz).

IR(KBr): 3338, 1707, 1616, 1556, 1537 cm$^{-1}$.

$[\alpha]_D^{23}$+97.2+1.4° (c=1.016, MeOH)

Elemental Analysis (C$_{30}$H$_{33}$NO$_3$S•0.3H$_2$O) Calcd.(%): C, 73.08; H, 6.87; N, 2.84; S, 6.50 Found(%): C, 73.19; H, 7.11; N, 2.98; S, 6.32

Compound I-157

300MHz ¹H-NMR(CDCl₃) δ: 1.03(1H, m), 1.17–1.29 (2H, m), 1.38–1.47(2H, m), 1.55–1.76(4H, m), 1.97–2.18 (5H, m), 2.33(2H, t, J=7.5Hz), 2.50(1H, m), 3.80(1H, m), 4.29(2H, s), 5.28–5.40(2H, m), 5.94(1H, d, J=7.5Hz), 6.81 (1H, d, J=3.9Hz), 7.32–7.39(2H, m), 7.42–7.50(2H, m), 7.69(1H, s), 7.77–7.83(3H, m).
IR(CHCl₃): 3516, 3446, 3427, 2665, 1739, 1709, 1643, 1543, 1506, 1458 cm⁻¹.
$[\alpha]_D^{23}$ +62.8±1.0° (c=1.005, MeOH)
Elemental Analysis (C₃₀H₃₂NO₃S•0.2H₂O) Calcd.(%): C, 73.35; H, 6.85; N, 2.85; S, 6.53 Found(%): C, 73.36; H, 6.84; N, 3.19; S, 6.55

Compound I-158

300MHz ¹H-NMR(CDCl₃) δ: 1.07(1H, m), 1.20–1.32 (2H, m), 1.42–1.50(2H, m), 1.57–1.84(4H, m), 2.00–2.23 (5H, m), 2.36(2H, t, J=7.5Hz), 2.53(1H, m), 2.95–3.00(2H, m), 3.06–3.12(2H, m), 3.82(1H, m),3.83(3H, s), 5.30–5.43 (2H, m), 5.95(1H, d, J=6.9Hz), 6.73(1H, d, J=3.6Hz), 6.84–6.89(2H, m), 7.09(1H, dd, J=1.5 and 7.5Hz), 7.20(1H, dt, J=1.5 and 7.5Hz), 7.34(1H, d, J=3.6Hz).
IR(Nujol): 3367, 3221, 3186, 3091, 3055, 2654, 1711, 1631, 1566, 1541, 1321 cm⁻¹.
$[\alpha]_D^{25}$ +61.3±1.0° (c=1.003, MeOH)
Elemental Analysis (C₂₈H₃₅NO₄S) Calcd.(%): C, 69.82; H, 7.32; N, 2.91; S, 6.66 Found(%): C, 69.93; H, 7.48; N, 3.09; S, 6.54

Compound I-159

300MHz ¹H-NMR(CDCl₃) δ: 1.07(1H, m), 1.18–1.30 (2H, m), 1.40–1.50(2H, m), 1.54–1.78(4H, m), 1.98–2.21 (5H, m), 2.33(2H, t, J=7.2Hz), 2.53(1H, m), 2.94–3.03(2H, m), 3.06–3.15(2H, m), 3.83(1H, m), 5.29–5.43(2H, m), 6.12(1H, d, J=7.5Hz), 6.72(1H, d, J=3.6Hz), 6.77–6.83(2H, m), 7.04–7.08(2H, m), 7.36(1H, d, J=3.6Hz).
IR(CHCl₃): 3599, 3444, 3425, 3195, 1709, 1635, 1543, 1508, 1456 cm⁻¹.
$[\alpha]_D^{25}$ +64.8±1.0° (c=1.006, MeOH)
Elemental Analysis (C₂₇H₃₃NO₄S•0.2H₂O) Calcd.(%): C, 68.82; H, 7.14; N, 2.97; S, 6.80 Found(%): C, 68.81; H, 7.10; N, 3.03; S, 6.88

Compound I-160 mp.139–141° C.
300MHz ¹H-NMR(CDCl₃) δ: 1.12(1H, m), 1.25–1.31 (2H, m), 1.45–1.51(2H, m), 1.60–1.78(4H, m), 2.02–2.22 (5H, m), 2.35(2H, t, J=7.5Hz), 2.57(1H, m), 3.87(1H, m), 4.09(2H, s), 5.31–5.45(2H, m), 6.22(1H, d, J=7.2Hz), 7.19–7.33(6H, m), 7.63(1H, m), 7.71(1H, d, J=8.7Hz), 7.73 (1H, s).
IR(KBr): 3338, 1705, 1616, 1560, 1537 cm⁻¹.
$[\alpha]_D^{25}$ +92.1±1.3° (c=1.006, MeOH)
Elemental Analysis (C₃₀H₃₃NO₃S) Calcd.(%): C, 73.89; H, 6.82; N, 2.87; S, 6.58 Found(%): C, 73.69; H, 6.75; N, 2.91; S, 6.58

Compound I-161

300MHz ¹H-NMR(CDCl₃) δ: 1.12(1H, m), 1.25–1.31 (2H, m), 1.47–1.51(2H, m), 1.60–1.76(4H, m), 2.03–2.20 (5H, m), 2.36(2H, t, J=7.2Hz), 2.57(1H, m), 3.87(1H, m), 4.08(2H, s), 5.31–5.45(2H, m), 6.22(1H, d, J=7.5Hz), 6.90 (1H, dd, J=1.2 and 4.8Hz), 6.93(1H, m), 7.25–7.29(2H, m), 7.61 and 7.71(each 1H, each s), 7.75(1H, d, J=8.4Hz).
IR(CHCl₃): 3512, 3444, 3423, 2671, 1709, 1649, 1531, 1502 cm⁻¹.
$[\alpha]_D^{25}$ +96.1±1.4° (c=1.005, MeOH)
Elemental Analysis (C₂₈H₃₁NO₃S₂) Calcd.(%): C, 68.12; H, 6.33; N, 2.84; S, 12.99 Found(%): C, 67.89; H, 6.32; N, 2.88; S, 12.88

Compound I-162

300MHz ¹H-NMR(CDCl₃) δ: 1.12(1H, m), 1.24–1.31 (2H, m), 1.45–1.51(2H, m), 1.60–1.78(4H, m), 2.03–2.22 (5H, m), 2.36(2H, t, J=7.2Hz), 2.57(1H, m), 3.87(1H, m), 4.25(2H, s), 5.31–5.45(2H, m), 6.25(1H, d, J=7.2Hz), 6.81 (1H, m), 6.93(1H, dd, J=3.3 and 5.4Hz), 7.15(1H, dd, J=1.5 and 5.4Hz), 7.31(1H, dd, J=1.5 and 8.1Hz), 7.65 and 7.71 (each 1H, each s), 7.76(1H, d, J=8.1Hz).
IR(CHCl₃): 3516, 3444, 3423, 1741, 1709, 1649, 1531, 1502 cm⁻¹.
$[\alpha]_D^{25}$ +98.5±1.4° (c=1.007, MeOH)
Elemental Analysis (C₂₈H₃₁NO₃S₂•0.1H₂O) Calcd.(%): C, 67.87; H, 6.35; N, 2.83; S, 12.94 Found(%): C, 67.83; H, 6.29; N, 3.00; S, 12.99

Compound I-163 mp.114–115° C.
300MHz ¹H-NMR(CDCl₃) δ: 1.09(1H, m), 1.20–1.30 (2H, m), 1.40–1.49(2H, m), 1.55–1.77(4H, m), 1.99–2.19 (5H, m), 2.34(2H, t, J=7.2Hz), 2.53(1H, m), 3.83(1H, m), 4.12(2H, s), 5.30–5.43(2H, m), 6.14(1H, d, J=7.5Hz), 6.81 and 6.93(each 1H, each m), 7.14–7.17(2H, m), 7.37(1H, d, J=1.8Hz).
IR(CHCl₃): 3516, 3444, 3428, 2671, 1709, 1645, 1550, 1508, 1435 cm⁻¹.
$[\alpha]_D^{25}$ +71.6±1.1° (c=1.002, MeOH)
Elemental Analysis (C₂₄H₂₉NO₃S₂•0.1H₂O) Calcd.(%): C, 64.72; H, 6.61; N, 3.14; S, 14.40 Found(%): C, 64.50; H, 6.54; N, 3.24; S, 14.45

Compound I-164

300MHz ¹H-NMR(CDCl₃) δ: 1.08(1H, m), 1.20–1.31 (2H, m), 1.41–1.49(2H, m), 1.56–1.77(4H, m), 1.99–2.19 (5H, m), 2.34(2H, t, J=7.2Hz), 2.53(1H, m), 3.83(1H, m), 3.94(2H, s), 5.30–5.43(2H, m), 6.08(1H, d, J=6.9Hz), 6.91 and 6.95(each 1H, each m), 7.08(1H, d, J=1.5Hz), 7.27(1H, m), 7.34(1H, d, J=1.5Hz).
IR(CHCl₃): 3512. 3444, 3429, 1739, 1709, 1644, 1550, 1508 cm⁻¹.
$[\alpha]_D^{25}$ +69.7±1.1° (c=1.000, MeOH)
Elemental Analysis (C₂₄H₂₉NO₃S₂•0.2H₂O) Calcd.(%): C, 64.45; H, 6.63; N, 3.13; S, 14.34 Found(%): C, 64.37; H, 6.49; N, 3.16; S, 14.41

Compound I-165

300MHz ¹H-NMR(CDCl₃) δ: 1.08(1H, m), 1.19–1.31 (2H, m), 1.41–1.51(2H, m), 1.55–1.74(4H, m), 1.99–2.16 (5H, m), 2.34(2H, t, J=7.2Hz), 2.53(1H, m), 3.73(2H, s), 3.83(1H, m), 5.30–5.42(2H, m), 6.15(1H, d, J=6.6Hz), 6.25, 7.10 and 7.24(each 1H, each s), 7.35–7.38(2H, m).
IR(CHCl₃): 3510. 3444, 3429, 2669, 1709, 1645, 1550, 1508 cm⁻¹.
$[\alpha]_D^{25}$ +71.6±1.1° (c=1.008, MeOH)

Elemental Analysis ($C_{24}H_{29}NO_4S \cdot 0.2H_2O$) Calcd.(%): C, 66.85; H, 6.78; N, 3.25; S, 7.44 Found(%): C, 66.94; H, 6.81; N, 3.26; S, 7.38

Compound I-166

300MHz $^1$H-NMR(CDCl$_3$) δ: 1.02(1H, m), 1.15–1.27 (2H, m), 1.36–1.45(2H, m), 1.53–1.76(4H, m), 1.96–2.14 (5H, m), 2.32(2H, t, J=7.2Hz), 2.49(1H, m), 3.78(1H, m), 4.58(2H, s), 5.27–5.39(2H, m), 5.92(1H, d, J=7.2Hz), 6.73 and 7.32(each 1H, each d, each J=3.9Hz), 7.37–7.51(4H, m), 7.80(1H, d, J=7.5Hz), 7.87 and 7.97(each 1H, each m).

IR(CHCl$_3$): 3516, 3446, 3427, 2669, 1739, 1709, 1641, 1543, 1508, 1458 cm$^{-1}$.

$[α]_D^{25.5}$+62.8±1.0° (c=1.012, MeOH)

Elemental Analysis ($C_{30}H_{33}NO_3S \cdot 0.1H_2O$) Calcd.(%): C, 73.62; H, 6.84; N, 2.86; S, 6.55 Found(%): C, 73.35; H, 6.54; N, 3.06; S, 6.51

Compound I-167 mp. 129–130° C.

300MHz $^1$H-NMR(CDCl$_3$) δ: 1.04(1H, m), 1.16–1.28 (2H, m), 1.38–1.46(2H, m), 1.54–1.73(4H, m), 1.97–2.15 (5H, m), 2.31(2H, t, J=7.2Hz), 2.51(1H, m), 3.81(1H, m), 4.37(2H, s), 5.28–5.41(2H, m), 6.04(1H, d, J=7.5Hz), 6.97 (1H, s), 7.30–7.50(5H, m), 7.77(1H, d, J=8.1Hz), 7.86 and 7.94(each 1H, each m).

IR(CHCl$_3$): 3514, 3444, 3427, 1739, 1709, 1645, 1549, 1508 cm$^{-1}$.

$[α]_D^{24}$+59.4±1.0° (c=1.011, MeOH)

Elemental Analysis ($C_{30}H_{33}NO_3S$) Calcd.(%): C, 73.89; H, 6.82; N, 2.87; S, 6.58 Found(%): C, 73.85; H, 6.90; N, 2.85; S, 6.81

Compound I-168

300MHz $^1$H-NMR(CDCl$_3$) δ: 1.10(1H, m), 1.21–1.33 (2H, m), 1.47–1.52(2H, m), 1.59–1.80(4H, m), 2.04–2.27 (5H, m), 2.36(2H, t, J=7.5Hz), 2.61(1H, m), 3.93(1H, m), 4.42(2H, s), 5.33–5.47(2H, m), 6.13(1H, d, J=7.5Hz), 6.88 (1H, m), 6.92(1H, m), 7.15(1H, dd, J=1.2 and 5.1Hz), 7.28(1H, d, J=7.5Hz), 7.43(1H, d, J=8.1Hz), 7.84(1H, s), 8.20(1H, d, J=8.1Hz).

IR(CHCl$_3$): 3512, 3438, 1709, 1651, 1518, 1495 cm$^{-1}$.

$[α]_D^{25}$+61.6±1.0° (c=1.003, MeOH)

Elemental Analysis ($C_{28}H_{31}NO_3S_2$) Calcd.(%): C, 68.12; H, 6.33; N, 2.84; S, 12.99 Found(%): C, 67.83; H, 6.28; N, 2.96; S, 12.76

Compound I-169

300MHz $^1$H-NMR(CDCl$_3$) δ: 1.10(1H, m), 1.22–1.32 (2H, m), 1.46–1.51(2H, m), 1.58–1.76(4H, m), 2.02–2.24 (5H, m), 2.35(2H, t, J=7.2Hz), 2.60(1H, m), 3.92(1H, m), 4.23(2H, s), 5.32–5.47(2H, m), 6.18(1H, d, J=8.1Hz), 6.92 (1H, dd, J=1.2 and 4.8Hz), 7.01(1H, m), 7.20–7.25(2H, m), 7.41(1H, t, J=8.1Hz), 7.84(1H, s), 8.18(1H, d, J=7.5Hz).

IR(CHCl$_3$): 3510, 3438, 2667, 1709, 1651, 1518, 1495 cm$^{-1}$.

$[α]_D^{25}$+61.3±1.0° (c=1.006, MeOH)

Elemental Analysis ($C_{28}H_{31}NO_3S_2$) Calcd.(%): C, 68.12; H, 6.33; N, 2.84; S, 12.99 Found(%): C, 67.94; H, 6.30; N, 2.97; S, 12.87

Compound I-170

300MHz $^1$H-NMR(CDCl$_3$) δ: 1.10(1H, m), 1.21–1.33 (2H, m), 1.47–1.52(2H, m), 1.59–1.79(4H, m), 2.03–2.27 (5H, m), 2.36(2H, t, J=7.5Hz), 2.61(1H, m), 3.93(1H, m), 4.03(2H, s), 5.33–5.48(2H, m), 6.15(1H, d, J=7.2Hz), 7.23 (1H, d, J=7.2Hz), 7.29(1H, m), 7.35(1H, t, J=1.5Hz), 7.42 (1H, t, J=7.8Hz), 7.85(1H, s), 8.18(1H, d, J=7.8Hz).

IR(CHCl$_3$): 3518, 3438, 2663, 1739, 1709, 1651, 1518, 1496 cm$^{-1}$.

$[α]_D^{25}$+60.3±1.0° (c=1.002, MeOH)

Elemental Analysis ($C_{28}H_{31}NO_4S \cdot 0.1H_2O$) Calcd.(%): C, 70.15; H, 6.56; N, 2.92; S, 6.69 Found(%): C, 70.03; H, 6.49; N, 2.92; S, 6.69

Compound I-171

300MHz $^1$H-NMR(CDCl$_3$) δ: 1.05(1H, m), 1.18–1.28 (2H, m), 1.41–1.46(2H, m), 1.56–1.79(4H, m), 2.00–2.15 (5H, m), 2.34(2H, t, J=7.2Hz), 2.45(3H, s), 2.50(1H, m), 3.80(1H, m), 4.25(2H, s), 5.29–5.42(2H, m), 5.95(1H, d, J=7.5Hz), 6.78(1H, d, J=3.6Hz), 7.11–7.27(4H, m), 7.36 (1H, d, J=3.6Hz).

IR(CHCl$_3$): 3512, 3446, 3427, 2669, 1739, 1709, 1643, 1543, 1506 cm$^{-1}$.

$[α]_D^{23.5}$+62.8±1.0° (c=1.005, MeOH)

Elemental Analysis ($C_{27}H_{33}NO_3S_2$) Calcd.(%): C, 67.05; H, 6.88; N, 2.90; S, 13.26 Found(%): C, 66.94; H, 7.05; N, 3.00; S, 13.14

Compound I-172

300MHz $^1$H-NMR(CDCl$_3$) δ: 1.07(1H, m), 1.19–1.29 (2H, m), 1.41–1.46(2H, m), 1.57–1.78(4H, m), 2.01–2.19 (5H, m), 2.34(2H, t, J=7.5Hz), 2.51(1H, m), 2.90(3H, s), 3.80(1H, m), 4.68(2H, s), 5.29–5.43(2H, m), 6.02(1H, d, J=7.5Hz), 6.84(1H, td, J=0.9 and 3.9Hz), 7.37(1H, d, J=3.9Hz), 7.42–7.51(2H, m), 7.62(1H, dt, J=1.5 and 7.5Hz), 8.08(1H, dd, J=1,5 and 7.5Hz).

IR(CHCl$_3$): 3518, 3444, 3427, 1709, 1643, 1543, 1508, 1311, 1153 cm$^{-1}$.

$[α]_D^{23.5}$+59.3±1.0° (c=1.007, MeOH)

Elemental Analysis ($C_{27}H_{33}NO_5S_2 \cdot 0.2H_2O$) Calcd.(%): C, 62.45; H, 6.48; N, 2.70; S, 12.35 Found(%): C, 62.47; H, 6.60; N, 2.73; S, 12.36

Compound I-173

300MHz $^1$H-NMR(CDCl$_3$) δ: 1.13(1H, m), 1.23–1.36 (2H, m), 1.43–1.80(6H, m), 2.03–2.24(5H, m), 2.36(2H, t, J=7.2Hz), 2.60(1H, m), 3.91(1H, m), 3.93(2H, s), 5.31–5.46 (2H, m), 6.31(1H, d, J=7.2Hz), 7.32–7.42(2H, m), 7.57(1H, d, J=6.9Hz), 7.73–7.82(3H, m), 7.94(1H, s).

IR(CHCl$_3$): 3516, 3446, 2665, 1709, 1649, 1616, 1514, 1481, 1468 cm$^{-1}$.

$[α]_D^{24}$+100.7±1.4° (c=1.008, MeOH)

Elemental Analysis ($C_{28}H_{31}NO_3 \cdot 0.2H_2O$) Calcd.(%): C, 77.64; H, 7.31; N, 3.23 Found(%): C, 77.64; H, 7.57; N, 3.29

Compound I-174

300MHz $^1$H-NMR(CDCl$_3$) δ: 1.06(1H, m), 1.19–1.28 (2H, m), 1.40–1.47(2H, m), 1.57–1.78(4H, m), 1.99–2.18 (5H, m), 2.35(2H, t, J=7.4Hz), 2.51(1H, s), 3.21(2H, t, J=8.7Hz), 3.81(1H, m), 4.01(2H, s), 4.58(2H, t, J=8.7Hz), 5.29–5.42(2H, m), 6.02(1H, d, J=7.5Hz), 6.80(1H, d, J=3.9Hz), 7.06(1H, d, J=1.8Hz), 7.18(1H, d, J=1.8Hz), 7.36(1H, d, J=3.9Hz).

IR(CHCl$_3$): 3512, 3446, 3427, 2669, 1709, 1641, 1543, 1506, 1477, 1460, 1173 cm$^{-1}$.

$[\alpha]_D^{25}$+53.8±0.9° (c=1.007, MeOH)

Elemental Analysis (C$_{28}$H$_{32}$BrNO$_4$S•0.1H$_2$O) Calcd.(%): C, 60.02; H, 5.79; Br, 14.26; N, 2.50; S, 5.72 Found(%): C, 59.87; H, 5.68; Br, 14.13; N, 2.59; S, 5.71

Compound I-175

300MHz $^1$H-NMR(CDCl$_3$) δ: 1.12(1H, m), 1.23–1.31 (2H, m), 1.44–1.51(2H, m), 1.60–1.78(4H, m), 2.03–2.28 (5H, m), 2.36(2H, t, J=7.4Hz), 2.56(1H, s), 3.87(1H, m), 4.21 (2H, s), 5.31–5.45(2H, m), 6.21(1H, d, J=7.2Hz), 7.18–7.37 (7H, m), 7.70(1H, d, J=7.2Hz), 7.80(1H, s).

IR(CHCl$_3$): 3514, 3444, 3423, 2667, 1709, 1649, 1537, 1502, 1454 cm$^{-1}$.

$[\alpha]_D^{25}$+78.2±1.2° (c=1.002, MeOH)

Elemental Analysis (C$_{30}$H$_{33}$BrNO$_3$S•0.1H$_2$O) Calcd.(%): C, 73.62; H, 6.84; N, 2.86; S, 6.55 Found(%): C, 73.49; H, 6.88; N, 2.89; S, 6.57

Compound I-176

300MHz $^1$H-NMR(CDCl$_3$) δ: 1.12(1H, m), 1.23–1.32 (2H, m), 1.44–1.51(2H, m), 1.61–1.78(4H, m), 2.03–2.28 (5H, m), 2.36(2H, t, J=7.4Hz), 2.57(1H, s), 3.88(1H, m), 4.21 (2H, s), 5.31–5.45(2H, m), 6.22(1H, d, J=7.2Hz), 6.94(1H, dd, J=1.5 and 4.8Hz), 7.04(1H, m), 7.21–7.25(2H, m), 7.35(1H, dd, J=7.2 and 7.8Hz), 7.71(1H, d, J=7.2Hz), 7.80 (1H, s).

IR(CHCl$_3$): 3512, 3444, 3423, 2669, 1709, 1647, 1539, 1504 cm$^{-1}$.

$[\alpha]_D^{25}$+77.1±1.2° (c=1.002, MeOH)

Elemental Analysis (C$_{28}$H$_{31}$NO$_3$S$_2$•0.2H$_2$O) Calcd.(%): C, 67.63; H, 6.36; N, 2.82; S, 12.90 Found(%): C, 67.57; H, 6.34; N, 2.97; S, 12.98

Compound I-177

300MHz $^1$H-NMR(CDCl$_3$) δ: 1.12(1H, m), 1.25–1.32 (2H, m), 1.44–1.51(2H, m), 1.60–1.78(4H, m), 2.03–2.28 (5H, m), 2.31(3H, s), 2.36(2H, t, J=7.2Hz), 2.56(1H, s), 3.87 (1H, m), 4.17(2H, s), 5.31–5.45(2H, m), 6.22(1H, d, J=7.2Hz), 7.09 and 7.15(each 2H, each d, J=8.1Hz), 7.19 (1H, d, J=7.2Hz), 7.34(1H, dd, J=7.2 and 7.8Hz), 7.69(1H, d, J=7.8Hz), 7.79(1H, s).

IR(CHCl$_3$): 3510, 3444, 3423, 2669, 1709, 1647, 1537, 1504 cm$^{-1}$.

$[\alpha]_D^{25}$+75.9±1.2° (c=1.004, MeOH)

Elemental Analysis (C$_{31}$H$_{35}$NO$_3$S) Calcd.(%): C, 74.22; H, 7.03; N, 2.79; S, 6.39 Found(%): C, 73.93; H, 7.13; N, 2.91; S, 6.38

Compound I-178

300MHz $^1$H-NMR(CDCl$_3$) δ: 1.13(1H, m), 1.24–1.31 (2H, m), 1.44–1.51(2H, m), 1.60–1.77(4H, m), 2.03–2.22 (5H, m), 2.36(2H, t, J=7.2Hz), 2.56(1H, s), 3.88(1H, m), 4.39 (2H, s), 5.31–5.45(2H, m), 6.26(1H, d, J=7.2Hz), 6.90–6.94 (2H, m), 7.15(1H, dd, J=1.5 and 5.1Hz), 7.27(1H, d, J=7.5Hz), 7.36(1H, t, J=7.5Hz), 7.71(1H, d, J=7.5Hz), 7.80 (1H, s).

IR(CHCl$_3$): 3510, 3444, 3423, 2667, 1709, 1649, 1537, 1504 cm$^{-1}$.

$[\alpha]_D^{25}$+76.6±1.2° (c=1.003, MeOH)

Elemental Analysis (C$_{28}$H$_{31}$NO$_3$S$_2$) Calcd.(%): C, 68.12; H, 6.33; N, 2.84; S, 12.99 Found(%): C, 67.83; H, 6.45; N, 3.04; S, 13.03

Compound I-179

300MHz $^1$H-NMR(CDCl$_3$) δ: 1.04(1H, m), 1.18–1.28 (2H, m), 1.39–1.47(2H, m), 1.56–1.78(4H, m), 1.98–2.18 (5H, m), 2.34(2H, t, J=7.2Hz), 2.50(1H, m), 3.80(1H, m), 4.08(2H, s), 5.29–5.41(2H, m), 5.95(1H, d, J=7.2Hz), 6.53 (1H, d, J=3.6Hz), 7.23–7.41(10H, m).

IR(CHCl$_3$): 3516, 3446, 3427, 1741, 1709, 1641, 1543, 1506, 1479, 1456 cm$^{-1}$.

$[\alpha]_D^{24.5}$+57.6±1.0° (c=1.007, MeOH)

Elemental Analysis (C$_{32}$H$_{35}$NO$_3$S•0.2H$_2$O) Calcd.(%): C, 74.30; H, 6.90; N, 2.71; S, 6.20 Found(%): C, 74.24; H, 6.89; N, 2.88; S, 6.47

Compound I-180

300MHz $^1$H-NMR(CDCl$_3$) δ: 1.17(1H, m), 1.24–1.35 (2H, m), 1.48–1.55(2H, m), 1.61–1.79(4H, m), 2.06–2.26 (5H, m), 2.37(2H, t, J=7.2Hz), 2.61(1H, m), 3.90(1H, m), 5.33–5.48(2H, m), 6.44(1H, d, J=7.2Hz), 7.31(1H, m), 7.47–7.65(5H, m), 7.90(1H, s).

IR(CHCl$_3$): 3516, 3440, 1714, 1655, 1604, 1514, 1473, 1446 cm$^{-1}$.

$[\alpha]_D^{25}$+92.1±1.3° (c=1.001, MeOH)

Elemental Analysis (C$_{28}$H$_{29}$NO$_4$•0.3H$_2$O) Calcd.(%): C, 74.91; H, 6.65; N, 3.12 Found(%): C, 74.81; H, 6.51; N, 3.29

Compound I-181

300MHz $^1$H-NMR(CDCl$_3$) δ: 1.04(1H, m), 1.18–1.28 (2H, m), 1.41–1.46(2H, m), 1.55–1.77(4H, m), 1.99–2.16 (5H, m), 2.34(2H, t, J=7.4Hz), 2.51(1H, s), 3.79(3H, s), 3.80 (1H, m), 4.08(2H, s), 5.29–5.42(2H, m), 5.97(1H, d, J=7.2Hz), 6.75(1H, d, J=3.9Hz), 6.85 and 7.15(each 2H, each d, J=8.4Hz), 7.37(1H, d, J=3.9Hz).

IR(CHCl$_3$): 3518, 3446, 3427, 1741, 1709, 1641, 1612, 1543, 1510, 1458 cm$^{-1}$.

$[\alpha]_D^{25}$+63.6±1.0° (c=1.000, MeOH)

Elemental Analysis (C$_{27}$H$_{33}$NO$_4$S•0.2H$_2$O) Calcd.(%): C, 68.88; H, 7.14; N, 2.97; S, 6.80 Found(%): C, 68.92; H, 7.02; N, 3.12; S, 6.96

Compound I-182

300MHz $^1$H-NMR(CDCl$_3$) δ: 1.04(1H, m), 1.18–1.27 (2H, m), 1.40–1.45(2H, m), 1.59–1.78(4H, m), 1.99–2.14 (5H, m), 2.34(2H, t, J=7.4Hz), 2.51(1H, s), 3.80(1H, m), 4.37 (2H, s), 5.29–5.41(2H, m), 5.97(1H, d, J=7.2Hz), 6.82(1H, d, J=3.6Hz), 7.20(1H, s), 7.34–7.37(3H, m), 7.69(1H, m), 7.86(1H, m).

IR(CHCl$_3$): 3512, 3444, 3427, 2669, 1709, 1643, 1543, 1508, 1458, 1431 cm$^{-1}$.

$[\alpha]_D^{25}$+60.7±1.0° (c=1.008, MeOH)

Elemental Analysis (C$_{28}$H$_{31}$NO$_3$S$_2$•0.3H$_2$O) Calcd.(%): C, 67.39; H, 6.38; N, 2.81; S, 12.85 Found(%): C, 67.44; H, 6.30; N, 3.15; S, 12.81

Compound I-183

300MHz $^1$H-NMR(CDCl$_3$) δ: 1.04(1H, m), 1.18–1.26 (2H, m), 1.39–1.44(2H, m), 1.54–1.75(4H, m), 1.99–2.15 (5H, m), 2.32(2H, t, J=7.4Hz), 2.50(1H, s), 3.80(1H, m), 4.12

(2H, s), 5.28–5.42(2H, m), 6.05(1H, d, J=7.5Hz), 6.78(1H, d, J=3.9Hz), 6.82–6.87(2H, m), 7.07–7.14(2H, m), 7.35(1H, d, J=3.9Hz).

IR(CHCl$_3$): 3508, 3444, 3197, 1707, 1635, 1543, 1508, 1456 cm$^{-1}$.

$[\alpha]_D^{25}$ +64.7±1.0° (c=1.004, MeOH)

Elemental Analysis (C$_{26}$H$_{31}$NO$_4$S•0.2H$_2$O) Calcd.(%): C, 68.30; H, 6.92; N, 3.06; S, 7.01 Found(%): C, 68.21; H, 6.96; N, 3.09; S, 6.93

Compound I-184

300MHz $^1$H-NMR(CDCl$_3$) δ: 1.15(1H, m), 1.26–1.35 (2H, m), 1.47–1.56(2H, m), 1.62–1.82(4H, m), 2.05–2.26 (5H, m), 2.37(2H, t, J=7.2Hz), 2.61(1H, m), 3.92(1H, m), 3.93(2H, s), 5.32–5.47(2H, m), 6.34(1H, d, J=6.9Hz), 7.31–7.43(2H, m), 7.53–7.59(2H, m), 7.67(1H, m), 7.5(1H, d, J=6.9Hz), 8.17(1H, s).

IR(CHCl$_3$): 3514, 3444, 2667, 1709, 1651, 1572, 1516, 1481, 1452 cm$^{-1}$.

$[\alpha]_D^{24}$ +81.2±1.2° (c=1.002, MeOH)

Elemental Analysis (C$_{28}$H$_{31}$NO$_3$•0.2H$_2$O) Calcd.(%): C, 77.64; H, 7.31; N, 3.23 Found(%): C, 77.59; H, 7.15; N, 3.44

Compound I-185

300MHz $^1$H-NMR(CDCl$_3$) δ: 1.06(1H, m), 1.21–1.28 (2H, m), 1.41–1.46(2H, m), 1.58–1.78(4H, m), 2.00–2.16 (5H, m), 2.35(2H, t, J=7.2Hz), 2.51(1H, m), 3.79(1H, m), 4.16(2H, s), 5.31–5.40(2H, m), 5.93(1H, d, J=7.8Hz), 6.80 (1H, d, J=3.6Hz), 7.03–7.12(2H, m), 7.20–7.28(2H, m), 7.35(1H, d, J=3.6Hz).

IR(CHCl$_3$): 3518, 3444, 3427, 1741, 1709, 1643, 1543, 1506, 1456 cm$^{-1}$.

$[\alpha]_D^{24}$ +56.2±0.9° (c=1.03, CHCl$_3$)

Elemental Analysis (C$_{26}$H$_{30}$FNO$_3$S•0.4H$_2$O) Calcd.(%): C, 67.48; H, 6.71; N, 3.03; S, 6.93; F, 4.11 Found(%): C, 67.49; H, 6.72; N, 3.09; S, 6.93; F, 4.11

Compound I-186

300MHz $^1$H-NMR(CDCl$_3$) δ: 1.04(1H, m), 1.19–1.29 (2H, m), 1.41–1.46(2H, m), 1.58–1.82(4H, m), 2.00–2.16 (5H, m), 2.34(2H, t, J=7.4Hz), 2.51(1H, s), 3.80(1H, m), 4.17 (2H, s), 5.08(2H, s), 5.28–5.41(2H, m), 5.90(1H, d, J=7.5Hz), 6.76(1H, d, J=3.9Hz), 6.90–6.95(2H, m), 7.18–7.25(2H, m), 7.31–7.38(6H, m).

IR(CHCl$_3$): 3516, 3446, 3427, 1741, 1709, 1641, 1601, 1543, 1502, 1454 cm$^{-1}$.

$[\alpha]_D^{24}$ +53.9±0.9° (c=1.005, MeOH)

Elemental Analysis (C$_{33}$H$_{37}$NO$_4$S) Calcd.(%): C, 72.90; H, 6.86; N, 2.58; S, 5.90 Found(%): C, 72.64; H, 6.92; N, 2.52; S, 5.74

Compound I-187

300MHz $^1$H-NMR(CDCl$_3$) δ: 1.04(1H, m), 1.18–1.28 (2H, m), 1.41–1.46(2H, m), 1.57–1.78(4H, m), 1.99–2.15 (5H, m), 2.34(2H, t, J=7.4Hz), 2.51(1H, s), 3.80(1H, m), 4.16 (2H, s), 4.54–4.57(2H, m), 5.24–5.41(4H, m), 5.94(1H, d, J=7.5Hz), 6.04(1H, m), 6.79(1H, d, J=3.9Hz), 6.85–6.93 (2H, m), 7.15–7.24(2H, m), 7.34(1H, d, J=3.9Hz).

IR(CHCl$_3$): 3516, 3446, 3427, 1739, 1709, 1641, 1543, 1506, 1477 cm$^{-1}$.

$[\alpha]_D^{24}$ +59.0±1.0° (c=1.007, MeOH)

Elemental Analysis (C$_{29}$H$_{35}$NO$_4$S•0.2H$_2$O) Calcd.(%): C, 70.05; H, 7.18; N, 2.82; S, 6.45 Found(%): C, 69.97; H, 7.16; N, 2.80; S, 6.52

Compound I-188 mp.84–85° C.

300MHz $^1$H-NMR(CDCl$_3$) δ: 1.04(1H, m), 1.18–1.29 (2H, m), 1.41–1.46(2H, m), 1.56–1.81(4H, m), 2.00–2.17 (5H, m), 2.35(2H, t, J=7.2Hz), 2.51(1H, s), 3.80(1H, m), 4.07 (2H, s), 5.05(2H, s), 5.29–5.42(2H, m), 5.93(1H, d, J=7.5Hz), 6.75(1H, d, J=3.9Hz), 6.92 and 7.15(each 2H, each d, J=8.7Hz), 7.31–7.44(6H, d, m).

IR(CHCl$_3$): 3521, 3446, 3427, 1741, 1709, 1643, 1612, 1543, 1510, 1456 cm$^{-1}$.

$[\alpha]_D^{24}$ +56.1±1.0° (c=1.002, MeOH)

Elemental Analysis (C$_{33}$H$_{37}$NO$_4$S) Calcd.(%): C, 72.90; H, 6.86; N, 2.58; S, 5.90 Found(%): C, 72.78; H, 6.88; N, 2.74; S, 5.84

Compound I-189

300MHz $^1$H-NMR(CDCl$_3$) δ: 1.04(1H, m), 1.19–1.29 (2H, m), 1.41–1.46(2H, m), 1.56–1.79(4H, m), 2.00–2.15 (5H, m), 2.35(2H, t, J=7.2Hz), 2.51(1H, s), 3.80(1H, m), 4.07 (2H, s), 4.51–4.53(2H, m), 5.26–5.44(4H, m), 5.94(1H, d, J=7.5Hz), 6.05(1H, m), 6.76(1H, d, J=3.9Hz), 6.87 and 7.14(each 2H, each d, J=8.7Hz), 7.36(1H, d, J=3.9Hz).

IR(CHCl$_3$): 3512, 3446, 3427, 1741, 1709, 1643, 1612, 1543, 1508, 1458 cm$^{-1}$.

$[\alpha]_D^{24}$ +61.6±1.0° (c=1.004, MeOH)

Elemental Analysis (C$_{29}$H$_{35}$NO$_4$S•0.4H$_2$O) Calcd.(%): C, 69.54; H, 7.20; N, 2.78; S, 6.40 Found(%): C, 69.47; H, 7.22; N, 2.84; S, 6.51

Compound I-190

300MHz $^1$H-NMR(CDCl$_3$) δ: 1.05(1H, m), 1.18–1.32 (2H, m), 1.39–1.48(2H, m), 1.54–1.80(4H, m), 1.98–2.20 (5H, m), 2.34(2H, t, J=7.2Hz), 2.51(1H, m), 3.81(1H, m), 4.04(2H, s), 5.29–5.42(2H, m), 5.93(1H, d, J=7.5Hz), 6.68–6.78(2H, m), 7.36(1H, d, J=3.6Hz).

IR(CHCl$_3$): 3517, 3446, 3427, 1741, 1709, 1643, 1543, 1504, 1489, 1444, 1250, 1041 cm$^{-1}$.

$[\alpha]_D^{24}$ +59.4±1.0° (c=1.011, MeOH)

Elemental Analysis (C$_{27}$H$_{31}$NO$_5$S) Calcd.(%): C, 67.34; H, 6.49; N, 2.91; S, 6.66 Found(%): C, 67.27; H, 6.45; N, 3.04; S, 6.63

Compound I-191

300MHz $^1$H-NMR(CDCl$_3$) δ: 1.06(1H, m), 1.18–1.32 (2H, m), 1.39–1.48(2H, m), 1.54–1.80(4H, m), 1.98–2.20 (5H, m), 2.34(2H, t, J=7.5Hz), 2.51(1H, m), 3.81(1H, m), 4.12(2H, s), 5.30–5.42(2H, m), 6.04(1H, d, J=7.2Hz), 6.77 (1H, d, J=3.6Hz), 6.89–7.04(3H, m), 7.28(1H, m), 7.38(1H, d, J=3.6Hz).

IR(CHCl$_3$): 3518, 3446, 3427, 1739, 1709, 1643, 1545, 1506 cm$^{-1}$.

$[\alpha]_D^{25}$ +62.6±1.0° (c=1.009, MeOH)

Elemental Analysis (C$_{26}$H$_{30}$FNO$_3$S) Calcd.(%): C, 68.54; H, 6.64; N, 3.07; S, 7.04; F, 4.17 Found(%): C, 68.25; H, 6.37; N, 3.19; S, 7.12; F, 4.12

Compound I-192

300MHz $^1$H-NMR(CDCl$_3$) δ: 1.06(1H, m), 1.18–1.32 (2H, m), 1.40–1.48(2H, m), 1.54–1.80(4H, m), 1.98–2.20 (5H, m), 2.35(2H, t, J=7.5Hz), 2.52(1H, m), 3.81(1H, m), 4.19(2H, s), 5.30–5.42(2H, m), 5.99(1H, d, J=7.2Hz), 6.78 and 7.37(each 1H, each d, each J=3.6Hz), 7.40–7.54(4H, m).

IR(CHCl$_3$): 3516, 3446, 3427, 1740, 1709, 1643, 1545, 1506, 1450, 1330, 1167, 1130, 1074 cm$^{-1}$.

$[\alpha]_D^{25}$+55.4±0.9° (c=1.029, MeOH)

Elemental Analysis (C$_{27}$H$_{30}$F$_3$NO$_3$S) Calcd.(%): C, 64.14; H, 5.98; N, 2.77; S, 6.34; F,11.27 Found(%): C, 63.95; H, 5.99; N, 2.90; S, 6.36; F,10.98

Compound I-193

300MHz $^1$H-NMR(CDCl$_3$) δ: 1.05(1H, m), 1.24–1.28 (2H, m), 1.42–1.46(2H, m), 1.58–1.79(4H, m), 2.01–2.21 (5H, m), 2.35(2H, t, J=7.2Hz), 2.51(1H, m), 3.80(1H, m), 4.26(2H, s), 5.33–5.38(2H, m), 5.94(1H, d, J=7.2Hz), 6.79 (1H, d, J=3.9Hz), 7.21–7.28(3H, m), 7.35–7.40(2H, m).

IR(CHCl$_3$): 3518, 3446, 3427, 1743, 1709, 1643, 1543, 1506 cm$^{-1}$.

$[\alpha]_D^{25}$+55.5±0.9° (c=1.06, CHCl$_3$)

Elemental Analysis (C$_{26}$H$_{30}$ClNO$_3$S•0.3H$_2$O) Calcd.(%): C, 65.41; H, 6.46; N, 2.93; S, 6.72; Cl, 7.43 Found(%): C, 65.41; H, 6.40; N, 3.08; S, 6.75; Cl, 7.31

Compound I-194

300MHz $^1$H-NMR(CDCl$_3$) δ: 1.04(1H, m), 1.18–1.28 (2H, m), 1.39–1.46(2H, m), 1.56–1.78(4H, m), 1.98–2.16 (5H, m), 2.30(6H, s), 2.34(2H, t, J=7.2Hz), 2.50(1H, m), 3.80(1H, m), 4.16(2H, s), 5.28–5.41(2H, m), 5.93(1H, d, J=6.9Hz), 6.78(1H, d, J=3.9Hz), 7.03–7.14(3H, m), 7.77 (1H, d, J=3.9Hz).

IR(CHCl$_3$): 3516, 3446, 3427, 2669, 1709, 1641, 1543, 1506, 1456 cm$^{-1}$.

$[\alpha]_D^{24}$+66.6±1.0° (c=1.009, MeOH)

Elemental Analysis (C$_{28}$H$_{35}$NO$_3$S•0.2H$_2$O) Calcd.(%): C, 71.67; H, 7.60; N, 2.98; S, 6.83 Found(%): C, 71.71; H, 7.54; N, 3.15; S, 6.81

Compound I-195

300MHz $^1$H-NMR(CDCl$_3$) δ: 1.05(1H, m), 1.22–1.28 (2H, m), 1.42–1.47(2H, m), 1.59–1.78(4H, m), 2.01–2.17 (5H, m), 2.35(2H, t, J=7.2Hz), 2.50(1H, m), 3.82(1H, m), 4.32(2H, s), 5.35–5.37(2H, m), 5.94(1H, d, J=6.9Hz), 6.76 (1H, d, J=3.9Hz), 7.33–7.39(3H, m), 7.50 (1H, m), 7.69(1H, d, J=3.9Hz).

IR(CHCl$_3$): 3316, 3446, 3427, 1743, 1709, 1643, 1543, 1506, 1456, 1163, 1126 cm$^{-1}$.

$[\alpha]_D^{25}$+54.5±1.0° (c=1.00, CHCl$_3$)

Elemental Analysis (C$_{27}$H$_{30}$F$_3$NO$_3$S•0.2H$_2$O) Calcd.(%): C, 63.93; H, 6.02; N, 2.75; S, 6.30 Found(%): C, 63.92; H, 5.85; N, 2.94; S, 6.38

Compound I-196

300MHz $^1$H-NMR(CDCl$_3$) δ: 1.05(1H, m), 1.22–1.28 (2H, m), 1.42–1.46(2H, m), 1.58–1.80(4H, m), 2.01–2.21 (5H, m), 2.35(2H, t, J=7.2Hz), 2.52(1H, m), 3.81(1H, m), 3.88(3H, s), 4.06(2H, s), 5.33–5.38(2H, m), 5.94(1H, d, J=10.2Hz), 6.70(1H, d, J=3.6Hz), 6.87–6.97(3H, m), 7.36 (1H, d, J=3.6Hz).

IR(CHCl$_3$): 3517, 3446, 3427, 2673, 1741, 1709, 1643, 1543, 1516, 1274 1030 cm$^{-1}$.

$[\alpha]_D^{25}$+54.2±0.9° (c=1.00, CHCl$_3$)

Elemental Analysis (C$_{27}$H$_{32}$FNO$_4$S•0.3H$_2$O) Calcd.(%): C, 66.04; H, 6.69; N, 2.85; S, 6.53; F, 3.87 Found(%): C, 66.16; H, 6.61; N, 2.82; S, 6.34; F, 3.66

Compound I-197

300MHz $^1$H-NMR(CDCl$_3$) δ: 1.05(1H, m), 1.18–1.27 (2H, m), 1.41–1.45(2H, m), 1.56–1.77(4H, m), 1.98–2.13 (5H, m), 2.34(2H, t, J=7.5Hz), 2.50(1H, s), 3.21(2H, t, J=8.7Hz), 3.80(1H, m), 4.07(2H, s), 4.57(2H, t, J=8.7Hz), 5.29–5.41(2H, m), 6.00(1H, d, J=7.5Hz), 6.79(1H, d, J=3.6Hz), 6.79(1H, dd, J=7.2 and 7.5Hz), 6.95(1H, d, J=7.5Hz), 7.09(1H, d, J=7.2Hz), 7.36(1H, d, J=3.6Hz).

IR(CHCl$_3$): 3514, 3446, 3427, 2669, 1739, 1709, 1641, 1543, 1506, 1477, 1456, 1441 cm$^{-1}$.

$[\alpha]_D^{25}$+61.1±1.0° (c=1.004, MeOH)

Elemental Analysis (C$_{28}$H$_{33}$NO$_4$S•0.2H$_2$O) Calcd.(%): C, 69.60; H, 6.97; N, 2.90; S, 6.63 Found(%): C, 69.68; H, 6.89; N, 3.19; S, 6.65

Compound I-198

300MHz $^1$H-NMR(CDCl$_3$) δ: 1.04(1H, m), 1.18–1.27 (2H, m), 1.40–1.46(2H, m), 1.56–1.76(4H, m), 1.98–2.13 (5H, m), 2.33(2H, t, J=7.5Hz), 2.50(1H, s), 3.21(2H, t, J=8.7Hz), 3.80(1H, m), 4.24(2H, s), 5.28–5.40(2H, m), 5.97(1H, d, J=7.2Hz), 6.79(1H, d, J=3.6Hz), 7.22(1H, dd, J=1.2 and 8.1Hz), 7.29(1H, d, J=5.4Hz), 7.38(1H, d,J=3.6Hz), 7.44(1H, d, J=5.4Hz), 7.68(1H, d, J=1.2Hz), 7.81(1H, d, J=8.1Hz).

IR(CHCl$_3$): 3516, 3446, 3427, 1741, 1709, 1643, 1543, 1506, 1547 cm$^{-1}$.

$[\alpha]_D^{25}$+62.0±1.0° (c=1.000, MeOH)

Elemental Analysis (C$_{28}$H$_{31}$NO$_3$S$_2$•0.2H$_2$O) Calcd.(%): C, 67.63; H, 6.36; N, 2.82; S, 12.90 Found(%): C, 67.55; H, 6.28; N, 2.97; S, 12.90

Compound I-199

300MHz $^1$H-NMR(CDCl$_3$) δ: 1.04(1H, m), 1.17–1.27 (2H, m), 1.40–1.45(2H, m), 1.54–1.77(4H, m), 1.98–2.15 (5H, m), 2.34(2H, t, J=7.2Hz), 2.51(1H, s), 3.80(1H, m),4.25 (2H, s), 5.28–5.41(2H, m), 5.97(1H, d, J=7.2Hz), 6.79(1H, d, J=3.9Hz), 7.24(1H, dd, J=1.5 and 8.1Hz), 7.30(1H, d, J=5.4Hz), 7.38(1H, d, J=3.6Hz), 7.41(1H, d, J=5.4Hz), 7.73(1H, m), 7.76(1H, d, J=8.1Hz).

IR(CHCl$_3$): 3516, 3447, 3427, 1741, 1709, 1643, 1543, 1506, 1458 cm$^{-1}$.

$[\alpha]_D^{25}$+62.1±1.0° (c=1.008, MeOH)

Elemental Analysis (C$_{28}$H$_{31}$NO$_3$S$_2$•0.3H$_2$O) Calcd.(%): C, 67.39; H, 6.38; N, 2.81; S, 12.85 Found(%): C, 67.42; H, 6.29; N, 2.99; S, 12.94

Compound I-200

300MHz $^1$H-NMR(CDCl$_3$) δ: 1.03(1H, m), 1.16–1.22 (2H, m), 1.39–1.44(2H, m), 1.53–1.76(4H, m), 1.97–2.14 (5H, m), 2.33(2H, t, J=7.5Hz), 2.49(1H, s), 3.79(1H, m),4.39 (2H, s), 5.28–5.40(2H, m), 5.98(1H, d, J=7.5Hz), 6.86(1H, d, J=3.9Hz), 7.21(1H, d, J=6.9Hz), 7.35(1H, dd, J=6.9 and 8.1Hz), 7.36(1H, d, J=5.4Hz), 7.36(1H, d, J=3.9Hz), 7.42 (1H, d, J=5.4Hz), 7.74(1H, d, J=8.1Hz).

IR(CHCl$_3$): 3516, 3446, 3427, 1739, 1709, 1643, 1543, 1506, 1458 cm$^{-1}$.

[α]$_D^{25}$+58.4±1.0° (c=1.003, MeOH)
Elemental Analysis (C$_{28}$H$_{31}$NO$_3$S$_2$•0.2H$_2$O) Calcd.(%): C, 67.63; H, 6.36; N, 2.82; S, 12.90 Found(%): C, 67.62; H, 6.27; N, 3.09; S, 12.92

Compound I-201

300MHz $^1$H-NMR(CDCl$_3$+CD$_3$OD) δ: 1.08(1H, m), 1.22–1.28(2H, m), 1.41–1.46(2H, m), 1.55–1.71(4H, m), 2.01–2.10(5H, m), 2.29(2H, t, J=7.4Hz), 2.51(1H, s), 3.77(1H, m), 4.29(2H, s), 5.34–5.40(2H, m), 6.80(1H, d, J=3.9Hz), 6.93(1H, dd, J=1.8 and 8.7Hz), 7.10(1H, d, J=1.8Hz), 7.22(1H, s), 7.36(1H, d, J=3.9Hz), 7.65(1H, d, J=8.7Hz).
IR(CHCl$_3$): 3508, 3423, 3236, 1709, 1633, 1601, 1545, 1510, 1441 cm$^{-1}$.
[α]$_D^{25}$+57.5±1.0° (c=1.006, MeOH)
Elemental Analysis (C$_{28}$H$_{31}$NO$_4$S$_2$•0.5H$_2$O) Calcd.(%): C, 64.84; H, 6.21; N, 2.70; S, 12.36 Found(%): C, 67.57; H, 6.20; N, 2.93; S, 12.38

Compound I-202

300MHz $^1$H-NMR(CDCl$_3$) δ: 1.05(1H, m), 1.24–1.28(2H, m), 1.41–1.48(2H, m), 1.58–1.79(4H, m), 2.02–2.22(5H, m), 2.33(2H, t, J=7.5Hz), 2.51(1H, m), 3.78(1H, m), 4.25(2H, s), 4.70(2H, s), 5.31–5.42(2H, m), 6.00(1H, d, J=7.2Hz), 6.74(1H, d, J=3.6Hz), 7.24–7.42(5H, m).
IR(CHCl$_3$): 3518, 3444, 3427, 1709, 1643, 1543, 1506, 1456 cm$^{-1}$.
[α]$_D^{26}$+51.9±0.9° (c=1.04, CHCl$_3$)
Elemental Analysis (C$_{27}$H$_{33}$FNO$_4$S•0.7H$_2$O) Calcd.(%): C, 67.53; H, 7.22; N, 2.92; S, 6.02 Found(%): C, 67.92; H, 7.13; N, 2.88; S, 6.11

Compound I-203

300MHz $^1$H-NMR(CDCl$_3$) δ: 1.02(1H, m), 1.22–1.28(2H, m), 1.40–1.42(2H, m), 1.57–1.72(4H, m), 1.82–1.85(4H, m), 2.01–2.13(5H, m), 2.27(2H, t, J=7.5Hz), 2.49(1H, m), 2.71–2.73(4H, m), 3.67(1H, d, J=13.2Hz), 3.76(1H,m), 3.83(1H, d, J=13.2Hz), 4.26(1H, d, J=16.5Hz), 4.34(1H, d, J=16.5Hz), 5.33–5.45(2H, m), 6.04(1H, d, J=7.2Hz), 6.70(1H, d, J=3.6Hz), 7.16–7.33(4H, m), 7.43((1H, d, J=3.6Hz).
IR(CHCl$_3$): 3518, 3446, 3424, 2472, 1707, 1643, 1545, 1506, 1456 cm$^{-1}$.
[α]$_D^{26}$+41.9±0.8° (c=1.03, CHCl$_3$)
Elemental Analysis (C$_{31}$H$_{40}$N$_2$O$_3$S•0.6H$_2$O) Calcd.(%): C, 70.05; H, 7.81; N, 5.27; S, 6.03 Found(%): C, 70.01; H, 7.81; N, 5.18; S, 5.86

Compound I-204

300MHz $^1$H-NMR(CDCl$_3$) δ: 1.06(1H, m), 1.22–1.29(2H, m), 1.41–1.46(2H, m), 1.58–1.72(4H, m), 2.03–2.17(5H, m), 2.31(2H, t, J=7.2Hz), 2.51(1H, m), 2.60(6H, s), 3.79(1H, m), 3.94(1H, d, J=13.2Hz), 3.99(1H, d, J=13.2Hz), 4.39(2H,s), 5.30–5.44(2H, m), 6.01(1H, d, J=7.2Hz), 6.72(1H, d, J=3.9Hz), 7.26–7.40(4H, m), 7.56(1H, d, J=7.2Hz).
IR(CHCl$_3$): 3519, 3444, 3425, 2455, 1753, 1712, 1643, 1545, 1508, 1458 cm$^{-1}$.
[α]$_D^{26}$+41.2±0.8° (c=1.02, CHCl$_3$)
Elemental Analysis (C$_{29}$H$_{38}$N$_2$O$_3$S•1.7H$_2$O•0.2CHCl$_3$) Calcd.(%): C, 63.86; H, 7.63; N, 5.10; S, 5.84; Cl, 3.87 Found(%): C, 63.88; H, 7.51; N, 4.94; S, 5.63; Cl, 4.22

Compound I-205

300MHz $^1$H-NMR(CDCl$_3$) δ: 1.14(1H, m), 1.24–1.36(2H, m), 1.45–1.54(2H, m), 1.60–1.79(4H, m), 2.03–2.26(5H, m), 2.36(2H, t, J=7.5Hz), 2.58(1H, m), 3.19–3.26(4H, m), 3.89(1H, m), 5.32–5.45(2H, m), 6.33(1H, d, J=6.3Hz), 7.24(1H, d, J=7.2Hz), 7.34 and 7.46(each 1H, each m), 7.61(1H, dd; J=1.5 and 8.4Hz), 7.68(1H, d, J=1.5Hz), 7.98–8.04(2H, m).
IR(CHCl$_3$): 3518, 3444, 2667, 1709, 1649, 1597, 1514, 1483, 1450, 1294 cm$^{-1}$.
[α]$_D^{25}$+78.7±1.2° (c=1.003, MeOH)
Elemental Analysis (C$_{30}$H$_{33}$NO$_4$) Calcd.(%): C, 75.54; H, 7.10; N, 2.94 Found(%): C, 75.62; H, 7.05; N, 2.94

Compound I-206

300MHz $^1$H-NMR(CDCl$_3$) δ: 1.10(1H, m), 1.22–1.36(2H, m), 1.40–1.52(2H, m), 1.56–1.81(4H, m), 2.00–2.24(5H, m), 2.35(2H, t, J=7.2Hz), 2.50(1H, m), 3.84(1H, m), 3.99(2H, s), 5.30–5.43(2H, m), 6.05(1H, d, J=3.3Hz), 6.29(1H, d, J=7.8Hz), 6.99–7.05(3H, m), 7.17–7.22(2H, m).
IR(CHCl$_3$): 3512, 3435, 1739, 1709, 1653, 1606, 1549, 1510 cm$^{-1}$.
[α]$_D^{26}$+71.0±1.1° (c=1.005, MeOH)
Elemental Analysis (C$_{26}$H$_{30}$FNO$_4$) Calcd.(%): C, 71.05; H, 6.88; N, 3.19; F,4.32 Found(%): C, 70.78; H, 6.97; N, 3.30; F,4.27

Compound I-207

300MHz $^1$H-NMR(CDCl$_3$) δ: 1.10(1H, m), 1.22–1.34(2H, m), 1.40–1.50(2H, m), 1.56–1.81(4H, m), 2.00–2.24(5H, m), 2.35(2H, t, J=7.2Hz), 2.50(1H, m), 3.84(1H, m), 4.02(2H, s), 5.30–5.43(2H, m), 6.07(1H, d, J=3.3Hz), 6.30(1H, d, J=7.5Hz), 7.02(1H, d, J=3.3Hz), 7.22–7.36(5H, m).
IR(CHCl$_3$): 3516, 3435, 2669, 1709, 1651, 1606, 1547, 1498 cm$^{-1}$.
[α]$_D^{24}$+76.5±1.2° (c=1.005, MeOH)
Elemental Analysis (C$_{26}$H$_{31}$FNO$_4$•0.1H$_2$O) Calcd.(%): C, 73.77; H, 7.43; N, 3.31 Found(%): C, 73.63; H, 7.27; N, 3.42

Compound I-208

300MHz $^1$H-NMR(CDCl$_3$) δ: 1.04(1H, m), 1.16–1.26(2H, m), 1.39–1.44(2H, m), 1.55–1.76(4H, m), 1.98–2.18(5H, m), 2.33(2H, t, J=7.2Hz), 2.50(1H, s), 3.79(1H, m), 4.42(2H, s), 5.28–5.40(2H, m), 5.98(1H, d, J=6.9Hz), 6.78(1H, d, J=2.1Hz), 6.84(1H, d, J=3.6Hz), 7.12–7.21(2H, m), 7.36(1H, d, J=3.6Hz), 7.50(1H, dd, J=1.5 and 7.5Hz), 7.63(1H, d, 2.1Hz).
IR(CHCl$_3$): 3516, 3446, 3427, 2665, 1741, 1709, 1643, 1523, 1506, 1458, 1427 cm$^{-1}$.
[α]$_D^{25}$+63.4±1.0° (c=1.006, MeOH)
Elemental Analysis (C$_{28}$H$_{31}$NO$_4$S•0.2H$_2$O) Calcd.(%): C, 69.89; H, 6.58; N, 2.91; S, 6.66 Found(%): C, 69.68; H, 6.48; N, 3.10; S, 6.62

Compound I-209

300MHz $^1$H-NMR(CDCl$_3$) δ: 1.07(1H, m), 1.22–1.29(2H, m), 1.42–1.47(2H, m), 1.59–1.82(4H, m), 2.01–2.20(5H, m), 2.35(2H, t, J=7.2Hz), 2.52(1H, m), 2.94(3H,s), 3.81(1H, m), 4.19(2H, s), 4.44(2H, s), 5.31–5.38(2H, m), 5.35(1H,d, J=7.2Hz), 6.63–6.72(4H, m), 7.16–7.25(6H, m), 7.36(1H, d, J=3.6Hz).

IR(CHCl$_3$): 3514, 3444, 3427, 1741, 1709, 1643, 1599, 1543, 1506, 1456 cm$^{-1}$.

$[\alpha]_D^{26}$+50.8±0.9° (c=1.04, CHCl$_3$)

Elemental Analysis (C$_{34}$H$_{40}$N$_2$O$_3$S•0.7H$_2$O) Calcd.(%): C, 71.72; H, 7.33; N, 4.92; S, 5.63 Found(%): C, 71.81; H, 7.29; N, 4.81; S, 5.54

Compound I-210

300MHz $^1$H-NMR(CDCl$_3$) δ: 1.14–1.68(11H, m), 1.91–2.16(9H, m), 2.21(2H, t, J=7.2Hz), 2.57(1H, m), 2.98 (1H, m), 3.71(1H, m), 3.89(2H, s), 4.28(1H, d, J=16.5Hz), 4.30(1H, d, J=16.5Hz), 5.28–5.50(3H, m), 6.56(1H, m), 6.75(1H, m), 7.20–7.33(2H, m), 7.49–7.55(2H, m).

IR(CHCl$_3$): 3518, 3425, 1753, 1711, 1641, 1545, 1508, 1456 cm$^{-1}$.

$[\alpha]_D^{26}$+35.6±0.7° (c=1.03, CHCl$_3$)

Compound I-211

300MHz $^1$H-NMR(CDCl$_3$) δ: 1.04(1H, m), 1.17–1.28 (2H, m), 1.39–1.46(2H, m), 1.54–1.78(4H, m), 1.98–2.19 (5H, m), 2.33(2H, t, J=7.2Hz), 2.51(1H, m), 3.80(1H, m), 4.29(2H, s), 5.28–5.40(2H, m), 5.95(1H, d, J=7.2Hz), 6.82 (1H, d, J=3.6Hz), 7.23(1H, dd, J=1.5 and 8.1Hz), 7.30–7.47 (4H, m), 7.55(1H, d, J=8.1Hz), 7.89(1H, d, J=7.8Hz), 7.93 (1H, dd, J=1.5 and 7.8Hz).

IR(CHCl$_3$): 3510, 3446, 3427, 2671, 1739, 1709, 1641, 1545, 1506, 1458, 1427 cm$^{-1}$.

$[\alpha]_D^{24}$+60.2±1.0° (c=1.006, MeOH)

Elemental Analysis (C$_{32}$H$_{33}$NO$_4$S•0.2H$_2$O) Calcd.(%): C, 72.34; H, 6.34; N, 2.64; S, 6.04 Found(%): C, 72.28; H, 6.25; N, 2.72; S, 5.93

Compound I-212

300MHz $^1$H-NMR(CDCl$_3$) δ: 1.05(1H, m), 1.18–1.30 (2H, m), 1.38–1.47(2H, m), 1.54–1.80(4H, m), 1.98–2.20 (5H, m), 2.34(2H, t, J=7.5Hz), 2.51(1H, m), 3.78(3H, s), 3.80(1H, m), 3.86(3H, s), 4.15(2H, s), 5.29–5.42(2H, m), 5.93(1H, d, J=7.5Hz), 6.78–6.85(3H, m), 7.01(1H, t, J=8.1Hz), 7.36(1H, d, J=3.9Hz).

IR(CHCl$_3$): 3516, 3446, 3425, 2667, 1739, 1709, 1641, 1543, 1506, 1481, 1273, 1076 cm$^{-1}$.

$[\alpha]_D^{25}$+60.8±1.0° (c=1.002, MeOH)

Elemental Analysis (C$_{28}$H$_{35}$NO$_5$S•0.1H$_2$O) Calcd.(%): C, 67.33; H, 7.10; N, 2.80; S, 6.42 Found(%): C, 67.21; H, 7.08; N, 2.92; S, 6.45

Compound I-213

300MHz $^1$H-NMR(CDCl$_3$) δ: 1.08(1H, m), 1.19–1.30 (2H, m), 1.42–1.47(2H, m), 1.58–1.78(4H, m), 2.01–2.16 (5H, m), 2.38(2H, t, J=7.2Hz), 2.39(3H, s), 2.53(1H, s),3.82 (1H, m), 4.15(2H, s), 5.31–5.44(2H, m), 5.87(1H, s), 6.05 (1H, d, J=7.2Hz), 6.86(1H, d, J=3.9Hz), 7.38(1H, d, J=3.9Hz).

IR(CHCl$_3$): 3516, 3444, 3427, 2669, 1709, 1643, 1608, 1545, 1508, 1456 cm$^{-1}$.

$[\alpha]_D^{25}$+64.3±1.0° (c=1.012, MeOH)

Elemental Analysis (C$_{24}$H$_{30}$N$_2$O$_4$S•0.2H$_2$O) Calcd.(%): C, 64.61; H, 6.87; N, 6.28; S, 7.19 Found(%): C, 64.70; H, 6.84; N, 6.34; S, 7.27

Compound I-214

300MHz $^1$H-NMR(CDCl$_3$) δ: 1.06(1H, m), 1.19–1.28 (2H, m), 1.41–1.46(2H, m), 1.58–1.79(4H, m), 2.00–2.15 (5H, m), 2.33–2.37(5H, m), 2.51(1H, s), 3.81–3.82(4H,m), 4.08(2H, s), 5.29–5.42(2H, m), 5.93(1H, d, J=6.9Hz), 6.70 (1H, s), 6.72(1H, d, J=7.8Hz), 6.77(1H, d, J=3.6Hz), 7.04 (1H, d, J=7.8Hz), 7.34(1H, d, J=3.6Hz).

IR(CHCl$_3$): 3516, 3446, 3427, 2669, 1741, 1709, 1641, 1614, 1583, 1506, 1458 cm$^{-1}$.

$[\alpha]_D^{25}$+58.9±1.0° (c=1.012, MeOH)

Elemental Analysis (C$_{28}$H$_{35}$NO$_4$S•0.2H$_2$O) Calcd.(%): C, 69.31; H, 7.35; N, 2.89; S, 6.61 Found(%): C, 69.21; H, 7.35; N, 3.03; S, 6.65

Compound I-215 mp. 128–129° C.

300MHz $^1$H-NMR(CDCl$_3$) δ: 1.05(1H, m), 1.19–1.28 (2H, m), 1.41–1.46(2H, m), 1.56–1.79(4H, m), 2.00–2.15 (5H, m), 2.34(2H, t, J=7.2Hz), 2.51(1H, s), 3.80(1H, m), 3.84(3H, s), 4.33(2H, s), 5.29–5.42(2H, m), 5.94(1H, d, J=6.9Hz), 6.83(1H, d, J=3.6Hz), 7.01(1H, dd, J=2.7 and 9.0Hz), 7.11(1H, d, J=2.7Hz), 7.21(1H, s), 7.36(1H, d, J=3.6Hz), 7.72(1H, d, J=9.0Hz).

IR(CHCl$_3$): 3516, 3446, 3427, 1739, 1709, 1643, 1601, 1543, 1506, 1458, 1427 cm$^{-1}$.

$[\alpha]_D^{25}$+55.7±1.0° (c=1.008, MeOH)

Elemental Analysis (C$_{29}$H$_{33}$NO$_4$S$_2$) Calcd.(%): C, 66.51; H, 6.35; N, 2.67; S, 12.25 Found(%): C, 66.41; H, 6.30; N, 2.96; S, 12.15

Compound I-216

300MHz $^1$H-NMR(CDCl$_3$) δ: 1.04(1H, m), 1.16–1.29 (2H, m), 1.39–1.46(2H, m), 1.55–1.79(4H, m), 1.98–2.19 (5H, m), 2.34(2H, t, J=7.2Hz), 2.51(1H, m), 3.80(1H, m), 3.87 and 4.20(each 2H, each s), 5.28–5.40(2H, m), 5.93(1H, d, J=8.1Hz), 6.81(1H, d, J=3.9Hz), 7.24–7.39(5H, m), 7.53 (1H, d, J=7.2Hz), 7.71–7.77(2H, m).

IR(CHCl$_3$): 3516, 3446, 3427, 1739, 1709, 1643, 1543, 1506, 1456 cm$^{-1}$.

$[\alpha]_D^{25}$+56.7±1.0° (c=1.000, MeOH)

Elemental Analysis (C$_{33}$H$_{35}$NO$_3$S•0.1H$_2$O) Calcd.(%): C, 75.14; H, 6.73; N, 2.66; S, 6.08 Found(%): C, 75.14; H, 6.80; N, 2.74; S, 5.83

Compound I-217

300MHz $^1$H-NMR(CDCl$_3$) δ: 1.07(1H, m), 1.19–1.32 (2H, m), 1.40–1.48(2H, m), 1.56–1.78(4H, m), 2.00–2.21 (5H, m), 2.34(2H, t, J=7.5Hz), 2.54(1H, m), 3.13–3.24(4H, m), 3.85(1H, m), 4.13(2H, s), 5.28–5.42(2H, m), 6.17(1H, d, J=7.2Hz), 7.06–7.17(4H, m), 7.22(1H, d, J=7.8Hz), 7.44 (1H, dd, J=1.8 and 7.8Hz), 7.53(1H, d, J=1.8Hz).

IR(CHCl$_3$): 3518, 3446, 1739, 1709, 1651, 1570, 1518, 1491, 1456 cm$^{-1}$.

$[\alpha]_D^{25}$+73.3±1.1° (c=1.000, MeOH)

Elemental Analysis (C$_{30}$H$_{35}$NO$_3$•0.2H$_2$O) Calcd.(%): C, 78.13; H, 7.44; N, 3.04 Found(%): C, 78.25; H, 7.76; N, 3.29

Compound I-218

300MHz $^1$H-NMR(CDCl$_3$) δ: 1.05(1H, m), 1.18–1.30 (2H, m), 1.39–1.48(2H, m), 1.54–1.81(4H, m), 1.98–2.20 (5H, m), 2.34(2H, t, J=7.2Hz), 2.51(1H, m), 3.80(1H, m), 3.82, 3.85 and 3.87(each 3H, each s), 4.07(2H, s), 5.29–5.42

(2H, m), 5.94(1H, d, J=7.5Hz), 6.62(1H, d, J=8.7Hz), 6.76 (1H, d, J=3.6Hz), 6.85(1H, d, J=8.7Hz), 7.35(1H, d, J=3.6Hz).
IR(CHCl$_3$): 3514, 3446, 3427, 1739, 1709, 1641, 1603, 1543, 1495, 1468, 1277, 1259, 1097 cm$^{-1}$.
$[\alpha]_D^{26}$+54.8±1.0° (c=1.013, MeOH)
Elemental Analysis (C$_{29}$H$_{37}$NO$_6$S•0.2H$_2$O) Calcd.(%): C, 65.56; H, 7.10; N, 2.64; S, 6.04 Found(%): C, 65.54; H, 6.96; N, 2.74; S, 5.98

Compound I-219

300MHz $^1$H-NMR(CDCl$_3$) δ: 1.04(1H, m), 1.17–1.30 (2H, m), 1.38–1.48(2H, m), 1.54–1.81(4H, m), 1.98–2.16 (5H, m), 2.17 and 2.29(each 3H, each s), 2.34(2H, t, J=7.2Hz), 2.51(1H, m), 3.80(1H, m), 4.14(2H, s), 5.29–5.41 (2H, m), 5.93(1H, d, J=7.5Hz), 6.68(1H, td, J=0.9 and 3.6Hz), 7.35(1H, d, J=3.6Hz).
IR(CHCl$_3$): 3514, 3446, 3427, 2669, 1739, 1709, 1641, 1543, 1506, 1458 cm$^{-1}$.
$[\alpha]_D^{26}$+66.9±1.1° (c=1.009, MeOH)
Elemental Analysis (C$_{28}$H$_{35}$NO$_3$S) Calcd.(%): C, 72.22; H, 7.58; N, 3.01; S, 6.89 Found(%): C, 71.93; H, 7.58; N, 3.12; S, 6.74

Compound I-220 mp.131–133° C.
300MHz $^1$H-NMR(CDCl$_3$) δ: 1.06(1H, m), 1.18–1.31 (2H, m), 1.40–1.48(2H, m), 1.56–1.82(4H, m), 2.00–2.21 (5H, m), 2.35(2H, t, J=7.5Hz), 2.52(1H, m), 3.82(1H, m), 3.83(3H, s), 3.84(6H, s), 4.07(2H, s), 5.30–5.42(2H, m), 5.95(1H, d, J=7.5Hz), 6.45(2H, s), 6.79(1H, d, J=3.6Hz), 7.36(1H, d, J=3.6Hz).
IR(CHCl$_3$): 3516, 3446, 3427, 1739, 1709, 1643, 1593, 1543, 1506, 1462, 1421, 1331, 1240, 1130 cm$^{-1}$.
$[\alpha]_D^{24}$+57.5±1.0° (c=1.007, MeOH)
Elemental Analysis (C$_{29}$H$_{37}$NO$_6$S) Calcd.(%): C, 66.01; H, 7.07; N, 2.65; S, 6.08 Found(%): C, 65.84; H, 6.93; N, 2.71; S, 6.06

Compound I-221

300MHz $^1$H-NMR(CDCl$_3$) δ: 1.05(1H, m), 1.17–1.30 (2H, m), 1.39–1.48(2H, m), 1.54–1.80(4H, m), 1.98–2.20 (5H, m), 2.34(2H, t, J=7.5Hz), 2.51(1H, m), 3.81(1H, m), 4.08(2H, s), 5.29–5.42(2H, m), 5.95(2H, s), 5.98(1H, d, J=7.5Hz), 6.68–6.80(4H, m), 7.35(1H, d, J=3.9Hz).
IR(CHCl$_3$): 3516, 3446, 3427, 1741, 1709, 1641, 1543, 1504, 1460, 1252, 1063 cm$^{-1}$.
$[\alpha]_D^{24}$+62.7±1.0° (c=1.006, MeOH)
Elemental Analysis (C$_{27}$H$_{31}$NO$_5$S) Calcd.(%): C, 67.34; H, 6.49; N, 2.91; S, 6.66 Found(%): C, 67.12; H, 6.37; N, 2.98; S, 6.55

Compound I-222

300MHz $^1$H-NMR(CDCl$_3$) δ: 1.08(1H, m), 1.24–1.28 (2H, m), 1.41–1.45(2H, m), 1.56–1.78(4H, m), 1.97–2.20 (5H, m), 2.14(3H, s), 2.33(2H, t, J=7.2Hz), 2.51(1H, m), 3.77(1H, m), 4.06(2H, s), 5.28–5.42(2H, m), 6.16(1H, d, J=7.2Hz), 6.74(1H, d, J=3.6Hz), 6.96(1H, d, J=7.5Hz), 7.24(1H, t, J=8.7Hz), 7.35–7.38(3H, m), 7.74(1H, br s).
IR(KBr): 3309, 1707, 1672, 1614, 1547, 1523, 1489, 1441, 1371, 1319 cm$^{-1}$.
$[\alpha]_D^{26}$+57.7±1.0° (c=1.012, MeOH)
Elemental Analysis (C$_{28}$H$_{34}$N$_2$O$_4$S•0.4H$_2$O) Calcd.(%): C, 67.01; H, 6.99; N, 5.58; S, 6.39 Found(%): C, 66.98; H, 6.72; N, 5.47; S, 6.27

Compound I-223

300MHz $^1$H-NMR(CDCl$_3$) δ: 1.05(1H, m), 1.22–1.28 (2H, m), 1.42–1.46(2H, m), 1.55–1.75(4H, m), 2.02–2.22 (5H, m), 2.34(2H, t, J=7.5Hz), 2.51(1H, m), 2.99(3H, s), 3.81(1H, m), 4.11(2H, s), 5.29–5.45(2H, m), 6.04(1H, d, J=7.2Hz), 6.78 (1H, d, J=3.6Hz), 7.04–7.06(2H, m), 7.16 (1H, m), 7.25(1H, br s), 7.29(1H, t, J=7.8Hz), 7.36 (1H, d, J=3.6Hz).
IR(CHCl$_3$): 3512, 3444, 3427, 3371, 1709, 1639, 1608, 1545, 1508, 1475, 1458, 1389, 1335, 1151 cm$^{-1}$.
$[\alpha]_D^{24}$+55.0±1.0° (c=1.003, MeOH)
Elemental Analysis (C$_{27}$H$_{34}$N$_2$O$_5$S$_2$•0.2H$_2$O) Calcd.(%): C, 60.69; H, 6.49; N, 5.24; S, 12.00 Found(%): C, 60.70; H, 6.44; N, 5.15; S, 11.56

Compound I-224

300MHz $^1$H-NMR(CDCl$_3$) δ: 1.07(1H, m), 1.22–1.28 (2H, m), 1.42–1.53(2H, m), 1.57–1.74(4H, m), 2.00–2.24 (5H, m), 2.35(2H, t, J=7.2Hz), 2.52(1H, m), 3.81(1H, m), 4.33(2H, s), 5.29–5.42(2H, m), 5.98(1H, d, J=7.8Hz), 6.86, 6.88 and 7.14(each 1H, each d, each J=3.6Hz), 7.22–7.37 (4H, m), 7.53–7.56(2H, m).

Compound I-225

300MHz $^1$H-NMR(CDCl$_3$) δ: 1.05(1H, m), 1.17–1.30 (2H, m), 1.39–1.48(2H, m), 1.54–1.81(4H, m), 1.98–2.20 (5H, m), 2.35(2H, t, J=7.5Hz), 2.51(1H, m), 3.81(1H, m), 4.08(2H, s), 4.23–4.30(4H, m), 5.29–5.42(2H, m), 5.95(1H, d, J=7.2Hz), 6.71–6.80(4H, m), 7.34(1H, d, J=3.6Hz).
IR(CHCl$_3$): 3514, 3446, 3427, 1739, 1709, 1641, 1603, 1543, 1506, 1475, 1456, 1284, 1090 cm$^{-1}$.
$[\alpha]_D^{24.5}$+58.9±1.0° (c=1.013, MeOH)
Elemental Analysis (C$_{28}$H$_{33}$NO$_5$S) Calcd.(%): C, 67.85; H, 6.71; N, 2.83; S, 6.47 Found(%): C, 68.01; H, 6.72; N, 2.97; S, 6.50

Compound I-226

300MHz $^1$H-NMR(CDCl$_3$) δ: 1.05(1H, m), 1.18–1.30 (2H, m), 1.38–1.47(2H, m), 1.54–1.81(4H, m), 1.98–2.20 (5H, m), 2.31(3H, s), 2.34(2H, t, J=7.5Hz), 2.51(1H, m), 3.70(3H, s), 3.80(1H, m), 4.16(2H, s), 5.29–5.42(2H, m), 5.95(1H, d, J=7.2Hz), 6.78(1H, d, J=3.6Hz), 6.96–7.11(3H, m), 7.37(1H, d, J=3.6Hz).
IR(CHCl$_3$): 3514, 3446, 3427, 2669, 1709, 1641, 1543, 1506, 1473, 1458, 1259, 1011 cm$^{-1}$.
$[\alpha]D^{24}$+62.7±1.0° (c=1.009, MeOH)
Elemental Analysis (C$_{28}$H$_{35}$NO$_4$S) Calcd.(%): C, 69.82; H, 7.32; N, 2.91; S, 6.66 Found(%): C, 69.55; H, 7.27; N, 3.09; S, 6.55

Compound I-227

300MHz $^1$H-NMR(CDCl$_3$) δ: 1.07(1H, m), 1.24–1.28 (2H, m), 1.41–1.46(2H, m), 1.56–1.79(4H, m), 2.00–2.17 (5H, m), 2.16(3H, s), 2.33(2H, t, J=7.5Hz), 2.51(1H, m), 3.79(1H, m), 4.08(2H, s), 5.28–5.42(2H, m), 6.05(1H, d, J=7.5Hz), 6.75(1H, d, J=3.6Hz), 7.16(2H, d, J=8.1Hz), 7.37(1H, d, J=3.6Hz), 7.43(2H, d, J=8.1Hz), 7.53(1H, br s).

IR(CHCl$_3$): 3512, 3437, 1707, 1639, 1543, 1516, 1410 cm$^{-1}$.

[α]$_D^{24.5}$+60.7±1.0° (c=1.012, MeOH)

Elemental Analysis (C$_{28}$H$_{34}$N$_2$O$_4$S•0.5H$_2$O) Calcd.(%): C, 67.77; H, 7.00; N, 5.56; S, 6.37 Found(%): C, 66.84; H, 6.91; N, 5.56; S, 6.26

Compound I-228

300MHz $^1$H-NMR(CDCl$_3$) δ: 1.06(1H, m), 1.22–1.29 (2H, m), 1.41–1.46(2H, m), 1.58–1.76(4H, m), 2.01–2.17 (5H, m), 2.34(2H, t, J=7.5Hz), 2.51(1H, m), 2.99(3H, s), 3.80(1H, m), 4.11(2H, s), 5.29–5.43(2H, m), 6.01(1H, d, J=7.5Hz), 6.78(1H, d, J=3.6Hz), 6.86(1H, br s), 7.17–7.23 (4H, m), 7.36(1H, d, J=3.6Hz).

IR(CHCl$_3$): 3510, 3444, 3427, 3371, 1709, 1639, 1543, 1510, 1456, 1389, 1338, 1155 cm$^{-1}$.

[α]$_D^{24.5}$+56.5±1.0° (c=0.953, MeOH)

Elemental Analysis (C$_{27}$H$_{34}$N$_2$O$_5$S$_2$•0.1H$_2$O) Calcd.(%): C, 60.90; H, 6.47; N, 5.26; S, 12.04 Found(%): C, 61.06; H, 6.45; N, 5.29; S, 11.52

Compound I-229 mp.103–105° C.

300MHz $^1$H-NMR(CDCl$_3$) δ: 1.02(1H, m), 1.15–1.27 (2H, m), 1.37–1.45(2H, m), 1.53–1.77(4H, m), 1.96–2.18 (5H, m), 2.33(2H, t, J=7.5Hz), 2.49(1H, m), 3.79(1H, m), 4.40(2H, s), 5.27–5.39(2H, m), 5.94(1H, d, J=7.8Hz), 6.89 (1H, d, J=3.9Hz), 7.32–7.37(2H, m), 7.43–7.48(3H, m), 7.84(1H, m), 8.08(1H, d, J=6.9Hz), 8.15(1H, m).

IR(CHCl$_3$): 3514, 3444, 3427, 2667, 1739, 1709, 1643, 1543, 1506, 1458, 1444 cm$^{-1}$.

[α]$_D^{24.5}$+58.9±1.0° (c=1.006, MeOH)

Elemental Analysis (C$_{32}$H$_{33}$NO$_3$S$_2$) Calcd.(%): C, 70.68; H, 6.12; N, 2.58; S, 11.79 Found(%): C, 70.52; H, 6.11; N, 2.67; S, 11.72

Compound I-230 mp.86–87° C.

300MHz $^1$H-NMR(CDCl$_3$) δ: 1.02(1H, m), 1.16–1.28 (2H, m), 1.37–1.45(2H, m), 1.54–1.77(4H, m), 1.97–2.17 (5H, m), 2.32(2H, t, J=7.5Hz), 2.49(1H, m), 3.78(1H, m), 3.79 and 4.26(each 2H, each s), 5.27–5.39(2H, m), 5.93(1H, d, J=7.2Hz), 6.78(1H, d, J=3.9Hz), 7.18(1H, d, J=7.2Hz), 7.29(1H, m), 7.34–7.40(3H, m), 7.52(1H, d, J=7.2Hz), 7.72 (1H, d, J=7.5Hz), 7.78(1H, d, J=7.2Hz).

IR(CHCl$_3$): 3514, 3446, 3427, 2669, 1709, 1641, 1543, 1506, 1456 cm$^{-1}$.

[α]$_D^{24.5}$+59.2±1.0° (c=1.006, MeOH)

Elemental Analysis (C$_{33}$H$_{35}$NO$_3$S) Calcd.(%): C, 75.40; H, 6.71; N, 2.66; S, 6.10 Found(%): C, 75.33; H, 6.73; N, 2.75; S, 6.06

Compound I-231

300MHz $^1$H-NMR(CDCl$_3$) δ: 1.04(1H, m), 1.16–1.30 (2H, m), 1.38–1.46(2H, m), 1.54–1.81(4H, m), 1.98–2.16 (5H, m), 2.21 and 2.50(each 3H, each s), 2.34(2H, t, J=7.2Hz), 2.51(1H, m), 3.66(3H, s), 3.80(1H, m), 4.13(2H, s), 5.29–5.42(2H, m), 5.93(1H, d, J=6.9Hz), 6.78(1H, d, J=3.6Hz), 6.89 and 6.96(each 1H, each d, each J=7.5Hz), 7.36(1H, d, J=3.6Hz).

IR(CHCl$_3$): 3516, 3446, 3425, 2669, 1709, 1641, 1545, 1506, 1458, 1263, 1084, 1009 cm$^{-1}$.

[α]$_D^{24}$+61.8±1.0° (c=1.006, MeOH)

Elemental Analysis (C$_{29}$H$_{37}$NO$_4$S•0.2H$_2$O) Calcd.(%): C, 69.76; H, 7.55; N, 2.81; S, 6.42 Found(%): C, 69.80; H, 7.59; N, 2.97; S, 6.34

Compound I-232

300MHz $^1$H-NMR(CDCl$_3$) δ: 1.02(1H, m), 1.16–1.27 (2H, m), 1.37–1.45(2H, m), 1.53–1.77(4H, m), 1.96–2.15 (5H, m), 2.33(2H, t, J=7.5Hz), 2.50(1H, m), 3.79(1H, m), 4.50(2H, s), 5.27–5.40(2H, m), 5.94(1H, d, J=7.5Hz), 6.88 (1H, d, J=3.9Hz), 7.29–7.38(4H, m), 7.47(1H, m), 7.58(1H, d, J=8.4Hz), 7.86(1H, m), 7.95(1H, d, J=7.8Hz).

IR(CHCl$_3$): 3512, 3444, 3427, 2669, 1739, 1708, 1641, 1543, 1506, 1475, 1452, 1423 cm$^{-1}$.

[α]$_D^{24}$+58.5±1.0° (c=1.006, MeOH)

Elemental Analysis (C$_{32}$H$_{33}$NO$_4$S•0.2H$_2$O) Calcd.(%): C, 72.34; H, 6.34; N, 2.64; S, 6.04 Found(%): C, 72.36; H, 6.16; N, 2.72; S, 5.94

Compound I-233 mp. 125–126° C.

300MHz $^1$H-NMR(CDCl$_3$) δ: 1.05(1H, m), 1.18–1.28 (2H, m), 1.41–1.45(2H, m), 1.57–1.78(4H, m), 2.00–2.20 (5H, m), 2.33(2H, t, J=7.4Hz), 2.51(1H, s), 3.80(1H, m), 4.05 (2H, s), 5.28–5.42(2H, m), 5.98(1H, d, J=6.6Hz), 6.76(1H, d, J=3.6Hz), 6.80 and 7.09(each 2H, each d, J=8.4Hz), 7.37(1H, d, J=3.6Hz).

IR(KBr): 3354, 3132, 2688, 1703, 1616, 1599, 1549, 1514, 1458, 1250 cm$^{-1}$.

[α]$_D^{25}$+67.7±1.1° (c=1.001, MeOH)

Elemental Analysis (C$_{26}$H$_{31}$NO$_4$S) Calcd.(%): C, 68.85; H, 6.89; N, 3.09; S, 7.07 Found(%): C, 69.12; H, 6.95; N, 3.10; S, 7.12

Compound II-2

300MHz $^1$H-NMR(CDCl$_3$) δ: 0.89(1H, d, J=10.2Hz), 1.05 and 1.19(each 3H, each s), 1.50–2.44(14H, m), 4.15 (1H, m), 5.31–5.50(2H, m), 6.31(1H, d, J=8.1Hz), 7.00(1H, d, J=1.8Hz), 7.42–7.47(2H, m), 7.54(1H, d, J=1.8Hz), 7.56 (1H, m), 7.76–7.79(2H, m), 8.29(1H, s).

IR(CHCl$_3$): 3509, 3446, 3360, 3108, 1708, 1639, 1515, 1448, 1330, 1164 cm$^{-1}$.

[α]$_D^{20}$+39.0±0.8° (c=1.006, MeOH)

Elemental Analysis (C$_{27}$H$_{34}$N$_2$O$_5$S$_2$•0.2H$_2$O) Calcd.(%): C, 60.09; H, 6.54; N, 5.19; S,11.88 Found(%): C, 60.07; H, 6.48; N, 5.31; S,11.92

Compound II-3

300MHz $^1$H-NMR(CDCl$_3$) δ: 0.73(1H, d, J=10.2Hz), 1.06 and 1.16(each 3H, each s), 1.43–2.36(14H, m), 4.07 (1H, m), 5.28–5.49(2H, m), 6.37(1H, d, J=8.7Hz), 7.28 and 7.33(each 1H, each d, each J=1.8Hz), 7.38–7.43(2H, m), 7.50(1H, m), 7.96–7.99(2H, m).

IR(CHCl$_3$): 3440, 3254, 3096, 3062, 1708, 1643, 1560, 1530, 1298 cm$^{-1}$.

[α]$_D^{20}$+49.0±0.9° (c=1.008, MeOH)

Elemental Analysis (C$_{28}$H$_{34}$N$_2$O$_4$S•0.4H$_2$O) Calcd.(%): C, 67.01; H, 6.99; N, 5.58; S,6.39 Found(%): C, 66.96; H, 7.04; N, 5.67; S,6.32

Compound II-4

300MHz $^1$H-NMR(CDCl$_3$) δ: 0.94(1H, d, J=10.2Hz), 1.08 and 1.21(each 3H, each s), 1.50–2.43(14H, m), 4.12

(2H, s), 4.22(1H, m), 5.33–5.49(2H, m), 6.06(1H, d, J=8.7Hz), 7.04(1H, d, J=1.2Hz), 7.22–7.34(2H, m), 7.63 (1H, d, J=1.2Hz).

IR(CHCl$_3$): 3517, 3451, 3087, 3065, 2670, 1708, 1708, 1647, 1549, 1508 cm$^{-1}$.

$[\alpha]_D^{21.5}$+41.9±0.8° (c=1.015, MeOH)

Elemental Analysis (C$_{28}$H$_{35}$NO$_3$S) Calcd.(%): C, 72.22; H, 7.58; N, 3.01; S,6.89 Found(%): C, 72.07; H, 7.57; N, 3.21; S,6.77

Compound II-5

300MHz $^1$H-NMR(CDCl$_3$) δ: 0.98(1H, d, J=10.2Hz), 1.14 and 1.24(each 3H, each s), 1.54–2.48(14H, m), 4.30 (1H, m), 5.35–5.52(2H, m), 6.26(1H, d, J=8.7Hz), 6.38 and 7.13 (each 2H, each t, J=2.1Hz), 7.44 and 7.79(each 2H, each d, each J=8.4Hz).

IR(CHCl$_3$): 3453, 2662, 1739, 1708, 1652, 1609, 1500, 1333 cm$^{-1}$.

$[\alpha]_D^{22}$+65.2±1.1° (c=1.006, MeOH)

Elemental Analysis (C$_{27}$H$_{34}$N$_2$O$_3$•0.3H$_2$O) Calcd.(%): C, 73.71; H, 7.93; N, 6.37 Found(%): C, 73.85; H, 7.88; N, 6.37

Compound II-6

300MHz $^1$H-NMR(CDCl$_3$) δ: 0.95(1H, d, J=10.2Hz), 1.10 and 1.22(each 3H, each s), 1.52–2.42(14H, m), 4.25 (1H, m), 5.34–5.51(2H, m), 6.35(1H, d, J=8.7Hz), 7.07–7.15 (3H, m), 7.21–7.26(2H, m), 7.73 and 7.77(each 2H, each d, each J=8.7Hz).

IR(CHCl$_3$): 3518, 3446, 3365, 3249, 2673, 1709, 1655, 1516, 1348, 1167 cm$^{-1}$.

$[\alpha]_D^{21.5}$+56.1±0.9° (c=1.000, MeOH)

Elemental Analysis (C$_{29}$H$_{36}$N$_2$O$_5$S•0.6H$_2$O) Calcd.(%): C, 65.05; H, 7.00; N, 5.23; S, 5.99 Found(%): C, 65.07; H, 6.94; N, 5.37; S, 6.03

Compound II-7

300MHz $^1$H-NMR(CDCl$_3$) δ: 0.94(1H, d, J=10.5Hz), 1.09 and 1.21(each 3H, each s), 1.50–2.44(14H, m), 4.24 (1H, m), 5.32–5.48(2H, m), 6.24(1H, d, J=8.7Hz), 7.17 and 7.60(each 2H, each d, each J=8.7Hz), 7.41–7.46(2H, m), 7.54(1H, m), 7.80–7.84(2H, m).

IR(CHCl$_3$): 3510, 3451, 3371, 3139, 1709, 1647, 1609, 1496, 1163 cm$^{-1}$.

$[\alpha]_D^{22.5}$+47.1±0.9° (c=1.006, MeOH)

Elemental Analysis (C$_{29}$H$_{36}$N$_2$O$_5$S•0.4H$_2$O) Calcd.(%): C, 65.49; H, 6.97; N, 5.27; S, 6.03 Found(%): C, 65.51; H, 6.87; N, 5.39; S, 5.89

Compound II-8

300MHz $^1$H-NMR(CDCl$_3$) δ: 0.96(1H, d, J=10.5Hz), 1.09 and 1.22(each 3H, each s), 1.52–2.44(14H, m), 4.26 (1H, m), 5.33–5.49(2H, m), 6.26(1H, d, J=8.4Hz), 6.31 and 7.15(each 2H, each t, each J=2.1Hz), 7.81 and 7.89(each 2H, each d, each J=8.4Hz).

IR(CHCl$_3$): 3514, 3446, 3144, 1708, 1663, 1514, 1377, 1173 cm$^{-1}$.

$[\alpha]_D^{22}$+64.1±0.9° (c=1.000, MeOH)

Elemental Analysis (C$_{27}$H$_{34}$N$_2$O$_5$S•0.2H$_2$O) Calcd.(%): C, 64.57; H, 6.90; N, 5.58; S, 6.38 Found(%): C, 64.50; H, 6.97; N, 5.71; S, 6.28

Compound II-9 mp.156–157° C.

300MHz $^1$H-NMR(CDCl$_3$) δ: 1.00(1H, d, J=10.2Hz), 1.17 and 1.25(each 3H, each s), 1.57–2.51(14H, m), 4.31 (1H, m), 5.34–5.54(2H, m), 6.37(1H, d, J=9.3Hz), 7.33–7.47 (3H, m), 7.61(1H, s), 7.64(1H, m), 7.70–7.73(2H, m), 7.87 (1H, d, J=8.4Hz), 8.15(1H, d, J=1.2Hz).

IR(CHCl$_3$): 3518, 3452, 1741, 1709, 1649, 1510 cm$^{-1}$.

$[\alpha]_D^{23}$+67.2±2.1° (c=0.503, MeOH)

Elemental Analysis (C$_{31}$H$_{35}$NO$_3$S•0.1H$_2$O) Calcd.(%): C, 73.95; H, 7.05; N, 2.78; S, 6.37 Found(%): C, 73.94; H, 7.08; N, 3.04; S, 6.53

Compound II-10

300MHz $^1$H-NMR(CDCl$_3$) δ: 0.96(1H, d, J=10.5Hz), 1.11 and 1.23(each 3H, each s), 1.54–2.49(14H, m), 4.25 (1H, m), 5.35–5.56(2H, m), 6.33(2H, t, J=2.4Hz), 6.56(1H, d, J=7.8Hz), 7.17(2H, t, J=2.4Hz), 7.58(1H, t, J=7.8Hz), 7.93(1H, m), 8.04(1H, d, J=7.8Hz), 8.24(1H, m).

IR(CHCl$_3$): 3513, 3389, 3144, 2669, 1726, 1709, 1659, 1515, 1470, 1455, 1375 cm$^{-1}$.

$[\alpha]_D^{25}$+54.0±0.9° (c=1.008, MeOH)

Elemental Analysis (C$_{27}$H$_{34}$N$_2$O$_5$S•0.2H$_2$O) Calcd.(%): C, 64.46; H, 6.90; N, 5.53; S,6.38 Found(%): C, 64.45; H, 6.89; N, 5.75; S,6.42

Compound II-11

300MHz $^1$H-NMR(CDCl$_3$) δ: 0.96(1H, d, J=10.2Hz), 1.10 and 1.23(each 3H, each s), 1.52–2.42(14H, m), 2.29 (3H, t), 4.26(1H, m), 5.35–5.49(2H, m), 5.96(1H, brs), 6.19(1H, t, J=3.2Hz), 6.26(1H, d, J=8.1Hz), 7.25(1H, m), 7.81(4H, s).

IR(CHCl$_3$): 3511, 3446, 3152, 1708, 1662, 1514, 1485, 1368, 1164 cm$^{-1}$.

$[\alpha]_D^{27}$+59.4±1.0° (c=1.006, MeOH)

Elemental Analysis (C$_{25}$H$_{36}$N$_2$O$_5$S) Calcd.(%): C, 65.60; H, 7.08; N, 5.46; S,6.25 Found(%): C, 65.41; H, 7.00; N, 5.67; S,6.24

Compound II-12

300MHz $^1$H-NMR(CDCl$_3$) δ: 0.97(1H, d, J=10.5Hz), 1.03 and 1.22(each 3H, each s), 1.452–2.46(14H, m), 4.26 (1H, m), 5.33–5.50(2H, m), 6.20(2H, t, J=2.1Hz), 6.22(1H, d, J=8.1Hz), 6.68(2H, t, J=2.1Hz), 7.15 and 7.67(each 2H, each d, each J=8.1Hz).

IR(CHCl$_3$): 3511, 3452, 3103, 2666, 1709, 1652, 1523, 1496 cm$^{-1}$.

$[\alpha]_D^{23}$+57.7±1.0° (c=1.010, MeOH)

Elemental Analysis (C$_{28}$H$_{36}$N$_2$O$_3$•0.1H$_2$O) Calcd.(%): C, 74.67; H, 8.10; N, 6.22 Found(%): C, 74.69; H, 8.21; N, 6.38

Compound II-13

300MHz $^1$H-NMR(CDCl$_3$) δ: 0.94(1H, d, J=10.2Hz), 1.06 and 1.20(each 3H, each s), 1.49–2.40(14H, m), 4.21 (1H, m), 5.31–5.45(2H, m), 6.19(1H, d, J=8.4Hz), 6.88(1H, d, J=3.6Hz), 7.22–7.35(2H, m), 7.52–7.55(2H, m), 7.74 and 7.91(each 2H, each d, each J=8.4Hz), 7.98(1H, d, J=8.4Hz).

IR(CHCl$_3$): 3481, 3440, 3145, 3116, 2661, 1709, 1660, 1516, 1485, 1446, 1377, 1261, 1178, 1130 cm$^{-1}$.

$[\alpha]_D^{26}$+56.6±1.0° (c=1.000, MeOH)

Elemental Analysis (C$_{31}$H$_{36}$N$_2$O$_5$S•0.1H$_2$O) Calcd.(%): C, 67.64; H, 6.63; N, 5.09; S, 5.82 Found(%): C, 67.68; H, 6.72; N, 5.35; S, 5.73

Compound II-14

300MHz $^1$H-NMR(CDCl$_3$) δ: 0.92(1H, d, J=10.2Hz), 1.09 and 1.21(each 3H, each s), 1.53–2.47(14H, m), 4.17 (1H, m), 5.35–5.55(2H, m), 6.35 and 7.17(each 2H, each t, each J=2.1Hz), 6.38(1H, d, J=8.7Hz), 8.09 and 8.17(each 1H, each d, each J=1.5Hz).
IR(CHCl$_3$): 3510, 3409, 3144, 3107, 1727, 1709, 1657, 1538, 1503, 1456, 1387, 1166 cm$^{-1}$.
[α]$_D^{26.5}$+46.1±0.9° (c=1.005, MeOH)
Elemental Analysis (C$_{25}$H$_{32}$N$_2$O$_5$S$_2$•0.2H$_2$O) Calcd.(%): C, 59.08; H, 6.43; N, 5.51; S, 12.62 Found(%): C, 59.10; H, 6.45; N, 5.69; S, 12.58

Compound II-15

300MHz $^1$H-NMR(CDCl$_3$) δ: 0.93(1H, d, J=10.2Hz), 1.08 and 1.21(each 3H, each s), 1.50–2.41(14H, m), 4.20 (1H, m), 5.35–5.47(2H, m), 6.16(1H, d, J=8.7Hz), 6.33 and 7.16(each 2H, each t, each J=2.4Hz), 7.30 and 7.56(each 1H, each d, each J=3.9Hz).
IR(CHCl$_3$): 3515, 3446, 3144, 3100, 1708, 1658, 1529, 1504, 1456, 1385, 1167 cm$^{-1}$.
[α]$_D^{26.5}$+54.1±0.9° (c=1.004, MeOH)
Elemental Analysis (C$_{25}$H$_{32}$N$_2$O$_5$S$_2$•0.2H$_2$O) Calcd.(%): C, 59.08; H, 6.43; N, 5.51; S, 12.62 Found(%): C, 59.12; H, 6.36; N, 5.57; S, 12.59

Compound II-16

300MHz $^1$H-NMR(CDCl$_3$) δ: 0.95(1H, d, J=10.2Hz), 1.09 and 1.22(each 3H, each s), 1.52–2.45(14H, m), 4.24 (1H, m), 4.63(2H, s), 5.34–5.50(2H, m), 6.25–6.27(2H, m), 6.40(1H, d, J=8.4Hz), 7.25(1H, dd, J=1.8 and 3.0Hz), 7.80 and 7.85(each 2H, each d, each J=8.7Hz).
IR(CHCl$_3$): 3581, 3518, 3445, 3149, 2666, 1709, 1661, 1515, 1472, 1371, 1182, 1150 cm$^{-1}$.
[α]$_D^{27}$+58.1±1.0° (c=1.007, MeOH)
Elemental Analysis (C$_{28}$H$_{36}$N$_2$O$_6$S) Calcd.(%): C, 63.61; H, 6.86; N, 5.30; S, 6.07 Found(%): C, 63.50; H, 6.84; N, 5.44; S, 5.89

Compound II-17 mp.119–121° C.
300MHz $^1$H-NMR(CDCl$_3$) δ: 0.97(1H, d, J=10.2Hz), 1.11 and 1.24(each 3H, each s), 1.53–2.49(14H, m), 4.29 (1H, m), 5.39–5.57(2H, m), 6.37 and 7.22(each 2H, each t, each J=2.1Hz), 7.13(1H, d, J=8.4Hz), 7.50 and 7.93(each 1H, each d, each J=3.9Hz).
IR(Nujol): 3365, 3145, 3100, 1739, 1621, 1548, 1405, 1367, 1187 cm$^{-1}$.
[α]$_D^{26.5}$+45.5±0.8° (c=1.012, MeOH)
Elemental Analysis (C$_{25}$H$_{32}$N$_2$O$_5$S$_2$) Calcd.(%): C, 59.74; H, 6.02; N, 5.57; S, 12.76 Found(%): C, 59.56; H, 6.33; N, 5.64; S, 12.76

Compound II-18

300MHz $^1$H-NMR(CDCl$_3$) δ: 0.93(1H, d, J=10.2Hz), 1.08 and 1.21(each 3H, each s), 1.50–2.41(14H, m), 4.21 (1H, m), 5.34–5.48(2H, m), 6.21(1H, d, J=8.4Hz), 7.36 and 7.63(each 1H, each d, each J=3.9Hz), 7.70(1H, dd, J=1.5 and 5.1Hz), 7.75(1H, dd, J=1.5 and 3.9Hz).
IR(CHCl$_3$): 3516, 3446, 3097, 1708, 1656, 1529, 1504, 1337, 1153 cm$^{-1}$.
[α]$_D^{25}$+54.1±0.9° (c=1.000, MeOH)
Elemental Analysis (C$_{25}$H$_{31}$NO$_5$S$_3$) Calcd.(%): C, 57.56; H, 5.99; N, 2.68; S, 18.44 Found(%): C, 57.33; H, 5.95; N, 2.68; S, 18.38

Compound II-19 mp.132–133° C.
300MHz $^1$H-NMR(CDCl$_3$) δ: 0.93(1H, d, J=10.2Hz), 1.08 and 1.21(each 3H, each s), 1.54–2.44(14H, m), 4.19 (1H, m), 5.33–5.50(2H, m), 6.03(1H, d, J=8.7Hz), 6.52(1H, dd, J=1.5 and 3.3Hz), 7.11(1H, dd, J=3.9 and 4.8Hz), 7.17(1H, dd, J=2.1 and 3.3Hz), 7.70–7.72(2H, m), 7.74(1H, dd, J=1.5 and 3.9Hz).
IR(CHCl$_3$): 3510, 3448, 3143, 3099, 1733, 1708, 1650, 1572, 1507, 1473, 1387, 1179 cm$^{-1}$.
[α]$_D^{24}$+39.1±0.8° (c=1.003, MeOH)
Elemental Analysis (C$_{25}$H$_{32}$N$_2$O$_5$S$_2$) Calcd.(%): C, 59.50; H, 6.39; N, 5.55; S, 12.71 Found(%): C, 59.49; H, 6.46; N, 5.47; S, 12.70

Compound II-20 mp.165–166° C.
300MHz $^1$H-NMR(CDCl$_3$) δ: 0.93(1H, d, J=10.2Hz), 1.08 and 1.20(each 3H, each s), 1.50–2.45(14H, m), 4.17 (1H, m), 5.33–5.51(2H, m), 6.04(1H, d, J=8.4Hz), 6.51(1H, dd, J=1.5 and 3.3Hz), 7.15(1H, dd, J=2.4 and 3.3Hz), 7.52–7.57(2H, m), 7.65(1H, m), 7.74(1H, dd, J=1.8 and 2.1Hz), 7.89–7.93(1H, m).
IR(CHCl$_3$): 3510, 3449, 3144, 1733, 1708, 1650, 1570, 1507, 1384, 1185, 1176 cm$^{-1}$.
[α]$_D^{24}$+33.8±0.7° (c=1.011, MeOH)
Elemental Analysis (C$_{27}$H$_{34}$N$_2$O$_5$S) Calcd.(%): C, 65.04; H, 6.87; N, 5.62; S, 6.43 Found(%): C, 64.95; H, 6.68; N, 5.69; S, 6.40

Compound II-21

300MHz $^1$H-NMR(CDCl$_3$) δ: 0.93(1H, d, J=10.2Hz), 1.07 and 1.21(each 3H, each s), 1.49–2.41(14H, m), 4.19 (1H, m), 5.33–5.47(2H, m), 5.99(1H, d, J=8.7Hz), 7.01(1H, dd, J=3.6 and 5.4Hz), 7.04 and 7.28(each 1H, each d, each J=3.6Hz), 7.29(1H, dd, J=1.2 and 3.6Hz), 7.43(1H, dd, J=1.2 and 5.4Hz).
IR(CHCl$_3$): 3518, 3449, 3430, 2672, 1708, 1646, 1530, 1500, 1421 cm$^{-1}$.
[α]$_D^{25.5}$+45.9±0.9° (c=1.010, MeOH)
Elemental Analysis (C$_{25}$H$_{31}$NO$_3$S$_3$) Calcd.(%): C, 61.32; H, 6.38; N, 2.86; S, 19.64 Found(%): C, 61.17; H, 6.42; N, 3.00; S, 19.80

Compound II-22

300MHz $^1$H-NMR(CDCl$_3$) δ: 0.93(1H, d, J=10.2Hz), 1.07 and 1.21(each 3H, each s), 1.49–2.41(14H, m), 2.46 (3H, d, J=1.2Hz), 4.18(1H, m), 5.33–5.47(2H, m), 5.99(1H, d, J=8.4Hz), 6.66(1H, m), 6.99(1H, d, J=3.9Hz), 7.10(1H, d, J=3.3Hz), 7.26(1H, d, J=3.9Hz).
IR(CHCl$_3$): 3509, 3449, 2671, 1708, 1645, 1530, 1500, 1420 cm$^{-1}$.
[α]$_D^{25.5}$+43.5±0.8° (c=1.002, MeOH)

Elemental Analysis (C$_{26}$H$_{33}$NO$_3$S$_3$) Calcd.(%): C, 61.99; H, 6.60; N, 2.78; S, 19.10 Found(%): C, 61.77; H, 6.68; N, 2.83; S, 18.91

Compound II-23 mp.118–120° C.

300MHz $^1$H-NMR(CDCl$_3$) δ: 0.94(1H, d, J=10.2Hz), 1.09 and 1.22(each 3H, each s), 1.51–2.42(14H, m), 2.53 (3H, d, J=0.9Hz), 4.20(1H, m), 5.35–5.48(2H, m), 6.17(1H, d, J=8.7Hz), 6.77(1H, m), 7.34(1H, d, J=3.9Hz), 7.57(1H, d, J=3.6Hz), 7.60(1H, d, J=3.9Hz).

IR(Nujol): 3399, 3082, 1733, 1613, 1543, 1328, 1318, 1151 cm$^{-1}$.

[α]$_D^{25.5}$+54.0±0.9° (c=1.012, MeOH)

Elemental Analysis (C$_{26}$H$_{33}$NO$_5$S$_3$) Calcd.(%): C, 58.29; H, 6.21; N, 2.61; S, 17.95 Found(%): C, 58.08; H, 6.18; N, 2.73; S, 17.66

Compound II-24 mp.126–127° C.

300MHz $^1$H-NMR(CDCl$_3$) δ: 0.93(1H, d, J=10.2Hz), 1.08 and 1.20(each 3H, each s), 1.50–2.46(14H, m), 4.17 (1H, m), 5.33–5.51(2H, m), 6.04(1H, d, J=8.4Hz), 6.51(1H, dd, J=1.5 and 3.3Hz), 7.13(1H, dd, J=2.7 and 3.3Hz), 7.22(1H, dd, J=7.8 and 9.0Hz), 7.73(1H, dd, J=1.5 and 2.1Hz), 7.91–7.96(2H, m).

IR(CHCl$_3$): 3513, 3449, 3144, 1733, 1709, 1651, 1592, 1507, 1496, 1385, 1181 cm$^{-1}$.

[α]$_D^{24}$+36.2±0.8° (c=1.005, MeOH)

Elemental Analysis (C$_{27}$H$_{33}$FN$_2$O$_5$S) Calcd.(%): C, 62.77; H, 6.44; N, 5.42; F, 3.68; S, 6.21 Found(%): C, 62.71; H, 6.49; N, 5.39; F, 3.69; S, 6.21

Compound II-25 mp.145–146° C.

300MHz $^1$H-NMR(CDCl$_3$) δ: 0.93(1H, d, J=10.2Hz), 1.08 and 1.20(each 3H, each s), 1.50–2.45(14H, m), 3.86 (3H, s), 4.17(1H, m), 5.33–5.51(2H, m), 6.04(1H, d, J=8.4Hz), 6.48(1H, dd, J=1.5 and 3.3Hz), 6.98 and 7.85 (each 2H, each d, each J=9.0Hz), 7.12(1H, dd, J=2.7 and 3.3Hz), 7.71(1H, dd, J=1.8 and 2.1Hz).

IR(CHCl$_3$): 3513, 3449, 3413, 3143, 1733, 1709, 1649, 1596, 1576, 1499, 1379, 1266, 1189, 1167 cm$^{-1}$.

[α]$_D^{24}$+34.5±0.7° (c=1.005, MeOH)

Elemental Analysis (C$_{28}$H$_{36}$N$_2$O$_6$S) Calcd.(%): C, 63.61; H, 6.86; N, 5.30; S, 6.07 Found(%): C, 63.54; H, 6.93; N, 5.18; S, 6.08

Compound II-26

300MHz $^1$H-NMR(CDCl$_3$) δ: 0.97(1H, d, J=10.5Hz), 1.12 and 1.23(each 3H, each s), 1.50–2.50(14H, m), 4.23 (1H, m), 5.39–5.51(2H, m), 6.09(1H, d, J=9.6Hz), 6.35(1H, dd, J=2.4 and 3.9Hz), 6.48(1H, dd, J=2.4 and 3.9Hz), 7.02(1H, dd, J=3.6 and 4.8Hz), 7.18(1H, dd, J=0.6 and 4.8Hz), 7.41(1H, dd, J=0.6 and 3.6Hz), 10.92(1H, brs).

IR(CHCl$_3$): 3506, 3447, 3220, 3164, 1704, 1617, 1537, 1508 cm$^{-1}$.

[α]$_D^{24}$+50.7±0.9° (c=1.009, MeOH)

Elemental Analysis (C$_{25}$H$_{32}$N$_2$O$_3$S•0.2H$_2$O) Calcd.(%): C, 67.59; H, 7.35; N, 6.31; S, 7.22 Found(%): C, 67.60; H, 7.23; N, 6.39; S, 7.34

Compound II-27 mp.138–139° C.

300MHz $^1$H-NMR(CDCl$_3$) δ: 0.97(1H, d, J=10.2Hz), 1.13 and 1.24(each 3H, each s), 1.50–2.47(14H, m), 4.24 (1H, m), 5.36–5.52(2H, m), 6.06(1H, d, J=8.4Hz), 6.98(1H, d, J=3.9Hz), 6.99 and 7.05(each 1H, each d, each J=16.2Hz), 7.28–7.34(3H, m), 7.37(1H, d, J=3.9Hz).

IR(CHCl$_3$): 3518, 3449, 3431, 2665, 1708, 1642, 1538, 1519, 1500 cm$^{-1}$.

[α]$_D^{24}$+49.1±0.9° (c=1.014, MeOH)

Elemental Analysis (C$_{27}$H$_{33}$NO$_3$S$_2$) Calcd.(%): C, 67.05; H, 6.88; N, 2.90; S, 13.26 Found(%): C, 67.94; H, 6.86; N, 2.99; S, 13.23

Compound II-28

300MHz $^1$H-NMR(CDCl$_3$) δ: 0.94(1H, d, J=9.9Hz), 1.07 and 1.22(each 3H, each s), 1.50–2.44(14H, m), 4.20(1H, m), 5.30–5.51(2H, m), 5.97(1H, d, J=9.0Hz), 6.58(2H, s), 6.95 (1H, d, J=3.9Hz), 7.02(1H, dd, J=1.5 and 4.8Hz), 7.25–7.31 (2H, m), 7.31(1H, d, J=3.9Hz).

IR(CHCl$_3$): 3517, 3449, 3430, 2664, 1708, 1642, 1536, 1519, 1501 cm$^{-1}$.

[α]$_D^{24}$+38.6±0.8° (c=1.006, MeOH)

Elemental Analysis (C$_{27}$H$_{33}$NO$_3$S$_2$•0.2H$_2$O) Calcd.(%): C, 66.55; H, 6.91; N, 2.87; S, 13.16 Found(%): C, 66.52; H, 6.81; N, 3.11; S, 12.93

Compound II-29

300MHz $^1$H-NMR(CDCl$_3$) δ: 0.94(1H, d, J=10.2Hz), 1.09 and 1.22(each 3H, each s), 1.50–2.39(14H, m), 2.44 (3H, d, J=0.9Hz), 4.20(1H, m), 5.34–5.49(2H, m), 5.98(1H, d, J=8.7Hz), 6.70(1H, m), 7.06(1H, d, J=3.9Hz), 7.10(1H, d, J=1.8Hz), 7.30(1H, d, J=3.9Hz).

IR(CHCl$_3$): 3518, 3450, 3430, 3110, 2669, 1740, 1708, 1645, 1530, 1499, 1420 cm$^{-1}$.

[α]$_D^{24}$+46.0±0.9° (c=0.968, MeOH)

Elemental Analysis (C$_{26}$H$_{33}$NO$_3$S$_3$) Calcd.(%): C, 61.99; H, 6.60; N, 2.78; S, 19.10 Found(%): C, 61.99; H, 6.61; N, 2.87; S, 19.18

Compound II-30

300MHz $^1$H-NMR(CDCl$_3$) δ: 0.94(1H, d, J=10.5Hz), 1.09 and 1.22(each 3H, each s), 1.51–2.42(14H, m), 2.47 (3H, d, J=0.9Hz), 4.21(1H, m), 5.35–5.49(2H, m), 6.18(1H, d, J=8.7Hz), 7.04(1H, m), 7.36 and 7.60(each 1H, each d, each J=3.9Hz), 7.91(1H, d, J=1.5Hz).

IR(CHCl$_3$): 3510, 3447, 3115, 2670, 1708, 1656, 1529, 1504, 1443, 1329, 1156, 1143 cm$^{-1}$.

[α]$_D^{24}$+53.8±0.9° (c=1.008, MeOH)

Elemental Analysis (C$_{26}$H$_{33}$NO$_5$S$_3$) Calcd.(%): C, 58.29; H, 6.21; N, 2.61; S, 17.96 Found(%): C, 58.07; H, 6.05; N, 2.69; S, 17.94

Compound II-31 mp.98–100° C.

300MHz $^1$H-NMR(CDCl$_3$) δ: 0.94(1H, d, J=10.2Hz), 1.08 and 1.21(each 3H, each s), 1.50–2.43(14H, m), 4.13 (2H, s), 4.20(1H, m), 5.33–5.49(2H, m), 5.97(1H, d, J=8.4Hz), 6.77(1H, m), 7.21–7.35(6H, m).

IR(KBr): 3407, 2674, 1703, 1630, 1511 cm$^{-1}$.

[α]$_D^{24}$+46.8±0.9° (c=1.006, MeOH)

Elemental Analysis ($C_{28}H_{35}NO_3S$) Calcd.(%): C, 72.22; H, 7.58; N, 3.01; S, 6.89 Found(%): C, 72.04; H, 7.36; N, 3.27; S, 6.91

Compound II-32

300MHz $^1$H-NMR(CDCl$_3$) δ: 0.94(1H, d, J=10.2Hz), 1.09 and 1.22(each 3H, each s), 1.50–2.45(14H, m), 4.22 (1H, m), 5.35–5.49(2H, m), 6.04(1H, d, J=8.7Hz), 6.52 and 6.69(each 1H, each d, each J=12.0Hz), 6.99(1H, dd, J=3.6 and 5.1Hz), 7.07(1H, d, J=3.9Hz), 7.13(1H, d, J=3.9Hz), 7.27(1H, dd, J=0.9 and 5.1Hz), 7.36(1H, d, J=3.9Hz).

IR(CHCl$_3$): 3510, 3449, 3430, 2664, 1708, 1643, 1536, 1501 cm$^{-1}$.

$[α]_D^{24}$+40.3±0.8° (c=1.011, MeOH)

Elemental Analysis ($C_{27}H_{33}NO_3S_2$•0.3H$_2$O) Calcd.(%): C, 66.31; H, 6.92; N, 2.86; S, 13.11 Found(%): C, 66.29; H, 6.81; N, 3.07; S, 13.13

Compound II-33 mp.117–118° C.

300MHz $^1$H-NMR(CDCl$_3$) δ: 0.97(1H, d, J=10.2Hz), 1.13 and 1.24(each 3H, each s), 1.50–2.47(14H, m), 4.24 (1H, m), 5.36–5.52(2H, m), 6.06(1H, d, J=8.7Hz), 6.97 and 7.15(each 1H, each d, each J=15.9Hz), 6.98(1H, d, J=3.9Hz), 7.01(1H, dd, J=3.3 and 4.8Hz), 7.09(1H, d, J=3.3Hz), 7.23(1H, d, J=4.8Hz), 7.36(1H, d, J=3.9Hz).

IR(CHCl$_3$): 3517, 3450, 2670, 1738, 1708, 1641, 1537, 1518, 1500 cm$^{-1}$.

$[α]_D^{24}$+55.7±1.0° (c=1.001, MeOH)

Elemental Analysis ($C_{27}H_{33}NO_3S_2$) Calcd.(%): C, 67.05; H, 6.88; N, 2.90; S, 13.26 Found(%): C, 66.91; H, 6.83; N, 2.97; S, 13.13

Compound II-34

300MHz $^1$H-NMR(CDCl$_3$) δ: 0.93(1H, d, J=10.5Hz), 1.08 and 1.22(each 3H, each s), 1.50–2.41(14H, m), 2.39 (3H, d, J=0.6Hz), 4.21(1H, m), 5.35–5.48(2H, m), 5.99(1H, m), 6.15(1H, d, J=8.7Hz), 6.20(1H, t, J=3.3Hz), 7.18(1H, dd, J=1.8 and 3.3Hz), 7.31 and 7.54(each 1H, each d, each J=3.9Hz).

IR(CHCl$_3$): 3511, 3446, 3150, 3101, 1708, 1658, 1529, 1504, 1375, 1183, 1160 cm$^{-1}$.

$[α]_D^{23}$+50.3±0.9° (c=1.007, MeOH)

Elemental Analysis ($C_{26}H_{34}N_2O_5S_2$•0.2H$_2$O) Calcd.(%): C, 59.79; H, 6.64; N, 5.36; S, 12.28 Found(%): C, 59.72; H, 6.61; N, 5.51; S, 12.37

Compound II-35

300MHz $^1$H-NMR(CDCl$_3$) δ: 0.93(1H, d, J=10.2Hz), 1.09 and 1.22(each 3H, each s), 1.51–2.44(14H, m), 4.20 (1H, m), 5.34–5.50(2H, m), 6.22 and 6.23(total 1H, each d, J=8.1 and 8.7Hz), 7.12(1H, dd, J=3.9 and 5.1Hz), 7.44(2H, m), 7.60(1H, m), 7.69(1H, m).

IR(CHCl$_3$): 3509, 3447, 3092, 1708, 1653, 1530, 1503 cm$^{-1}$.

$[α]_D^{23}$+49.3±0.9° (c=1.002, MeOH)

Elemental Analysis ($C_{25}H_{31}NO_4S_3$•0.4H$_2$O) Calcd.(%): C, 58.54; H, 6.25; N, 2.73; S, 18.75 Found(%): C, 58.62; H, 6.16; N, 2.88; S, 18.72

Compound II-36

300MHz $^1$H-NMR(CDCl$_3$) δ: 0.94(1H, d, J=10.2Hz), 1.09 and 1.10(total 3H, each s), 1.22 and 1.23(total 3H, each s), 1.51–2.44(14H, m), 2.52 and 2.53(total 3H, each d, J=0.6Hz), 4.20(1H, m), 5.35–5.50(2H, m), 6.23 and 6.24 (total 1H, each d, J=8.7 and 8.4Hz), 6.77(1H, m), 7.39–7.46 (3H, m).

IR(CHCl$_3$): 3510, 3447, 3429, 3093, 2665, 1708, 1652, 1530, 1502, 1437 cm$^{-1}$.

$[α]_D^{23}$+47.4±0.9° (c=1.008, MeOH)

Elemental Analysis ($C_{26}H_{33}NO_4S_3$•0.3H$_2$O) Calcd.(%): C, 59.47; H, 6.45; N, 2.67; S, 18.32 Found(%): C, 59.59; H, 6.16; N, 2.76; S, 18.11

Compound II-37

300MHz $^1$H-NMR(CDCl$_3$) δ: 0.93(1H, d, J=10.5Hz), 1.08 and 1.21(each 3H, each s), 1.50–2.42(14H, m), 3.84 (3H, s), 4.12(2H, s), 4.19(1H, m), 5.33–5.48(2H, m), 5.98 (1H, d, J=9.0Hz), 6.77(1H, dt, J=0.9 and 3.9Hz), 6.88(1H, d, J=8.1Hz), 9.90(1H, m), 7.15(1H, m), 7.23(1H, m), 7.28(1H, d, J=3.9Hz).

IR(CHCl$_3$): 3509, 3450, 3431, 2664, 1739, 1708, 1639, 1544, 1506, 1464 cm$^{-1}$.

$[α]_D^{24}$+40.4°±0.8° (c=1.003, MeOH)

Elemental Analysis ($C_{29}H_{37}NO_4S$•0.1H$_2$O) Calcd.(%): C, 70.02; H, 7.53; N, 2.81; S, 6.45 Found(%): C, 69.92; H, 7.53; N, 2.96; S, 6.46

Compound II-38

300MHz $^1$H-NMR(CDCl$_3$) δ: 0.93(1H, d, J=10.2Hz), 1.08 and 1.21(each 3H, each s), 1.50–2.47(14H, m), 4.13 (2H, s), 4.20(1H, m), 5.33–5.50(2H, m), 6.01(1H, d, J=9.0Hz), 6.80(1H, m), 6.82(1H, m), 6.86(1H, m), 7.12(1H, m), 7.15(1H, m), 7.31(1H, d, J=3.9Hz).

IR(CHCl$_3$): 3597, 3510, 3448, 3427, 3190, 1709, 1633, 1545, 1508, 1456 cm$^{-1}$.

$[α]_D^{24}$+41.8°±0.8° (c=1.004, MeOH)

Elemental Analysis ($C_{28}H_{35}NO_4S$•0.3H$_2$O) Calcd.(%): C, 69.11; H, 7.37; N, 2.88; S, 6.59 Found(%): C, 68.94; H, 7.42; N, 2.96; S, 6.73

Compound II-39

300MHz $^1$H-NMR(CDCl$_3$) δ: 0.93(1H, d, J=10.2Hz), 1.08 and 1.21(each 3H, each s), 1.50–2.44(14H, m), 2.27 (3H, s), 4.05(2H, s), 4.20(1H, m), 5.33–5.49(2H, m), 6.01 (1H, d, J=8.7Hz), 6.71(1H, d, J=3.9Hz), 7.09(1H, dd, J=1.2 and 7.8Hz), 7.17–7.32(3H, m), 7.28(1H, d, J=3.9Hz).

IR(CHCl$_3$): 3516, 3450, 3431, 2669, 1747, 1709, 1641, 1543, 1506, 1456, 1369 cm$^{-1}$.

$[α]_D^{24}$+40.2°±0.8° (c=1.006, MeOH)

Elemental Analysis ($C_{30}H_{37}NO_5S$•0.2H$_2$O) Calcd.(%): C, 68.34; H, 7.15; N, 2.66; S, 6.08 Found(%): C, 68.33; H, 6.94; N, 2.83; S, 6.31

Compound II-40

300MHz $^1$H-NMR(CDCl$_3$) δ: 0.93(1H, d, J=10.5Hz), 1.08 and 1.21(each 3H, each s), 1.50–2.41(14H, m), 4.20 (1H, m), 5.39–5.47(2H, m), 6.19(1H, d, J=8.4Hz), 7.35(1H, d, J=3.9Hz), 7.51–7.64(4H, m), 7.98(2H, m).

IR(CHCl$_3$): 3516, 3446, 2667, 1709, 1657, 1529, 1504, 1327, 1157 cm$^{-1}$.

$[α]_D^{20}$+55.6°±1.0° (c=1.004, MeOH)

Elemental Analysis (C$_{27}$H$_{33}$NO$_5$S•0.2H$_2$O) Calcd.(%): C, 62.45; H, 6.48; N, 2.70; S, 12.35 Found(%): C, 62.46; H, 6.40; N, 2.75; S, 12.19

Compound II-41

300MHz $^1$H-NMR(CDCl$_3$) δ: 0.95(1H, d, J=10.5Hz), 1.09 and 1.22(each 3H, each s), 1.50–2.44(14H, m), 2.31 (3H, s), 4.22(1H, m), 5.35–5.49(2H, m), 6.01(1H, d, J=8.7Hz), 7.03–7.21(4H, m), 7.38(1H, d, J=3.9Hz).
IR(CHCl$_3$): 3516, 3448, 3429, 1739, 1709, 1647, 1529, 1500, 1473, 1421 cm$^{-1}$.
[α]$_D^{20}$+46.2°±1.0° (c=1.003, MeOH)
Elemental Analysis (C$_{28}$H$_{35}$NO$_3$S$_2$•0.2H$_2$O) Calcd.(%): C, 67.08; H, 7.12; N, 2.79; S, 12.79 Found(%): C, 67.12; H, 7.04; N, 2.94; S, 12.88

Compound II-42 mp.111.2–115° C.
300MHz $^1$H-NMR(CDCl$_3$) δ: 0.93(1H, d, J=10.2Hz), 1.08 and 1.21(each 3H, each s), 1.50–2.39(14H, m), 2.42 (3H, s), 4.20(1H, m), 5.34–5.47(2H, m), 6.17(1H, d, J=8.7Hz), 7.34(1H, d, J=3.9Hz), 7.41(2H, m), 7.59(1H, d, J=3.9Hz), 7.78(2H, m).
IR(CHCl$_3$): 3516, 3446, 1739, 1707, 1655, 1529, 1504, 1331, 1151 cm$^{-1}$.
[α]$_D^{20}$+53.0°±0.9° (c=1.002, MeOH)
Elemental Analysis (C$_{28}$H$_{35}$NO$_5$S$_2$•0.2H$_2$O) Calcd.(%): C, 63.06; H, 6.69; N, 2.63; S, 12.02 Found(%): C, 63.07; H, 6.62; N, 2.73; S, 12.04

Compound II-43

300MHz $^1$H-NMR(CDCl$_3$) δ: 0.95(1H, d, J=10.2Hz), 1.09 and 1.22(each 3H, each s), 1.50–2.44(14H, m), 3.77 (3H, s), 4.22(1H, m), 5.35–5.49(2H, m), 6.04(1H, d, J=8.7Hz), 6.74–6.89(3H, m), 7.17–7.23(2H, m), 7.40(1H, d, J=3.9Hz).
IR(CHCl$_3$): 3514, 3448, 3431, 1739, 1707, 1649, 1529, 1500, 1477 cm$^{-1}$.
[α]$_D^{20}$+45.8°±0.9° (c=1.011, MeOH)
Elemental Analysis (C$_{28}$H$_{35}$NO$_4$S$_2$•0.3H$_2$O) Calcd.(%): C, 64.78; H, 6.91; N, 2.70; S, 12.35 Found(%): C, 64.62; H, 6.83; N, 2.85; S, 12.65

Compound II-44

300MHz $^1$H-NMR(CDCl$_3$) δ: 0.93(1H, d, J=10.5Hz), 1.08 and 1.21(each 3H, each s), 1.50–2.41(14H, m), 3.86 (3H, s), 4.20(1H, m), 5.34–5.47(2H, m), 6.17(1H, d, J=8.7Hz), 7.12(1H, m), 7.35(1H, d, J=3.9Hz), 7.40–7.48 (2H, m), 7.56(1H, m), 7.60(1H, d, J=3.9Hz).
IR(CHCl$_3$): 3514, 3446, 2667, 1707, 1657, 1599, 1529, 1504, 1481, 1329, 1252, 1151 cm$^{-1}$.
[α]$_D^{20}$+52.6°±0.9° (c=1.011, MeOH)
Elemental Analysis (C$_{28}$H$_{35}$NO$_6$S$_2$•0.2H$_2$O) Calcd.(%): C, 61.22; H, 6.50; N, 2.55; S, 11.67 Found(%): C, 61.10; H, 6.36; N, 2.65; S, 11.73

Compound II-45

300MHz $^1$H-NMR(CDCl$_3$) δ: 0.92(1H, d, J=10.5Hz), 1.07 and 1.20(each 3H, each s), 1.52–2.43(14H, m), 4.18 (1H, m), 5.33–5.50(2H, m), 6.42(1H, d, J=8.4Hz), 7.07(1H, m), 7.33–7.39(2H, m), 7.46–7.51(2H, m), 7.56(1H, d, J=3.9Hz).
IR(CHCl$_3$): 3587, 3442, 3280, 1707, 1643, 1531, 1329, 1308, 1149 cm$^{-1}$.
[α]$_D^{20}$+53.2°±0.9° (c=1.010, MeOH)
Elemental Analysis (C$_{27}$H$_{33}$NO$_6$S$_2$•0.4H$_2$O) Calcd.(%): C, 60.18; H, 6.32; N, 2.60; S, 11.90 Found(%): C, 60.19; H, 6.06; N, 2.63; S, 11.99

Compound II-46

300MHz $^1$H-NMR(CDCl$_3$) δ: 0.91(1H, d, J=10.2Hz), 1.08 and 1.21(each 3H, each s), 1.50–2.45(14H, m), 4.20 (1H, m), 5.33–5.50(2H, m), 6.17(1H, d, J=8.7Hz), 6.72(2H, m), 6.79(1H, m), 7.11(2H, m), 7.38(1H, d, J=3.9Hz).
IR(CHCl$_3$): 3342, 2669, 1707, 1622, 1583, 1535 cm$^{-1}$.
[α]$_D^{23}$+45.6°±0.9° (c=1.007, MeOH)
Elemental Analysis (C$_{27}$H$_{33}$NO$_4$S$_2$•0.2H$_2$O) Calcd.(%): C, 64.44; H, 6.69; N, 2.78; S, 12.74 Found(%): C, 64.33; H, 6.59; N, 2.83; S, 13.07

Compound II-47

300MHz $^1$H-NMR(CDCl$_3$) δ: 0.94(1H, d, J=10.5Hz), 1.08 and 1.21(each 3H, each s), 1.50–2.43(14H, m), 3.79 (3H, s), 4.10(2H, s), 4.20(1H, m), 5.33–5.49(2H, m), 5.98 (1H, d, J=8.7Hz), 6.76–6.85(4H, m), 7.24(1H, m), 7.32(1H, d, J=3.9Hz).
IR(CHCl$_3$): 3516, 3450, 3431, 2669, 1738, 1709, 1641, 1600, 1437, 1261 cm$^{-1}$.
[α]$_D^{23.5}$+42.8°±0.8° (c=1.005, MeOH)
Elemental Analysis (C$_{29}$H$_{37}$NO$_4$S) Calcd.(%): C, 70.27; H, 7.52; N, 2.83; S, 6.47 Found(%): C, 70.05; H, 7.55; N, 2.84; S, 6.45

Compound II-48

300MHz $^1$H-NMR(CDCl$_3$) δ: 0.94(1H, d, J=10.2Hz), 1.09 and 1.21(each 3H, each s), 1.51–2.43(14H, m), 3.38 (3H, s), 4.18(1H, m), 5.33–5.50(2H, m), 5.83(1H, d, J=8.7Hz), 6.16(1H, d, J=3.9Hz), 7.14(1H, m), 7.21–7.27 (4H, m), 7.33–7.39(2H, m).
IR(CHCl$_3$): 3514, 3450, 2661, 1739, 1709, 1628, 1597, 1495, 1479, 1415, 1132 cm$^{-1}$.
[α]$_D^{23.5}$+50.8°±0.9° (c=1.005, MeOH)
Elemental Analysis (C$_{28}$H$_{36}$N$_2$O$_3$S•0.2H$_2$O) Calcd.(%): C, 69.45; H, 7.58; N, 5.78; S, 6.62 Found(%): C, 69.45; H, 7.39; N, 5.99; S, 6.65

Compound II-49

300MHz $^1$H-NMR(CDCl$_3$) δ: 0.93(1H, d, J=9.9Hz), 1.08 and 1.21(each 3H, each s), 1.50–2.42(14H, m), 2.28(3H, s), 4.12(2H, s), 4.20(1H, m), 5.33–5.48(2H, m), 5.98(1H, d, J=9.0Hz), 6.71(1H, d, J=3.6Hz), 7.17(4H, s), 7.30(1H, d, J=3.6Hz).
IR(CHCl$_3$): 3518, 3450, 3430, 1739, 1709, 1641, 1543, 1506, 1471, 1458 cm$^{-1}$.
[α]$_D^{22.5}$+42.9°±0.8° (c=1.000, MeOH)
Elemental Analysis (C$_{29}$H$_{37}$NO$_3$S) Calcd.(%): C, 72.61; H, 7.77; N, 2.92; S, 6.68 Found(%): C, 72.43; H, 7.78; N, 3.09; S, 6.62

Compound II-50

300MHz $^1$H-NMR(CDCl$_3$) δ: 0.93(1H, d, J=10.2Hz), 1.08 and 1.21(each 3H, each s), 1.50–2.46(14H, m), 4.19 (1H, m), 5.33–5.50(2H, m), 6.03(1H, d, J=8.7Hz), 6.52(1H, dd, J=1.5 and 3.3Hz), 7.11(1H, dd, J=3.9 and 4.8Hz), 7.17(1H, dd, J=2.1 and 3.3Hz), 7.70–7.72(2H, m), 7.74(1H, dd, J=1.2 and 3.9Hz).

IR(CHCl$_3$): 3510, 3448, 3143, 2666, 1733, 1708, 1650, 1572, 1507, 1387, 1179 cm$^{-1}$.

$[\alpha]_D^{24}$+39.1°+0.8° (c=1.003, MeOH)

Elemental Analysis (C$_{25}$H$_{32}$N$_2$O$_5$S$_2$) Calcd.(%): C, 59.50; H, 6.39; N, 5.55; S, 12.71 Found(%): C, 59.49; H, 6.46; N, 5.47; S, 12.70

Compound II-51

300MHz $^1$H-NMR(CDCl$_3$) δ: 0.94(1H, d, J=9.9Hz), 1.09 and 1.22(each 3H, each s),1.50–2.42(14H, m), 2.43(3H, s), 4.20(1H, m), 4.24(2H, s), 5.34–5.49(2H, m), 5.99(1H, d, J=8.7Hz), 6.58(1H, m), 6.67(1H, d, J=3.3Hz), 6.83(1H, d, J=3.9Hz), 7.32(1H, d, J=3.9Hz).

IR(CHCl$_3$): 3516, 3450, 3431, 2667, 1709, 1643, 1545, 1508, 1471, 1458 cm$^{-1}$.

$[\alpha]_D^{22}$+42.8±0.8° (c=1.006, MeOH)

Elemental Analysis (C$_{27}$H$_{35}$NO$_3$S$_2$) Calcd.(%): C, 66.77; H, 7.26; N, 2.88; S, 13.20 Found(%): C, 66.60; H, 7.23; N, 2.93; S, 13.19

Compound II-52

300MHz $^1$H-NMR(CDCl$_3$) δ: 0.94(1H, d, J=10.5Hz), 1.09 and 1.22(each 3H, each s), 1.50–2.44(14H, m), 2.31 (3H, s), 4.21(1H, m), 4.25(2H, s), 5.34–5.49(2H, m), 6.01 (1H, d, J=8.7Hz), 6.83(1H, d, J=3.9Hz), 7.03(1H, m), 7.11–7.20(3H, m), 7.27(1H, d, J=3.9Hz).

IR(CHCl$_3$): 3516, 3450, 3431, 2665, 1739, 1709, 1643, 1543, 1508, 1473 cm$^{-1}$.

$[\alpha]D^{22}$+42.6+1.0°(c=0.861, MeOH)

Elemental Analysis (C$_{29}$H$_{37}$NO$_3$S$_2$H$_2$O) Calcd.(%): C, 67.59; H, 7.31; N, 2.72; S, 12.44 Found(%): C, 67.49; H, 7.27; N, 2.82; S, 12.35

Compound II-53

300MHz $^1$H-NMR(CDCl$_3$) δ: 0.93(1H, d, J=9.9Hz), 1.08 and 1.21(each 3H, each s), 1.50–2.41(14H, m), 2.60(3H, s), 4.20(1H, m), 5.34–5.48(2H, m), 6.18(1H, d, J=8.7Hz), 7.28 (1H, d-like), 7.36(1H, d, J=3.9Hz), 7.40(1H, t-like), 7.51 (1H, dt, J=1.2 and 7.2Hz), 7.61(1H, d, J=3.9Hz), 8.15(1H, dd, J=1.2 and 8.1Hz).

IR(CHCl$_3$): 3512, 3446, 1739, 1709, 1655, 1529, 1504, 1325, 1157 cm$^{-1}$.

$[\alpha]_D^{24}$+51.1+0.9° (c=1.010, MeOH)

Elemental Analysis (C$_{28}$H$_{35}$NO$_5$S$_2$) Calcd.(%): C, 63.49; H, 6.66; N, 2.64; S, 12.11 Found(%): C, 63.23; H, 6.53; N, 2.70; S, 12.17

Compound II-54

300MHz $^1$H-NMR(CDCl$_3$) δ: 0.93(1H, d, J=10.2Hz), 1.07 and 1.21(each 3H, each s), 1.50–2.40(14H, m), 2.42 (3H, s), 4.20(1H, m), 5.34–5.47(2H, m), 6.17(1H, d, J=8.7Hz), 7.32(1H, d-like), 7.34 and 7.57(each 1H, each d, each J=4.2Hz), 7.86(2H, d-like).

IR(CHCl$_3$): 3512, 3446, 1741, 1707, 1655, 1529, 1504, 1331, 1153 cm$^{-1}$.

$[\alpha]_D^{24}$+54.9±0.9° (c=1.008, MeOH) Elemental Analysis (C$_{28}$H$_{35}$NO$_5$S$_2$) Calcd.(%): C, 63.49; H, 6.66; N, 2.64; S, 12.11 Found(%): C, 63.16; H, 6.54; N, 2.70; S, 12.16

Compound II-55

300MHz $^1$H-NMR(CDCl$_3$) δ: 0.95(1H, d, J=10.5Hz), 1.09 and 1.21(each 3H, each s), 1.50–2.44(14H, m), 4.15 (2H, s), 4.20(1H, m), 5.33–5.49(2H, m), 6.01(1H, d, J=9.3Hz), 6.13(1H, dd, J=0.6 and 3.0Hz), 6.32(1H, dd, J=1.8 and 3.0Hz), 6.84 and 7.22(each 1H, each d, each J=3.6Hz), 7.47(1H, dd, J=0.6 and 1.8Hz).

IR(CHCl$_3$): 3518, 3450, 3431, 2669, 1739, 1709, 1643, 1545, 1506 cm$^{-1}$.

$[\alpha]_D^{23}$+45.8±0.9° (c=1.003, MeOH)

Elemental Analysis (C$_{26}$H$_{33}$NO$_4$S•0.6H$_2$O) Calcd.(%): C, 66.95; H, 7.39; N, 3.00; S, 6.87 Found(%): C, 67.04; H, 7.17; N, 3.11; S, 7.03

Compound II-56

300MHz $^1$H-NMR(CDCl$_3$) δ: 0.95(1H, d, J=10.5Hz), 1.10 and 1.22(each 3H, each s), 1.52–2.45(14H, m), 3.96 (2H, s), 4.20(1H, m), 5.33–5.49(2H, m), 6.00(1H, d, J=8.7Hz), 6.30(1H, dd, J=0.9 and 1.8Hz), 6.81(1H, d, J=3.6Hz), 7.31–7.33(2H, m), 7.38(1H, t, J=1.8Hz).

IR(CHCl$_3$): 3516, 3450, 3431, 2663, 1739, 1709, 1643, 1545, 1506 cm$^{-1}$.

$[\alpha]_D^{21}$+46.5±0.9° (c=1.002, MeOH)

Elemental Analysis (C$_{26}$H$_{33}$NO$_4$S•0.1H$_2$O) Calcd.(%): C, 68.27; H, 7.32; N, 3.06; S, 7.01 Found(%): C, 68.08; H, 7.14; N, 3.21; S, 7.19

Compound II-57

300MHz $^1$H-NMR(CDCl$_3$) δ: 0.94(1H, d, J=10.2Hz), 1.09 and 1.21(each 3H, each s), 1.50–2.42(14H, m), 4.20 (1H, m), 4.41(2H, s), 5.33–5.49(2H, m), 6.01(1H, d, J=8.7Hz), 6.91(1H, d, J=3.6Hz), 7.11(1H, s), 7.27–7.35(3H, m), 7.68–7.77(2H, m).

IR(CHCl$_3$): 3512, 3446, 3431, 1709, 1645, 1543, 1508 cm$^{-1}$.

$[\alpha]_D^{24}$+44.9±0.9° (c=1.002, MeOH)

Elemental Analysis (C$_{30}$H$_{35}$NO$_3$S$_2$•0.3H$_2$O) Calcd.(%): C, 68.35; H, 6.81; N, 2.66; S, 12.17 Found(%): C, 68.17; H, 6.52; N, 2.68; S, 12.04

Compound II-58

300MHz $^1$H-NMR(CDCl$_3$) δ: 0.94(1H, d, J=10.5Hz), 1.09 and 1.21(each 3H, each s), 1.50–2.41(14H, m), 4.19 (1H, m), 4.29(2H, s), 5.33–5.48(2H, m), 6.02(1H, d, J=8.4Hz), 6.51(1H, s), 6.91(1H, d, J=3.6Hz), 7.16–7.25(2H, m), 7.34(1H, d, J=3.6Hz), 7.42(1H, d, J=8.4Hz), 7.50(1H, m).

IR(CHCl$_3$): 3516, 3450, 3431, 1739, 1709, 1643, 1545, 1508, 1454 cm$^{-1}$.

$[\alpha]_D^{23}$+42.3±0.8° (c=1.001, MeOH)

Elemental Analysis (C$_{30}$H$_{35}$NO$_4$S•0.3H$_2$O) Calcd.(%): C, 70.50; H, 7.02; N, 2.74; S, 6.27 Found(%): C, 70.36; H, 6.94; N, 2.70; S, 6.17

Compound II-59

300MHz $^1$H-NMR(CDCl$_3$) δ: 0.94(1H, d, J=10.2Hz), 1.08 and 1.20(each 3H, each s), 1.49–2.42(14H, m), 4.20 (1H, m), 4.19(2H, s), 5.33–5.48(2H, m), 5.99(1H, d, J=9.0Hz), 6.80(1H, d, J=3.6Hz), 7.22(1H, d, J=7.5Hz), 7.31–7.50(7H, m), 7.57(2H, m).

IR(CHCl$_3$): 3518, 3450, 3431, 2671, 1739, 1709, 1643, 1543, 1506, 1471, 1456 cm$^{-1}$.

Compound II-60

300MHz $^1$H-NMR(CDCl$_3$) δ: 0.97(1H, d, J=10.2Hz), 1.06 and 1.22(each 3H, each s),1.52–2.48(14H, m), 4.11(2H, s), 4.31(1H, m), 5.34–5.51(2H, m), 6.15(1H, d, J=9.0Hz), 7.19–7.30(6H, m), 7.76(1H, d, J=8.1Hz), 7.83(1H, s), 8.15 (1H, s)
IR(CHCl$_3$): 3516, 3442, 2667, 1739, 1709, 1651, 1514, 1495, 1471, 1454, 1435 cm$^{-1}$.
$[α]_D^{24}$+42.8±0.8° (c=1.001, MeOH)
Elemental Analysis (C$_{32}$H$_{37}$NO$_3$S) Calcd.(%): C, 74.53; H, 7.23; N, 2.72; S, 6.22 Found(%): C, 74.25; H, 7.20; N, 2.97; S, 6.05

Compound II-61

300MHz $^1$H-NMR(CDCl$_3$) δ: 0.98(1H, d, J=10.2Hz), 1.10 and 1.23(each 3H, each s),1.52–2.49(14H, m), 4.10(2H, s), 4.32(1H, m), 5.35–5.53(2H, m), 6.17(1H, d, J=8.7Hz), 7.19–7.32(6H, m), 7.64(1H, d, J=0.9Hz), 7.76(1H, s), 8.21 (1H, d, J=8.4Hz).
IR(CHCl$_3$): 3518, 3442, 2671, 1739, 1707, 1651, 1514, 1493, 1469, 1454, 1404 cm$^{-1}$.
$[α]_D^{24}$+47.1±0.9° (c=1.001, MeOH)
Elemental Analysis (C$_{32}$H$_{37}$NO$_3$S•0.2H$_2$O) Calcd.(%): C, 74.01; H, 7.26; N, 2.70; S, 6.17 Found(%): C, 73.89; H, 7.44; N, 2.93; S, 6.04

Compound II-62 mp.134–135° C.
300MHz $^1$H-NMR(CDCl$_3$) δ: 0.93(1H, d, J=10.5Hz), 0.98 and 1.15(each 3H, each s),1.48–2.43(14H, m), 4.20(1H, m), 4.40 and 4.54(each 1H, each d, J=16.5Hz), 5.33–5.50 (2H, m), 6.04(1H, d, J=8.4Hz), 6.99–7.30(6H, m), 7.55(1H, s), 7.73(1H, d, J=8.4Hz).
IR(CHCl$_3$): 3518, 3437, 2669, 1741, 1709, 1653, 1510, 1471, 1454 cm$^{-1}$.
$[α]_D^{25}$+54.2±0.9° (c=1.003, MeOH)
Elemental Analysis (C$_{32}$H$_{37}$NO$_3$S•0.1H$_2$O) Calcd.(%): C, 74.27; H, 7.25; N, 2.71; S, 6.20 Found(%): C, 74.11; H, 7.16; N, 3.15; S, 6.25

Compound II-63

300MHz $^1$H-NMR(CDCl$_3$) δ: 0.94(1H, d, J=10.5Hz), 1.08 and 1.21(each 3H, each s),1.49–2.43(14H, m), 3.94(2H, s), 4.22(1H, m), 5.33–5.49(2H, m), 6.03(1H, d, J=8.7Hz), 7.04(1H, s), 7.17–7.33(6H, m).
IR(CHCl$_3$): 3516, 3448, 3433, 2669, 1739, 1709, 1645, 1549, 1508, 1471, 1454 cm$^{-1}$.
$[α]_D^{25}$+40.5±0.8° (c=1.003, MeOH)
Elemental Analysis (C$_{28}$H$_{35}$NO$_3$S•0.1H$_2$O) Calcd.(%): C, 71.95; H, 7.59; N, 3.00; S, 6.86 Found(%): C, 71.82; H, 7.49; N, 3.37; S, 6.83

Compound II-64

300MHz $^1$H-NMR(CDCl$_3$) δ: 0.98(1H, d, J=10.5Hz), 1.10 and 1.23(each 3H, each s),1.53–2.50(14H, m), 4.24(2H, s), 4.33(1H, m), 5.35–5.54(2H, m), 6.18(1H, d, J=8.4Hz), 7.19–7.30(6H, m), 7.42(1H, t, J=7.8Hz), 7.78(1H, s), 8.18 (1H, d, J=7.8Hz).
IR(CHCl$_3$): 3514, 3442, 2671, 1709, 1651, 1516, 1495, 1471, 1454, cm$^{-1}$.
$[α]_D^{25}$+53.6±0.9° (c=1.003, MeOH),
Elemental Analysis (C$_{32}$H$_{37}$NO$_3$S•0.1H$_2$O) Calcd.(%): C, 74.27; H, 7.25; N, 2.71; S, 6.20 Found(%): C, 74.18; H, 7.24; N, 2.90; S, 6.14

Compound II-65 mp.117–118° C.
300MHz $^1$H-NMR(CDCl$_3$) δ: 0.94(1H, d, J=9.9Hz), 1.09 and 1.21(each 3H, each s), 1.55–2.42(14H, m), 3.87(3H, s), 4.06(2H, s), 4.18(1H, m), 5.35–5.49(2H, m), 5,56(1H, brs), 5.89(1H, d, J=8.7Hz), 6.72–6.77(3H, m), 6.87(1H, d, J=8.1Hz), 7.31(1H, d, J=3.6Hz).
IR(Nujol): 3373, 3184, 2667, 1705, 1622, 1599, 1547, 1520, 1286 cm$^{-1}$.
$[α]_D^{23}$+42.0±0.8° (c=1.008, MeOH)
Elemental Analysis (C$_{29}$H$_{37}$NO$_5$S) Calcd.(%): C, 68.07; H, 7.29; N, 2.74; S, 6.27 Found(%): C, 67.84; H, 7.43; N, 2.71; S, 6.18

Compound II-66

300MHz $^1$H-NMR(CDCl$_3$) δ: 0.95(1H, d, J=9.9Hz), 1.10 and 1.23(each 3H, each s), 1.53–2.45(14H, m), 3.87(3H, s), 2.96–3.01(2H, m), 3.10–3.16(2H, m), 4.22(1H, m), 5.34–5.50(2H, m), 6.01(1H, d, J=8.4Hz), 6.71(1H, d, J=3.9Hz), 7.16–7.32(6H, m).
IR(CHCl$_3$): 3518, 3450, 3431, 2671, 1739, 1709, 1641, 1545, 1508 cm$^{-1}$.
$[α]_D^{22}$+44.3±0.8° (c=1.006, MeOH)
Elemental Analysis (C$_{29}$H$_{37}$NO$_3$S•0.1H$_2$O) Calcd.(%): C, 72.34; H, 7.79; N, 2.91; S, 6.66 Found(%): C, 72.24; H, 7.68; N, 3.11; S, 6.73

Compound II-67

300MHz $^1$H-NMR(CDCl$_3$) δ: 0.95(1H, d, J=10.2Hz), 1.10 and 1.23(each 3H, each s), 1.52–2.45(14H, m), 2.43 (3H, d, J=0.9Hz), 3.07–3.18(4H, m), 4.21(1H, m), 5.35–5.50 (2H, m), 6.02(1H, d, J=8.4Hz), 6.53–6.57(2H, m), 6.76 and 7.30(each 1H, each d, each J=3.9Hz).
IR(CHCl$_3$): 3516, 3450, 3431, 2667, 1709, 1641, 1543, 1508 cm$^{-1}$.
$[α]_D^{22}$+43.1±0.8° (c=1.005, MeOH)
Elemental Analysis (C$_{28}$H$_{37}$NO$_3$S$_2$•0.3H$_2$O) Calcd.(%): C, 66.58; H, 7.50; N, 2.77; S, 12.70 Found(%): C, 66.47; H, 7.46; N, 2.99; S, 12.62

Compound II-68

300MHz $^1$H-NMR(CDCl$_3$) δ: 0.95(1H, d, J=10.2Hz), 1.10 and 1.23(each 3H, each s), 1.52–2.45(14H, m), 3.19 (4H, s), 4.21(1H, m), 5.34–5.50(2H, m), 6.01(1H, d, J=8.4Hz), 6.75(1H, d, J=3.9Hz), 6.79(1H, m), 6.91(1H, dd, J=3.6 and 5.1Hz), 7.13(1H, dd, J=0.9 and 5.1Hz), 7.29(1H, d, J=3.9Hz).
IR(CHCl$_3$): 3514, 3450, 3433, 2667,n 1739, 1709, 1641, 1545, 1508 cm$^{-1}$.
$[α]_D^{24}$+33.5±0.8° (c=1.009, MeOH)
Elemental Analysis (C$_{27}$H$_{35}$NO$_3$S$_2$) Calcd.(%): C, 66.77; H, 7.26; N, 2.88; S, 13.20 Found(%): C, 66.48; H, 7.31; N, 2.97; S, 13.22

Compound II-69

300MHz $^1$H-NMR(CDCl$_3$) δ: 0.97(1H, d, J=9.9Hz), 1.12 and 1.23(each 3H, each s), 1.53–2.47(14H, m), 3.00–3.06 (2H, m), 3.12–3.17(2H, m), 4.27(1H, m), 5.34–5.51(2H, m), 6.24(1H, d, J=9.0Hz), 6.75(1H, m), 6.90(1H, dd, J=3.6 and 5.4Hz), 7.12(1H, dd, J=1.2 and 5.4Hz), 7.25 and 7.64(each 2H, each d-like).

IR(CHCl$_3$): 3516, 3452, 2665, 1738, 1709, 1649, 1523, 1495 cm$^{-1}$.

$[α]_D^{24}$+54.5±0.9° (c=1.016, MeOH) Elemental Analysis (C$_{25}$H$_{37}$NO$_3$S) Calcd.(%): C, 72.61; H, 7.77; N, 2.92; S, 6.68 Found(%): C, 72.51; H, 7.69; N, 2.98; S, 6.62

Compound II-70

300MHz $^1$H-NMR(CDCl$_3$) δ: 0.95(1H, d, J=10.2Hz), 1.10 and 1.23(each 3H, each s), 1.51–2.45(14H, m), 2.92–2.97(2H, m), 3.08–3.13(2H, m), 4.22(1H, m), 5.34–5.50(2H, m), 6.00(1H, d, J=8.7Hz), 6.69(1H, d, J=3.6Hz), 6.92–7.00(2H, m), 7.09–7.15(2H, m), 7.28(1H, d, J=3.6Hz).

IR(CHCl$_3$): 3516, 3450, 3431, 1741, 1709, 1641, 1543, 1510, 1471 cm$^{-1}$.

$[α]_D^{23}$+42.6±0.8° (c=1.014, MeOH)

Elemental Analysis (C$_{29}$H$_{36}$FNO$_3$S) Calcd.(%): C, 69.99; H, 7.29; N, 2.81; S, 6.44; F, 3.82 Found(%): C, 69.87; H, 7.29; N, 2.88; S, 6.50; F, 3.85

Compound II-71 mp.93–95° C.

300MHz $^1$H-NMR(CDCl$_3$) δ: 0.96(1H, d, J=10.2Hz), 1.13 and 1.23(each 3H, each s), 1.52–2.47(14H, m), 4.08 (2H, s), 4.27(1H, m), 5.34–5.51(2H, m), 6.21(1H, d, J=8.7Hz), 7.18–7.32(6H, m), 7.61 and 7.66(each 1H, each s), 7.74(1H, d, J=8.4Hz).

IR(KBr): 3367, 1705, 1618, 1556, 1533, 1508 cm$^{-1}$.

$[α]_D^{23}$+60.4±0.8° (c=1.012, MeOH)

Elemental Analysis (C$_{32}$H$_{37}$NO$_3$S) Calcd.(%): C, 74.53; H, 7.23; N, 2.72; S, 6.22 Found(%): C, 74.31; H, 7.37; N, 2.99; S, 6.10

Compound II-72

300MHz $^1$H-NMR(CDCl$_3$) δ: 0.92(1H, d, J=10.2Hz), 1.06 and 1.19(each 3H, each s), 1.47–2.42(14H, m), 4.20 (1H, m), 4.28(2H, s), 5.32–5.47(2H, m), 5.98(1H, d, J=8.7Hz), 6.80(1H, d, J=3.3Hz), 7.32–7.36(2H, m), 7.41–7.50(2H, m), 7.68(1H, s), 7.77–7.83(3H, m).

IR(CHCl$_3$): 3518, 3450, 3431, 1739, 1709, 1641, 1545, 1508, 1471 cm$^{-1}$.

$[α]_D^{23}$+42.7±0.8° (c=1.003, MeOH)

Elemental Analysis (C$_{32}$H$_{37}$NO$_3$S•0.2H$_2$O) Calcd.(%): C, 74.01; H, 7.26; N, 2.70; S, 6.17 Found(%): C, 73.94; H, 7.30; N, 2.89; S, 6.15

Compound II-73

300MHz $^1$H-NMR(CDCl$_3$) δ: 0.95(1H, d, J=10.5Hz), 1.11 and 1.22(each 3H, each s), 1.51–2.45(14H, m), 2.94–3.00(2H, m), 3.06–3.12(2H, m), 3.83(3H, s), 4.22(1H, m), 5.34–5.50(2H, m), 6.00(1H, d, J=8.7Hz), 6.73(1H, d, J=3.6Hz), 6.84–6.89(2H, m), 7.09(1H, dd, J=1.5 and 7.8Hz), 7.20(1H, dt, J=1.5 and 7.8Hz), 7.30(1H, d, J=3.6Hz).

IR(CHCl$_3$): 3518, 3450, 3431, 1741, 1709, 1639, 1545, 1506, 1496, 1466 cm$^{-1}$.

$[α]_D^{25}$+41.3±0.8° (c=1.007, MeOH)

Elemental Analysis (C$_{30}$H$_{39}$FNO$_4$S) Calcd.(%): C, 70.69; H, 7.71; N, 2.75; S, 6.29 Found(%): C, 70.42; H, 7.64; N, 2.78; S, 6.37

Compound II-74

300MHz $^1$H-NMR(CDCl$_3$) δ: 0.94(1H, d, J=10.2Hz), 1.10 and 1.22(each 3H, each s), 1.53–2.48(14H, m), 2.96–3.04(2H, m), 3.07–3.16(2H, m), 4.22(1H, m), 5.34–5.52(2H, m), 6.04(1H, d, J=8.7Hz), 6.74(1H, d, J=3.6Hz), 6.77–6.85(2H, m), 7.05–7.11(2H, m), 7.31(1H, d, J=3.6Hz).

IR(CHCl$_3$): 359, 3510, 3429, 3190, 1709, 1636, 1545, 1508, 1456 cm$^{-1}$.

$[α]_D^{25}$+42.7±0.8° (c=1.009, MeOH)

Elemental Analysis (C$_{29}$H$_{37}$NO$_4$S•0.3H$_2$O) Calcd.(%): C, 69.51; H, 7.56; N, 2.80; S, 6.40 Found(%): C, 69.25; H, 7.43; N, 2.89; S, 6.43

Compound II-75 mp.91–92° C.

300MHz $^1$H-NMR(CDCl$_3$) δ: 0.95(1H, d, J=10.5Hz), 1.09 and 1.22(each 3H, each s), 1.51–2.44(14H, m), 4.16(2H, s), 4.20(1H, m), 5.34–5.49(2H, m), 5.99(1H, d, J=8.7Hz), 6.79(1H, d, J=3.9Hz), 6.96(1H, dd, J=1.2 and 4.8Hz), 7.05 (1H, m), 7.28(1H, dd, J=3.0 and 4.8Hz), 7.32(1H, d, J=3.9Hz).

IR(Nujol): 3408, 2677, 1703, 1626, 1541, 1514, 1246 cm$^{-1}$.

$[α]_D^{26}$+43.8±0.8° (c=1.005, MeOH)

Elemental Analysis (C$_{26}$H$_{33}$NO$_3$S$_2$) Calcd.(%): C, 66.21; H, 7.05; N, 2.97; S, 13.60 Found(%): C, 66.00; H, 7.81; N, 3.11; S, 13.69

Compound II-76 mp.125–126° C.

300MHz $^1$H-NMR(CDCl$_3$) δ: 0.96(1H, d, J=10.2Hz), 1.13 and 1.23(each 3H, each s), 1.52–2.47(14H, m), 4.10 (2H, s), 4.27(1H, m), 5.34–5.51(2H, m), 6.20(1H, d, J=9.0Hz), 7.19–7.33(6H, m), 7.62 and 7.69(each 1H, each s), 7.73(1H, d, J=8.4Hz).

IR(KBr): 3415, 3199, 1736, 1703, 1633, 1523 cm$^{-1}$.

$[α]_D^{25}$+53.3±0.8° (c=1.002, MeOH)

Elemental Analysis (C$_{32}$H$_{37}$NO$_3$S•0.1H$_2$O) Calcd.(%): C, 74.27; H, 7.25; N, 2.71; S, 6.23 Found(%): C, 74.19; H, 7.16; N, 2.81; S, 6.23

Compound II-77 mp.98–101° C.

300MHz $^1$H-NMR(CDCl$_3$) δ: 0.97(1H, d, J=10.5Hz), 1.14 and 1.24(each 3H, each s), 1.53–2.47(14H, m), 4.08 (2H, s), 4.27(1H, m), 5.35–5.51(2H, m), 6.21(1H, d, J=8.7Hz), 6.90(1H, dd, J=1.2 and 5.1Hz), 6.93(1H, m), 7.24–7.29(2H, m), 7.63(1H, s), 7.75(1H, d, J=8.1Hz).

IR(KBr): 3394, 3097, 1707, 1643, 1533, 1500 cm$^{-1}$.

$[α]_D^{25}$+58.7±1.0° (c=1.006, MeOH)

Elemental Analysis (C$_{30}$H$_{35}$NO$_3$S$_2$•0.3H$_2$O) Calcd.(%): C, 68.35; H, 6.81; N, 2.66; S, 12.17 Found(%): C, 68.27; H, 6.76; N, 2.94; S, 12.17

Compound II-78 mp.106–109° C.

300MHz $^1$H-NMR(CDCl$_3$) δ: 0.97(1H, d, J=10.2Hz), 1.14 and 1.24(each 3H, each s), 1.53–2.47(14H, m), 4.26 (2H, s), 4.27(1H, m), 5.35–5.51(2H, m), 6.22(1H, d, J=8.7Hz), 6.82(1H, m), 6.93(1H, dd, J=3.6 and 5.1Hz), 7.16(1H, dd, J=1.2 and 5.1Hz), 7.32(1H, dd, J=8.1 and 1.8Hz), 7.68(2H, m), 7.76(1H, d, J=8.1Hz).

IR(KBr): 3396, 3070, 1707, 1645, 1535, 1500 cm$^{-1}$.

$[α]_D^{25}$+59.9±1.0° (c=1.005, MeOH)

Elemental Analysis (C$_{30}$H$_{35}$NO$_3$S$_2$•0.2H$_2$O) Calcd.(%): C, 68.59; H, 6.79; N, 2.67; S, 12.21 Found(%): C, 68.57; H, 6.62; N, 2.76; S, 12.17

Compound II-79

300MHz $^1$H-NMR(CDCl$_3$) δ: 0.94(1H, d, J=10.2Hz), 1.09 and 1.22(each.3H, each S), 1.49–2.44(14H, m), 4.12 (2H, s), 4.23(1H, m), 5.34–5.49(2H, m), 6.09(1H, d, J=8.7Hz), 6.82 and 6.93(each 1H, each m), 7.13–7.17(2H, m), 7.34(1H, d, J=1.5Hz).

IR(CHCl$_3$): 3512, 3448, 3431, 1739, 1709, 1645, 1550, 1508, 1471, 1456 cm$^{-1}$.

$[α]_D^{25}$+43.3±0.8° (c=1.007, MeOH)

Elemental Analysis (C$_{26}$H$_{33}$NO$_3$S$_2$•0.1H$_2$O) Calcd.(%): C, 65.95; H, 7.07; N, 2.96; S, 13.54 Found(%): C, 66.12; H, 7.06; N, 3.04; S, 13.66

Compound II-80

300MHz $^1$H-NMR(CDCl$_3$) δ: 0.94(1H, d, J=10.5Hz), 1.09 and 1.22(each 3H, each s), 1.49–2.44(14H, m), 3.95 (2H, s), 4.22(1H, m), 5.34–5.49(2H, m), 6.06(1H, d, J=8.7Hz), 6.92 and 6.96(each 1H, each m), 7.07(1H, d, J=1.5Hz), 7.28(1H, m), 7.30(1H, d, J=1.5Hz).

IR(CHCl$_3$): 3510, 3431, 1739, 1709, 1645, 1550, 1508, 1471 cm$^{-1}$.

$[α]D^{25}$+41.1±0.8° (c=1.009, MeOH)

Elemental Analysis (C$_{26}$H$_{33}$NO$_3$S$_2$•0.2H$_2$O) Calcd.(%): C, 65.70; H, 7.08; N, 2.95; S, 13.49 Found(%): C, 65.57; H, 6.97; N, 3.08; S, 13.63

Compound II-81

300MHz $^1$H-NMR(CDCl$_3$) δ: 0.98(1H, d, J=10.5Hz), 1.10 and 1.23(each 3H, each s),1.53–2.50(14H, m), 4.23(2H, s), 4.33(1H, m), 5.35–5.54(2H, m), 6.18(1H, d, J=8.7Hz), 6.92(1H, dd, J=1.2 and 4.8Hz), 7.01(1H, m), 7.22(1H, d, J=7.8Hz), 7.24(1H, dd, J=3.0 and 4.8Hz), 7.42(1H, d, J=7.8 and 8.1Hz), 7.79(1H, s), 8.18(1H, d, J=8.1Hz).

IR(CHCl$_3$): 3516, 3442, 2667, 1709, 1651, 1516, 1495, 1471 cm$^{-1}$.

$[α]_D^{26}$+50.9±0.9° (c=1.009, MeOH),

Elemental Analysis (C$_{30}$H$_{35}$NO$_3$S$_2$•0.2H$_2$O) Calcd.(%): C, 68.59; H, 6.79; N, 2.67; S, 12.21 Found(%): C, 68.51; H, 6.69; N, 2.73; S, 12.39

Compound II-82

300MHz $^1$H-NMR(CDCl$_3$) δ: 0.95(1H, d, J=10.2Hz), 1.10 and 1.22(each 3H, each s), 1.50–2.44(14H, m), 3.74 (2H, s), 4.23(1H, m), 5.34–5.50(2H, m), 6.07(1H, d, J=8.0Hz), 6.23(1H, s), 7.08(1H, d, J=1.5Hz), 7.24(1H, s), 7.31(1H, d, J=1.5Hz), 7.36(1H, m).

IR(CHCl$_3$): 3510, 3448, 3431, 2663, 1709, 1645, 1550, 1508, 1471 cm$^{-1}$.

$[α]_D^{25}$+44.2±0.8° (c=1.001, MeOH)

Elemental Analysis (C$_{26}$H$_{33}$NO$_4$S•0.2H$_2$O) Calcd.(%): C, 68.00; H, 7.33; N, 3.05; S, 6.98 Found(%): C, 68.00; H, 7.30; N, 3.15; S, 7.12

Compound II-83

300MHz $^1$H-NMR(CDCl$_3$) δ: 0.92(1H, d, J=10.2Hz), 1.05 and 1.19(each 3H, each s), 1.48–2.40(14H, m), 4.17 (1H, m), 4.58(2H, s), 5.31–5.46(2H, m), 5.96(1H, d, J=8.7Hz), 6.72 and 7.26(each 1H, each d, each J=3.9Hz), 7.37–7.51(4H, m), 7.79(1H, d, J=8.1Hz), 7.87 and 7.97(each 1H, each m).

IR(CHCl$_3$): 3516, 3450, 3431, 2667, 1739, 1709, 1641, 1543, 1508, 1471 cm$^{-1}$.

$[α]_D^{25.5}$+41.9±0.8° (c=1.011, MeOH)

Elemental Analysis (C$_{32}$H$_{37}$NO$_3$S•0.2H$_2$O) Calcd.(%): C, 74.01; H, 7.26; N, 2.70; S, 6.17 Found(%): C, 74.10; H, 7.13; N, 2.99; S, 6.15

Compound II-84

300MHz $^1$H-NMR(CDCl$_3$) δ: 0.93(1H, d, J=10.2Hz), 1.05 and 1.20(each 3H, each s), 1.48–2.42(14H, m), 4.20 (1H, m), 4.39(2H, m), 5.31–5.46(2H, m), 6.00(1H, d, J=9.0Hz), 6.96(1H, s), 7.30–7.33(2H, m), 7.40–7.50(3H, m), 7.78(1H, d, J=8.1Hz), 7.87 and 7.95(each 1H, each m).

IR(CHCl$_3$): 3518, 3448, 3431, 2665, 1738, 1709, 1645, 1549, 1508, 1471 cm$^{-1}$.

$[α]_D^{24}$+37.9±0.8° (c=1.004, MeOH)

Elemental Analysis (C$_{32}$H$_{37}$NO$_3$S•0.1H$_2$O) Calcd.(%): C, 74.27; H, 7.25; N, 2.71; S, 6.20 Found(%): C, 74.13; H, 7.18; N, 2.87; S, 6.26

Compound II-85

300MHz $^1$H-NMR(CDCl$_3$) δ: 0.99(1H, d, J=10.2Hz), 1.11 and 1.24(each 3H, each s), 1.53–2.50(14H, m), 4.03 (2H, s), 4.34(1H, m), 5.36–5.54(2H, m), 6.20(1H, d, J=8.4Hz), 7.24(1H, d, J=8.4Hz), 7.24(1H, d, J=7.2Hz), 7.30(1H, m), 7.35(1H, t, J=1.8Hz), 7.42(1H, dd, J=7.2 and 8.1Hz), 7.81(1H, s), 8.19(1H, d, J=7.2Hz).

IR(CHCl$_3$): 3518, 3442, 1739, 1709, 1651, 1516, 1496, 1471 cm$^{-1}$.

$[α]_D^{25}$+54.3±1.0° (c=1.002, MeOH)

Elemental Analysis (C$_{30}$H$_{35}$NO$_4$S•0.1H$_2$O) Calcd.(%): C, 71.00; H, 6.99; N, 2.76; S, 6.32 Found(%): C, 70.95; H, 6.82; N, 2.74; S, 6.35

Compound II-86

300MHz $^1$H-NMR(CDCl$_3$) δ: 0.99(1H, d, J=10.5Hz), 1.16 and 1.24(each 3H, each s), 1.53–2.48(14H, m), 3.93 (2H, s), 4.32(1H, m), 5.34–5.52(2H, m), 6.35(1H, d, J=8.7Hz), 7.31–7.42(2H, m), 7.56(1H, d, J=6.9Hz), 7.71 (1H, dd, J=1.5 and 8.1Hz), 7.78–7.83(2H, m), 7.92(1H, s).

IR(CHCl$_3$): 3516, 3452, 3026, 2667, 1738, 1709, 1649, 1641, 1514, 1481, 1469, 1454 cm$^{-1}$.

$[α]_D^{24}$+67.5±1.1° (c=1.005, MeOH)

Elemental Analysis (C$_{30}$H$_{35}$NO$_3$•0.1H$_2$O) Calcd.(%): C, 78.43; H, 7.72; N, 3.05 Found(%): C, 78.36; H, 7.99; N, 3.24

Compound II-87

300MHz $^1$H-NMR(CDCl$_3$) δ: 0.96(1H, d, J=10.2Hz), 1.14 and 1.25(each 3H, each s),1.53–2.47(14H, m), 4.25(1H, m), 5.37–5.52(2H, m), 6.23(1H, d, J=8.7Hz), 7.16–7.22(2H, m), 7.36(1H, m), 7.46(1H, s), 7.45–7.49(1H, m).

IR(CHCl$_3$): 3516, 3446, 3429, 1734, 1703, 1652, 1606, 1521, 1496, 1457, 1419 cm$^{-1}$.

$[\alpha]_D^{25}$+72.8°±1.1° (c=1.005, MeOH),

Elemental Analysis (C$_{28}$H$_{31}$NO$_4$S•0.3H$_2$O) Calcd.(%): C, 69.63; H, 6.59; N, 2.90; S, 6.63 Found(%): C, 69.51; H, 6.72; N, 3.30; S, 6.56

Compound II-88

300MHz $^1$H-NMR(CDCl$_3$) δ: 0.97(1H, d, J=10.2Hz), 1.14 and 1.24(each 3H, each s),1.53–2.47(14H, m), 4.22 ((2H, s), 4.27(1H, m), 5.35–5.51(2H, m), 6.22(1H, d, J=8.7Hz), 6.94(1H, dd, J=1.2 and 4.8Hz), 7.05(1H, m), 7.21–7.26(2H, m), 7.35(1H, dd, J=7.5 and 8.1Hz), 7.71(1H, d, J=7.5Hz), 7.75(1H, s).

IR(CHCl$_3$): 3512, 3448, 3427, 2665, 1709, 1649, 1539, 1504, 1469 cm$^{-1}$.

$[\alpha]_D^{25}$+46.1±0.9° (c=1.011, MeOH),

Elemental Analysis (C$_{30}$H$_{35}$NO$_3$S$_2$) Calcd.(%): C, 69.06; H, 6.76; N, 2.68; S, 12.29 Found(%): C, 68.77; H, 6.84; N, 2.78; S, 12.30

Compound II-89

300MHz $^1$H-NMR(CDCl$_3$) δ: 0.96(1H, d, J=10.2Hz), 1.14 and 1.23(each 3H, each s),1.52–2.46(14H, m), 4.21 ((2H, s), 4.28(1H, m), 5.34–5.51(2H, m), 6.23(1H, d, J=9.0Hz), 6.94(1H, dd, J=1.2 and 4.8Hz), 7.05(1H, m), 7.21–7.26(2H, m), 7.35(1H, dd, J=7.5 and 8.1Hz), 7.71(1H, d, J=7.5Hz), 7.75(1H, s).

IR(CHCl$_3$): 3510, 3448, 3427, 2665, 1709, 1649, 1539, 1504, 1469, 1454 cm$^{-1}$.

$[\alpha]_D^{25}$+47.4±0.90° (c=1.005, MeOH),

Elemental Analysis (C$_{32}$H$_{37}$NO$_3$S•0.1H$_2$O) Calcd.(%): C, 74.27; H, 7.25; N, 2.71; S, 6.20 Found(%): C, 74.15; H, 7.14; N, 2.89; S, 6.26

Compound II-90

300MHz $^1$H-NMR(CDCl$_3$) δ: 0.96(1H, d, J=10.2Hz), 1.14 and 1.24(each 3H, each s),1.53–2.46(14H, m), 2.31(3H, s), 4.17((2H, s), 4.28(1H, m), 5.34–5.51(2H, m), 6.22(1H, d, J=9.0Hz), 7.09 and 7.15(each 2H, each d, J=7.8Hz), 7.19 (1H, d, J=7.2Hz), 7.34(1H, dd, J=7.2 and 7.8Hz), 7.70(1H, d, J=7.8Hz), 7.75(1H, s).

IR(CHCl$_3$): 3510, 3448, 3427, 2669, 1709, 1649, 1537, 1504, 1469 cm$^{-1}$.

$[\alpha]_D^{25}$+45.6±0.9° (c=1.005, MeOH),

Elemental Analysis (C$_{33}$H$_{39}$NO$_3$S•0.1H$_2$O) Calcd.(%): C, 74.57; H, 7.43; N, 2.64; S, 6.03 Found(%): C, 74.46; H, 7.48; N, 2.78; S, 6.15

Compound II-91

300MHz $^1$H-NMR(CDCl$_3$) δ: 0.97(1H, d, J=10.2Hz), 1.14 and 1.24(each 3H, each s),1.53–2.47(14H, m), 2.31(3H, s), 4.28(1H, m), 4.40((2H, s), 5.35–5.51(2H, m), 6.23(1H, d, J=8.7Hz), 6.92–6.94(2H, m), 7.16(1H, dd, J=1.5 and 5.1Hz), 7.28(1H, d, J=7.5Hz), 7.36(1H, t, J=7.5Hz), 7.72(1H, d, J=7.5Hz), 7.75(1H, s).

IR(CHCl$_3$): 3508, 3448, 3427, 2663, 1709, 1649, 1539, 1504, 1469 cm$^{-1}$.

$[\alpha]_D^{25}$+46.2±0.9° (c=1.005, MeOH),

Elemental Analysis (C$_{30}$H$_{35}$NO$_3$S$_2$) Calcd.(%): C, 69.06; H, 6.76; N, 2.68; S, 12.29 Found(%): C, 68.84; H, 6.86; N, 2.79; S, 12.28

Compound II-92

300MHz $^1$H-NMR(CDCl$_3$) δ: 0.94(1H, d, J=10.5Hz), 1.08 and 1.21(each 3H, each s), 1.51–2.42(14H, m), 4.09 (2H, s), 4.18(1H, m), 5.33–5.48(2H, m), 5.96(1H, d, J=9.3Hz), 6.54(1H, d, J=3.6Hz), 7.24–7.42(10H, m).

IR(CHCl$_3$): 3510, 3450, 3431, 1739, 1709, 1641, 1543, 1506, 1479, 1458 cm$^{-1}$.

$[\alpha]_D^{24.5}$+39.4±0.8° (c=1.007, MeOH)

Elemental Analysis (C$_{34}$H$_{39}$NO$_3$S•0.1H$_2$O) Calcd.(%): C, 75.13; H, 7.27; N, 2.58; S, 5.90 Found(%): C, 75.05; H, 7.32; N, 2.69; S, 6.17

Compound II-93

300MHz $^1$H-NMR(CDCl$_3$) δ: 1.00(1H, d, J=10.2Hz), 1.15 and 1.26(each 3H, each s), 1.55–2.49(14H, m), 4.30 (1H, m), 5.37–5.53(2H, m), 6.38(1H, d, J=8.1Hz), 7.32(1H, m), 7.49–7.58(3H, m), 7.64–7.67(2H, m), 7.92(1H, s).

IR(CHCl$_3$): 3514, 3446, 1714, 1655, 1618, 1514, 1469, 1446 cm$^{-1}$.

$[\alpha]_D^{25}$+66.7±1.1° (c=1.005, MeOH)

Elemental Analysis (C$_{30}$H$_{33}$NO$_4$•0.2H$_2$O) Calcd.(%): C, 75.83; H, 7.08; N, 2.95 Found(%): C, 75.69; H, 7.05; N, 3.08

Compound II-94 mp.103–104° C.

300MHz $^1$H-NMR(CDCl$_3$) δ: 0.93(1H, d, J=10.2Hz), 1.08 and 1.21(each 3H, each s),1.49–2.42(14H, m), 3.79(3H, s), 4.07((2H, s), 4.20(1H, m), 5.33–5.48(2H, m), 5.98(1H, d, J=8.7Hz), 6.75(1H, d, J=3.6Hz), 6.85 and 7.15(each 2H, each d, J=8.4Hz), 7.31(1H, d, J=3.6Hz).

IR(CHCl$_3$): 3519, 3450, 3431, 1741, 1709, 1641, 1612, 1543, 1510, 1464 cm$^{-1}$.

$[\alpha]_D^{25}$+43.8±0.8° (c=1.009, MeOH)

Elemental Analysis (C$_{29}$H$_{37}$NO$_4$S) Calcd.(%): C, 70.27; H, 7.52; N, 2.83; S, 6.47 Found(%): C, 70.33; H, 7.55; N, 3.05; S, 6.46

Compound II-95

300MHz $^1$H-NMR(CDCl$_3$) δ: 0.93(1H, d, J=10.5Hz), 1.07 and 1.21(each 3H, each s),1.49–2.42(14H, m), 4.20(1H, m), 4.37(2H, s), 5.33–5.48(2H, m), 5.99(1H, d, J=8.4Hz), 6.82(1H, d, J=3.6Hz), 7.21(1H, s), 7.30(1H, d, J=3.6Hz), 7.34–7.37(2H, m), 7.69(1H, m), 7.86(1H, m).

IR(CHCl$_3$): 3512, 3450, 3431, 2671, 1739, 1709, 1643, 1543, 1508, 1471, 1460 cm$^{-1}$.

$[\alpha]_D^{25}$+40.2±0.8° (c=1.005, MeOH),

Elemental Analysis (C$_{30}$H$_{35}$NO$_3$S$_2$•0.4H$_2$O) Calcd.(%): C, 68.12; H, 6.82; N, 2.64; S, 12.12 Found(%): C, 68.05; H, 6.70; N, 2.87; S, 12.00

Compound II-96

300MHz $^1$H-NMR(CDCl$_3$) δ: 0.92(1H, d, J=10.2Hz), 1.08 and 1.20(each 3H, each s),1.50–2.43(14H, m), 4.04(2H, s), 4.20(1H, m), 5.32–5.49(2H, m), 6.03(1H, d, J=9.0Hz), 6.75(1H, d, J=3.6Hz), 6.80 and 7.06(each 2H, each d, J=8.7Hz), 7.32(1H, d, J=3.6Hz).

IR(CHCl$_3$): 3446, 3510, 3182, 2673, 1709, 1635, 1614, 1545, 1512, 1471, 1458 cm$^{-1}$.

$[α]_D^{25}$ +43.8±0.8° (c=1.000, MeOH),
Elemental Analysis ($C_{28}H_{35}NO_4S$) Calcd.(%): C, 69.82; H, 7.32; N, 2.91; S, 6.66 Found(%): C, 69.57; H, 7.43; N, 3.00; S, 6.61

Compound II-97

300MHz $^1$H-NMR(CDCl$_3$) δ: 1.00(1H, d, J=10.5Hz), 1.17 and 1.25(each 3H, each s), 1.55–2.50(14H, m), 3.93 (2H, s), 4.32(1H, m), 5.35–5.49(2H, m), 6.37(1H, d, J=8.7Hz), 7.31–7.43(2H, m), 7.54–7.63(3H, m), 7.84(1H, d, J=7.2Hz), 8.16(1H,
IR(CHCl$_3$): 3514, 3450, 2667, 1709, 1651, 1572, 1514, 1481, 1452 cm$^{-1}$.
$[α]_D^{24}$ +58.3±1.0° (c=1.003, MeOH)
Elemental Analysis ($C_{30}H_{35}NO_3$•0.1$H_2O$) Calcd.(%): C, 78.43; H, 7.72; N, 3.05 Found(%): C, 78.26; H, 7.73; N, 3.28

Compound II-98

300MHz $^1$H-NMR(CDCl$_3$) δ: 0.94(1H, d, J=10.2Hz), 1.09 and 1.21(each 3H, each s), 1.52–2.42(14H, m), 4.16 (2H, s), 4.19(1H, m), 5.33–5.47(2H, m), 5.99(1H, d, J=9.3Hz), 6.78(1H, d, J=3.6Hz), 7.00–7.12(2H, m), 7.20–7.27(2H, m), 7.30(1H, d, J=3.6Hz).
IR(CHCl$_3$): 3510, 3450, 3431, 1741, 1709, 1643, 1543, 1508, 1456 cm$^{-1}$.
$[α]_D^{24}$ +38.0±0.8° (c=1.03, CHCl$_3$)
Elemental Analysis ($C_{28}H_{34}FNO_3S$•0.5$H_2O$) Calcd.(%): C, 68.26; H, 7.16; N, 2.86; S, 6.51; F, 3.86 Found(%): C, 68.24; H, 7.08; N, 2.93; S, 6.50; F, 3.80

Compound II-99 mp.53–55° C.
300MHz $^1$H-NMR(CDCl$_3$) δ: 0.94(1H, d, J=10.2Hz), 1.08 and 1.21(each 3H, each s),1.51–2.42(14H, m), 4.07(2H, s), 4.19(1H, m), 5.05(2H, s), 5.33–5.48(2H, m), 5.98(1H, d, J=9.0Hz), 6.76(1H, d, J=3.6Hz), 6.92 and 7.15(each 2H, each d, J=8.7Hz), 7.31(1H, d, J=3.6Hz), 7.32.–7.43(5H, m)
IR(CHCl$_3$): 3518, 3450, 3431, 1741, 1709, 1641, 1612, 1545, 1510, 1469, 1456 cm$^{-1}$.
$[α]_D^{24}$ +36.0±0.8° (c=1.005, MeOH),
Elemental Analysis ($C_{35}H_{41}NO_4S$•0.4$H_2O$) Calcd.(%): C, 72.61; H, 7.28; N, 2.42; S, 5.54 Found(%): C, 72.58; H, 7.33; N, 2.65; S, 5.53

Compound II-100

300MHz $^1$H-NMR(CDCl$_3$) δ: 0.94(1H, d, J=10.5Hz), 1.08 and 1.21(each 3H, each s),1.51–2.42(14H, m), 4.07(2H, s), 4.19(1H, m), 4.51–4.53(2H, m), 5.26–5.46(4H, m), 5.98 (1H, d, J=8.7Hz), 6.05(1H, m), 6.76(1H, d, J=3.6Hz), 6.87 and 7.14(each 2H, each d, J=8.7Hz), 7.31(1H, d, J=3.6Hz).
IR(CHCl$_3$): 3511, 3450, 3431, 1741, 1709, 1641, 1612, 1543, 1508, 1471, 1458 cm$^{-1}$.
$[α]_D^{24}$ +39.7±0.8° (c=1.008, MeOH),
Elemental Analysis ($C_{31}H_{39}NO_4S$•0.2$H_2O$) Calcd.(%): C, 70.88; H, 7.56; N, 2.67; S, 6.10 Found(%): C, 70.86; H, 7.60; N, 2.68; S, 6.17

Compound II-101

300MHz $^1$H-NMR(CDCl$_3$) δ: 0.94(1H, d, J=10.2Hz), 1.09 and 1.21(each 3H, each s),1.50–2.43(14H, m), 4.04(2H, s), 4.20(1H, m), 5.33–5.49(2H, m), 5.94(2H, s), 5.98(1H, d, J=8.7Hz), 6.68–6.78(4H, m), 7.31(1H, d, J=3.9Hz).
IR(CHCl$_3$): 3518, 3450, 3431, 1739, 1709, 1641, 1543, 1504, 1489, 1444, 1250, 1041 cm$^{-1}$.
$[α]_D^{24}$ +42.2±0.8° (c=1.010, MeOH),
Elemental Analysis ($C_{29}H_{35}NO_5S$) Calcd.(%): C, 68.34; H, 6.92; N, 2.75; S, 6.29 Found(%): C, 68.19; H, 6.88; N, 2.86; S, 6.20

Compound II-102 mp.76–80° C.
300MHz $^1$H-NMR(CDCl$_3$) δ: 0.94(1H, d, J=9.9Hz), 1.09 and 1.21(each 3H, each s),1.51–2.43(14H, m), 4.13(2H, s), 4.20(1H, m), 5.34–5.49(2H, m), 6.00(1H, d, J=8.4Hz), 6.78 (1H, d, J=3.9Hz), 6.90–7.04(3H, m), 7.27(1H, m), 7.32(1H, d, J=3.9Hz).
IR(Nujol): 3408, 1703, 1631, 1514, 1250 cm$^{-1}$.
$[α]_D^{25}$ +51.0±0.9° (c=1.001, MeOH),
Elemental Analysis ($C_{28}H_{34}FNO_3S$) Calcd.(%): C, 69.54; H, 7.09; N, 2.90; S, 6.63; F, 3.93 Found(%): C, 69.77; H, 7.23; N, 2.95; S, 6.55; F, 3.93

Compound II-103

300MHz $^1$H-NMR(CDCl$_3$) δ: 0.94(1H, d, J=10.2Hz), 1.09 and 1.22(each 3H, each s),1.51–2.44(14H, m), 4.19(2H, s), 4.20(1H, m), 5.34–5.49(2H, m), 6.00(1H, d, J=8.4Hz), 6.78 and 7.32(each 1H, each d, each J=3.6Hz), 7.40–7.54 (4H, m).
IR(CHCl$_3$): 3516, 3450, 3431, 1739, 1709, 1643, 1543, 1508, 1331, 1167, 1130 cm$^{-1}$.
$[α]_D^{25}$ +39.5±0.8° (c=1.012, MeOH),
Elemental Analysis ($C_{29}H_{34}F_3NO_3S$) Calcd.(%): C, 65.27; H, 6.42; N, 2.62; S, 6.01; F,10.68 Found(%): C, 65.05; H, 6.46; N, 2.74; S, 6.02; F,10.63

Compound II-104

300MHz $^1$H-NMR(CDCl$_3$) δ: 0.94(1H, d, J=10.2Hz), 1.09 and 1.21(each 3H, each s), 1.51–2.26(14H, m), 4.19 (1H, m), 4.26(2H, s), 5.33–5.49(2H, m), 6.00(1H, d, J=8.4Hz), 6.79(1H, d, J=3.9Hz), 7.20–7.25(3H, m), 7.30 (1H, d, J=3.9Hz), 7.37–7.40(1H, m).
IR(CHCl$_3$): 3516, 3450, 3431, 1741, 1709, 1643, 1543, 1508, 1471 cm$^{-1}$.
$[α]_D^{25}$ +38.5±0.8° (c=1.00, CHCl$_3$) Elemental Analysis ($C_{28}H_{34}FNO_3S$•0.5$H_2O$) Calcd.(%): C, 66.06; H, 6.93; N, 2.75; S, 6.30; Cl, 6.96 Found(%): C, 66.21; H, 6.87; N, 2.97; S, 6.24; Cl, 6.75

Compound II-105

300MHz $^1$H-NMR(CDCl$_3$) δ: 0.93(1H, d, J=10.5Hz), 1.07 and 1.20(each 3H, each s), 1.49–2.42(14H, m), 2.30 (6H, s), 4.15(2H, s), 4.19(1H, m), 5.33–5.48(2H, m), 5.97 (1H, d, J=8.7Hz), 6.56(1H, d, J=3.9Hz), 7.03–7.13(3H, m), 7.26(1H, d, J=3.9Hz).
IR(CHCl$_3$): 3518, 3450, 3431, 2671, 1739, 1709, 1641, 1543, 1506, 1471 cm$^{-1}$.
$[α]_D^{24}$ +43.7±0.8° (c=1.004, MeOH)
Elemental Analysis ($C_{30}H_{39}FNO_3S$•0.1$H_2O$) Calcd.(%): C, 72.72; H, 7.97; N, 2.83; S, 6.47 Found(%): C, 72.68; H, 7.95; N, 2.96; S, 6.48

Compound II-106

300MHz $^1$H-NMR(CDCl$_3$) δ: 0.94(1H, d, J=9.9Hz), 1.09 and 1.21(each 3H, each s), 1.53–2.50(14H, m), 4.19(1H, m), 4.32(2H, s), 5.34–5.47(2H, m), 6.00(1H, d, J=8.7Hz), 6.76 (1H, d, J=3.6Hz), 7.28–7.39(3H, m), 7.50(1H, m), 7.66(1H, d, J=3.6Hz).

IR(CHCl$_3$): 3516, 3450, 3431, 2669, 1741, 1709, 1643, 1543, 1508, 1456, 1315, 1163, 1126, 1059, 1038 cm$^{-1}$.

$[\alpha]_D^{25}$+36.4±0.7° (c=1.03, CHCl$_3$)

Elemental Analysis (C$_{29}$H$_{34}$F$_3$NO$_3$S) Calcd.(%): C, 65.27; H, 6.42; N, 2.62; S, 6.01 Found(%): C, 65.34; H, 6.30; N, 2.82; S, 6.00

Compound II-107

300MHz $^1$H-NMR(CDCl$_3$) δ: 0.93(1H, d, J=10.2Hz), 1.09 and 1.21(each 3H, each s),1.50–2.42(14H, m), 3.21(2H, t, J=8.7Hz), 4.02(2H, s), 4.20(1H, m), 4.59(2H, t, J=8.7Hz), 5.34–5.49(2H, m), 6.01(1H, d, J=8.7Hz), 6.80(1H, d, J=3.6Hz), 7.06(1H, d, J=1.8Hz), 7.19(1H, m), 7.30(1H, d, J=3.6Hz).

IR(CHCl$_3$): 3512, 3450, 3431, 2667, 1739, 1709, 1641, 1543, 1508, 1460 cm$^{-1}$.

$[\alpha]_D^{25}$+35.7±0.8° (c=1.002, MeOH),

Elemental Analysis (C$_{30}$H$_{36}$BrNO$_4$S) Calcd.(%): C, 61.43; H, 6.19; Br, 13.62; N, 2.39; S, 5.47 Found(%): C, 61.26; H, 6.11; Br, 13.54; N, 2.46; S, 5.47

Compound II-108

300MHz $^1$H-NMR(CDCl$_3$) δ: 0.93(1H, d, J=10.5Hz), 1.08 and 1.20(each 3H, each s),1.49–2.42(14H, m), 3.22(2H, t, J=8.7Hz), 4.07(2H, s), 4.20(1H, m), 4.57(2H, t, J=8.7Hz), 5.33–5.48(2H, m), 5.99(1H, d, J=9.0Hz), 6.79(1H, t, J=7.5Hz), 6.80(1H, d, J=3.6Hz), 6.95(1H, d, J=7.5Hz), 7.09(1H, d, J=7.5Hz), 7.30(1H, d, J=3.6Hz).

IR(CHCl$_3$): 3514, 3450, 3431, 2667, 1739, 1709, 1641, 1545, 1506, 1458 cm$^{-1}$.

$[\alpha]_D^{25}$+42.0±0.8° (c=1.004, MeOH),

Elemental Analysis (C$_{30}$H$_{37}$NO$_4$S•0.1H$_2$O) Calcd.(%): C, 70.72; H, 7.36; N, 2.75; S, 6.29 Found(%): C, 70.59; H, 7.39; N, 2.95; S, 6.31

Compound II-109

300MHz $^1$H-NMR(CDCl$_3$) δ: 0.93(1H, d, J=10.5Hz), 1.07 and 1.20(each 3H, each s),1.49–2.42(14H, m), 4.20(1H, m), 4.27(2H, s), 5.32–5.48(2H, m), 5.99(1H, d, J=8.7Hz), 6.80(1H, d, J=3.6Hz), 7.24(1H, dd, J=1.5 and 8.1Hz), 7.31 (1H, dd, J=0.6 and 5.4Hz), 7.33(1H, d, J=3.6Hz), 7.40(1H, d, J=5.4Hz), 7.73(1H, m), 7.77(1H, d, J=8.1Hz) .

IR(CHCl$_3$): 3516, 3450, 3431, 1741, 1709, 1641, 1543, 1508, 1469 cm$^{-1}$.

$[\alpha]_D^{25}$+41.5±0.8° (c=1.002, MeOH),

Elemental Analysis (C$_{30}$H$_{35}$NO$_3$S$_2$•0.3H$_2$O) Calcd.(%): C, 68.36; H, 6.81; N, 2.66; S, 12.17 Found(%): C, 68.37; H, 6.73; N, 2.86; S, 12.21

Compound II-110

300MHz $^1$H-NMR(CDCl$_3$) δ: 0.92(1H, d, J=10.5Hz), 1.07 and 1.19(each 3H, each s),1.47–2.41(14H, m), 4.20(1H, m), 4.24(2H, s), 5.32–5.47(2H, m), 6.00(1H, d, J=8.7Hz), 6.78(1H, d, J=3.9Hz), 7.21(1H, dd, J=1.8 and 8.4Hz), 7.26 (1H, d, J=5.7Hz), 7.33(1H, d, J=3.9Hz), 7.43(1H, d, J=5.7Hz), 7.67(1H, d, J=1.8Hz), 7.81(1H, d, J=8.4Hz)

IR(CHCl$_3$): 3516, 3450, 3431, 1739, 1709, 1641, 1545, 1458 cm$^{-1}$.

$[\alpha]_D^{25}$+40.9±0.8° (c=1.002, MeOH),

Elemental Analysis (C$_{30}$H$_{35}$NO$_3$S$_2$•0.3H$_2$O) Calcd.(%): C, 68.36; H, 6.81; N, 2.66; S, 12.17 Found(%): C, 68.30; H, 6.68; N, 2.94; S, 12.25

Compound II-111

300MHz $^1$H-NMR(CDCl$_3$) δ: 0.93(1H, d, J=10.2Hz), 1.06 and 1.19(each 3H, each s),1.48–2.41(14H, m), 4.19(1H, m), 4.39(2H, s), 5.32–5.47(2H, m), 5.99(1H, d, J=8.7Hz), 6.86(1H, d, J=3.6Hz), 7.21(1H, d, J=7.2Hz), 7.30(1H, d, J=3.6Hz), 7.35(1H, t, J=7.2Hz), 7.36(1H, d, J=5.4Hz), 7.42 (1H, d, J=5.4Hz), 7.74(1H, d, J=7.2Hz)

IR(CHCl$_3$): 3516, 3450, 3431, 1739, 1709, 1641, 1543, 1508, 1471, 1460 cm$^{-1}$.

$[\alpha]_D^{25}$+42.0±0.8° (c=1.001, MeOH),

Elemental Analysis (C$_{30}$H$_{35}$NO$_3$S$_2$•0.3H$_2$O) Calcd.(%): C, 68.36; H, 6.81; N, 2.66; S, 12.17 Found(%): C, 68.63; H, 6.78; N, 2.84; S, 12.26

Compound II-112

300MHz $^1$H-NMR(CDCl$_3$) δ: 0.92(1H, d, J=10.2Hz)., 1.07 and 1.20(each 3H, each s),1.52–2.47(14H, m), 4.20(1H, m), 4.23(2H, s), 5.32–5.51(2H, m), 6.08(1H, d, J=8.7Hz), 6.75(1H, d, J=3.6Hz), 6.95(1H, dd, J=2.4 and 9.0Hz), 7.10 (1H, d, J=2.4Hz), 7.19(1H, s), 7.27(1H, d, J=3.6Hz), 7.66 (1H, d, J=9.0Hz).

IR(CHCl$_3$): 3427, 3249, 1707, 1633, 1601, 1545, 1510, 1442 cm$^{-1}$.

$[\alpha]_D^{25}$+40.1±0.8° (c=1.007, MeOH),

Elemental Analysis (C$_{10}$H$_{35}$NO$_4$S$_2$•0.3H$_2$O) Calcd.(%): C, 66.34; H, 6.61; N, 2.58; S, 11.81 Found(%): C, 66.21; H, 6.70; N, 2.70; S, 11.75

Compound II-113

300MHz $^1$H-NMR(CDCl$_3$) δ: 0.93(1H, d, J=10.2Hz), 1.08 and 1.21(each 3H, each s), 1.53–2.45(14H, m), 4.17 (1H, m), 4.24(2H, m), 4.69(2H, m), 5.35–5.47(2H, m), 6.02(1H, d, J=9.3Hz), 6.72(1H, d, J=3.9Hz), 7.23–7.31(4H, m), 7.40(1H, m).

IR(CHCl$_3$): 3516, 3450, 3431, 1709, 1641, 1527, 1508, 1456 cm$^{-1}$.

$[\alpha]_D^{26}$+32.7±0.7° (c=1.00, CHCl$_3$)

Compound II-114

300MHz $^1$H-NMR(CDCl$_3$) δ: 0.92(1H, d, J=10.2Hz), 1.08 and 1.21(each 3H, each s), 1.54–2.48(18H, m), 3.20 (4H, m), 4.11–4.22(3H, m), 4.43(2H, s), 5.33–5.55(2H, m), 5.99(1H, d, J=8.4Hz), 6.67(1H, d, J=4.2Hz), 7.30–7.43(4H, m), 7.64(1H, d, J=4.2Hz).

IR(CHCl$_3$): 3514, 3448, 3420, 2555, 2459, 1711, 1643, 1543, 1508, 1456 cm$^{-1}$.

$[\alpha]_D^{26}$+20.4±0.6° (c=1.05, CHCl$_3$)

Elemental Analysis (C$_{33}$H$_{44}$N$_2$O$_3$S•1.1H$_2$O) Calcd.(%): C, 69.71; H, 8.19; N, 4.93; S, 5.64 Found(%): C, 69.69; H, 8.08; N, 4.92; S, 5.54

Compound II-115

300MHz $^1$H-NMR(CDCl$_3$) δ: 0.93(1H, d, J=10.5Hz), 1.07 and 1.21(each 3H, each s), 1.53–2.46(14H, m), 2.49 (6H,s), 3.79(1H, d, J=10.8Hz), 3.84(1H, d, J=10.8Hz), 4.19 (1H, m), 4.35(1H, d, J=20.1Hz), 4.37(1H, d, J=20.1Hz), 5.36–5.54 (2H, m), 5.94(1H, d, J=9.0Hz), 6.71(1H, d, J=3.6Hz), 7.25–7.43(5H, m).

IR(CHCl$_3$): 3516, 3448, 3429, 2553, 2459, 1711, 1643, 1545, 1506, 1471 cm$^{-1}$.

$[\alpha]_D^{26}$+20.9±0.6° (c=1.03, CHCl$_3$)

Elemental Analysis (C$_{31}$H$_{42}$N$_2$O$_3$S•3.1 H$_2$O) Calcd.(%): C, 64.35; H, 8.40; N, 4.84; S, 5.54 Found(%): C, 64.36; H, 7.87; N, 4.63; S, 5.17

Compound II-116

300MHz $^1$H-NMR(CDCl$_3$) δ: 0.98(1H, d, J=10.5Hz), 1.13 and 1.24(each 3H, each s), 1.53–2.47(14H, m), 3.20–3.27(4H, m), 4.28(1H, m), 5.35–5.51(2H, m), 6.32(1H, d, J=8.4Hz), 7.24(1H, d, J=7.5Hz), 7.34 and 7.46(each 1H, each m), 7.55(1H, dd, J=1.8 and 8.4Hz), 7.67(1H, d, J=1.8Hz), 8.00–8.04(2H, m).

IR(CHCl$_3$): 3518, 3448, 1709, 1649, 1597, 1514, 1294 cm$^{-1}$.

$[\alpha]_D^{25}$+58.8±1.0° (c=1.001, MeOH)

Elemental Analysis (C$_{32}$H$_{37}$NO$_4$•0.2H$_2$O) Calcd.(%): C, 76.37; H, 7.49; N, 2.78 Found(%): C, 76.33; H, 7.50; N, 2.88

Compound II-117

300MHz $^1$H-NMR(CDCl$_3$) δ: 0.95(1H, d, J=10.2Hz), 1.07 and 1.22(each 3H, each s), 1.51–2.43(14H, m), 3.97 (2H, s), 4.21(1H, m), 5.34–5.49(2H, m), 6.07(1H, d, J=3.3Hz), 6.38(1H, d, J=9.3Hz), 6.98–7.04(3H, m), 7.13–7.22(2H, m).

IR(CHCl$_3$): 3518, 3438, 1739, 1709, 1651, 1606, 1549, 1508 cm$^{-1}$.

$[\alpha]_D^{26}$+57.2±1.0° (c=1.016, MeOH)

Elemental Analysis (C$_{28}$H$_{34}$FNO$_4$•0.1H$_2$O) Calcd.(%): C, 71.65; H, 7.34; N, 2.98; F, 4.05 Found(%): C, 71.57; H, 7.44; N, 3.14; F, 4.01

Compound II-118

300MHz $^1$H-NMR(CDCl$_3$) δ: 0.96(1H, d, J=10.5Hz), 1.07 and 1.21(each 3H, each s), 1.52–2.43(14H, m), 4.00 (2H, s), 4.21(1H, m), 5.34–5.49(2H, m), 6.09(1H, d, J=3.3Hz), 6.40(1H, d, J=9.6Hz), 7.01(1H, d, J=3.3Hz), 7.22–7.36(5H, m).

IR(CHCl$_3$): 3516, 3439, 2667, 1738, 1709, 1651, 1606, 1547, 1498 cm$^{-1}$.

$[\alpha]_D^{24}$+62.2±1.0° (c=1.007, MeOH)

Elemental Analysis (C$_{28}$H$_{35}$NO$_4$•0.2H$_2$O) Calcd.(%): C, 74.21; H, 7.87; N, 3.09 Found(%): C, 74.14; H, 7.81; N, 3.25

Compound II-119

300MHz $^1$H-NMR(CDCl$_3$) δ: 0.92(1H, d, J=10.2Hz), 1.07 and 1.20(each 3H, each s),1.48–2.42(14H, m), 4.19(1H, m), 4.42(2H, s), 5.32–5.47(2H, m), 5.98(1H, d, J=8.7Hz), 6.78(1H, d, J=2.1Hz), 6.84(1H, d, J=3.9Hz), 7.13(1H, dd, J=1.5 and 7.5Hz), 7.19(1H, t, J=7.5Hz), 7.30(1H, d, J=3.9Hz), 7.50(1H, dd, J=1.5 and 7.5Hz), 7.63(1H, d, 2.1Hz).

IR(CHCl$_3$): 3516, 3450, 3431, 1741, 1709, 1641, 1543, 1508, 1471, 1458, 1427 cm$^{-1}$.

$[\alpha]_D^{25}$+43.5±0.8° (c=1.010, MeOH),

Elemental Analysis (C$_{30}$H$_{35}$NO$_4$S•0.2H$_2$O) Calcd.(%): C, 70.75; H, 7.01; N, 2.75; S, 6.30 Found(%): C, 70.80; H, 7.02; N, 2.96; S, 6.26

Compound II-120

300MHz $^1$H-NMR(CDCl$_3$) δ: 0.94(1H, d, J=10.2Hz), 1.09 and 1.22(each 3H, each s), 1.55–2.41(14H, m), 2.95 (3H, s), 4.18–4.21(3H, m), 4.45(2H, s), 5.39–5.43(2H, m), 6.00(1H, d, J=8.7Hz), 6.63–6.71(4H, m), 7.16–7.26(6H, m), 7.32(1H, m).

IR(CHCl$_3$): 3516, 3450, 3431, 1739, 1709, 1643, 1599, 1543, 1505, 1454 cm$^{-1}$.

$[\alpha]_D^{26}$+32.2±0.7° (c=1.00, CHCl$_3$)

Elemental Analysis (C$_{36}$H$_{44}$N$_2$O$_3$S•0.6H$_2$O) Calcd.(%): C, 72.59; H, 7.65; N, 4.70; S, 5.38 Found(%): C, 72.68; H, 7.47; N, 4.74; S, 5.29

Compound II-121

300MHz $^1$H-NMR(CDCl$_3$) δ: 0.93(1H, d, J=9.9Hz), 1.07 and 1.20(each 3H, each s), 1.49–2.41(14H, m), 4.19(1H, m), 4.30(2H, s), 5.32–5.48(2H, m), 5.99(1H, d, J=9.0Hz), 6.82 (1H, d, J=3.6Hz), 7.24(1H, dd, J=1.5 and 8.1Hz), 7.30–7.36 (2H, m), 7.41–7.47(2H, m), 7.55(1H, d, J=8.1Hz), 7.87–7.94 (2H, m).

IR(CHCl$_3$): 3510, 3450, 3431, 2669, 1739, 1709, 1641, 1545, 1506, 1458, 1429 cm$^{-1}$.

$[\alpha]_D^{24}$+39.4±0.8° (c=1.002, MeOH)

Elemental Analysis (C$_{34}$H$_{37}$NO$_4$S•0.1H$_2$O) Calcd.(%): C, 73.25; H, 6.73; N, 2.51; S, 5.75 Found(%): C, 73.13; H, 6.53; N, 2.69; S, 5.79

Compound II-122

300MHz $^1$H-NMR(CDCl$_3$) δ: 0.93(1H, d, J=10.2Hz), 1.08 and 1.21(each 3H, each s), 1.50–2.43(14H, m), 3.79 and 3.86(each 3H, each s), 4.14(2H, s), 4.19(1H, m), 5.33–5.48(2H, m), 5.96(1H, d, J=8.4Hz), 6.78–6.85(3H, m), 7.00(1H, t, J=8.1Hz), 7.30(1H, d, J=3.6Hz).

IR(CHCl$_3$): 3516, 3450, 3431, 2667, 1739, 1709, 1641, 1543, 1506, 1481, 1273, 1076 cm$^{-1}$.

$[\alpha]_D^{26}$+39.6±0.8° (c=1.007, MeOH)

Elemental Analysis (C$_{30}$H$_{39}$NO$_5$S•0.1H$_2$O) Calcd.(%): C, 68.31; H, 7.49; N, 2.66; S, 6.08 Found(%): C, 68.17; H, 7.50; N, 2.76; S, 6.13

Compound II-123

300MHz $^1$H-NMR(CDCl$_3$) δ: 0.94(1H, d, J=10.2Hz), 1.09 and 1.22(each 3H, each s),1.51–2.45(14H, m), 2.39(3H, s), 4.15(2H, s), 4.21(1H, m), 5.34–5.50(2H, m), 5.87(1H, s), 6.04(1H, d, J=8.7Hz), 6.86(1H, d, J=3.6Hz), 7.32(1H, d, J=3.6Hz).

IR(CHCl$_3$): 3514, 3450, 3431, 1709, 1645, 1608, 1545, 1508, 1471, 1456 cm$^{-1}$.

$[\alpha]_D^{25}$+47.0±0.9° (c=1.017, MeOH),

Elemental Analysis (C$_{26}$H$_{34}$N$_2$O$_4$S•0.3H$_2$O) Calcd.(%): C, 65.60; H, 7.33; N, 5.88; S, 6.74 Found(%): C, 65.49; H, 7.31; N, 6.00; S, 6.86

Compound II-124

300MHz $^1$H-NMR(CDCl$_3$) δ: 0.93(1H, d, J=10.2Hz), 1.08 and 1.21(each 3H, each s),1.50–2.42(14H, m), 2.33(3H, s), 3.82(3H, s), 4.07(2H, s), 4.18(1H, m), 5.33–5.48(2H, m), 5.96(1H, d, J=8.7Hz), 6.69(1H, s), 6.74(1H, d, J=7.8Hz), 6.76(1H, d, J=3.6Hz), 7.03(1H, d, J=7.8Hz), 7.28(1H, d, J=3.6Hz).

IR(CHCl$_3$): 3516, 3450, 3431, 1741, 1709, 1639, 1614, 1543, 1506, 1464 cm$^{-1}$.

[α]$_D^{24}$+43.3±0.8° (c=1.012, MeOH),
Elemental Analysis (C$_{30}$H$_{39}$NO$_4$S•0.1H$_2$O) Calcd.(%): C, 70.45; H, 7.73; N, 2.74; S, 6.27 Found(%): C, 70.35; H, 7.78; N, 2.96; S, 6.20

Compound II-125

300MHz $^1$H-NMR(CDCl$_3$) δ: 0.93(1H, d, J=10.2Hz), 1.07 and 1.21(each 3H, each s),1.49–2.43(14H, m), 3.84(3H, s), 4.20(1H, m), 4.32(2H, s), 5.33–5.48(2H, m), 5.99(1H, d, J=8.4Hz), 6.83(1H, d, J=3.6Hz), 7.01(1H, dd, J=2.4 and 8.7Hz), 7.12(1H, d,J=2.4Hz), 7.21(1H, s), 7.31(1H, d, J=3.6Hz), 7.71(1H, d, J=8.7Hz).
IR(CHCl$_3$): 3516, 3450, 3431, 1739, 1709, 1643, 1601, 1543, 1508, 1458, 1427 cm$^{-1}$.
[α]$_D^{25}$+38.5±0.8° (c=1.004, MeOH),
Elemental Analysis (C$_{31}$H$_{37}$NO$_4$S$_2$•0.1H$_2$O) Calcd.(%): C, 67.26; H, 6.72; N, 2.53; S, 11.58 Found(%): C, 67.24; H, 6.73; N, 2.77; S, 11.51

Compound II-126

300MHz $^1$H-NMR(CDCl$_3$) δ: 0.94(1H, d, J=10.5Hz), 1.07 and 1.20(each 3H, each s), 1.50–2.42(14H, m), 3.87 (2H, s), 4.18(1H, m), 4.20(2H, s), 5.32–5.48(2H, m), 5.98 (1H, d, J=7.2Hz), 6.81(1H, d, J=3.6Hz), 7.23–7.41(5H, m), 7.53(1H, d, J=7.5Hz), 7.71–7.77(2H, m).
IR(CHCl$_3$): 3514, 3450, 3431, 1739, 1709, 1641, 1545, 1506, 1469, 1456 cm$^{-1}$.
[α]$_D^{25}$+38.5±0.8° (c=1.007, MeOH)
Elemental Analysis (C$_{35}$H$_{39}$NO$_3$S•0.2H$_2$O) Calcd.(%): C, 75.42; H, 7.13; N, 2.51; S, 5.75 Found(%): C, 75.36; H, 7.18; N, 2.79; S, 5.50

Compound II-127

300MHz $^1$H-NMR(CDCl$_3$) δ: 0.96(1H, d, J=10.2Hz), 1.10 and 1.21(each 3H, each s), 1.52–2.44(14H, m), 3.14–3.24(4H, m), 4.13(2H, s), 4.24(1H, m), 5.32–5.49(2H, m), 6.19(1H, d, J=9.0Hz), 7.06–7.18(4H, m), 7.22(1H, d, J=8.1Hz), 7.39(1H, dd, J=1.8 and 8.1Hz), 7.51(1H, d, J=1.8Hz).
IR(CHCl$_3$): 3516, 3452, 1738, 1709, 1649, 1570, 1518, 1491, 1471 cm$^{-1}$.
[α]$_D^{25}$+54.4±0.9° (c=1.002, MeOH)
Elemental Analysis (C$_{32}$H$_{39}$NO$_4$•0.1H$_2$O) Calcd.(%): C, 78.85; H, 8.11; N, 2.87 Found(%): C, 78.74; H, 8.14; N, 3.17

Compound II-128

300MHz $^1$H-NMR(CDCl$_3$) δ: 0.94(1H, d, J=10.2Hz), 1.08 and 1.21(each 3H, each s), 1.50–2.43(14H, m), 3.83, 3.85 and 3.86(each 3H, each s), 4.07(2H, s), 4.19(1H, m), 5.33–5.49(2H, m), 5.97(1H, d, J=9.0Hz), 6.62(1H, d, J=8.7Hz), 6.76(1H, td, J=0.9 and 3.6Hz), 6.87(1H, d, J=8.7Hz), 7.30(1H, d, J=3.6Hz).
IR(CHCl$_3$): 3516, 3450, 3431, 1739, 1709, 1641, 1603, 1543, 1495, 1469, 1277, 1259, 1097 cm$^{-1}$.
[α]$_D^{26}$+38.4±0.8° (c=1.013, MeOH)
Elemental Analysis (C$_{31}$H$_{41}$NO$_6$S•0.2H$_2$O) Calcd.(%): C, 66.57; H, 7.46; N, 2.50; S, 5.73 Found(%): C, 66.54; H, 7.42; N, 2.61; S, 5.71

Compound II-129

300MHz $^1$H-NMR(CDCl$_3$) δ: 0.94(1H, d, J=10.2Hz), 1.08 and 1.21(each 3H, each s), 1.50–2.42(14H, m), 2.18 and 2.29(each 3H, each s), 4.14(2H, s), 4.19(1H, m), 5.33–5.49(2H, m), 5.96(1H, d, J=8.4Hz), 6.67(1H, td, J=0.9 and 3.6Hz), 7.02–7.12(3H, m), 7.29(1H, t, J=3.6Hz).
IR(CHCl$_3$): 3516, 3450, 3431, 1741, 1709, 1641, 1543, 1506, 1471 cm$^{-1}$.
[α]$_D^{26}$+42.8±0.8° (c=1.007, MeOH)
Elemental Analysis (C$_{30}$H$_{39}$NO$_3$S) Calcd.(%): C, 72.98; H, 7.96; N, 2.84; S, 6.50 Found(%): C, 72.67; H, 7.98; N, 2.94; S, 6.38

Compound II-130

300MHz $^1$H-NMR(CDCl$_3$) δ: 0.95(1H, d, J=10.2Hz), 1.09 and 1.22(each 3H, each s), 1.51–2.44(14H, m), 3.83 (3H, s), 3.84(6H, s), 4.07(2H, s), 4.20(1H, m), 5.34–5.49 (2H, m), 6.00(1H, d, J=8.7Hz), 6.45(2H, s), 6.79 and 7.31 (each 1H, each d, each J=3.6Hz).
IR(CHCl$_3$): 3516, 3450, 3431, 1741, 1709, 1641, 1593, 1543, 1506, 1464, 1421, 1331, 1240, 1130 cm$^{-1}$.
[α]$_D^{24}$+38.3±0.8° (c=1.004, MeOH)
Elemental Analysis (C$_{31}$H$_{41}$NO$_6$S•0.2H$_2$O) Calcd.(%): C, 66.57; H, 7.46; N, 2.50; S, 5.73 Found(%): C, 66.48; H, 7.37; N, 2.59; S, 5.63

Compound II-131

300MHz $^1$H-NMR(CDCl$_3$) δ: 0.94(1H, d, J=10.2Hz), 1.08 and 1.21(each 3H, each s), 1.50–2.43(14H, m), 4.08 (2H, s), 4.20(1H, m), 5.33–5.49(2H, m), 5.95(2H, s), 5.99 (1H, d, J=8.7Hz), 6.68–6.82(4H, m), 7.30(1H, d, J=3.6Hz).
IR(CHCl$_3$): 3512, 3450, 3431, 1739, 1709, 1641, 1545, 1506, 1460, 1252, 1063 cm$^{-1}$.
[α]$_D^{24}$+41.8±0.8° (c=1.007, MeOH)
Elemental Analysis (C$_{29}$H$_{35}$NO$_5$S) Calcd.(%): C, 68.34; H, 6.92; N, 2.75; S, 6.29 Found(%): C, 68.04; H, 6.90; N, 2.79; S, 6.29

Compound II-132

300MHz $^1$H-NMR(CDCl$_3$) δ: 0.92(1H, d, J=10.5Hz), 1.09 and 1.21(each 3H, each s), 1.51–2.45(14H, m), 2.14 (3H, s), 4.08(2H, s), 4.18(1H, m), 5.32–5.50(2H, m), 6.08 (1H, d, J=8.4Hz), 6.76(1H, d, J=3.6Hz), 6.97(1H, d, J=7.8Hz), 7.24(1H, t, J=8.4Hz), 7.30(1H, d, J=3.6Hz), 7.38–7.40(2H, m), 7.74(1H, br s).
IR(CHCl$_3$): 3514, 3435, 3311, 1705, 1639, 1612, 1534, 1508, 1439 cm$^{-1}$.
[α]$_D^{25}$+40.1±0.8° (c=1.008, MeOH)
Elemental Analysis (C$_{30}$H$_{38}$N$_2$O$_4$S•0.4H$_2$O) Calcd.(%): C, 68.00; H, 7.38; N, 5.29; S, 6.05 Found(%): C, 68.11; H, 7.17; N, 5.22; S, 5.93

Compound II-133

300MHz $^1$H-NMR(CDCl$_3$) δ: 0.94(1H, d, J=10.5Hz), 1.09 and 1.22(each 3H, each s), 1.53–2.50(14H, m), 2.99 (3H, s), 4.13(2H, s), 4.21(1H, m), 5.34–5.52(2H, m), 6.02 (1H, d, J=9.3Hz), 6.80(1H, d, J=3.9Hz), 7.04–7.07(2H, m), 7.16(1H, m), 7.25–7.32(3H, m).
IR(CHCl$_3$): 3510, 3440, 3431, 3371, 1709, 1639, 1608, 1543, 1508, 1471, 1386, 1335, 1151 cm$^{-1}$.
[α]$_D^{24}$+38.3±0.8° (c=1.006, MeOH)
Elemental Analysis (C$_{29}$H$_{38}$N$_2$O$_5$S$_2$•0.2H$_2$O) Calcd.(%): C, 61.94; H, 6.88; N, 4.98; S, 11.40 Found(%): C, 61.99; H, 6.92; N, 4.95; S, 10.97

Compound II-134

300MHz 1H-NMR(CDCl$_3$) δ: 0.94(1H, d, J=10.2Hz), 1.09 and 1.21(each 3H, each s), 1.50–2.44(14H, m), 4.21 (1H, m), 4.32(2H, s), 5.34–5.50(2H, m), 6.01(1H, d, J=9.0Hz), 6.86, 6.88 and 7.14(each 1H, each d, each J=3.6Hz), 7.23–7.37(4H, m), 7.53–7.56(2H, m).

Compound II-135

300MHz $^1$H-NMR(CDCl$_3$) δ: 0.94(1H, d, J=10.2Hz), 1.08 and 1.21(each 3H, each s), 1.50–2.43(14H, m), 4.08 (2H, s), 4.17–4.30(5H, m), 5.33–5.49(2H, m), 5.98(1H, d, J=8.4Hz), 6.71–6.80(4H, m), 7.28(1H, d, J=3.6Hz).

IR(CHCl$_3$): 3516, 3450, 3431, 1739, 1709, 1639, 1602, 1543, 1506, 1475, 1456, 1284, 1090 cm$^{-1}$.

[α]$_D^{24.5}$+40.2±0.8° (c=1.011, MeOH)

Elemental Analysis (C$_{30}$H$_{37}$NO$_5$S•S0.2H$_2$O) Calcd.(%): C, 68.34; H, 7.15; N, 2.66; S, 6.08 Found(%): C, 68.35; H, 7.03; N, 2.71; S, 6.17

Compound II-136

300MHz $^1$H-NMR(CDCl$_3$) δ: 0.94(1H, d, J=10.2Hz), 1.08 and 1.21(each 3H, each s), 1.50–2.43(14H, m), 2.31 and 3.70(each 3H, each s), 4.15(2H, s), 4.19(1H, m), 5.33–5.49(2H, m), 5.98(1H, d, J=8.7Hz), 6.77(1H, d, J=3.9Hz), 6.96–7.11(3H, m), 7.31(1H, d, J=3.9Hz).

IR(CHCl$_3$): 3516, 3450, 3431, 2669, 1738, 1709, 1641, 1545, 1506, 1471, 1259, 1011 cm$^{-1}$.

[α]$_D^{24}$+41.2±0.8° (c=1.003, MeOH)

Elemental Analysis (C$_{30}$H$_{39}$NO$_4$S) Calcd.(%): C, 70.69; H, 7.71; N, 2.75; S, 6.29 Found(%): C, 70.41; H, 7.76; N, 2.97; S, 6.04

Compound II-137

300MHz $^1$H-NMR(CDCl$_3$) δ: 0.93(1H, d, J=10.2Hz), 1.08 and 1.21(each 3H, each s), 1.51–2.42(14H, m), 2.16 (3H, s), 4.09(2H, s), 4.18(1H, m), 5.32–5.50(2H, m), 6.01 (1H, d, J=8.7Hz), 6.77(1H, d, J=3.6Hz), 7.17(2H, d, J=8.1Hz), 7.32(1H, d, J=3.6Hz), 7.43(1H, br s), 7.44(2H, d, J=8.1Hz).

IR(CHCl$_3$): 3514, 3435, 3311, 1705, 1639, 1541, 1513, 1410 cm$^{-1}$.

[α]$_D^{24.5}$+40.8±0.8° (c=1.000, MeOH)

Elemental Analysis (C$_{30}$H$_{35}$N$_2$O$_4$S•0.4H$_2$O) Calcd.(%): C, 68.00; H, 7.38; N, 5.29; S, 6.05 Found(%): C, 68.06; H, 7.38; N, 5.28; S, 5.92

Compound II-138

300MHz $^1$H-NMR(CDCl$_3$) δ: 0.94(1H, d, J=9.9Hz), 1.09 and 1.21(each 3H, each s), 1.51–2.42(14H, m), 2.99(3H, s), 4.11(2H, s), 4.20(1H, m), 5.33–5.49(2H, m), 6.01(1H, d, J=9.3Hz), 6.78(1H, d, J=3.6Hz), 6.86(1H, br s), 7.17–7.25 (4H, m), 7.31(1H, d, J=3.6Hz).

IR(CHCl$_3$): 3510, 3448, 3431, 3371, 1707, 1639, 1543, 1510, 1471, 1456, 1387, 1330, 1155 cm$^{-1}$.

[α]$_D^{24.5}$+37.6±0.8° (c=1.006, MeOH)

Elemental Analysis (C$_{29}$H$_{35}$N$_2$O$_5$S$_2$•0.3H$_2$O) Calcd.(%): C, 61.74; H, 6.90; N, 4.97; S, 11.37 Found(%): C, 61.84; H, 6.93; N, 5.03; S, 11.14

Compound II-139 mp.149–150° C.

300MHz $^1$H-NMR(CDCl$_3$) δ: 0.92(1H, d, J=10.5Hz), 1.05 and 1.19(each 3H, each s), 1.47–2.40(14H, m), 4.18 (1H, m), 4.40(2H, s), 5.31–5.46(2H, m), 5.98(1H, d, J=8.4Hz), 6.88(1H, d, J=3.9Hz), 7.30–7.35(2H, m), 7.42–7.48(3H, m), 7.58(1H, m), 8.08(1H, d, J=6.6Hz), 8.14 (1H, m).

IR(CHCl$_3$): 3514, 3450, 3431, 2667, 1738, 1707, 1643, 1543, 1508, 1471, 1458, 1444 cm$^{-1}$.

[α]$_D^{24.5}$+39.7±0.8° (c=1.008, MeOH)

Elemental Analysis (C$_{34}$H$_{37}$NO$_3$S$_2$) Calcd.(%): C, 71.42; H, 6.52; N, 2.45; S, 11.22 Found(%): C, 71.21; H, 6.53; N, 2.51; S, 10.97

Compound II-140

300MHz $^1$H-NMR(CDCl$_3$) δ: 0.92(1H, d, J=10.5Hz), 1.06 and 1.19(each 3H, each s), 1.48–2.40(14H, m), 3.79 (2H, s), 4.18(1H, m), 4.26(2H, s), 5.21–5.47(2H, m), 5.96 (1H, d, J=8.4Hz), 6.78(1H, d, J=3.6Hz), 7.18(1H, d, J=7.2Hz), 7.27–7.40(4H, m), 7.53(1H, d, J=7.2Hz), 7.72 (1H, d, J=7.8Hz), 7.78(1H, d, J=6.9Hz).

IR(CHCl$_3$): 3510, 3450, 3431, 2669, 1739, 1709, 1641, 1543, 1506, 1471, 1456 cm$^{-1}$.

[α]$_D^{24}$+36.6±0.8° (c=1.006, MeOH)

Elemental Analysis (C$_{35}$H$_{39}$NO$_3$S•0.2H$_2$O) Calcd.(%): C, 75.42; H, 7.13; N, 2.51; S, 5.75 Found(%): C, 75.46; H, 7.15; N, 2.73; S, 5.55

Compound II-141

300MHz $^1$H-NMR(CDCl$_3$) δ: 0.93(1H, d, J=9.9Hz), 1.08 and 1.21(each 3H, each s), 1.50–2.43(14H, m), 2.20, 2.45 and 3.67(each 3H, each s), 4.13(2H, s), 4.19(1H, m), 5.33–5.49(2H, m), 5.97(1H, d, J=8.4Hz), 6.77(1H, td, J=0.9 and 3.9Hz), 6.89 and 6.95(each 1H, each d, each J=7.8Hz), 7.31(1H, d, J=3.6Hz).

IR(CHCl$_3$): 3516, 3450, 3431, 1738, 1709, 1641, 1545, 1506, 1458, 1263, 1084, 1009 cm$^{-1}$.

[α]$_D^{24}$+39.8±0.8° (c=1.006, MeOH)

Elemental Analysis (C$_{31}$H$_{41}$NO$_4$S) Calcd.(%): C, 71.09; H, 7.89; N, 2.67; S, 6.12 Found(%): C, 70.80; H, 8.02; N, 2.92; S, 6.06

Compound II-142

300MHz $^1$H-NMR(CDCl$_3$) δ: 0.93(1H, d, J=10.2Hz), 1.06 and 1.19(each 3H, each s), 1.49–2.41(14H, m), 4.18 (1H, m), 4.50(2H, s), 5.32–5.47(2H, m), 5.98(1H, d, J=9.0Hz), 6.89(1H, d, J=3.9Hz), 7.29–7.38(4H, m), 7.47 (1H, m), 7.59(1H, d, J=8.4Hz), 7.86(1H, m), 7.95(1H, d, J=7.8Hz).

IR(CHCl$_3$): 3510, 3450, 3431, 2669, 1739, 1709, 1641, 1545, 1508, 1471, 1450, 1423 cm$^{-1}$.

[α]$_D^{24}$+40.3±0.8° (c=1.007, MeOH)

Elemental Analysis (C$_{34}$H$_{37}$NO$_4$S•0.2H$_2$O) Calcd.(%): C, 73.01; H, 6.74; N, 2.50; S, 5.73 Found(%): C, 72.91; H, 6.58; N, 2.59; S, 5.75

Compound II-143

300MHz $^1$H-NMR(CDCl$_3$) δ: 0.94(1H, d, J=10.5Hz), 1.08 and 1.21(each 3H, each s),1.18(3H, t, J=7.8Hz), 1.50–2.42(14H, m), 2.64(2H, q, J=7.8Hz), 4.15(2H, s), 4.19(1H, m), 5.33–5.48(2H, m), 5.96(1H, d, J=9.3Hz), 6.68 (1H, d, J=3.6Hz), 7.16–7.25(4H, m), 7.29(1H, d, J=3.6Hz).

IR(CHCl$_3$): 3516, 3450, 3431, 2667, 1739, 1709, 1641, 1543, 1506, 1471, 1456 cm$^{-1}$.

[α]$_D^2$+41.9±0.8° (c=1.013, MeOH)

Elemental Analysis (C$_{30}$H$_{39}$NO$_3$S•0.1H$_2$O) Calcd.(%): C, 72.72; H, 7.97; N, 2.83; S, 6.47 Found(%): C, 72.55; H, 7.88; N, 3.19; S, 6.62

Compound III-1

300MHz $^1$H-NMR(CDCl$_3$) δ: 0.88(1H, d, J=10.2Hz), 1.07 and 1.23(each 3H, each s), 1.56–2.51(13H, m), 2.67 (1H, m), 4.41(1H, m), 5.29–5.41(2H, m), 6.07(1H, d, J=8.1Hz), 6.34 and 7.16(each 2H, each t, each J=2.1Hz), 7.35 and 7.52(each 1H, each d, each J=3.9Hz).

IR(CHCl$_3$): 3511, 3431, 3144, 3101, 2668, 1708, 1656, 1530, 1505, 1455, 1384, 1167 cm$^{-1}$.

[α]$_D^{24}$ +34.2±0.7° (c=1.007, MeOH)

Elemental Analysis (C$_{25}$H$_{32}$N$_2$O$_5$S$_2$•0.5H$_2$O) Calcd.(%): C, 58.46; H, 6.48; N, 5.45; S, 12.48 Found(%): C, 58.77; H, 6.40; N, 5.65; S, 12.72

Compound III-2

300MHz $^1$H-NMR(CDCl$_3$) δ: 0.90(1H, d, J=9.9Hz), 1.06 and 1.23(each 3H, each s), 1.58–2.48(13H, m), 2.67(1H, m), 4.41(1H, m), 5.29–5.42(2H, m), 6.27(1H, d, J=8.1Hz), 7.38–7.44(3H, m), 6.34(1H, d, J=3.9Hz), 8.14(1H, dd, J=1.5 and 3.0Hz).

IR(CHCl$_3$): 3517, 3431, 3361, 3114, 1708, 1654, 1530, 1504, 1332, 1151 cm$^{-1}$.

[α]D$^{24}$+33.7±0.7° (c=1.003, MeOH)

Elemental Analysis (C$_{25}$H$_{31}$NO$_5$S$_3$•0.2H$_2$O) Calcd.(%): C, 57.16; H, 6.02; N, 2.67; S, 18.31 Found(%): C, 57.09; H, 5.88; N, 2.76; S, 18.15

Compound III-3

300MHz $^1$H-NMR(CDCl$_3$) δ: 0.94(1H, d, J=9.9Hz), 1.07 and 1.23(each 3H, each s), 1.56–2.48(13H, m), 2.68(1H, m), 4.42(1H, m), 5.29–5.42(2H, m), 6.16(1H, d, J=8.4Hz), 7.16 (1H, dd, J=3.9 and 5.1Hz), 7.42 and 7.63(each 1H, each d, each J=3.9Hz), 7.70(1H, dd, J=1.5 and 5.1Hz), 7.76(1H, dd, J=1.5 and 3.9Hz).

IR(CHCl$_3$): 3516, 3431, 3365, 3097, 1708, 1654, 1530, 1505, 1402, 1336, 1153 cm$^{-1}$.

[α]$_D^{24}$ +34.5±0.7° (c=1.010, MeOH)

Elemental Analysis (C$_{25}$H$_{31}$NO$_6$S$_3$•0.1H$_2$O) Calcd.(%): C, 57.36; H, 6.01; N, 2.68; S, 18.38 Found(%): C, 57.16; H, 5.88; N, 2.76; S, 18.36

Compound III-4

300MHz $^1$H-NMR(CDCl$_3$) δ: 0.88(1H, d, J=9.9Hz), 1.07 and 1.23(each 3H, each s), 1.58–2.34(12H, m), 2.39(3H, s), 2.44(1H, m), 2.68(1H, m), 4.41(1H, m), 5.29–5.42(2H, m), 5.99(1H, m), 6.08(1H, d, J=8.4Hz), 6.20(1H, t, J=3.3Hz), 7.19(1H, m), 7.38 and 7.55(each 1H, each d, each J=3.9Hz).

IR(CHCl$_3$): 3510, 3431, 3150, 3100, 1708, 1656, 1530, 1505, 1375, 1161 cm$^{-1}$.

[α]$_D^{24}$+30.9±0.7° (c=1.000, MeOH)

Elemental Analysis (C$_{26}$H$_{34}$N$_2$O$_5$S$_2$•0.3H$_2$O) Calcd.(%): C, 59.58; H, 6.65; N, 5.35; S, 12.24 Found(%): C, 59.57; H, 6.48; N, 5.51; S, 12.22

Compound IV-1

300MHz $^1$H-NMR(CDCl$_3$) δ: 0.85 and 1.22(each 3H, each s), 1.44(1H, d, J=10.2Hz), 1.54–2.51(14H, m), 4.10 (1H, m), 5.31–5.41(2H, m), 6.21(1H, d, J=8.4Hz), 7.11( 1H, dd, J=3.9 and 4.8Hz), 7.44 and 7.63(each 1H, each d, each J=3.9Hz), 7.70(1H, dd, J=1.2 and 4.8Hz), 7.75(1H, dd, J=1.2 and 3.9Hz).

IR(CHCl$_3$): 3517, 3423, 3366, 3097, 2665, 1708, 1655, 1530, 1505, 1335, 1153 cm$^{-1}$.

[α]$_D^{23}$−46.4±0.9° (c=1.010, MeOH)

Elemental Analysis (C$_{25}$H$_{31}$NO$_5$S$_3$•0.3H$_2$O) Calcd.(%): C, 56.97; H, 6.04; N, 2.66; S, 18.25 Found(%): C, 57.10; H, 5.96; N, 2.70; S, 18.02

Compound IV-2

300MHz $^1$H-NMR(CDCl$_3$) δ: 0.84 and 1.22(each 3H, each s), 1.43(1H, d, J=10.5Hz), 1.53–2.50(14H, m), 4.09 (1H, m), 5.30–5.41(2H, m), 6.17(1H, d, J=8.7Hz), 6.33 and 7.16(each 2H, each t-like), 7.40 and 7.57(each 1H, each d, each J=3.9Hz).

IR(CHCl$_3$): 3514, 3432, 3144, 3102, 1708, 1657, 1531, 1506, 1456, 1384, 1167 cm$^{-1}$.

[α]$_D^{23}$45.4±0.9° (c=1.010, MeOH)

Elemental Analysis (C$_{25}$H$_{30}$N$_2$O$_5$S$_2$•0.3H$_2$O) Calcd.(%): C, 59.10; H, 6.07; N, 5.51; S, 12.62 Found(%): C, 59.12; H, 5.83; N, 5.53; S, 12.41

Compound V-1

300MHz $^1$H-NMR(CDCl$_3$) δ: 1.24–2.13(13H, m), 2.22 (1H, m), 2.32(2H, t, J=7.2Hz), 3.41(1H, m), 3.44(1H, m), 5.18–5.36(2H, m), 6.19(1H, m), 6.33 and 7.15(each 2H, each t, each J=2.4Hz), 7.28 and 7.55(each 2H, each t, each J=3.9Hz).

IR(CHCl$_3$): 3512, 3439, 3144, 3100, 1708, 1658, 1535, 1508, 1446, 1167 cm$^{-1}$.

[α]$_D^{26}$+69.5±1.1° (c=1.012, MeOH)

Elemental Analysis (C$_{23}$H$_{28}$N$_2$O$_5$S•0.5H$_2$O) Calcd.(%): C, 56.89; H, 6.02; N, 5.77; S, 13.21 Found(%): C, 56.91; H, 5.96; N, 5.91; S, 13.37

Compound V-2

300MHz $^1$H-NMR(CDCl$_3$) δ: 1.14–2.16(13H, m), 2.23 (1H, m), 2.30–2.37(2H, m), 3.41(1H, m), 3.45(1H, m), 5.18–5.36(2H, m), 6.19(1H, m), 7.11(1H, dd, J=3.9 and 5.1Hz), 7.32 and 7.62(each 1H, each d, each J=3.9Hz), 7.39(1H, dd, J=1.5 and 5.1Hz), 7.75(1H, dd, J=1.5 and 3.9Hz).

IR(CHCl$_3$): 3512, 3440, 3096, 1708, 1657, 1534, 1507, 1402, 1336, 1153 cm$^{-1}$.

[α]$_D^{25}$+69.2±1.1° (c=1.006, MeOH)

Elemental Analysis (C$_{23}$H$_{27}$NO$_5$S$_3$•0.1H$_2$O) Calcd.(%): C, 55.57; H, 5.51; N, 2.83; S, 19.42 Found(%): C, 55.55; H, 5.32; N, 2.85; S, 19.21

Compound V-3

300MHz $^1$H-NMR(CDCl$_3$) δ: 1.16–2.14(13H, m), 2.23 (1H, m), 2.28–2.36(2H, m), 3.54–3.46(2H, m), 5.17–5.37 (2H, m), 6.14(1H, m), 7.32(1H, d, J=3.9Hz), 7.38–7.44(2H, m), 7.61(1H, d, J=3.9Hz), 8.15(1H, dd, J=1.2 and 3.0Hz).

IR(CHCl$_3$): 3508, 3431, 3114, 1708, 1656, 1534, 1508, 1331, 1152, 1102 cm$^{-1}$.

[α]$_D^{24}$+66.5±1.1° (c=1.003, MeOH)

Elemental Analysis ($C_{23}H_{27}NO_5S_3 \cdot 0.3H_2O$) Calcd.(%): C, 55.35; H, 5.57; N, 2.81; S, 19.28 Found(%): C, 55.29; H, 5.54; N, 2.85; S, 19.01

Compound V-4

300MHz $^1$H-NMR(CDCl$_3$) δ: 1.18–2.18(13H, m), 2.23 (1H, m), 2.31–2.35(2H, m), 2.38(3H, s), 3.43(2H, m), 5.18–5.36(2H, m), 5.98(1H, m), 6.14(1H, m), 6.19(1H, t, J=3.3Hz), 7.17(1H, m), 7.29 and 7.53(each 1H, each d, each J=3.9Hz).
IR(CHCl$_3$): 3512 3440, 3150, 3101, 1708, 1658, 1535, 1508, 1375, 1161 cm$^{-1}$.
$[α]_D^{24}$+30.9±0.7° (c=1.000, MeOH)
Elemental Analysis ($C_{26}H_{34}N_2O_5S_2 \cdot 0.3H_2O$) Calcd.(%): C, 59.58; H, 6.65; N, 5.35; S, 12.24 Found(%): C, 59.57; H, 6.48; N, 5.51; S, 12.22

Compound V-5

300MHz $^1$H-NMR(CDCl$_3$) δ: 1.18–2.10(13H, m), 2.11 (1H, m), 2.21–2.35(2H, m), 3.35(1H, m), 3.46(1H, m), 4.12(2H, s), 5.17–5.34(2H, m), 5.88(1H, m), 6.74(1H, d, J=3.9Hz), 7.21–7.38(6H, m).
IR(CHCl$_3$): 3511, 3432, 3065, 1708, 1642, 1547, 1515, 1455 cm$^{-1}$.
$[α]_D^{23}$+69.1±1.1° (c=1.009, MeOH)
Elemental Analysis ($C_{26}H_{31}NO_3S \cdot 0.1H_2O$) Calcd.(%): C, 71.07; H, 7.16; N, 3.19; S, 7.30 Found(%): C, 70.91; H, 7.18; N, 3.19; S, 7.34

Compound V-6

300MHz $^1$H-NMR(CDCl$_3$) δ: 1.18–2.15(14H, m), 2.24–2.34(2H, m), 3.36(1H, m), 3.58(1H, m), 5.19–5.40(2H, m), 6.07(1H, m), 7.28–7.42(3H, m), 7.51(1H, d, J=0.6Hz), 7.56–7.59(2H, m), 7.72(1H, d, J=0.6Hz).
IR(CHCl$_3$): 3514, 3446, 1709, 1649, 1550, 1520, 1491 cm$^{-1}$.
$[α]_D^{22}$+79.4±1.2° (c=1.004, MeOH)
Elemental Analysis ($C_{25}H_{29}NO_3S \cdot 0.2H_2O$) Calcd.(%): C, 70.29; H, 6.94; N, 3.28; S, 7.51 Found(%): C, 70.26; H, 6.68; N, 3.48; S, 7.44

Compound V-7

300MHz $^1$H-NMR(CDCl$_3$) δ: 1.18–2.14(13H, m), 2.26 (1H, m), 2.31–2.36(2H, m), 3.30(1H, m), 3.64(1H, m), 3.82(3H, s), 5.19–5.39(2H, m), 6.06(1H, m), 6.89–7.01(6H, m), 7.66(2H, d, J=8.1Hz).
IR(CHCl$_3$): 3514, 3446, 1709, 1649, 1550, 1520, 1491 cm$^{-1}$.
$[α]_D^{22}$+76.3±1.2° (c=1.009, MeOH)
Elemental Analysis ($C_{28}H_{33}NO_5 \cdot 0.2H_2O$) Calcd.(%): C, 71.99; H, 7.21; N, 3.00 Found(%): C, 72.05; H, 7.35; N, 2.93

Compound V-8

300MHz $^1$H-NMR(CDCl$_3$) δ: 1.18–2.14(13H, m), 2.25 (1H, m), 2.31–2.39(2H, m), 3.32(1H, m), 3.56(1H, m), 4.09(2H, d, J=0.3Hz), 5.18–5.38(2H, m), 5.89(1H, m), 6.68 (1H, d, J=3.6Hz), 6.94(1H, dd, J=3.6 and 5.1Hz), 7.02(1H, dd, J=1.5 and 3.6Hz), 7.23(1H, d, J=3.6Hz), 7.35(1H, dd, J=1.5 and 5.1Hz).
IR(CHCl$_3$): 3514, 3433, 1709, 1645, 1545, 1516, 1458 cm$^{-1}$.
$[α]_D^{23}$+61.8±1.0° (c=1.008, MeOH)
Elemental Analysis ($C_{24}H_{29}NO_3S_3 \cdot 0.2H_2O$) Calcd.(%): C, 60.14; H, 6.18; N, 2.92; S, 20.07 Found(%): C, 60.08; H, 6.11; N, 2.90; S, 20.05

Compound V-9

300MHz $^1$H-NMR(CDCl$_3$) δ: 1.06–2.15(13H, m), 2.23 (1H, m), 2.28–2.38(2H, m), 3.35(1H, m), 3.54(1H, m), 5.20(2H, s), 5.19–5.37(2H, m), 5.95(1H, m), 6.94–7.04(4H, m), 7.27–7.35(3H, m).
IR(CHCl$_3$): 3514, 3433, 1709, 1647, 1599, 1547, 1518, 1495 cm$^{-1}$.
$[α]_D^{24}$+67.8±1.1° (c=1.008, MeOH)
Elemental Analysis ($C_{26}H_{31}NO_4S \cdot 0.2H_2O$) Calcd.(%): C, 68.30; H, 6.92; N, 3.06; S, 7.01 Found(%): C, 68.31; H, 6.84; N, 3.16; S, 7.11

Compound V-10

300MHz $^1$H-NMR(CDCl$_3$) δ: 1.06–2.14(13H, m), 2.24 (1H, m), 2.30–2.37(2H, m), 3.31(1H, m), 3.53(1H, m), 4.50(2H, d, J=0.9Hz), 5.15–5.36(2H, m), 5.89(1H, m), 6.65–6.79(3H, m), 6.95(1H, d, J=3.9Hz), 7.15–7.21(2H, m), 7.33(1H, d, J=3.9Hz).
IR(CHCl$_3$): 3512, 3440, 1707, 1643, 1603, 1547, 1506 cm$^{-1}$.
$[α]_D^{22}$+67.3±1.1° (c=1.009, MeOH)
Elemental Analysis ($C_{26}H_{32}N_2O_3S \cdot 0.3H_2O$) Calcd.(%): C, 68.18; H, 7.17; N, 6.20; S, 7.00 Found(%): C, 68.04; H, 7.09; N, 6.25; S, 7.02

Compound V-11

300MHz $^1$H-NMR(CDCl$_3$) δ: 1.06–2.15(13H, m), 2.27 (1H, m), 2.28–2.38(2H, m), 3.31(1H, m), 3.54(1H, m), 4.24(2H, d, J=0.6Hz), 5.17–5.36(2H, m), 5.87(1H, m), 6.78 (1H, d, J=3.6Hz), 7.21–7.42(6H, m).
IR(CHCl$_3$): 3514, 3433, 3062, 2669, 1709, 1643, 1545, 1514 cm$^{-1}$.
$[α]_D^{22}$+64.3±1.0° (c=1.000, MeOH)
Elemental Analysis ($C_{26}H_{31}NO_3S_2 \cdot 0.5H_2O$) Calcd.(%): C, 65.24; H, 6.74; N, 2.93; S, 13.40 Found(%): C, 65.23; H, 6.55; N, 3.00; S, 13.46

Compound V-12

300MHz $^1$H-NMR(CDCl$_3$) δ: 1.18–1.81(7H, m), 1.85–1.94(2H, m), 2.01–2.13(2H, m), 2.22–2.33(3H, m), 3.41(1H, m), 3.33(1H, m), 3.49(2H, s), 3.54(1H, m), 4.15 (2H, s), 5.17–5.37(2H, m), 5.90(1H, m), 6.12(1H, dd, J=0.9 and 3.0Hz), 6.31(1H, dd, J=1.8 and 3.0Hz), 6.81 and 7.30 (each 1H, each d, each J=3.6Hz), 7.34(1H, dd, J=0.9 and 1.8Hz).
IR(CHCl$_3$): 3516, 3433, 1709, 1643, 1547, 1516 cm$^{-1}$.
$[α]_D^{23}$+71.3±1.1° (c=1.004, MeOH)
Elemental Analysis ($C_{24}H_{29}NO_4S \cdot 0.3H_2O$)
Calcd.(%): C, 66.58; H, 6.89; N, 3.24; S, 7.41
Found(%): C, 66.55; H, 6.63; N, 3.37; S, 7.51

Compound VI-1 mp.105–106° C..
300MHz $^1$H-NMR(CDCl$_3$) δ: 1.06(1H, m), 1.19–1.29 (2H, m), 1.42–1.47(2H, m), 1.58–1.78(4H, m), 2.00–2.19 (5H, m), 2.35(2H, t, J=7.2Hz), 2.52(1H, m), 3.82(1H, m), 4.16(2H, s), 5.30–5.42(2H, m), 5.99(1H, d, J=7.5Hz), 6.79

(1H, dt, J=0.9 and 3.9Hz), 6.96(1H, dd, J=1.5 and 4.8Hz), 7.05(1H, m), 7.28(1H, dd, J=3.0 and 4.8Hz), 7.37(1H. d, J=3.9Hz).

IR(KBr): 3367, 2667, 1700, 1612, 1543, 1520, 1317, 1244 cm$^{-1}$.

$[\alpha]_D^{24}$+70.2±1.1° (c=1.006, MeOH)

Elemental Analysis ($C_{24}H_{29}NO_3S_2$)

Calcd.(%): C, 64.98; H, 6.59; N, 3.16; S, 14.46

Found(%): C, 64.92; H, 6.52; N, 3.32; S, 14.48

The compounds prepared in Examples above were tested for determining the in vivo and in vitro activities according to the method as shown in Experimental examples below.

Experiment 1 Binding activity to $PGD_2$ Receptor (1) Preparation of Human Platelet Membrane Fraction Blood was collected using a plastic syringe containing 3.8% sodium citrate from the vein of healthy volunteers (adult male and female), then put into a plastic test tube and mixed by slow-reversion. The sample was then centrifuged at 1800 rpm, for 10 min at room temperature, and the supernatant containing PRP (platelet-rich plasma) was collected. The PRP was recentrifuged at 2300 rpm, for 22 min at room temperature to obtain platelets. The platelets were homogenized using a homogenizer (Ultra-Turrax) followed by centrifugation 3 times at 20,000 rpm, 10 min at 4° C.. to obtain a platelet membrane fraction. After protein determination, the membrane fraction was adjusted to 2 mg/ml and preserved in a refrigerator at −80° C.. until using for the binding test.

(2) Binding to $PGD_2$ Receptor

To a binding-reaction solution (50 mM Tris/HCl, pH 7.4, 5 mM $MgCl_2$) (0.2 ml) were added the human platelet membrane fraction (0.1 mg) and 5 nM [$^3$H]$PGD_2$ (115 Ci/mmol), and the mixture was reacted at 4° C. for 90 min. After the reaction, the mixture was filtered through a glass fiber filter paper and washed several times with cooled physiological saline, then the radioactivity retained on the filter paper was measured. The specific-binding ratio was calculated by subtracting the non-specific binding ratio which is the radioactivity similarly measured in the presence of 10 µM $PGD_2$ from the total binding. The inhibitory activity of each compound was expressed as the concentration required for 50% inhibition ($IC_{50}$), which was determined by depicting a substitution curve by plotting the binding ratio (%) in the presence of each compound, where the binding ratio in the absence of a test compound is 100%.

Experiment 2 Binding activity to $TXA_2$ Receptor (1) Preparation of Human Platelet Membrane Fraction The human platelet membrane fraction was prepared in accordance with Experiment 1 (1).

(2) Binding to $TXA_2$ Receptor

To a binding-reaction solution (50 mM Tris/HCl, pH 7.4, 10 mM $MgCl_2$) (0.2 ml) were added the human platelet membrane fraction (0.05 mg) and 2 nM Sodium [$^3$H](+)-(5Z)-7- [3-endo- [(phenylsulfonyl)amino]bicyclo[2.2.1] hept-2-exo-yl]heptenoate (Japanese Patent Publication (Kokoku) No.79060/1993, hereinafter referred to as (+)—S—145 sodium salt) (26.4 Ci/mmol), and the mixture was reacted at room temperature for 90 min. After the reaction, the resultant mixture was filtered through a glass fiber filter paper and washed several times with cooled physiological saline, then the radioactivity retained on the filter paper was measured. The specific-binding ratio was calculated by subtracting the non-specific binding ratio (the radio activity similarly determined in the presence of 10 µM (+)—S—145 sodium salt) from the total binding. The inhibitory activity of each compound was expressed as the concentration required for 50% inhibition ($IC_{50}$), which was determined by depicting a substitution curve by plotting the binding ratio (%) in the presence of each compound, where the binding ratio in the absence of a test compound is 100%.

Experiment 3 Evaluation of Antagonistic Activity Against $PGD_2$ Receptor Using Human Platelet Peripheral blood was collected from a healthy volunteer using a syringe in which 1/9 volume of a citric acid/dextrose solution was previously added. The sample was subjected to centrifugation at 180 g for 10 min to obtain the supernatant (PRP: platelet rich plasma). The resultant PRP was washed 3 times with a washing buffer and the number of platelets was counted with a micro cell counter. A suspension adjusted to contain the platelets at a final concentration of $5 \times 10^8$/ml was warmed at 37° C., then subjected to the pre-treatment with 3-isobutyl-1-methylxanthine (0.5 mM) for 5 min. To the suspension was added a test compound diluted at various concentration, and 10 minutes later, 0.1 µM $PGD_2$ was added to induce the reaction 2 minutes later, hydrochloric acid was added to terminate the reaction. The platelet was destroyed with an ultrasonic homogenizer. After centrifugation, the cAMP in the supernatant was determined by radioimmunoassay. $PGD_2$ receptor antagonism of a drug was evaluated as follows: the inhibition rate regarding cAMP increased by the addition of $PGD_2$ was determined at each concentration, and the concentration of the drug required for 50% inhibition ($IC_{50}$) was calculated.

The results of Experiment 1–3 are shown below.

TABLE 31

| Compound No. | Binding activity to $PGD_2$ receptor in human platelet membrane fraction $IC_{50}$ (µM) | Binding activity to $TXA_2$ receptor in human platelet membrane fraction $IC_{50}$ (µM) | Inhibitory activity for the increase of cAMP caused by $PGD_2$ in human platelet $IC_{50}$ (µM) |
|---|---|---|---|
| I-1b | 0.0043 | 0.003 | 0.0013 |
| I-10 | 0.0016 | 0.092 | 0.0018 |
| I-31 | 0.0082 | 0.130 | 0.0057 |
| I-47 | 0.0041 | 0.0062 | 0.007 |
| I-59 | 0.00041 | 0.016 | 0.0046 |
| I-66 | 0.0046 | 0.034 | 0.044 |
| I-79 | 0.00042 | 0.015 | 0.024 |
| I-80 | 0.0066 | 0.0052 | 0.039 |
| I-82 | 0.032 | 0.0018 | 0.053 |
| I-88 | 0.0076 | 0.078 | 0.0047 |
| I-93 | 0.0070 | 0.072 | 0.0084 |
| I-94 | 0.001 | 0.083 | 0.01 |
| I-104 | 0.0001 | 0.039 | 0.0016 |
| I-106 | 0.013 | 0.013 | 0.0093 |
| I-117 | 0.0091 | 0.0038 | 0.047 |
| I-128 | 0.020 | 0.048 | 0.01 |
| I-129 | 0.011 | 0.052 | 0.022 |
| I-131 | 0.044 | 0.019 | 0.041 |
| I-132 | 0.032 | 0.012 | 0.043 |
| I-136 | 0.023 | 0.016 | 0.015 |
| I-143 | 0.0027 | 0.028 | 0.0019 |
| I-146 | 0.044 | 0.019 | 0.073 |
| I-160 | 0.028 | 0.02 | 0.085 |
| I-168 | 0.00046 | 0.034 | 0.029 |
| I-169 | 0.00061 | 0.032 | 0.026 |
| I-170 | 0.00092 | 0.027 | 0.017 |
| I-182 | 0.061 | 0.028 | 0.011 |

TABLE 32

| Compound No. | Binding activity to PGD$_2$ receptor in human platelet membrane fraction IC$_{50}$ (μM) | Binding activity to TXA$_2$ receptor in human platelet membrane fraction IC$_{50}$ (μM) | Inhibitory activity for the increase of cAMP caused by PGD$_2$ in Human Platelet IC$_{50}$ (μM) |
|---|---|---|---|
| II-11 | 0.0079 | 0.030 | 0.0003 |
| II-15 | 0.002 | 0.012 | 0.011 |
| II-18 | 0.00096 | 0.0036 | 0.004 |
| II-21 | 0.0001 | 0.014 | 0.024 |
| II-30 | 0.072 | 0.0040 | 0.045 |
| II-34 | 0.0015 | 0.0044 | 0.0039 |
| II-37 | 0.0046 | 0.045 | 0.004 |
| II-40 | 0.026 | 0.0043 | 0.035 |
| II-45 | 0.022 | 0.0026 | 0.024 |
| II-59 | 0.032 | 0.072 | 0.025 |

Experiments for comparing the present compound having a dual antagonistic activity against PGD$_2$/TXA$_2$ receptors (e.g., I-1b, I-1c) with a PGD$_2$ receptor antagonist (e.g., B-1, B-2) and a TXA$_2$ antagonist (e.g., A) are shown below.

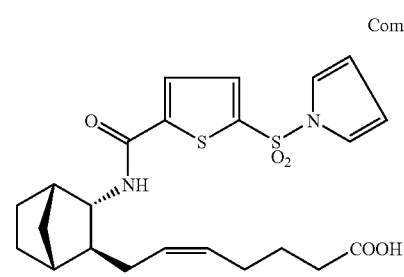

Compound (I-1b)

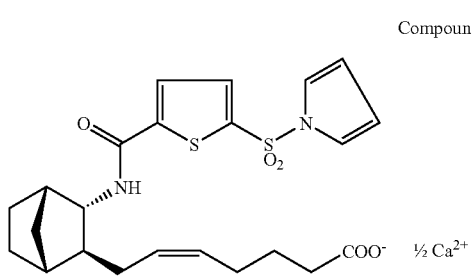

Compound (I-1c)

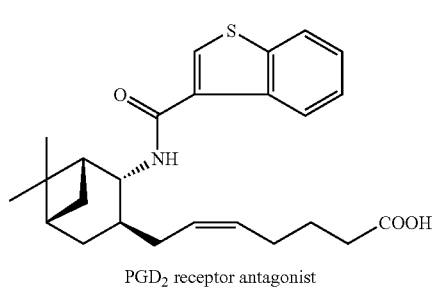

(B-1)

PGD$_2$ receptor antagonist

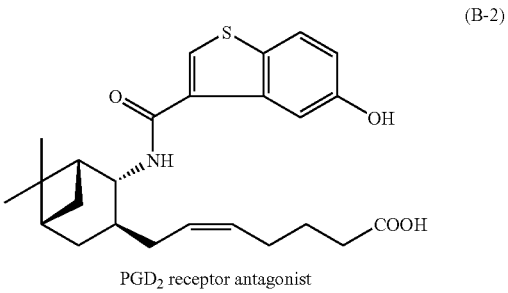

(B-2)

PGD$_2$ receptor antagonist

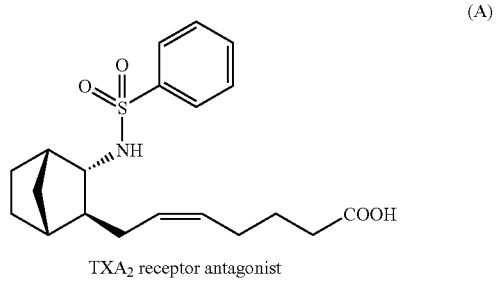

(A)

TXA$_2$ receptor antagonist

Comparative Experiment 1

The experiments were carried out in accordance with the above Experiment 1–3 for the purpose of comparing the compound having a dual antagonistic activity against PGD$_2$/TXA$_2$ receptor with a PGD$_2$ receptor antagonist and a TXA$_2$ receptor antagonist.

TABLE 33

| Compound | Experiment 1 Antaginistic activity against PGD$_2$ receptor IC$_{50}$ (μM) | Experiment 2 Antaginistic activity against TXA$_2$ receptor IC$_{50}$ (μM) | Experiment 3 Antaginistic activity against PGD$_2$ receptor IC$_{50}$ (μM) |
|---|---|---|---|
| Compound (I-1b) | 0.0043 | 0.003 | 0.0013 |
| TXA$_2$ receptor antagonist (A) | >10 | 0.0038 | >10 |
| PGD$_2$ receptor antagonist (B-1) | 0.0082 | 3.8 | 0.041 |

Comparative Experiment 2

Antigen-induced bronchial hyperresponsiveness

Male Hartley guinea pigs were actively sensitized to ovalbumin (OVA) by inhalation of aerosolized solution of 1% ovalbumin twice at a week interval. One week after the second sensitization, the animals were treated with antihistamine, diphenhydramine (10 mg/kg, i.p.), and then challenged with 1% OVA aerosol for 5 min. Twenty four hours later, acetylcholine at doses at 3.13, 6. 25, 12.5, 25, 50 and 100 micro g/kg was sequentially injected into the animals which were anesthetized with pentobarbital (30 mg/kg, i.p.). The bronchoconstriction induced by each dose of acetylcholine was monitored by the modified method of Konzett-Rössler technique, and made a dose-response curve of acetylcholine. Using the dose-response curve, the dose required for 200% increase in bronchoconstriction from baseline ($PD_{200}$) was calculated in each animal and used as an indication of bronchial responsiveness. Compounds were orally administered 1 hour before antigen challenge. **: P<0.01 vs Vehicle(Dunnett's test), ##: P<0.01 vs Vehicle (Student's t test).

TABLE 34

|  | Log $PD_{200}$ |
| --- | --- |
| Vehicle | 1.14 ± 0.03 |
| Compound (I-1b) 1 mg/kg | 1.25 ± 0.05 |
| Compound (I-1b) 10 mg/kg | 1.52 ± 0.06** |
| Negative control | 1.59 ± 0.08## |

TABLE 35

|  | Log $PD_{200}$ |
| --- | --- |
| Vehicle | 1.23 ± 0.06 |
| Compound (B-2) 10 mg/kg | 1.17 ± 0.05 |
| Negative control | 1.61 ± 0.06## |

TABLE 36

|  | Log $PD_{200}$ |
| --- | --- |
| Vehicle | 1.11 ± 0.06 |
| Compound (A) 1 mg/kg | 1.29 ± 0.04 |
| Compound (A) 10 mg/kg | 1.61 ± 0.09** |
| Negative control | 1.69 ± 0.06## |

As shown in Table 34, 35 and 36, a $PGD_2$ receptor antagonist (B-2) did not inhibit the induction of bronchial hyperresponsiveness, but $TXA_2$ receptor antagonist (A) and $PGD_2/TXA_2$ dual receptor antagonist, (e.g., I-1b) suppressed it, indicating that $TXA_2$ receptor antagonism is necessary for improvement of bronchial hyperresponsiveness.

Comparative Experiment 3

Antigen-induced increase in the eosinophil number in bronchoalveolar lavage fluid.

As described above, the animals were sensitized and challenged with antigen, seventy-two hours later, bronchoalveolar lavage was performed with 10 mL of saline. After the number of total cells in the recovered fluid was counted, smear samples were made. The samples were stained with May Grünward-Giemsa Stain, and differential cell count was performed by counting 500 cells/each sample. The eosinophil number was calculated by the ratio of the number of eosinophils, macrophages, neutrophils and lymphocytes. Compounds were orally administered three times 1 hour before and 24 and 48 hours after the challenge. The results are shown as follows. *: P<0.05, * *: P<0.01 vs Vehicle (Dunnett's test), : P<0. 01 vs Vehicle(Student's t test). ( ): inhibition %.

TABLE 37

|  | Cell number (×$10^6$ cells/animal) | |
| --- | --- | --- |
|  | Total cells | Eosinophils |
| Vehicle | 18.99 ± 1.69 | 6.06 ± 0.81 |
| Compound (I-1c) 1 mg/kg | 12.40 ± 1.27**(50%) | 4.33 ± 0.45 (38%) |
| Compound (I-1c) 10 mg/kg | 8.27 ± 0.65**(81%) | 2.64 ± 0.16**(75%) |
| Negative control | 5.72 ± 0.36## | 1.49 ± 0.09## |

TABLE 38

|  | Cell number (×$10^6$ cells/animal) | |
| --- | --- | --- |
|  | Total cells | Eosinophils |
| Vehicle | 18.47 ± 0.70 | 6.56 ± 0.60 |
| Compound (B-2) 10 mg/kg | 13.01 ± 1.58**(45%) | 4.49 ± 0.63*(43%) |
| Negative control | 6.32 ± 0.31## | 1.78 ± 0.18## |

TABLE 39

|  | Cell number (×$10^6$ cells/animal) | |
| --- | --- | --- |
|  | Total cells | Eosinophils |
| Vehicle | 12.10 ± 1.91 | 4.23 ± 0.75 |
| Compound (A) 10 mg/kg | 13.78 ± 1.75 (−18%) | 4.90 ± 0.73 (−18%) |
| Negative control | 2.98 ± 0.28## | 0.55 ± 0.13## |

As shown in Table 37, 38 and 39, $PGD_2$ receptor antagonist (B-2) and $PGD_2/TXA_2$ dual receptor antagonist (I-1c) significantly suppressed the eosinophil infiltration. But a $TXA_2$ receptor antagonist (A) did not show any inhibitory actions. These results indicate that $PGD_2$ receptor antagonism is necessary for suppression of inflammatory cell infiltration.

Comparative Experiment 4

Antigen-induced bronchoconstriction

Male Hartley guinea pigs were passively sensitized by intravenous injection of anti-OVA serum (antibody titer: 1: 3200), and 48 hours later, the animals were challenged by intravenous injection of OVA (70 micro g/kg). The bronchoconstriction induced by antigen was continuously monitored by means of modified method of Konzett-Rössler technique. The peak value of bronchoconstriction in each animal was used for evaluation of compounds. Compound (I-1b) and compound (B-2) were orally administered 1 hour before, compound (A) 2 hours before antigen challenge. The results are shown as follows. *: P<0.05 vs Vehicle, ##: P<0.01 vs Vehicle. ( ): inhibition %.

TABLE 40

|  | Peak bronchoconstriction (cm $H_2O$) |
| --- | --- |
| Vehicle | 68.3 ± 9.2 |
| Compound (I-1b) 1 mg/kg | 47.4 ± 11.4 (31%) |
| Compound (I-1b) 10 mg/kg | 28.4 ± 12.9*(58%) |

TABLE 41

|  | Peak bronchoconstriction (cm H$_2$O) |
| --- | --- |
| Vehicle | 30.3 ± 7.4 |
| Compound (B-2) 1 mg/kg | 36.5 ± 18.2 (−20%) |
| Compound (B-2) 30 mg/kg | 51.8 ± 16.3 (−71%) |

TABLE 42

|  | Peak bronchoconstriction (cm H$_2$O) |
| --- | --- |
| Vehicle | 59.2 ± 7.3 |
| Compound (A) 3 mg/kg | 55.3 ± 6.7 (7%) |
| Compound (A) 10 mg/kg | 18.8 ± 3.3**(68%) |

As shown in Table 40, 41 and 42, PGD$_2$ receptor antagonist (B-2) did not suppress the antigen-induced bronchoconstriction in this model but TXA$_2$ receptor antagonist (A) and PGD$_2$/TXA$_2$ dual receptor antagonist (I-1b) dramatically suppressed it. These results indicate that TXA$_2$ receptor antagonism is necessary for inhibition of bronchoconstrition.

Formulation Example

It is to be noted that the following Formulation Examples 1 to 8 are mere illustration, but not intended to limit the scope of the invention. The term "Active ingredient" means a compound of the present invention, the prodrug thereof, their pharmaceutically acceptable salt, or their hydrate.

Formulation Example 1

Hard gelatin capsules are prepared using the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

Tablet are prepared using the following ingredients:

|  | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The ingredients are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients is generally administered intravenously to a subject at a rate of 1 ml per minute.

Industrial Applicability

The pharmacological effect of the compound of the present invention is compared with that of $TXA_2$ receptor antagonist and $PGD_2$ receptor antagonist in the following table.

TABLE 43

| | $TXA_2$ receptor antagonist | $PGD_2$ receptor antagonist | Compound (I) |
|---|---|---|---|
| Bronchial asthma | | | |
| Eosinophilic infiltration | x | ⊚ | ⊚ |
| Advance of respiratory anaphylaxis | ⊚ | x | ⊚ |
| Respiratory contraction | ⊚ | x | ⊚ |

In bronchial asthma, a $TXA_2$ receptor antagonist itself can inhibit advance of respiratory anaphylaxis and respiratory contraction, but has no effect for eosinophilic infiltration. A $PGD_2$ receptor antagonist itself can inhibit eosinophilic infiltration, but has no effect for advance of respiratory anaphylaxis and respiratory contraction. On the other hand, a compound having a dual antagonistic activity against $PGD_2/TXA_2$ receptors like the compound (I) is efficient for all of eosinophilic infiltration, advance of respiratory anaphylaxis and respiratory contraction.

The compound having a dual antagonistic activity against $PGD_2/TXA_2$ receptors is useful for treating systemic mastocytosis and disorder of systemic mast cell activation as well as tracheal contraction, asthma, allergic rhinitis, allergic conjunctivitis, urticaria, itching, atopic dermatitis, alimentary allergy, ischemic reperfusion injury, cerebrovascular disorder, and inflammation, and effective for treating or improving condition of diseases such as arteriosclerosis, myocardial infarction, acute myocardial ischemia angina, cardiovascular shock or preventing unexpected death and the like, especially asthma or nasal blockage.

With a dual antagonistic activity against both a $TXA_2$ receptor and a $PGD_2$ receptor, the present compound can overcome some problems such as that due to the metabolic rate difference of each compound, which occur upon simultaneous administration of both a $TXA_2$ receptor antagonist and a $PGD_2$ receptor antagonist.

What is claimed:
1. A compound selected from the group consisting of:
7-(3-{[5-(Pyrrole-1-sulfonyl)-thiophene-2-carbonyl]-amino}-bicyclo[2.2.1]hept-2-yl)-hept-5-enoic acid (I-1b),
7-(3-{[5-(Thiophene-2-sulfonyl)-thiophene-2-carbonyl]-amino}-bicyclo[2.2.1]hept-2-yl)-hept-5-enoic acid (I-47),
7-(3-{[5-(Thiophen-2-ylsulfanyl)-thiophene-2-carbonyl]-amino}-bicyclo[2.2.1]hept-2-yl)-hept-5-enoic acid (I-59),
7-(3-{[5-(Thiophen-3-ylsulfanyl)-thiophene-2-carbonyl]-amino}-bicyclo[2.2.1]hept-2-yl)-hept-5-enoic acid (I-79),
7-(3-{[5-(Thiophene-3-sulfonyl)-thiophene-2-carbonyl]-amino}-bicyclo[2.2.1]hept-2-yl)-hept-5-enoic acid (I-80),
7-(3-{[5-(5-Methyl-thiophene-2-sulfonyl)-thiophene-2carbonyl]-amino}-bicyclo[2.2.1]hept-2-yl)-hept-5-enoic acid (I-82),
7-(3-{[5-(Thiophen-3-ylmethyl)-thiophene-2-carbonyl]-amino}-bicyclo[2.2.1]hept-2-yl)-hept-5-enoic acid (I-88),
7-(3-{[5-(Thiophen-2-ylmethyl)-thiophene-2-carbonyl]-amino}-bicyclo[2.2.1]hept-2-yl)-hept-5-enoic acid (I-93),
7-(3-{[1-(Thiophene-2-sulfonyl)-1H-pyrrole-3-carbonyl]-amino}-bicyclo[2.2.1]hept-2-yl)-hept-5-enoic acid (I-94),
7-(3-{[5-(Thiophen-2-ylsulfanylmethyl)-thiophene-2-carbonyl]amino}-bicyclo[2.2.1]hept-2-yl)-hept-5-enoic acid (I-104),
7-(3-{[5-(Thiophen-2-ylmethylsulfanyl)-thiophen-2-carbonyl]-amino}-bicyclo[2.2.1]hept-2-yl)-hept-5-enoic acid (I-106),
7-(3-{[5-(5-Methyl-thiophen-2-ylmethyl)-thiophene-2-carbonyl]-amino}-bicyclo[2.2.1]hept-2-yl)-hept-5-enoic acid (I-129),
7-(3-{[5-(Benzofuran-2-ylmethyl)-thiophene-2-carbonyl]-amino}bicyclo[2.2.1]hept-2-yl)-hept-5-enoic acid (I-136),

7-(3-{[7-(Thiophen-2-ylmethyl)-benzo[b]thiophene-3-carbonyl]-amino}-bicyclo[2.2.1]hept-2-yl)-hept-5-enoic acid (I-168), 7-(3-{[7-(Thiophen-3-ylmethyl)-benzo[b]thiophene-3-carbonyl]-amino}-bicyclo[2.2.1]hept-2-yl)-hept-5-enoic acid (I-169), 7-(3-{[7-(Furan-3-ylmethyl)-benzo[b]thiophene-3-carbonyl]amino}-bicyclo[2.2.1]hept-2-yl)-hept-5-enoic acid (1–170), 7-(3-{[5-(Benzo[b]thiophen-3-ylmethyl)-thiophene-2-carbonyl]-amino}-bicyclo[2.2.1]hept-2-yl)-hept-5-enoic acid (I-182), 7-(6,6-Dimethyl-2-{[5-(pyrrole-1-sulfonyl)-thiophene-2-carbonyl]-amino}-bicyclo[3.1.1]hept-3-yl)-hept-5-enoic acid (II-15), 7-(6,6-Dimethyl-2-{[5-(thiophene-2-sulfonyl)-thiophene-2-carbonyl]-amino}-bicyclo[3.1.1]hept-3-yl)-hept-5-enoic acid (II-18), 7-(6,6-Dimethyl-2-{[5-(thiophen-2-ylsulfanyl)-thiophene-2-carbonyl]-amino}-bicyclo[3.1.1]hept-3-yl)-hept-5-enoic acid (II-21), 7-(6,6-Dimethyl-2-([5-(5-methyl-thiophene-3-sulfonyl)-thiophene-2-carbonyl]-amino)-bicyclo[3.1.1]hept-3-yl)-hept-5-enoic acid (II-30), and 7-(6,6-Dimethyl-2-([5-(2-methyl-pyrrole-1-sulfonyl)-thiophene-2-carbonyl]-amino)-bicyclo[3.1.1]hept-3-yl)-hept-5-enoic acid (II-34), or a pharmaceutically acceptable salt, or a hydrate thereof.

2. A pharmaceutical composition which comprises a compound according to claim 1.

3. A method for treating a mammal to alleviate the pathological effects of asthma or nasal blockage which comprises administering to said mammal an effective amount of the compound according to claim 1.

* * * * *